US011185441B2

(12) United States Patent
Mandell

(10) Patent No.: US 11,185,441 B2
(45) Date of Patent: Nov. 30, 2021

(54) OCULAR DEVICE DELIVERY METHODS AND SYSTEMS

(71) Applicant: LayerBio, Inc., Lexington, MA (US)

(72) Inventor: Kenneth Jason Mandell, Lexington, MA (US)

(73) Assignee: LAYERBIO, INC., Lexington, MA (US)

(*) Notice: Subject to any disclaimer, the term of this patent is extended or adjusted under 35 U.S.C. 154(b) by 0 days.

(21) Appl. No.: 16/935,027

(22) Filed: Jul. 21, 2020

(65) Prior Publication Data
US 2020/0405538 A1 Dec. 31, 2020

Related U.S. Application Data

(63) Continuation of application No. PCT/US2020/039990, filed on Jun. 26, 2020.

(60) Provisional application No. 62/867,233, filed on Jun. 27, 2019, provisional application No. 63/012,994, filed on Apr. 21, 2020.

(51) Int. Cl.
| A61F 9/00 | (2006.01) |
| A61F 2/16 | (2006.01) |
| A61K 9/00 | (2006.01) |
| A61K 47/34 | (2017.01) |
| A61K 31/365 | (2006.01) |
| A61K 31/366 | (2006.01) |
| A61L 31/04 | (2006.01) |
| A61L 31/12 | (2006.01) |
| A61L 31/16 | (2006.01) |

(52) U.S. Cl.
CPC .............. *A61F 9/0017* (2013.01); *A61F 2/16* (2013.01); *A61K 9/0051* (2013.01); *A61K 31/365* (2013.01); *A61K 31/366* (2013.01); *A61K 47/34* (2013.01); *A61L 31/04* (2013.01); *A61L 31/041* (2013.01); *A61L 31/125* (2013.01); *A61L 31/16* (2013.01); *A61F 2002/1681* (2013.01); *A61F 2002/1683* (2013.01); *A61F 2250/0067* (2013.01); *A61L 2300/41* (2013.01)

(58) Field of Classification Search
CPC ...... A61F 2002/1681; A61F 2002/1683; A61F 2/16; A61F 9/0017; A61F 2250/0067; A61K 31/365; A61K 31/366; A61K 9/0051; A61L 2300/41; A61L 2430/16; A61L 27/54; A61L 31/04; A61L 31/125; C08L 67/04

See application file for complete search history.

(56) References Cited

U.S. PATENT DOCUMENTS

| 4,681,102 A | 7/1987 | Bartell |
| 4,834,750 A | 5/1989 | Gupta |
| 4,938,763 A | 7/1990 | Dunn et al. |
| 5,290,892 A | 3/1994 | Namdaran et al. |
| 5,378,475 A | 1/1995 | Smith et al. |
| 5,443,505 A | 8/1995 | Wong et al. |
| 5,554,187 A | 9/1996 | Rizzo, III |
| 6,679,605 B2 | 1/2004 | Zhou et al. |
| 6,699,493 B2 | 3/2004 | Wong |
| 6,713,081 B2 | 3/2004 | Robinson et al. |
| 6,726,918 B1 | 4/2004 | Wong et al. |
| 7,033,605 B2 | 4/2006 | Wong |
| 7,090,888 B2 | 8/2006 | Snyder et al. |
| 7,625,582 B2 | 12/2009 | Wong |
| 7,655,038 B2 | 2/2010 | Luthra et al. |
| 7,767,223 B2 | 8/2010 | Wong |
| 7,799,336 B2 | 9/2010 | Hughes |
| 7,931,909 B2 | 4/2011 | Hughes et al. |
| 8,039,010 B2 | 10/2011 | Trogden et al. |
| 8,043,628 B2 | 10/2011 | Wong |
| 8,063,031 B2 | 11/2011 | Wong et al. |
| 8,071,120 B2 | 12/2011 | Wong |
| 8,088,407 B2 | 1/2012 | Wong |
| 8,119,154 B2 | 2/2012 | Huang et al. |
| 8,147,865 B2 | 4/2012 | Huang et al. |
| 8,206,736 B2 | 6/2012 | Hughes |
| 8,216,603 B2 | 7/2012 | Kaufman |
| 8,242,099 B2 | 8/2012 | Wong et al. |
| 8,263,110 B2 | 9/2012 | Huang et al. |
| 8,293,741 B2 | 10/2012 | Burke et al. |
| 8,298,570 B2 | 10/2012 | Huang et al. |
| 8,318,169 B2 | 11/2012 | Trogden et al. |
| 8,343,214 B2 | 1/2013 | Kleinman |
| 8,389,597 B2 | 3/2013 | Blackwell et al. |
| 8,404,267 B2 | 3/2013 | Hughes et al. |
| 8,409,607 B2 | 4/2013 | Hughes et al. |
| 8,425,929 B2 | 4/2013 | Huang et al. |
| 8,455,656 B2 | 6/2013 | Spada et al. |
| 8,506,962 B2 | 8/2013 | Trogden et al. |
| 8,506,987 B2 | 8/2013 | Shiah et al. |
| 8,512,738 B2 | 8/2013 | Edelman et al. |
| 8,637,068 B2 | 1/2014 | Hughes |
| 8,663,194 B2 | 3/2014 | Ambati et al. |
| 8,668,920 B2 | 3/2014 | Kaufman |
| 8,673,341 B2 | 3/2014 | Hughes |
| 8,685,435 B2 | 4/2014 | Nivaggioli et al. |
| 8,702,794 B2 | 4/2014 | Hoffmann et al. |
| 8,715,713 B2 | 5/2014 | Ghebremeskel et al. |

(Continued)

FOREIGN PATENT DOCUMENTS

| EP | 1289740 B1 | 8/2005 |
| EP | 1339438 B1 | 10/2005 |

(Continued)

OTHER PUBLICATIONS

Allergan Acular (2012) Highlights of prescribing Information.

(Continued)

*Primary Examiner* — Anna R Falkowitz
(74) *Attorney, Agent, or Firm* — Wilson Sonsini Goodrich & Rosati

(57) ABSTRACT

The present disclosure provides an ophthalmic article. The ophthalmic article may comprise a biocompatible matrix comprising a copolymer derived from a caprolactone monomer and at least one other monomer. The ophthalmic article may also comprise an active agent or a diagnostic agent. The ophthalmic article may be configured to associate to a haptic of an intraocular lens (IOL).

30 Claims, 67 Drawing Sheets

(56) References Cited

U.S. PATENT DOCUMENTS

| | | |
|---|---|---|
| 8,771,722 B2 | 7/2014 | Huang et al. |
| 8,828,446 B2 | 9/2014 | Wong |
| 8,834,884 B2 | 9/2014 | Trogden et al. |
| 8,956,655 B2 | 2/2015 | Lyons et al. |
| 8,968,766 B2 | 3/2015 | Hughes et al. |
| 8,969,415 B2 | 3/2015 | Robinson et al. |
| 8,974,812 B2 | 3/2015 | Nivaggioli et al. |
| 9,012,437 B2 | 4/2015 | Wong et al. |
| 9,084,662 B2 | 7/2015 | Gifford, III et al. |
| 9,149,428 B2 | 10/2015 | Spada et al. |
| 9,192,511 B2 | 11/2015 | Shiah et al. |
| 9,233,070 B2 | 1/2016 | Edelman et al. |
| 9,283,178 B2 | 3/2016 | Wong |
| 9,327,059 B2 | 5/2016 | Huang et al. |
| 9,421,126 B2 | 8/2016 | Alster et al. |
| 9,592,242 B2 | 3/2017 | Wong |
| 9,610,246 B2 | 4/2017 | Shiah et al. |
| 9,668,917 B2 | 6/2017 | Gifford, III et al. |
| 9,775,849 B2 | 10/2017 | Wong et al. |
| 9,782,346 B2 | 10/2017 | Venkatraman et al. |
| 9,877,973 B2 | 1/2018 | Ambati et al. |
| 9,889,142 B2 | 2/2018 | Hughes et al. |
| 10,064,819 B2 | 9/2018 | Ambati et al. |
| 10,076,492 B2 | 9/2018 | Edelman et al. |
| 10,201,641 B2 | 2/2019 | Huang et al. |
| 10,206,934 B2 | 2/2019 | Wong et al. |
| 10,231,926 B2 | 3/2019 | Shiah et al. |
| 10,245,178 B1 | 4/2019 | Heitzmann et al. |
| 10,363,214 B2 | 7/2019 | Whitcup et al. |
| 10,383,721 B2 | 8/2019 | Marcos Celestino et al. |
| 10,449,145 B2 | 10/2019 | Csaky |
| 10,456,293 B2 | 10/2019 | Rubin et al. |
| 10,548,766 B2 | 2/2020 | Cuevas |
| 10,588,855 B2 | 3/2020 | Ambati et al. |
| 10,603,274 B2 | 3/2020 | Utkhede et al. |
| 2002/0164374 A1 | 11/2002 | Jackson et al. |
| 2006/0008506 A1 | 1/2006 | Cipriano De Sousa et al. |
| 2008/0050421 A1 | 2/2008 | Wong |
| 2008/0233172 A1 | 9/2008 | Whitcup et al. |
| 2009/0130176 A1 | 5/2009 | Bossy-Nobs et al. |
| 2010/0074942 A1 | 3/2010 | Ratner et al. |
| 2012/0329850 A1 | 12/2012 | Whitcup et al. |
| 2013/0209538 A1 | 8/2013 | Venkatraman et al. |
| 2013/0273137 A1 | 10/2013 | Mandell et al. |
| 2013/0302420 A1 | 11/2013 | Bowyer et al. |
| 2014/0199366 A1 | 7/2014 | Huang et al. |
| 2014/0316009 A1 | 10/2014 | Hughes |
| 2014/0336164 A1 | 11/2014 | Pal et al. |
| 2015/0174062 A1 | 6/2015 | Lyons et al. |
| 2015/0209274 A1* | 7/2015 | Venkatraman ........ A61F 9/0017 424/427 |
| 2015/0272877 A1 | 10/2015 | Shi et al. |
| 2015/0290170 A1 | 10/2015 | Liu et al. |
| 2016/0296627 A1 | 10/2016 | Garcia et al. |
| 2018/0177634 A1 | 6/2018 | De Juan, Jr. et al. |
| 2018/0177718 A1 | 6/2018 | Garcia et al. |
| 2018/0250311 A1 | 9/2018 | Ambati et al. |
| 2018/0325812 A1 | 11/2018 | Thakur et al. |
| 2019/0046434 A1 | 2/2019 | Mota Leite Machado Mariz et al. |
| 2019/0053892 A1* | 2/2019 | Siney .................. A61L 27/54 |
| 2019/0125581 A1 | 5/2019 | Heitzmann et al. |
| 2019/0133934 A1 | 5/2019 | Jacob et al. |
| 2019/0192341 A1 | 6/2019 | Robinson et al. |
| 2019/0254964 A1 | 8/2019 | Nivaggioli et al. |
| 2019/0336441 A1 | 11/2019 | Whitcup et al. |
| 2019/0358028 A1 | 11/2019 | Marcos Celestino et al. |
| 2019/0388339 A1 | 12/2019 | Csaky |
| 2020/0038240 A1 | 2/2020 | De Juan, Jr. et al. |
| 2020/0038326 A1 | 2/2020 | Spada et al. |
| 2020/0069577 A1 | 3/2020 | Liu et al. |
| 2020/0222317 A1 | 7/2020 | Utkhede et al. |
| 2020/0261358 A1 | 8/2020 | Wu et al. |
| 2020/0281767 A1 | 9/2020 | Zhu |
| 2020/0297530 A1 | 9/2020 | Cohen et al. |

FOREIGN PATENT DOCUMENTS

| | | |
|---|---|---|
| EP | 1296645 B1 | 9/2006 |
| EP | 1750688 B1 | 12/2007 |
| EP | 1758552 B1 | 7/2011 |
| EP | 2329811 B1 | 3/2013 |
| EP | 1773350 B1 | 5/2013 |
| EP | 2276439 A4 | 11/2013 |
| EP | 2361617 B1 | 6/2014 |
| EP | 2777693 A1 | 9/2014 |
| EP | 2307055 B1 | 1/2016 |
| EP | 2792362 B1 | 3/2016 |
| EP | 2364127 B1 | 8/2016 |
| EP | 2493459 B1 | 8/2016 |
| EP | 2591025 B1 | 10/2016 |
| EP | 1637126 B1 | 12/2016 |
| EP | 2026764 B1 | 7/2017 |
| EP | 1740153 B2 | 8/2017 |
| EP | 2086503 B1 | 12/2017 |
| EP | 3062775 B1 | 12/2017 |
| EP | 3067015 B1 | 6/2018 |
| EP | 3338743 A1 | 6/2018 |
| EP | 2305261 B1 | 9/2018 |
| EP | 2900250 B1 | 11/2018 |
| EP | 2571526 B1 | 3/2019 |
| EP | 3456323 A1 | 3/2019 |
| EP | 3068372 B1 | 5/2019 |
| EP | 3378505 A4 | 8/2019 |
| EP | 3524270 A1 | 8/2019 |
| EP | 3494959 A3 | 9/2019 |
| EP | 3566693 A1 | 11/2019 |
| EP | 3351239 B1 | 4/2020 |
| EP | 3656374 A1 | 5/2020 |
| EP | 3562489 A4 | 7/2020 |
| EP | 3167872 B1 | 10/2020 |
| WO | WO-2016196365 A1 | 12/2016 |
| WO | WO-2017015675 A1 | 1/2017 |
| WO | WO-2017053686 A1 | 3/2017 |
| WO | WO-2017137934 A1 | 8/2017 |
| WO | WO-2017184881 A1 | 10/2017 |
| WO | WO-2018064648 A1 | 4/2018 |
| WO | WO-2018175268 A1 | 9/2018 |
| WO | WO-2019033336 A1 | 2/2019 |
| WO | WO-2019056751 A1 | 3/2019 |
| WO | WO-2019094652 A1 | 5/2019 |
| WO | WO-2019164834 A1 | 8/2019 |
| WO | WO-2020047144 A3 | 3/2020 |
| WO | WO-2020104200 A1 | 5/2020 |
| WO | WO-2020128062 A1 | 6/2020 |
| WO | WO-2020128067 A1 | 6/2020 |
| WO | WO-2020191318 A1 | 9/2020 |

OTHER PUBLICATIONS

Assia, et al., Effect of expandable full-size intraocular lenses on lens centration and capsule opacification in rabbits, J Cataract Refract Surg (1999) vol. 25 pp. 347-356.

Baumeister, et al., Tilt and Decentration of Three-Piece Foldable High-Refractive Silicone and Hydrophobic Acrylic Intraocular Lenses With 6-mm Optics in an Intraindividual Comparison), American Journal of Ophthalmology, (2005) 1052-1058.

Beeley, et al., Fabrication, implantation, elution, and retrieval of a steroid-loaded polycaprolactone subretinal implant, Wiley InterScience (2005).

Schindler, et al., Biodegradable Polymers for Sustained Drug Delivery, Contemporary Topics in Polymer Science (1997) 251-289.

Cho, et al., The behavior of vascular smooth muscle cells an dplatelets onto epigallocatechin gallate-releasing poly(L-lactide-co-e-caprolactone) as stent-coating materials, Biomaterials 29 (2008) 884-893.

Donnelly, et al., Instilling eyedrops: difficulties experienced by patients following cataract surgery, Journal of Advanced Nursing, (1987) 12, 235-243.

Dunham, et al., The contralateral reduction of intraocular pressure by timolol British Journal of Ophthalmology (1994); 78:38-40.

(56) References Cited

OTHER PUBLICATIONS

Sellman, et al., Effect of a plano-convex posterior chamber lens on capsular opacification from Elschnig pearl formation J Cataract Refract Surg—vol. 14, (1988) 68-72.
Eperon, et al., A biodegradable drug delivery system for the treatment of postoperative inflammation, International Journal of Pharmaceutics, 352 (2008) 240-247.
Eperon, et al., A new drug delivery system inhibits uveitis in a animal model after cataract surgery, International Journal of Pharmaceutics 443 (2013) 254-261.
Fernandez, et al., Synthesis, structure and properties of poly(L-lactide-co-e-caprolactone) statistical copolymers, Journal of the Mechanical Behavior of Biomedical Materials 9 (2012) 100-112.
Grijpma, et al., High molecular weight copolymers of L-lactide and e-caprolactone as biodegradable elastomeric implants materials, Polymer Bulletin 25, (1991) 327-333.
Grijpma, et al., Polymerization temperature effects on the properties of L-lactide and E-caprolactone copolymers (1991) Polymer Bulletin 25, 335-341.
Perego, Gabriele et al., Preparation of a new nerve guide from a poly(L-lactide-co-6-caprolactone), Biomaterials, 1994, vol. 15, No. 189-193.
Guan, et al., Preparation and characterization of a highly macroporous biodegradable composite tissue engineering scaffold Wiley InterScience, (2004) 481-487.
Hackett, et al., Assessing Ocular Irritation (1996) Chapter 44 p. 557-567.
Hiljanen-Vainio, et al., Properties of E-caprolactone-DL-lactide (E-CL/DL-LA) copolymers with a minor E-CL content), Journal of Biomedical Materials Research (1997) vol. 34 39-46.
Silva-Cunba, et al., Poly-e-Caprolactone Intravitreous Devices: An In vivo Study IVOS, (2009) vol. 50, No. 5, 2312-2318.
Siqueira, et al., Pharmacokinetic and Toxicity Investigations of a New Intraocular Lens with a Dexamethasone Drug Delivery System: A Pilot Study, Ophthalmologica (2006); 220:338-342.
Kim, et al., Biocompatibility and Pharmacokinetic Analysis of an Intracameral Polycaprolactone Drug Delivery Implant for Glaucoma IOVS (2016) vol. 57, No. 10, 4341-4346.
Kimura, et al., Assessment of tilt and decentration of crystalline lens and intraocular lens relative to the corneal topographic axis using anterior segment optical coherence tomography Department of Ophthalmology, plos One (2017) 1-12.
Kleinmann, et al., hydrophilic acrylic intraocular lens as a drug-delivery system for fourth-generation fluoroquinolones J Cataract Refract Surg (2006) vol. 32.
Kugelberg, et al., Intraocular lens as a drug delivery system for dexamethasone, ACTA Ophthalmologica (2010) 88: 241-244.
Lee, et al., Elastic Biodegradable poly(glycolide-co-caprolactone) scaffold for tissue engineering, (2003) Wiley Periodicals, Inc. 29-37.
Lindstrom, et al., Dropless Cataract Surgery: An Overview, Bentham Science, Current Pharmaceutical Design (2017) 23, 558-564.
Smith, et al., Difficulties patients have at home after cataract surgery Can J Ophthalmol—col. 19, No. 1 (1994).
Mohammadi, et al., Injectable drug depot engineered to release multiple ophthalmic therapeutic agents with precise time profiles for postoperative treatment following ocular surgery Acta Biomater. (2018) 73: p. 90-102.
Omeros Copration (2018) OMIDRIA Highlights of Prescribing Information.
Pandita, et al., Contrast sensitivity and glare disability after implantation of AcrySof IQ Natural aspherical intraocular lens, J Cataract Refract Surg (2007) 33: 603-610.
Standardization of Uveitis Nomenclature for Reporting Clinical Data. Results of the First International Workshop The Standardization of Uveitis Nomenclature (SUN) Working Group, J Ophthalmol (2005) 140: 509-516.
Vainio, et al., Biodegradable Lactone Copolymers. I. Characterization and Mechanical Behavior of E-Caprolactone and Lactide Copolymers, Journal of Applied Polymer Science, (1996) Vo. 59, 1281-1288.
Wache, et al., Development of a polymer stent with shape memory effect as a drug delivery system, Journal of Materials Science: Materials in Medicine (2003) 14 109-112.
Woodward, et al., Hydrolytic Degradation and Erosion of Polyester Biomaterials ACS Macro Lett. (2018) 7(8): 976-982.
"Gantrade "Caprolactone Monomer: A Gateway Building Block for Advanced Performance Intermediates" Jan. 25, 2019".
"International Search Report and Written Opinion in corresponding PCT Application No. PCT/US2020/039990 dated Dec. 9, 2020".
"Jung, et al., "Physicochemical and surface properties of acrylic intraocular lenses and their clinical significance" Journal of Pharmaceutical Investigation (2017), vol. 47, No. 5".
"Wikipedia "Flexural Stength" Oct. 10, 2018 retrieved from ,http://en/wikipedia.org/w/index.php?title=Flexural_strength&oldid=863375722.".
"Wikipedia "Lactide" Jun. 12, 2018 retrieved from http://en/wikipedia.org/w/index.php?title=Lactide&oldid=863375722.".
Bhubalan et al., Chapter 8, Polyhydroxyalkanoate, Biodegradable Polymers In Clinical Use and Clinical Development, First Edition, pp. 249-316, 2011.
Cooper et al., Chapter 11, Poly($\epsilon$-Caprolactone-CO-Glycolide): Biomedical Applications of a Unique Elastomer, Biodegradable Polymers In Clinical Use and Clinical Development, First Edition, pp. 401-416, 2011.
Jain et al., Chapter 1, Biodegradable Polymers In Drug Delivery, Biodegradable Polymers In Clinical Use and Clinical Development, First Edition, pp. 1-76, 2011.
Letchford et al., Chapter 9, Lactide and Glycolide Polymers, Biodegradable Polymers In Clinical Use and Clinical Development, First Edition, pp. 319-366, 2011.

\* cited by examiner

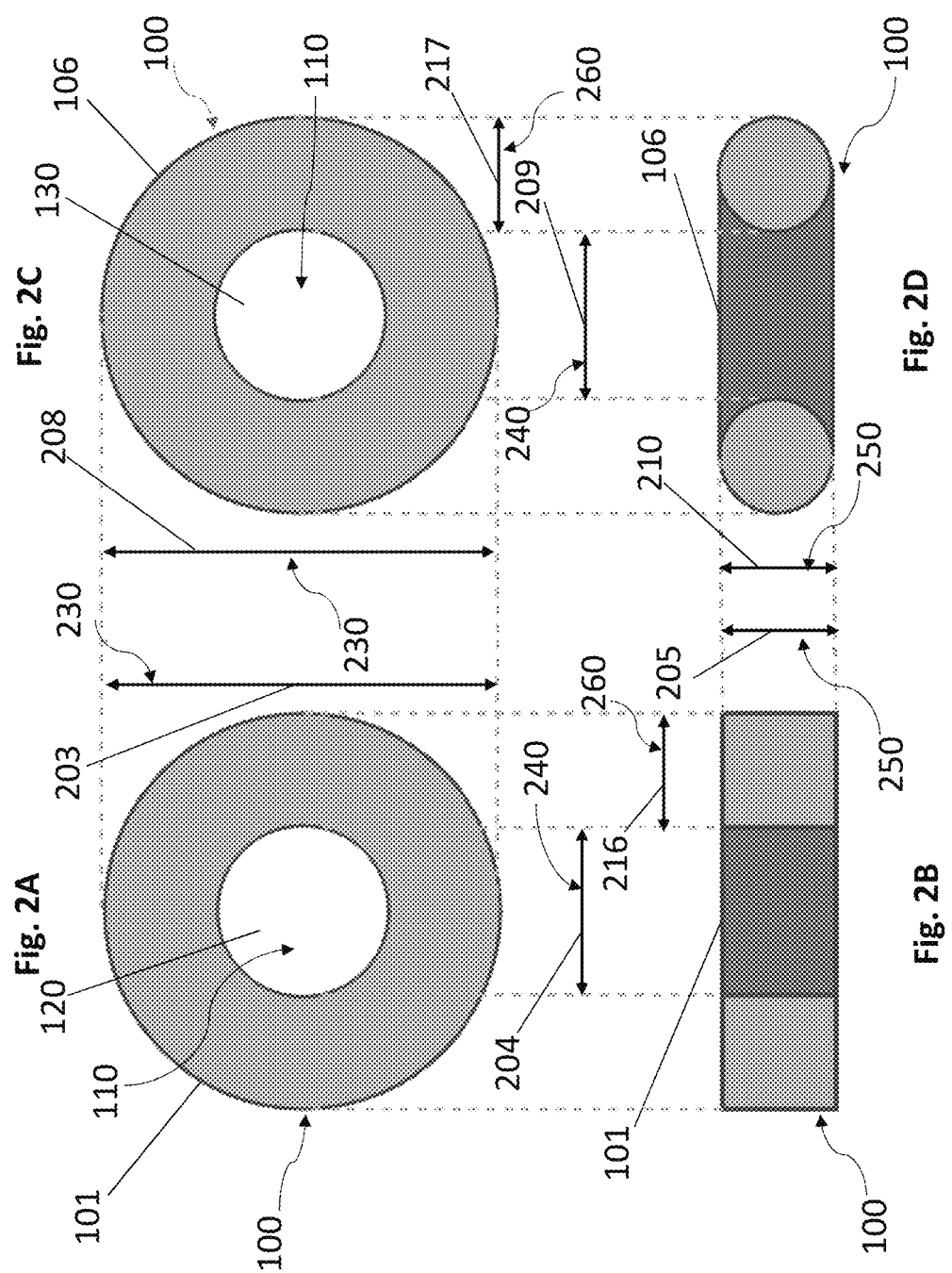

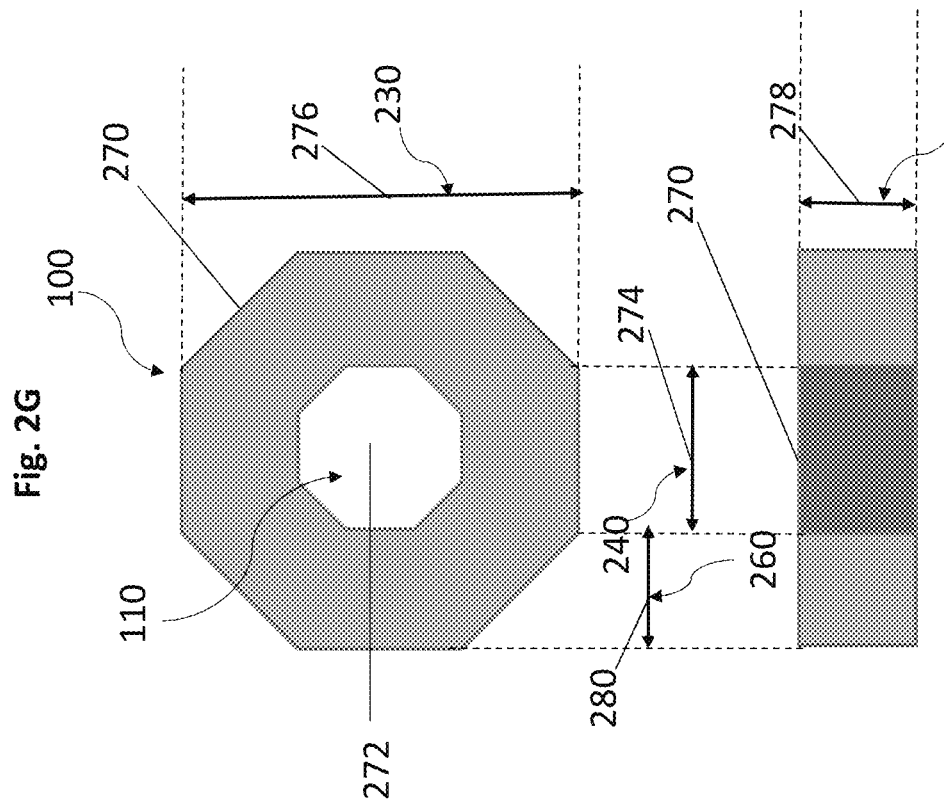
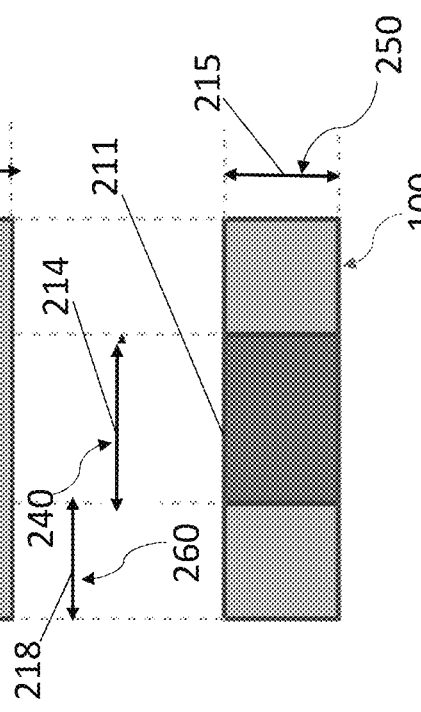

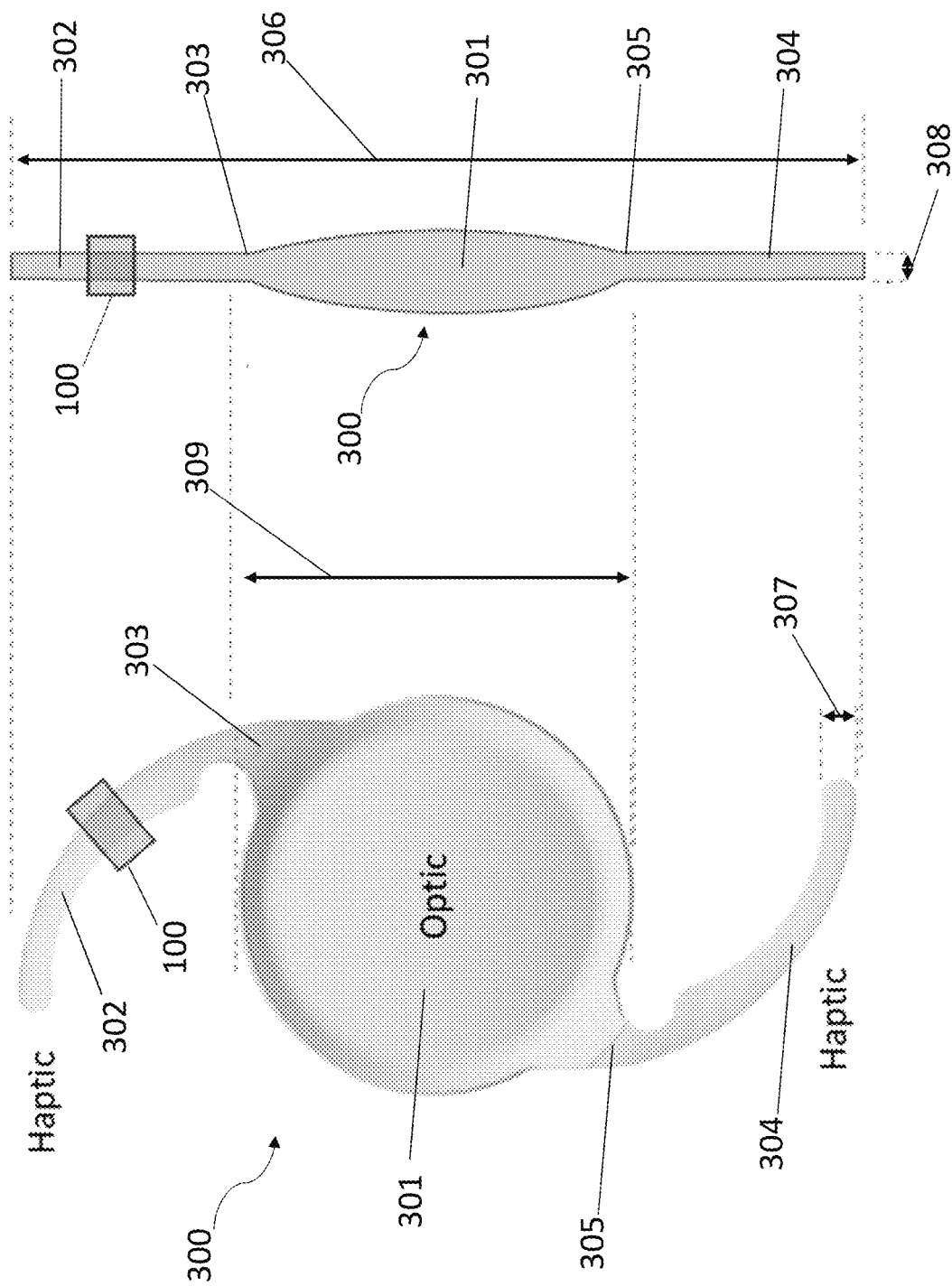

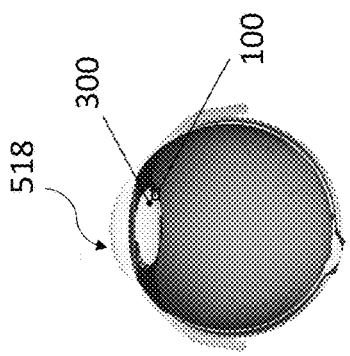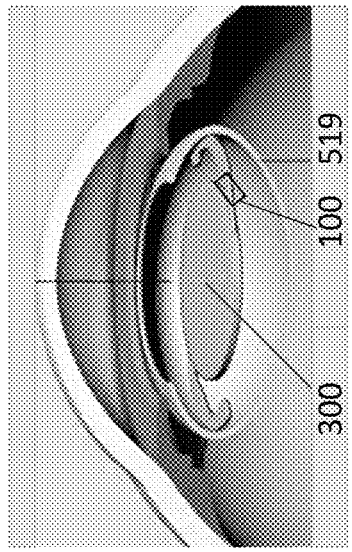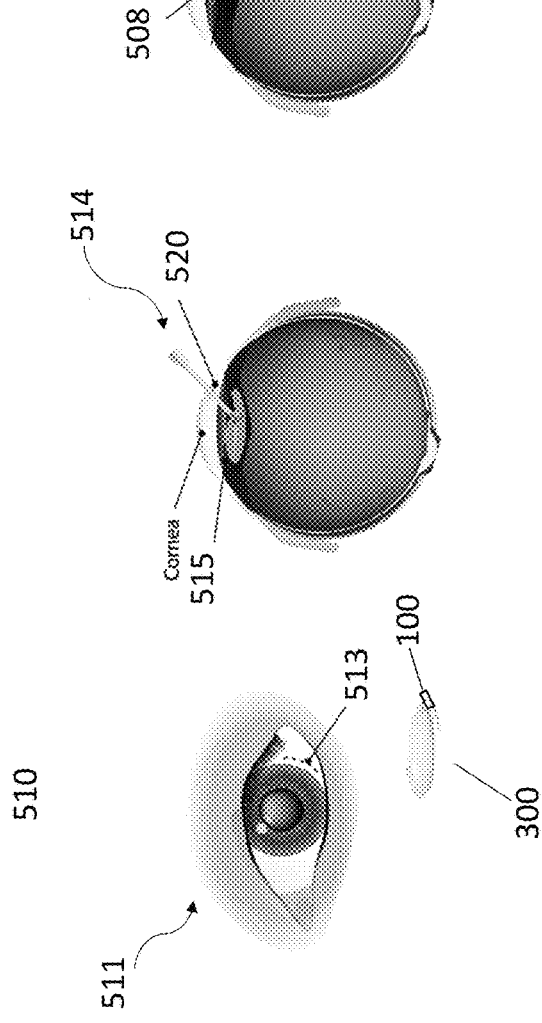

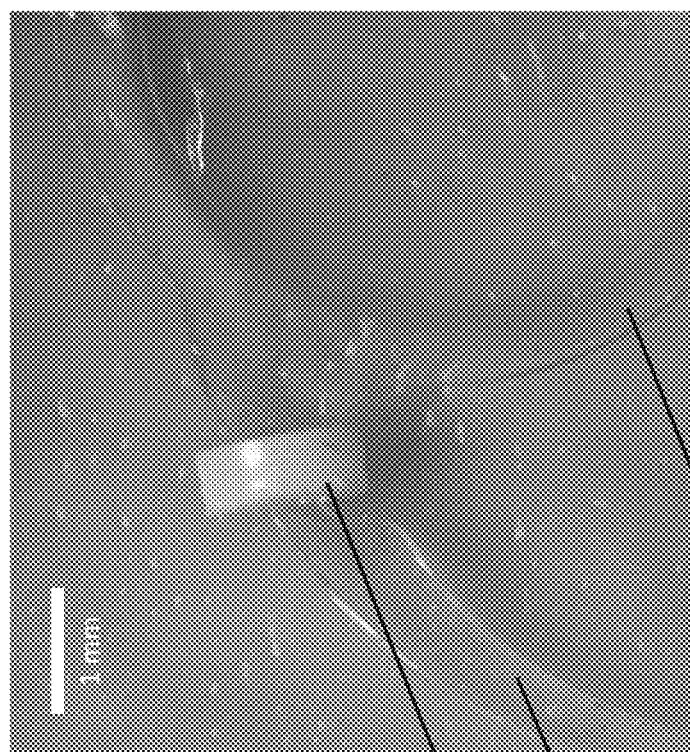
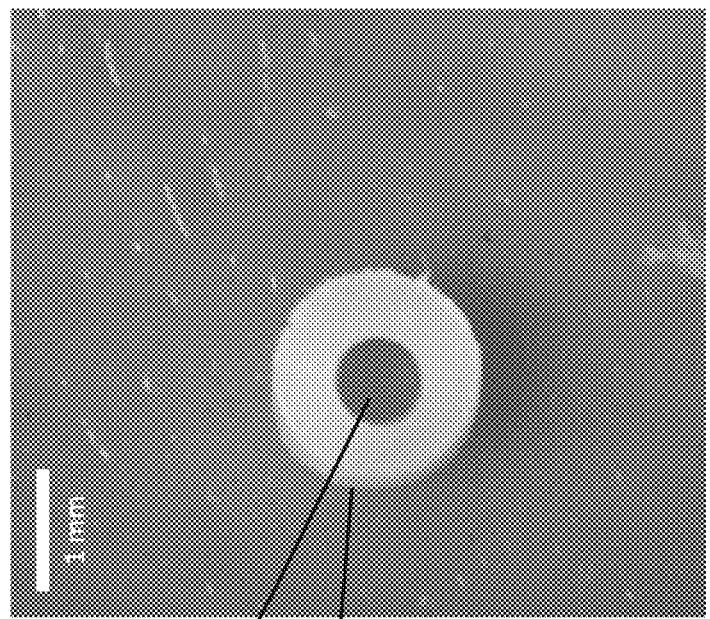
Fig. 7A
Fig. 7B

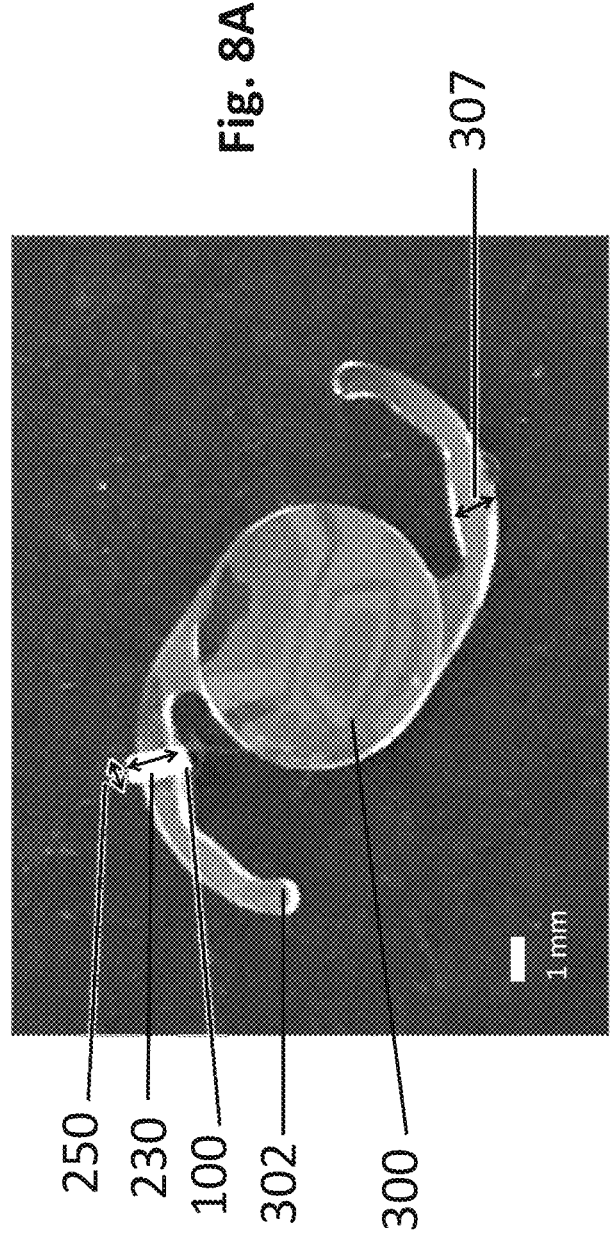
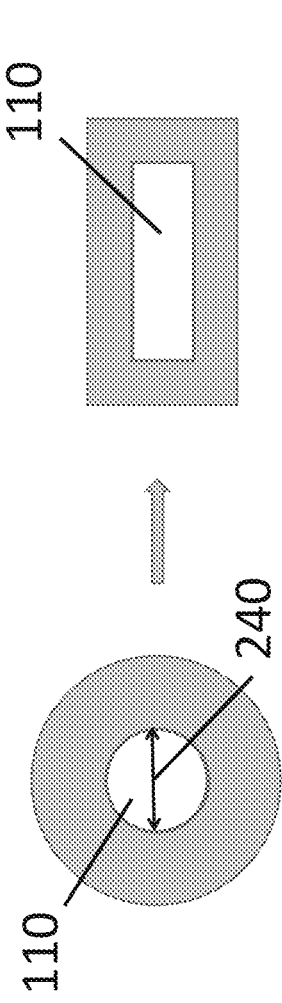

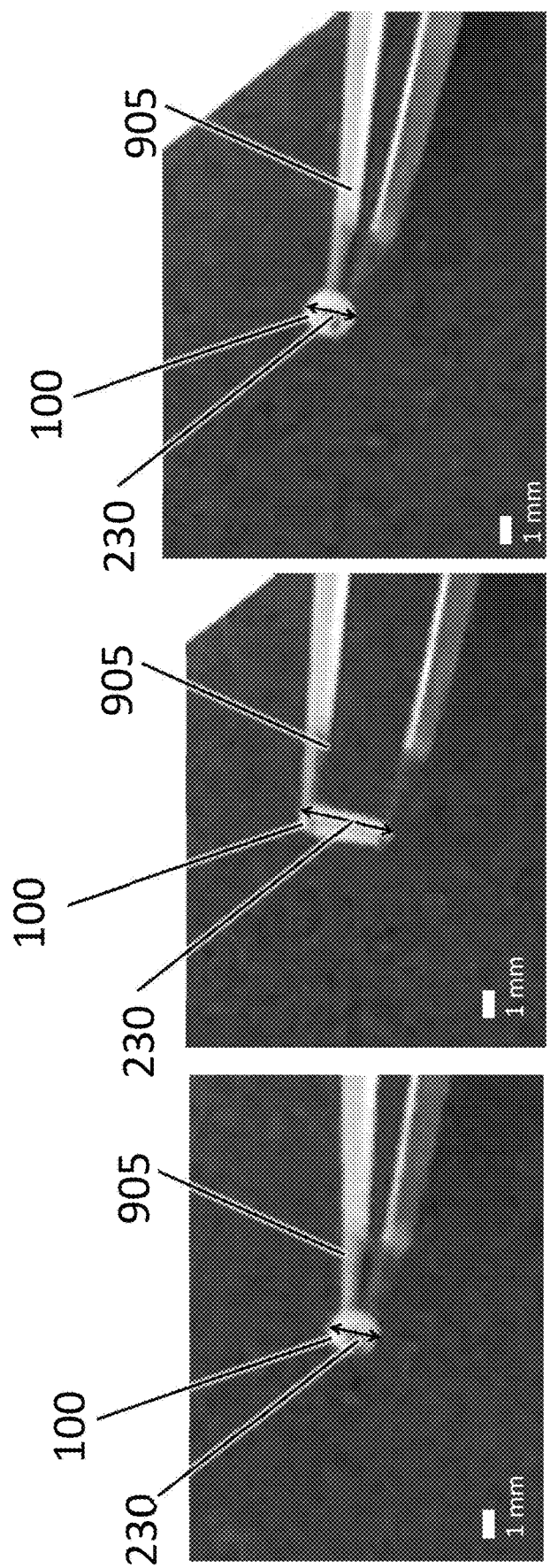

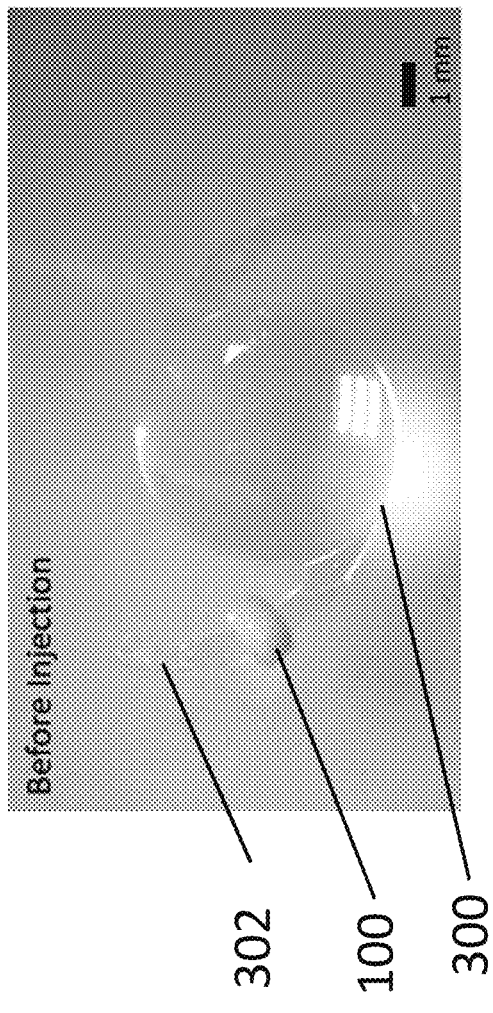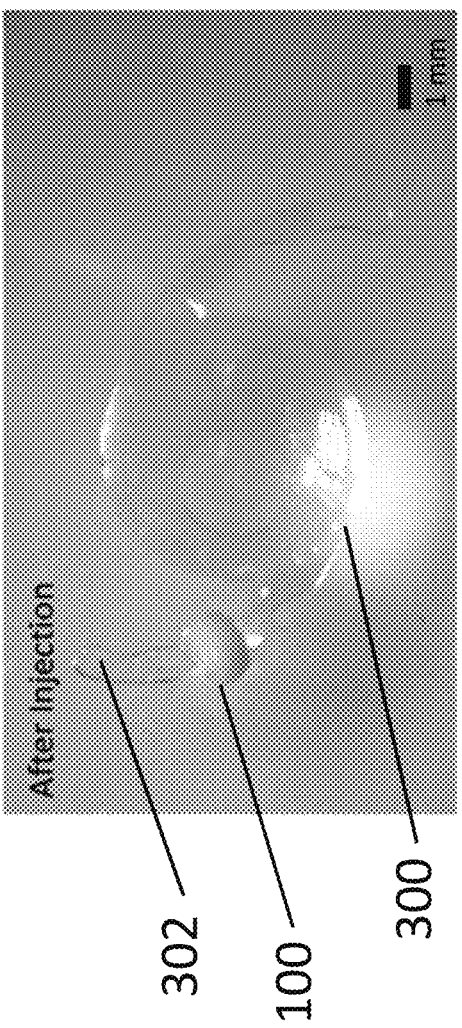

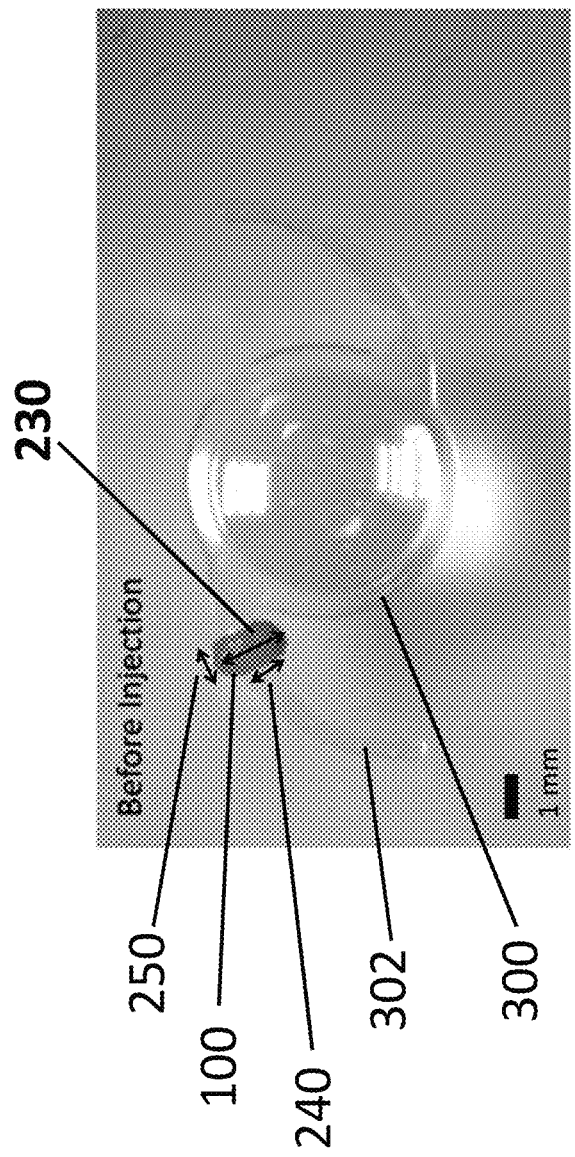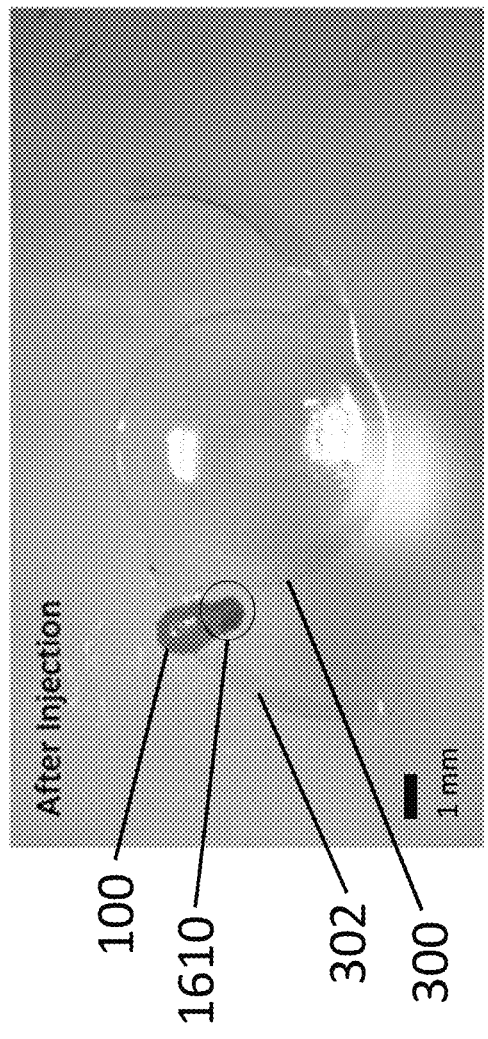

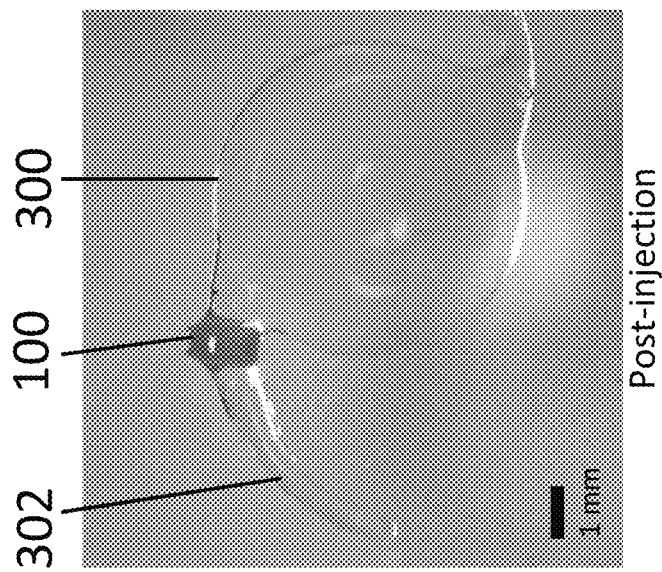
Fig. 17B Post-injection
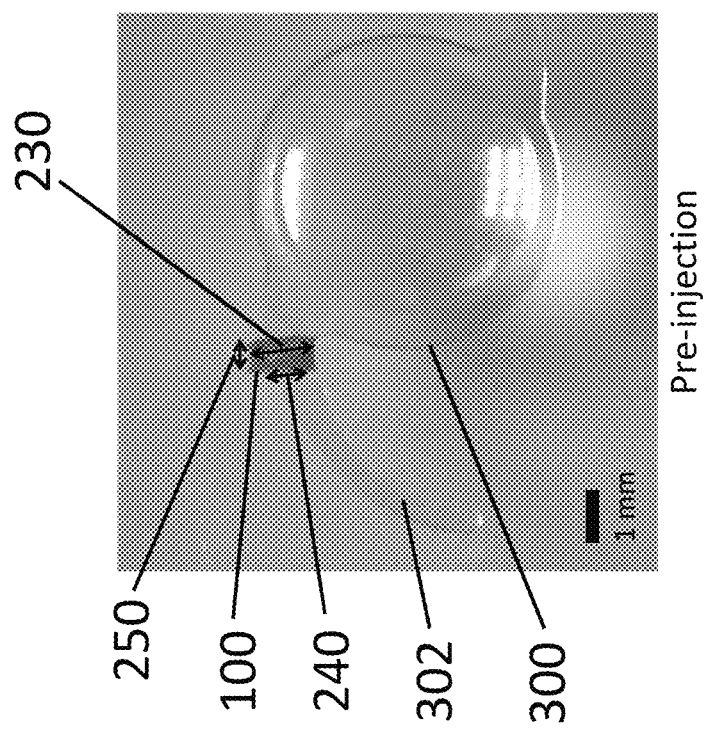
Fig. 17A Pre-injection

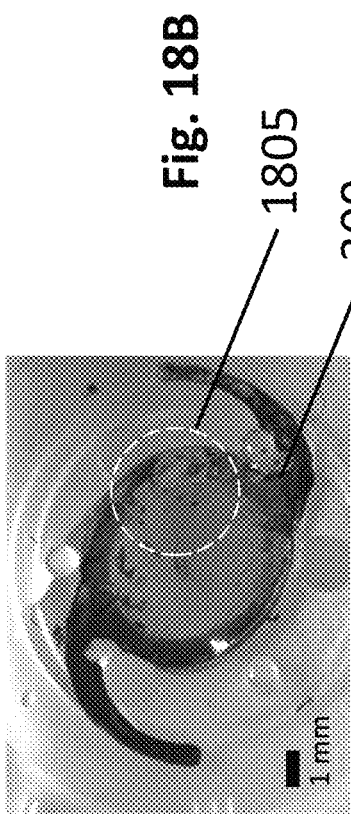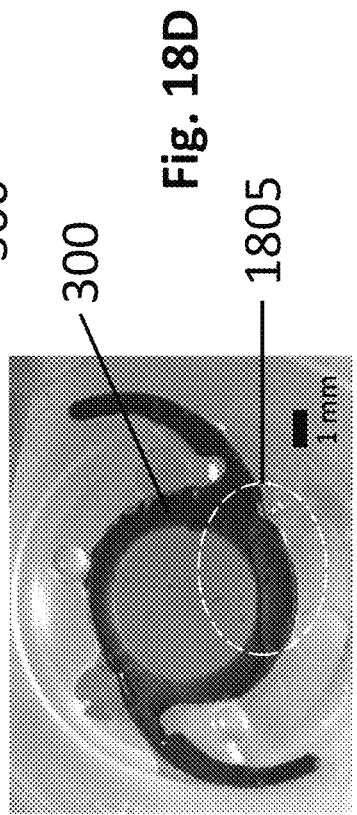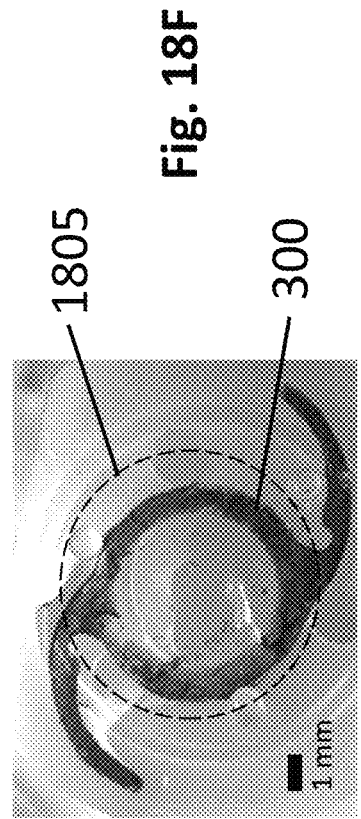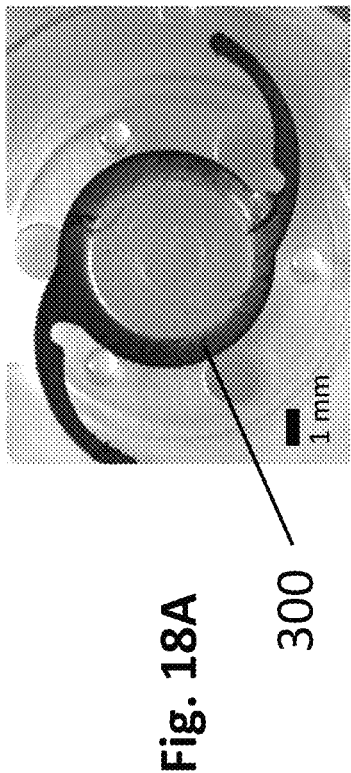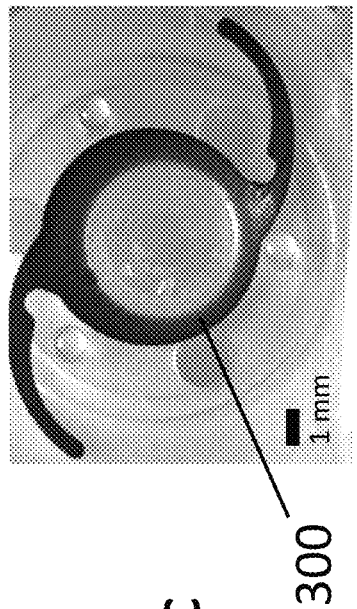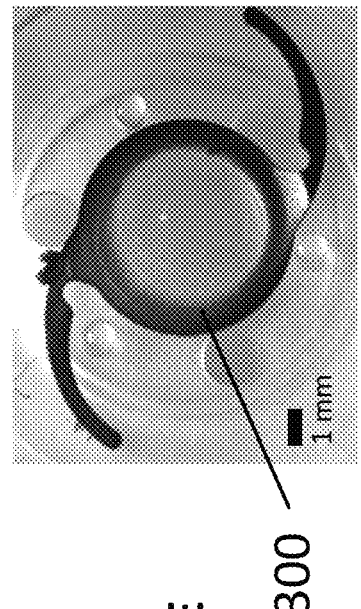

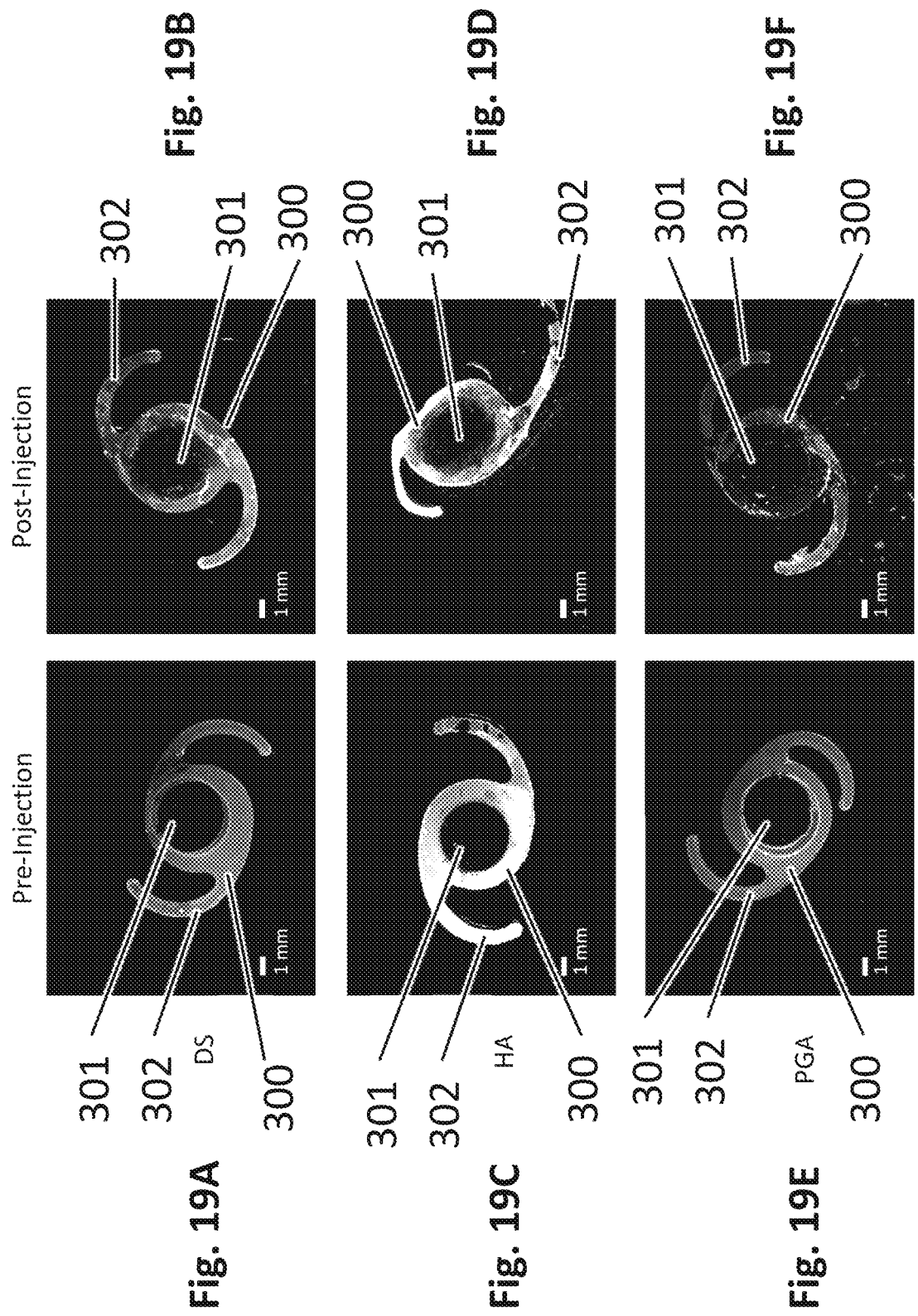

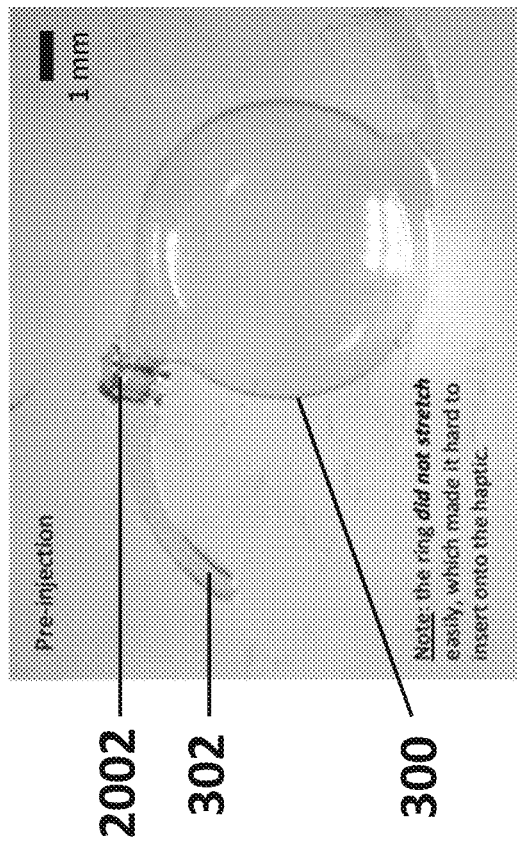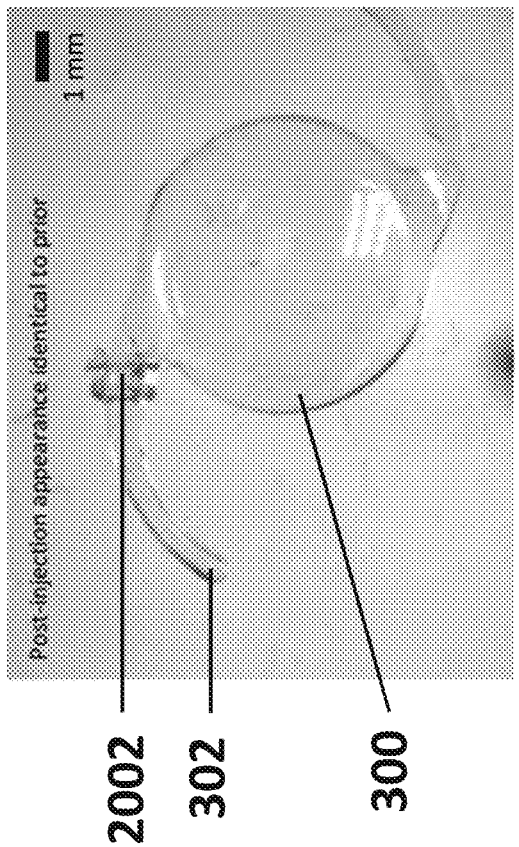

Mostly recovered original shape

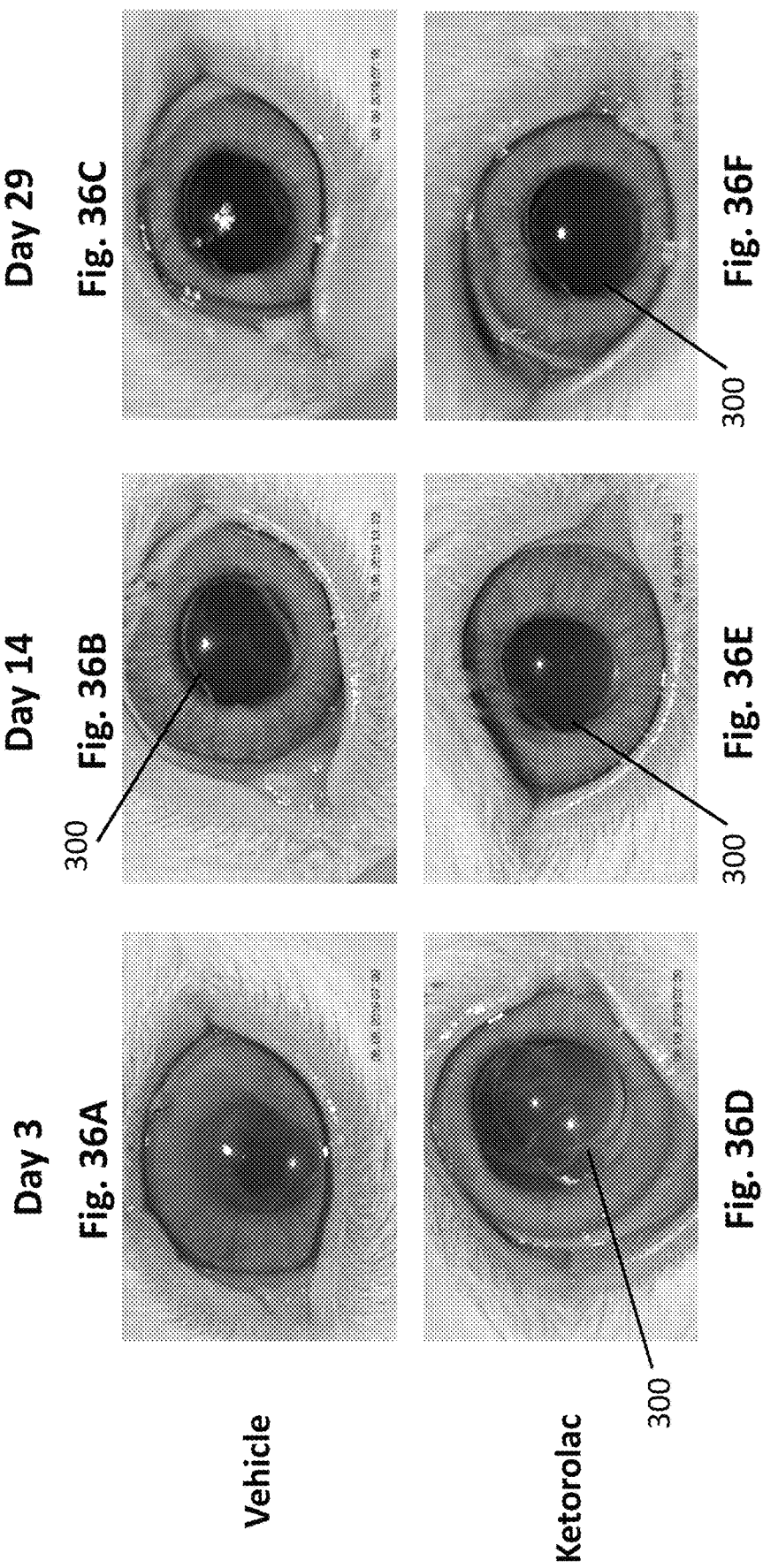

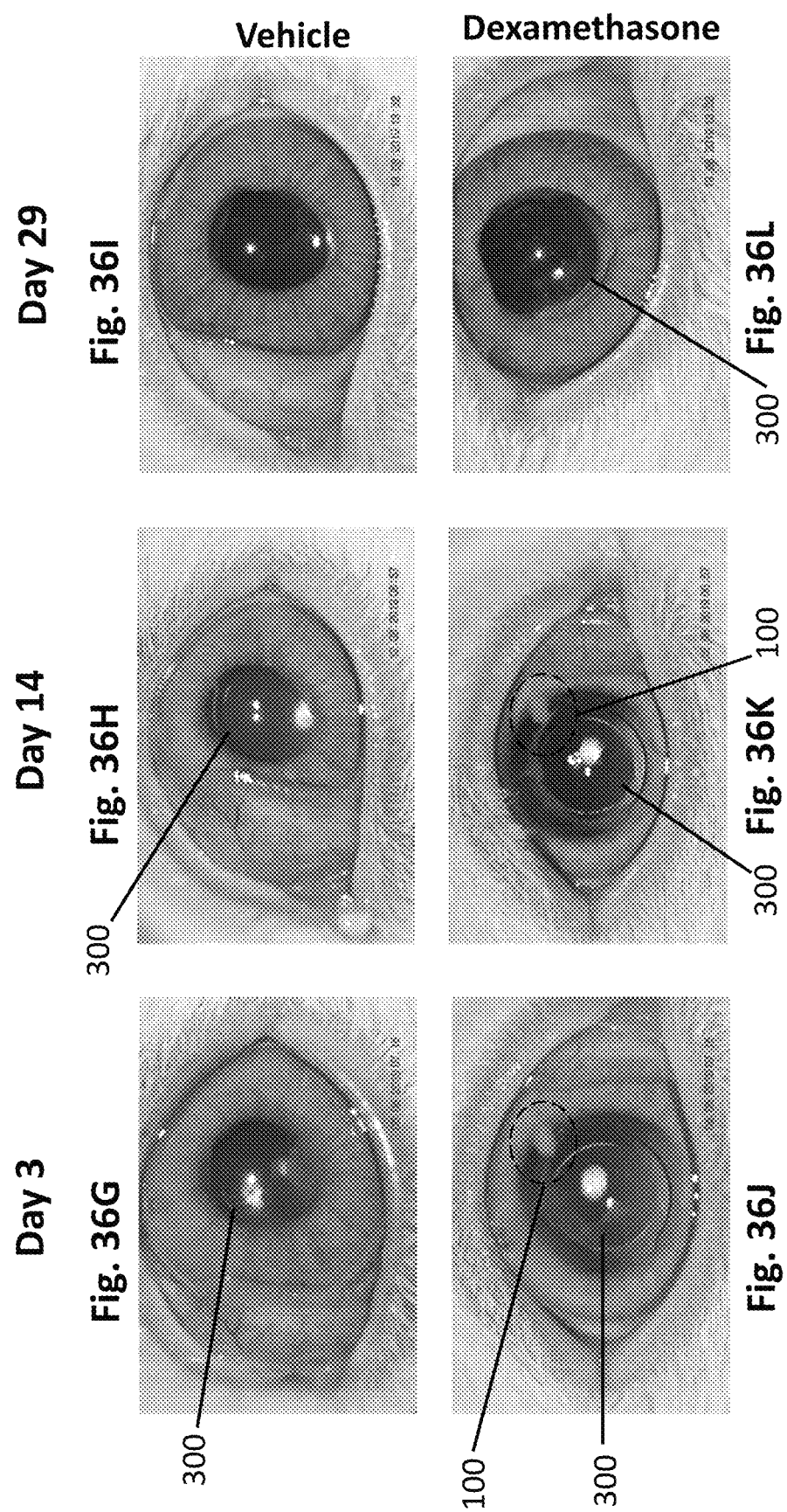

Iris and Ciliary Body

Vitreous and Retina

Vehicle

Dexamethasone

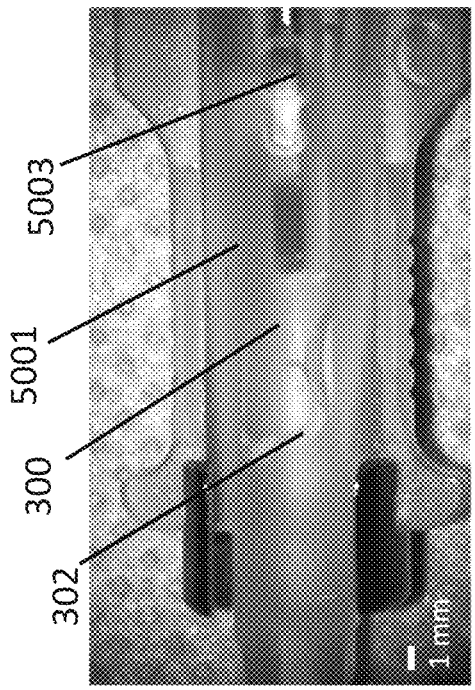
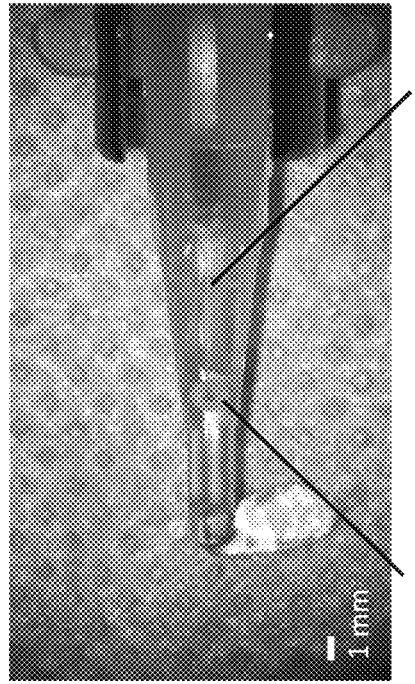
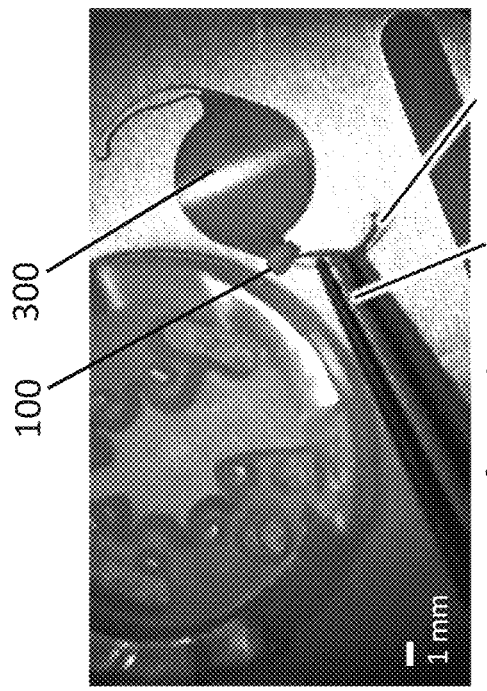
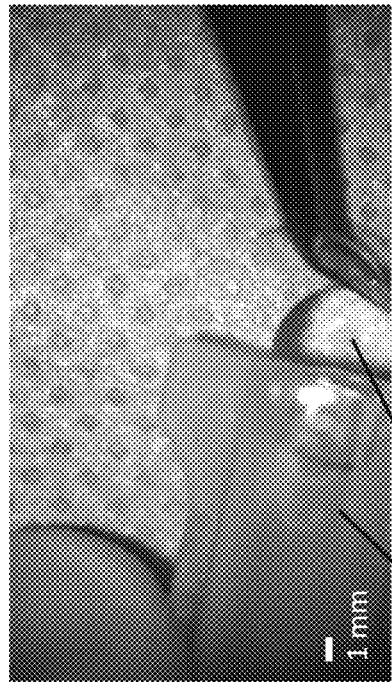
Fig. 50A
Fig. 50B
Fig. 50C
Fig. 50D

OCULAR DEVICE DELIVERY METHODS AND SYSTEMS

CROSS-REFERENCE

This application is a continuation application of International Patent Application No. PCT/US20/39990, filed on Jun. 26, 2020, which claims priority to and the benefit of U.S. Provisional Patent Application Ser. No. 62/867,233, filed Jun. 27, 2019 and U.S. Provisional Patent Application Ser. No. 63/012,994, filed Apr. 21, 2020, each of which is entirely incorporated herein by reference.

BACKGROUND

Cataract surgery is the second most common outpatient surgical procedure in the United States. Patients who undergo cataract surgery may receive a postoperative regimen of topical eye drops to be self-administered for many weeks following cataract surgery. These eye drops usually consist of an antibiotic agent to prevent infection and a corticosteroid and/or non-steroidal anti-inflammatory drug (NSAID) to prevent inflammation.

Compliance with postoperative eye drop regimens among patients (e.g., elderly patients) undergoing cataract surgery may be difficult. Typical postoperative prophylaxis for cataract surgery can comprise a complex and lengthy regimen of corticosteroid, non-steroidal anti-inflammatory drugs (NSAIDs) and antibiotic eye drops. In addition to their visual impairment, patients, especially the elderly population, may have physical and cognitive deficits that limit their ability to read labels, follow directions and physically instill eye drops into their own eyes. Furthermore, many elderly patients live alone and cannot rely on a caregiver to administer their medications. There is therefore a need to develop systems that automatically deliver drug to the eye and eliminate the issue of patient non-compliance.

Drug penetration into the eye by topical eye drops may be inefficient. It is estimated that only 1-3% of any drop actually penetrates the eye, and once inside the eye, such drugs are cleared very rapidly. This can result in a pulsatile delivery profile that does not provide continuous coverage by the dispensed medication. A more efficient approach may be to release a drug inside the eye closer to the target tissue and with continuous release kinetics.

A cataract is an opacification of the crystalline lens inside of the eye that interferes with visual function. Cataracts occur as a normal part of aging, and also as a side effect of some medications, systemic diseases and hereditary conditions. However, cataracts may also be related to eye trauma, long-term diabetes, corticosteroid medications or radiation treatments. The standard treatment for cataracts may be a surgical procedure in which the opacified lens is removed and replaced with an artificial lens (e.g., an intraocular lens) made of transparent acrylic or other synthetic material.

Intraocular lens (IOL) devices are comprised of two parts, the central optic and the haptics. The optic is the lens portion in the center of the IOL. Haptics are flexible arms that stabilize the IOL inside the lens capsule of the eye. The cataract surgery employs foldable IOLs, which can be injected into the eye using very small incisions (2.2 to 2.8 mm). As a result, sutures are not usually required to close the eye after cataract surgery.

IOL-based drug delivery strategies have been investigated previously, but none have succeeded in engineering such a system without significantly modifying the IOL design, requiring changes to the usual surgical technique or adding additional steps to manufacturing process. For example, one prior IOL comprised two dexamethasone-PLGA pellets embedded in the optic, but implantation required a 6 mm wound with two sutures, which is three times the size of the current standard for sutureless corneal incisions. Thus, this approach is not practical for modern cataract surgery.

Prior ring-shaped drug-release devices were attached to haptics of a 3-piece IOL, but its size and rigidity were not compatible with standard cataract surgery technique because the device required delivery through a larger corneal incision than is currently used. Thus, this approach was also not ideal.

Other prior approaches required soaking IOLs in drug solutions prior to surgery but this approach is limited by compatibility of specific drugs with specific IOL matrix materials (e.g., water soluble antibiotics with acrylic lenses; corticosteroids with silicone lenses). Furthermore, this approach does not offer controlled release; rather, it is purely diffusion limited burst release.

In another example, a system was previously proposed, in which an ultra-thin transparent film that releases a drug is manufactured on the surface of the IOL without disrupting the optical properties of the lens. While it is plausible that this device could provide adequate drug release function and not require changes to the usual cataract surgical procedure, this system adds additional steps to the manufacturing process which has implications for the overall cost of goods. Furthermore, it is not readily applied to IOLs of varying sizes, shapes and refractive powers or material, and to do so would require the manufacturers to add this feature to each individual make and model of IOL separately.

Improved ophthalmic articles, devices, methods, systems, and kits for delivery or administration of active agents and/or diagnostic agents from an ocular device to an eye and/or that address at least some of the above disadvantages would be desirable.

SUMMARY

Embodiments of the present disclosure provide articles, methods, devices, systems, and kits for intraocular agent (e.g., active agent and/or diagnostic agent) delivery. The present disclosure provides articles, methods, systems, and kits for delivery or administration of active agents and/or diagnostic agents from an ocular device to an eye. The present disclosure also provides articles, methods, systems, and kits for diagnosis and/or treatment of ocular diseases, conditions, and/or complications.

In an aspect, the present disclosure provides an ophthalmic article. In one embodiment, the ophthalmic article comprises: (a) a biocompatible matrix comprising a copolymer derived from a caprolactone monomer and at least one other monomer; and (b) an active agent or a diagnostic agent; wherein the ophthalmic article is configured to associate to a haptic of an intraocular lens (IOL). In some embodiments, the copolymer is derived from about 20 wt % to about 60 wt % of the caprolactone monomer and from about 40 wt % to 80 wt % of the at least one other monomer. In some embodiments, the copolymer is derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the biocompatible matrix is a random copolymer, a block copolymer, or a gradient copolymer. In some embodiments, the copolymer comprises a random copolymer. In some embodiments, the biocompatible matrix is biodegradable. In some embodiments, ophthalmic article has a tensile strength of at least about 0.5 megapascal (MPa). In some embodiments, ophthalmic article has a tensile strength from about 25 MPa to 35 MPa. In some embodiments, the ophthalmic article has a glass transition temperature of at most about 24° C. as measured by differential scanning calorimetry. In some embodiments, the ophthalmic article has a glass transition temperature from about −20° C. to 24° C. as measured by differential scanning calorimetry. In some embodiments, the ophthalmic article has an elasticity modulus of at most about 3 MPa. In some embodiments, the ophthalmic article has an elasticity modulus from about 0.5 MPa to 3 MPa. In some embodiments, the ophthalmic article has an elongation at break of at least about 100% as measured by tensile testing. In some embodiments, the ophthalmic article has an elongation at break from about 500% to 1500% at from about 18° C. to 24° C. In some embodiments, the shape of the ophthalmic article is an annulus, an extruded annulus, a torus, or a prism with a hole in the center. In some embodiments, the prism is a round prism, rectangular prism, a prism with three or more sides, or a prism with another shape. In some embodiments, the ophthalmic article comprises an internal structure for associating around the haptic of the IOL. In some embodiments, a perimeter or widest dimension of the internal structure is less than or equal to a perimeter or widest dimension of the haptic of the IOL. In some embodiments, a perimeter of the internal structure is less than or equal to a perimeter of the haptic of the IOL. In some embodiments, a widest dimension of the internal structure is less than or equal to a widest dimension of the haptic of the IOL. In some embodiments, the ophthalmic article extends no more than about 0.32 mm beyond the haptic of the IOL once the ophthalmic article is associated to the haptic of the IOL. In some embodiments, a shape of the internal structure is the same as a shape of the haptic of the IOL. In some embodiments, the ophthalmic article comprises an internal structure for securing around a notched region of the haptic of the IOL. In some embodiments, the ophthalmic article comprises an outer diameter of at most 1.5 mm. In some embodiments, the ophthalmic article comprises an internal hole with a diameter of at most 0.7 mm. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the ophthalmic article is configured such that the active agent or diagnostic agent is released from the biocompatible matrix. In some embodiments, the active agent or diagnostic agent is released from the biocompatible matrix over at least about 7 days. In some embodiments, active agent or diagnostic agent is released from the biocompatible matrix over from about 5-30 days, 5-21 days, 5-14 days, 5-10 days, 7-30 days, 7-21 days, 7-14 days, or 7-10 days. In some embodiments, the active agent or diagnostic agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, biocompatible matrix is sufficiently elastic such that it recovers its original shape after injection through an IOL injector that comprises an injector tip inner diameter from about 0.5 mm to 3 mm. In some embodiments, biocompatible matrix is sufficiently elastic such that the ophthalmic article recovers its shape once implanted inside an eye. In some embodiments, ophthalmic article is sufficiently physically stable in a physiologic environment such that it does not significantly change shape within at least 7 days after implantation of the ophthalmic article in an eye of a subject. In some embodiments, the ophthalmic article comprises from about 1 μg to 800 μg of the one or more active agents and/or diagnostic agent.

In another aspect, the present disclosure provides an ophthalmic article. In one embodiment, the ophthalmic article comprises (a) a biocompatible material; and (b) an active agent or a diagnostic agent, wherein the ophthalmic article has an equivalent elasticity, compressibility, tensile strength, shape recovery, or reshapability to another article comprising a biocompatible matrix comprising a copolymer derived from about 40 wt % of a caprolactone monomer and about 60 wt % of a lactide monomer, and wherein the ophthalmic article is configured to associate to a haptic of an intraocular lens (IOL). In some embodiments, the biocompatible material comprises a copolymer matrix. In some embodiments, the biocompatible material comprises a copolymer derived from about 20 wt % to about 60 wt % of a caprolactone monomer and from about 40 wt % to 80 wt % of at least one other monomer. In some embodiments, the at least one other monomer is lactide, glycolide, or trimethylene carbonate. In some embodiments, the biocompatible material or the another article comprising the biocompatible matrix comprises a random copolymer, a block copolymer, or a gradient copolymer. In some embodiments, the biocompatible material or the another article comprising the biocompatible matrix comprises a random copolymer. In some embodiments, the biocompatible material or the another article comprising the biocompatible matrix is biodegradable. In some embodiments, the another article comprises another active agent or diagnostic agent. In some embodiments, the another article comprising the biocompatible matrix has a tensile strength of at least about 0.5 megapascal (MPa). In some embodiments, the another article comprising the biocompatible matrix has a tensile strength from about 25 MPa to 35 MPa. In some embodiments, the another article comprising the biocompatible matrix has a glass transition temperature of at most about 24° C. as measured by differential scanning calorimetry. In some embodiments, the another article comprising the biocompatible matrix has a glass transition temperature from about −20° C. to 24° C. as measured by differential scanning calorimetry. In some embodiments, the another article comprising the biocompatible matrix has an elasticity modulus of at most about 3 MPa. In some embodiments, the another article comprising the biocompatible matrix has an elasticity modulus from about 0.5 MPa to 3 MPa. In some embodiments, the another article comprising the biocompatible matrix has an elongation at break of at least about 100% as measured at from about 18° C. to 24° C. In some embodiments, the another article comprising the biocompatible matrix has an elongation at break from about 500% to 1500% at from about 18° C. to 24° C. In some embodiments, a shape of the ophthalmic article is an annulus, an extruded annulus, a torus, or a prism with a hole in the center. In some embodiments, the prism is a round prism, rectangular prism, a prism with three or more sides, or a prism with another shape. In some embodiments, the ophthalmic article comprises an internal structure for associating around the haptic of the IOL. In some embodiments, a perimeter or widest dimension of the internal structure is less than or equal to a perimeter or widest dimension of the haptic of the IOL. In some embodiments, a perimeter of the internal structure is less than or equal to a perimeter of the haptic of the IOL. In some embodiments, a widest dimension of the internal structure is less than or equal to a widest dimension of the haptic of the IOL. In some embodiments, the ophthalmic article extends no more than about 0.32 mm beyond the haptic of the IOL once the ophthalmic article is associated to the haptic of the IOL. In some embodiments, a shape of the internal structure is the same as a shape of the haptic of the IOL. In some embodiments, the ophthalmic article comprises an internal structure for securing around a notched region of the haptic of the IOL. In some embodiments, the ophthalmic article comprises an outer diameter of at most 1.5 mm. In some embodiments, the ophthalmic article comprises an internal hole with a diameter of at most 0.7 mm. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the ophthalmic article is configured such that the active agent or diagnostic agent is released from the biocompatible material. In some embodiments, the active agent or diagnostic agent is released from the biocompatible material over at least about 7 days. In some embodiments, the active agent or diagnostic agent is released from the biocompatible material over from about 5-30 days, 5-21 days, 5-14 days, 5-10 days, 7-30 days, 7-21 days, 7-14 days, or 7-10 days. In some embodiments, the active agent or diagnostic agent is released from the biocompatible material through degradation of the biocompatible material. In some embodiments, the ophthalmic article or the another article comprising the biocompatible matrix is sufficiently compressible such that it is compatible with injection through an IOL injector that comprises an injector tip inner diameter from about 0.5 mm to 3 mm. In some embodiments, ophthalmic article or the another article comprising the biocompatible matrix is sufficiently flexible such that it is compatible with injection through an IOL injector that comprises an injector tip inner diameter from about 0.5 mm to 3 mm. In some embodiments, the ophthalmic article or the another article comprising the biocompatible matrix is sufficiently elastic such that it recovers its original shape after injection through an IOL injector that comprises an injector tip inner diameter from about 0.5 mm to 3 mm. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In an aspect, the present disclosure provides an ophthalmic system. In one embodiment, the ophthalmic delivery system comprises (a) one or more ophthalmic articles comprising (1) a biocompatible matrix comprising a copolymer derived from a caprolactone monomer and at least one other monomer, and (2) one or more active agents or diagnostic agents; and (b) one or more intraocular lenses (IOL) comprising one or more haptics, wherein the one or more ophthalmic articles is associated to the one or more haptics of the IOL. In some embodiments, about one of the one or more ophthalmic articles is associated with the one or more haptics of the IOL. In some embodiments, about two of the one or more ophthalmic articles are associated with the one or more haptics of the IOL. In some embodiments, about 3, 4, 5, 6, 7, 8, 9, or 10 of the one or more ophthalmic articles are associated with the one or more haptics of the IOL. In some embodiments, about one of the one or more ophthalmic articles is associated with one of the one or more haptics of the IOL. In some embodiments, two of the one or more ophthalmic articles are associated with one of the one or more haptics of the IOL. In some embodiments, about 3, 4, 5, 6, 7, 8, 9, or 10 of the one or more ophthalmic articles are associated with one of the one or more haptics of the IOL. In some embodiments, the copolymer is derived from about 20 wt % to about 60 wt % of the caprolactone monomer and from about 40 wt % to 80 wt % of the at least one other monomer. In some embodiments, the copolymer is derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, copolymer is a random copolymer. In some embodiments, the biocompatible matrix is biodegradable. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3 MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the one or more ophthalmic articles comprises an internal structure for associating around the one or more haptics of the IOL. In some embodiments, a perimeter or widest dimension of the internal structure is less than or equal to a perimeter or widest dimension of the haptic of the IOL. In some embodiments, a perimeter of the internal structure is less than or equal to a perimeter of the one or more haptics of the IOL. In some embodiments, a widest dimension of the internal structure is less than or equal to a widest dimension of the one or more haptics of the IOL. In some embodiments, the one or more ophthalmic articles extends no more than about 0.32 mm beyond the one or more haptics of the IOL once the one or more ophthalmic articles is associated to the one or more haptics of the IOL. In some embodiments, a shape of the internal structure is the same as a shape of the one or more haptics of the IOL. In some embodiments, the one or more ophthalmic articles comprises an internal structure for securing around a notched region of the one or more haptics of the IOL. In some embodiments, the one or more ophthalmic articles comprises an outer diameter of at most 1.5 mm. In some embodiments, the one or more ophthalmic articles comprises an inner diameter of at most 0.7 mm. In some embodiments, the one or more ophthalmic articles is configured such that the active agent or diagnostic agent is released from the biocompatible matrix. In some embodiments, the active agent or diagnostic agent is released from the biocompatible matrix over at least about 7 days. In some embodiments, the active agent or diagnostic agent is released from the biocompatible matrix over from about 5-30 days, 5-21 days, 5-14 days, 5-10 days, 7-30 days, 7-21 days, 7-14 days, or 7-10 days. In some embodiments, the active agent or diagnostic agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 μg to 800 μg of the one or more active agents and/or diagnostic agents.

In another aspect, the present disclosure provides a method of treating or preventing a disease. In one embodiment, the method comprises implanting into an eye of a subject in need thereof an intraocular lens (IOL) for sustained intraocular drug delivery, which IOL comprises one or more drug release articles associated thereto, wherein the one or more drug release articles comprises one or more active agents, wherein within 7 days after implantation the one or more drug release articles releases the one or more active agents and results in an inflammation score of at most 1 as measured by an anterior chamber cell score using slit lamp biomicroscopy or absence of eye pain as measured by a 10-point visual analog scale. In some embodiments, within 7 days after implantation the one or more drug release articles releases the one or more active agents and results in an inflammation score of at most 1 as measured by an anterior chamber cell score using slit lamp biomicroscopy. In some embodiments, within 7 days after implantation the one or more drug release articles releases the one or more active agents and results in an absence of eye pain as measured by a 10-point visual analog scale. In some embodiments, the one or more drug release articles is associated to one or more haptics of the IOL. In some embodiments, about one of the one or more drug release articles is associated with the one or more haptics of the IOL. In some embodiments, about two of the one or more drug release articles are associated with the one or more haptics of the IOL. In some embodiments, about 3, 4, 5, 6, 7, 8, 9, or 10 of the one or more drug release articles are associated with the one or more haptics of the IOL. In some embodiments, about one of the one or more drug release articles is associated with one of the one or more haptics of the IOL. In some embodiments, about two of the one or more drug release articles are associated with one of the one or more haptics of the IOL. In some embodiments, about 3, 4, 5, 6, 7, 8, 9, or 10 of the one or more drug release articles are associated with one of the one or more haptics of the IOL. In some embodiments, the one or more drug release articles comprises a biocompatible matrix. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more drug release articles is configured such that the active agent is released from the biocompatible matrix. In some embodiments, the active agent is released from the biocompatible matrix over at least about 7 days. In some embodiments, the active agent is released from the biocompatible matrix over from about 5-30 days, 5-21 days, 5-14 days, 5-10 days, 7-30 days, 7-21 days, 7-14 days, or 7-10 days. In some embodiments, the active agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the one or more drug release articles has a tensile strength of at least about 0.5 megapascal (MPa). In some embodiments, the one or more drug release articles has a tensile strength from about 25 MPa to 35 MPa. In some embodiments, the one or more drug release articles has a glass transition temperature of at most about 24° C. as measured by differential scanning calorimetry. In some embodiments, the one or more drug release articles has a glass transition temperature from about −20° C. to 24° C. as measured by differential scanning calorimetry. In some embodiments, the one or more drug release articles has an elasticity modulus of at most about 3 MPa. In some embodiments, the one or more drug release articles has an elasticity modulus from about 0.5 MPa to 3 MPa. In some embodiments, the one or more drug release articles has an elongation at break of at least about 100% as measured by tensile testing. In some embodiments, the one or more drug release articles has an elongation at break from about 500% to 1500% at from about 18° C. to 24° C. In some embodiments, a shape of the one or more drug release articles is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the one or more drug release articles comprises an internal structure for associating around one or more haptics of the IOL. In some embodiments, a perimeter or widest dimension of the internal structure is less than or equal to a perimeter or widest dimension of the haptic of the IOL. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more drug release articles extends no more than about 0.32 mm beyond the one or more haptics once the one or more drug release articles is associated to the one or more haptics. In some embodiments, a shape of the internal structure is the same as a shape of the one or more haptics. In some embodiments, the one or more drug release articles comprises an internal structure for securing around a notched region of the one or more haptics. In some embodiments, the one or more drug release articles comprises an outer diameter of at most 1.5 mm. In some embodiments, the internal structure comprises a diameter of at most 0.7 mm. In some embodiments, the one or more drug release articles is compressively associated to an outward surface of the one or more haptics. In some embodiments, the one or more drug release articles is associated to the one or more haptics of the IOL. In some embodiments, prior to implanting into the eye of the subject, compressing the IOL having the one or more drug release articles associated thereto through an IOL injector that comprises an injector tip inner diameter from about 0.5 mm to 3 mm. In some embodiments, the compressing comprises folding the IOL having the one or more drug release articles associated thereto into a tubular shape through the IOL injector that comprises the injector tip inner diameter from about 0.5 mm to 3 mm. In some embodiments, the subject is concurrently undergoing or has undergone ophthalmic surgery. In some embodiments, the subject is concurrently undergoing or has undergone cataract surgery. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In another aspect, the present disclosure provides a method of treating or preventing a disease. In one embodiment, the method comprises (a) associating one or more ophthalmic articles to one or more haptics of at least one intraocular lens (IOL), thereby generating at least one active agent-releasing intraocular lens; (b) implanting the at least one active agent-releasing intraocular lens into an eye of a subject in need thereof for sustained intraocular active agent delivery, wherein within 7 days after implantation the one or more ophthalmic articles releases the one or more active agents and results in an inflammation score of at most 1 as measured by an anterior chamber cell score using slit lamp biomicroscopy or absence of eye pain as measured by a 10-point visual analog scale. In some embodiments, within 7 days after implantation the one or more ophthalmic articles releases the one or more active agents and results in an inflammation score of at most 1 as measured by an anterior chamber cell score using slit lamp biomicroscopy. In some embodiments, within 7 days after implantation the one or more ophthalmic articles releases the one or more active agents and results in an absence of eye pain as measured by a 10-point visual analog scale. In some embodiments, about one of the one or more ophthalmic articles is associated with the one or more haptics. In some embodiments, about two of the one or more ophthalmic articles are associated with the one or more haptics. In some embodiments, about 3, 4, 5, 6, 7, 8, 9, or 10 of the one or more ophthalmic articles are associated with the one or more haptics. In some embodiments, about one of the one or more ophthalmic articles is associated with one of the one or more haptics. In some embodiments, about two of the one or more ophthalmic articles are associated with one of the one or more haptics. In some embodiments, about 3, 4, 5, 6, 7, 8, 9, or 10 of the one or more ophthalmic articles are associated with one of the one or more haptics. In some embodiments, one or more ophthalmic articles comprises a biocompatible matrix. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic articles is configured such that the active agent is released from the biocompatible matrix. In some embodiments, the active agent is released from the biocompatible matrix over at least about 7 days. In some embodiments, the active agent is released from the biocompatible matrix over from about 5-30 days, 5-21 days, 5-14 days, 5-10 days, 7-30 days, 7-21 days, 7-14 days, or 7-10 days. In some embodiments, the active agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3 MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the associating comprises indirect association between the one or more ophthalmic articles and the one or more haptics. In some embodiments, the one or more ophthalmic articles comprises an internal structure for associating around the one or more haptics. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure is the same as a shape of the one or more haptics. In some embodiments, one or more ophthalmic articles comprises an internal structure for securing around a notched region of the one or more haptics. In some embodiments, the one or more ophthalmic articles comprises an outer diameter of at most 1.5 mm. In some embodiments, the internal structure comprises a diameter of at most 0.7 mm. In some embodiments, the one or more ophthalmic articles is compressively associated to an outward surface of the one or more haptics. In some embodiments, prior to implanting into the eye of the subject, compressing the at least one active agent-releasing intraocular lens through an IOL injector that comprises an injector tip inner diameter from about 0.5 mm to 3 mm. In some embodiments, the compressing comprises folding the at least one active agent-releasing intraocular lens into a tubular shape through the IOL injector that comprises the injector tip inner diameter from about 0.5 mm to 3 mm. In some embodiments, the subject is concurrently undergoing or has undergone ophthalmic surgery. In some embodiments, the subject is concurrently undergoing or has undergone cataract surgery. In some embodiments, the associating comprises direct association between the one or more ophthalmic articles and the one or more haptics through a chemical bond, physical bond, compressive forces, or contractile forces. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In another aspect, the present disclosure provides method of treating or preventing a disease. In one embodiments, the method comprises (a) combining one or more active agents with a biocompatible matrix, thereby generating one or more ophthalmic articles; (b) associating the one or more ophthalmic articles to one or more haptics of at least one intraocular lens, thereby generating at least one active agent-releasing intraocular lens; (c) implanting the at least one active agent-releasing intraocular lens into an eye of a subject in need thereof for sustained intraocular active agent delivery, wherein within 7 days after implantation the one or more ophthalmic articles releases the one or more active agents and results in an inflammation score of at most 1 as measured by an anterior chamber cell score using slit lamp biomicroscopy or absence of eye pain as measured by a 10-point visual analog scale. In some embodiments, within 7 days after implantation the one or more ophthalmic articles releases the one or more active agents and results in an inflammation score of at most 1 as measured by an anterior chamber cell score using slit lamp biomicroscopy. In some embodiments, within 7 days after implantation the one or more ophthalmic articles releases the one or more active agents and results in an absence of eye pain as measured by a 10-point visual analog scale. In some embodiments, about one of the one or more ophthalmic articles is associated with the one or more haptics. In some embodiments, about two of the one or more ophthalmic articles are associated with the one or more haptics. In some embodiments, about 3, 4, 5, 6, 7, 8, 9, or 10 of the one or more ophthalmic articles are associated with the one or more haptics. In some embodiments, about one of the one or more ophthalmic articles is associated with one of the one or more haptics. In some embodiments, about two of the one or more ophthalmic articles are associated with one of the one or more haptics. In some embodiments, about 3, 4, 5, 6, 7, 8, 9, or 10 of the one or more ophthalmic articles are associated with one of the one or more haptics. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3 MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the one or more active agents is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the one or more active agents is dexamethasone, ketorolac, diclofenac, moxifloxacin, travoprost, 5-fluorouracil, or methotrexate. In some embodiments, the associating comprises indirect association between the one or more ophthalmic articles and the one or more haptics. In some embodiments, the one or more ophthalmic articles comprises an internal structure for associating around the one or more haptics. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure is the same as a shape of the one or more haptics. In some embodiments, the one or more ophthalmic articles comprises an internal structure for securing around a notched region of the one or more haptics. In some embodiments, the one or more ophthalmic articles comprises an outer diameter of at most 1.5 mm. In some embodiments, the internal structure comprises a diameter of at most 0.7 mm. In some embodiments, the one or more ophthalmic articles is configured such that the active agent is released from the biocompatible copolymer matrix. In some embodiments, the active agent is released from the biocompatible matrix over at least about 7 days. In some embodiments, the active agent is released from the biocompatible matrix over from about 5-30 days, 5-21 days, 5-14 days, 5-10 days, 7-30 days, 7-21 days, 7-14 days, or 7-10 days. In some embodiments, the active agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm wherein the one or more ophthalmic articles is compressively associated to an outward surface of the one or more haptics. In some embodiments, prior to implanting the at least one active agent-releasing intraocular lens into the eye of the subject, compressing the at least one active agent-releasing intraocular lens through an IOL injector that comprises an injector tip inner diameter from about 0.5 mm to 3 mm. In some embodiments, the compressing comprises folding the at least one active agent-releasing intraocular lens into a tubular shape through the IOL injector that comprises the injector tip inner diameter from about 0.5 mm to 3 mm. In some embodiments, the subject is concurrently undergoing or has undergone ophthalmic surgery. In some embodiments, the subject is concurrently undergoing or has undergone cataract surgery. In some embodiments, the associating comprises direct association between the one or more ophthalmic articles and the one or more haptics through a chemical bond, physical bond, compressive forces, or contractile forces. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In another aspect, the present disclosure provides a method of preparing at least one ophthalmic article. In one embodiment, the method comprises (a) combining one or more active agents or diagnostic agents in a solvent with a biocompatible matrix in the solvent, thereby generating a combined mixture in the solvent; (b) removing the solvent from the combined mixture, thereby generating an evaporated mixture; (c) using a weighted tool to compress the evaporated mixture, thereby generating a compressed mixture; and (d) using a shaping tool and an orifice tool to extract the at least one ophthalmic article from the compressed mixture. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, biocompatible matrix is biodegradable. In some embodiments, the at least one ophthalmic article has a tensile strength of at least about 0.5 megapascal (MPa). In some embodiments, the at least one ophthalmic article has a tensile strength from about 25 MPa to 35 MPa. In some embodiments, the at least one ophthalmic article has a glass transition temperature of at most about 24° C. as measured by differential scanning calorimetry. In some embodiments, the at least one ophthalmic article has a glass transition temperature from about −20° C. to 24° C. as measured by differential scanning calorimetry. In some embodiments, the at least one ophthalmic article has an elasticity modulus of at most about 3 MPa. In some embodiments, the at least one ophthalmic article has an elasticity modulus from about 0.5 MPa to 3 MPa. In some embodiments, the at least one ophthalmic article has an elongation at break of at least about 100% as measured by tensile testing. In some embodiments, the at least one ophthalmic article has an elongation at break from about 500% to 1500% at from about 18° C. to 24° C. In some embodiments, a shape of the at least one ophthalmic article is an annulus, an extruded annulus, a torus, or a prism with a hole in the center. In some embodiments, the prism is a round prism, rectangular prism, a prism with three or more sides, or a prism with another shape. In some embodiments, the one or more active agents is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the one or more active agents is dexamethasone, ketorolac, diclofenac, moxifloxacin, travoprost, 5-fluorouracil, or methotrexate. In some embodiments, the at least one ophthalmic article comprises an internal structure for associating around one or more haptics of an intraocular lens. In some embodiments, the at least one ophthalmic article comprises an outer diameter of at most 1.5 mm. In some embodiments, the internal structure comprises a diameter of at most 0.7 mm. In some embodiments, the at least one ophthalmic article is configured such that the one or more active agents or diagnostic agents is released from the biocompatible matrix. In some embodiments, the one or more active agents or diagnostic agents is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, prior to the combining in (a), suspending the one or more active agents or diagnostic agents in the solvent, thereby generating a suspension. In some embodiments, the weighted tool is a steel plate. In some embodiments, the weighted tool is a heated steel plate. In some embodiments, the weighted tool is a heated steel plate with Teflon. In some embodiments, the weighted tool compresses the evaporated mixture into a sheet. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In another aspect, the present disclosure provides a method of preparing at least one agent-releasing intraocular lens. In one embodiment, the method comprises (a) combining one or more active agents or diagnostic agents with a biocompatible matrix comprising a copolymer derived from a caprolactone monomer and at least one other monomer, thereby generating one or more ophthalmic articles; (b) associating the one or more ophthalmic articles to one or more haptics of at least one intraocular lens (IOL). In some embodiments, about one of the one or more ophthalmic articles is associated with the one or more haptics of the IOL. In some embodiments, about two of the one or more ophthalmic articles are associated with the one or more haptics of the IOL. In some embodiments, about 3, 4, 5, 6, 7, 8, 9, or 10 of the one or more ophthalmic articles are associated with the one or more haptics of the IOL. In some embodiments, about one of the one or more ophthalmic articles is associated with one of the one or more haptics of the IOL. In some embodiments, about two of the one or more ophthalmic articles are associated with one of the one or more haptics of the IOL. In some embodiments, about 3, 4, 5, 6, 7, 8, 9, or 10 of the one or more ophthalmic articles are associated with one of the one or more haptics of the IOL. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3 MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the associating comprises indirect association between the one or more ophthalmic articles and the one or more haptics. In some embodiments, the one or more ophthalmic articles comprises an internal structure for associating around the one or more haptics. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a perimeter or widest dimension of the internal structure is less than or equal to a perimeter or widest dimension of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure is the same as a shape of the one or more haptics. In some embodiments, the one or more ophthalmic articles comprises an internal structure for securing around a notched region of the one or more haptics. In some embodiments, the one or more ophthalmic articles comprises an outer diameter of at most 1.5 mm. In some embodiments, the internal structure comprises a diameter of at most 0.7 mm. In some embodiments, the one or more ophthalmic articles is configured such that the one or more active agents or diagnostic agents is released from the biocompatible matrix. In some embodiments, the active agent or diagnostic agent is released from the biocompatible matrix over at least about 7 days. In some embodiments, the active agent or diagnostic agent is released from the biocompatible matrix over from about 5-30 days, 5-21 days, 5-14 days, 5-10 days, 7-30 days, 7-21 days, 7-14 days, or 7-10 days. In some embodiments, the active agent or diagnostic agent is released from the biocompatible matrix through degradation of the biocompatible copolymer matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the one or more ophthalmic articles is compressively associated to an outward surface of the one or more haptics. In some embodiments, prior to implanting into the eye of the subject, compressing the IOL having the one or more ophthalmic articles associated thereto through an IOL injector that comprises an injector tip inner diameter from about 0.5 mm to 3 mm. In some embodiments, the compressing comprises folding the IOL having the one or more ophthalmic articles associated thereto into a tubular shape through the IOL injector that comprises the injector tip inner diameter from about 0.5 mm to 3 mm. In some embodiments, the associating comprises direct association between the one or more ophthalmic articles and the one or more haptics through a chemical bond, physical bond, compressive forces, or contractile forces. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In another aspect, the present disclosure provides a method of administering an active agent or diagnostic agent. In one embodiment, the method comprises (a) associating one or more ophthalmic articles to one or more haptics of at least one intraocular lens, thereby generating at least one agent-releasing intraocular lens; (b) compressing the at least one agent-releasing intraocular lens through an intraocular lens injector comprising an injector tip inner diameter from about 0.5 mm to 3 mm; and (c) implanting the at least one agent-releasing intraocular lens into an eye of a subject in need thereof for sustained intraocular active agent or diagnostic agent delivery. In some embodiments, about one of the one or more ophthalmic articles is associated with the one or more haptics of the IOL. In some embodiments, about two of the one or more ophthalmic articles are associated with the one or more haptics of the IOL. In some embodiments, about 3, 4, 5, 6, 7, 8, 9, or 10 of the one or more ophthalmic articles are associated with the one or more haptics of the IOL. In some embodiments, about one of the one or more ophthalmic articles is associated with one of the one or more haptics of the IOL. In some embodiments, about two of the one or more ophthalmic articles are associated with one of the one or more haptics of the IOL. In some embodiments, about 3, 4, 5, 6, 7, 8, 9, or 10 of the one or more ophthalmic articles are associated with one of the one or more haptics of the IOL. In some embodiments, the one or more ophthalmic articles comprises a biocompatible matrix. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic articles is configured such that the active agent or diagnostic agent is released from the biocompatible matrix. In some embodiments, the active agent or diagnostic agent is released from the biocompatible matrix over at least about 7 days. In some embodiments, the active agent or diagnostic agent is released from the biocompatible matrix over from about 5-30 days, 5-21 days, 5-14 days, 5-10 days, 7-30 days, 7-21 days, 7-14 days, or 7-10 days. In some embodiments, the active agent or diagnostic agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3

MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the associating comprises indirect association between the one or more ophthalmic articles and the one or more haptics. In some embodiments, the one or more ophthalmic articles comprises an internal structure for associating around the one or more haptics. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure is the same as a shape of the one or more haptics. In some embodiments, the one or more ophthalmic articles comprises an internal structure for securing around a notched region of the one or more haptics. In some embodiments, the one or more ophthalmic articles comprises an outer diameter of at most 1.5 mm. In some embodiments, the one or more ophthalmic articles comprises an inner diameter of at most 0.7 mm. In some embodiments, the one or more ophthalmic articles is compressively associated to an outward surface of the one or more haptics. In some embodiments, the compressing comprises folding the at least one agent-releasing intraocular lens into a tubular shape through the IOL injector that comprises the injector tip inner diameter from about 0.5 mm to 3 mm. In some embodiments, the subject is concurrently undergoing or has undergone ophthalmic surgery. In some embodiments, the subject is concurrently undergoing or has undergone cataract surgery. In some embodiments, the associating comprises direct association between the one or more ophthalmic articles and the one or more haptics through a chemical bond, physical bond, compressive forces, or contractile forces. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 μg to 800 μg of the one or more active agents and/or diagnostic agents.

In another aspect, the present disclosure provides a method of administering an active agent or diagnostic agent. In one embodiment, the method comprises (a) compressing an intraocular lens (IOL) having one or more ophthalmic articles associated thereto through an IOL injector that comprises an injector tip inner diameter from about 0.5 mm to 3 mm, thereby generating a compressed IOL having one or more ophthalmic articles associated thereto, which one or more ophthalmic articles comprises one or more active agents or diagnostic agents; and (b) implanting the compressed IOL having one or more ophthalmic articles associated thereto into an eye of a subject in need thereof for sustained intraocular active agent or diagnostic agent delivery. In some embodiments, about one of the one or more ophthalmic articles is associated with one or more haptics of the IOL. In some embodiments, about two of the one or more ophthalmic articles are associated with one or more haptics of the IOL. In some embodiments, about 3, 4, 5, 6, 7, 8, 9, or 10 of the one or more ophthalmic articles are associated with one or more haptics of the IOL. In some embodiments, about one of the one or more ophthalmic articles is associated with one of one or more haptics of the IOL. In some embodiments, about two of the one or more ophthalmic articles are associated with one of one or more haptics of the IOL. In some embodiments, about 3, 4, 5, 6, 7, 8, 9, or 10 of the one or more ophthalmic articles are associated with one of one or more haptics of the IOL. In some embodiments, the one or more ophthalmic articles comprises a biocompatible matrix. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic articles is configured such that the one or more active agents or diagnostic agents is released from the biocompatible matrix. In some embodiments, the one or more active agents or diagnostic agents is released from the biocompatible matrix over at least about 7 days. In some embodiments, the one or more active agents or diagnostic agents is released from the biocompatible matrix over from about 5-30 days, 5-21 days, 5-14 days, 5-10 days, 7-30 days, 7-21 days, 7-14 days, or 7-10 days. In some embodiments, the one or more active agents or diagnostic agents is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3 MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the one or more ophthalmic articles is indirectly associated with one or more haptics of the IOL. In some embodiments, the one or more ophthalmic articles comprises an internal structure for associating around one or more haptics of the intraocular lens. In some embodiments, a perimeter or widest dimension of the internal structure is less than or equal to a perimeter or widest dimension of the one or more haptics of the IOL. In some embodiments, a perimeter dimension of the internal structure is less than or equal to a perimeter of the one or more haptics of the IOL. In some embodiments, a widest dimension of the internal structure is less than or equal to a widest dimension of the one or more haptics of the IOL. In some embodiments, the one or more ophthalmic articles extends no more than about 0.32 mm beyond the one or more haptics of the IOL once the one or more ophthalmic articles is associated to the one or more haptics of the IOL. In some embodiments, a shape of the internal structure is the same as a shape of the one or more haptics of the IOL. In some embodiments, the one or more ophthalmic articles comprises an internal structure for securing around a notched region of one or more haptics of the IOL. In some embodiments, the one or more ophthalmic articles comprises an outer diameter of at most 1.5 mm. In some embodiments, the internal structure comprises a diameter of at most 0.7 mm. In some embodiment, the one or more ophthalmic articles is associated to one or more haptics of the IOL. In some embodiments, the one or more ophthalmic articles is compressively associated to an outward surface of the one or more haptics of the IOL. In some embodiments, the one or more ophthalmic articles is directly associated between the one or more ophthalmic articles and the one or more haptics through a chemical bond, physical bond, compressive forces, or contractile forces. In some embodiments, the compressing comprises folding the IOL having the one or more ophthalmic articles associated thereto into a tubular shape through the IOL injector that comprises the injector tip inner diameter from about 0.5 mm to 3 mm. In some embodiments, the subject is concurrently undergoing or has undergone ophthalmic surgery. In some embodiments, the subject is concurrently undergoing or has undergone cataract surgery. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In another aspect, the present disclosure provides kit. In one embodiment, the kit comprises a container comprising one or more ophthalmic articles comprising (1) a biocompatible matrix comprising a copolymer derived from a caprolactone monomer and at least one other monomer, and (2) one or more active agents or diagnostic agents; and instructions for use. In some embodiments, the kit further comprises another container comprising one or more intraocular lenses, which each of the one or more intraocular lenses comprises one or more haptics. In some embodiments, the container further comprises one or more intraocular lenses comprising one or more haptics associated with the one or more ophthalmic articles. In some embodiments, the one or more ophthalmic articles is associated with the one or more haptics of the one or more IOLs. In some embodiments, about one of the one or more ophthalmic articles is associated with the one or more haptics. In some embodiments, about two of the one or more ophthalmic articles are associated with the one or more haptics. In some embodiments, about 3, 4, 5, 6, 7, 8, 9, or 10 of the one or more ophthalmic articles are associated with the one or more haptics. In some embodiments, about one of the one or more ophthalmic articles is associated with one of the one or more haptics. In some embodiments, about two of the one or more ophthalmic articles are associated with one of the one or more haptics. In some embodiments, about 3, 4, 5, 6, 7, 8, 9, or 10 of the one or more ophthalmic articles are associated with one of the one or more haptics. In some embodiments, the biocompatible matrix comprises a copolymer derived from about 20 wt % to about 60 wt % of the caprolactone monomer and from about 40 wt % to 80 wt % of the at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3 MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the one or more active agents is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the one or more active agents is dexamethasone, ketorolac, diclofenac, moxifloxacin, travoprost, 5-fluorouracil, or methotrexate. In some embodiments, the one or more ophthalmic articles comprises an internal structure for associating around the one or more haptics. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure is the same as a shape of the one or more haptics. In some embodiments, the one or more ophthalmic articles comprises an internal structure for securing around a notched region of the one or more haptics. In some embodiments, the one or more ophthalmic articles comprises an outer diameter of at most 1.5 mm. In some embodiments, the internal structure comprises a diameter of at most 0.7 mm. In some embodiments, the one or more ophthalmic articles is configured such that the active agent or diagnostic agent is released from the biocompatible matrix. In some embodiments, the active agent or diagnostic agent is released from the biocompatible matrix over at least about 7 days. In some embodiments, the active agent or diagnostic agent is released from the biocompatible matrix over from about 5-30 days, 5-21 days, 5-14 days, 5-10 days, 7-30 days, 7-21 days, 7-14 days, or 7-10 days. In some embodiments, the active agent or diagnostic agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 μg to 800 μg of the one or more active agents and/or diagnostic agents.

In another aspect, the present disclosure provides a method of diagnosing a disease or condition of an eye. In one embodiment, the method comprises administering into an eye of a subject in need thereof an intraocular lens (IOL) for delivery of one or more diagnostic agents to the eye of the subject, which IOL comprises one or more ophthalmic articles associated thereto, wherein the one or more ophthalmic articles comprises the one or more diagnostic agents selected from the group consisting of paramagnetic molecules, fluorescent compounds, magnetic molecules, radionuclides, x-ray imaging agents, and contrast media. In some embodiments, the method further comprises capturing an image in which the one or more diagnostic agents indicate the disease or condition. In some embodiments, prior to administering the IOL comprising one or more ophthalmic articles associated thereto, associating the one or more ophthalmic articles to one or more haptics of the IOL. In some embodiments, prior to administering the IOL comprising one or more ophthalmic articles associated thereto, combining one or more diagnostic agents with a biocompatible copolymer matrix, thereby generating one or more ophthalmic articles. In some embodiments, prior to administering the IOL comprising one or more ophthalmic articles associated thereto, compressing the IOL comprising one or more ophthalmic articles associated thereto through an IOL injector that comprises an injector tip inner diameter from about 0.5 mm to 3 mm. In some embodiments, the one or more diagnostic agents is a fluorescent compound. In some embodiments, the one or more ophthalmic articles comprises a biocompatible matrix. In some embodiments, the one or more ophthalmic articles is associated to one or more haptics of the IOL. In some embodiments, about one of the one or more ophthalmic articles is associated with the one or more haptics of the IOL. In some embodiments, about two of the one or more ophthalmic articles are associated with the one or more haptics of the IOL. In some embodiments, about 3, 4, 5, 6, 7, 8, 9, or 10 of the one or more ophthalmic articles are associated with the one or more haptics of the IOL. In some embodiments, about one of the one or more ophthalmic articles is associated with one of the one or more haptics of the IOL. In some embodiments, about two of the one or more ophthalmic articles are associated with one of the one or more haptics of the IOL. In some embodiments, about 3, 4, 5, 6, 7, 8, 9, or 10 of the one or more ophthalmic articles are associated with one of the one or more haptics of the IOL. In some embodiments, the one or more ophthalmic articles comprises a biocompatible matrix. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic articles is configured such that the diagnostic agent is released from the biocompatible matrix. In some embodiments, the diagnostic agent is released from the biocompatible matrix through degradation of the biocompatible matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the one or more ophthalmic articles has a tensile strength of at least about 0.5 megapascal (MPa). In some embodiments, the one or more ophthalmic articles has a tensile strength from about 25 MPa to 35 MPa. In some embodiments, the one or more ophthalmic articles has a glass transition temperature of at most about 24° C. as measured by differential scanning calorimetry. In some embodiments, the one or more ophthalmic articles has a glass transition temperature from about −20° C. to 24° C. as measured by differential scanning calorimetry. In some embodiments, the one or more ophthalmic articles has an elasticity modulus of at most about 3 MPa. In some embodiments, the one or more ophthalmic articles has an elasticity modulus from about 0.5 MPa to 3 MPa. In some embodiments, the one or more ophthalmic articles has an elongation at break of at least about 100% as measured by tensile testing. In some embodiments, the one or more ophthalmic articles has an elongation at break from about 500% to 1500% at from about 18° C. to 24° C. In some embodiments, a shape of one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, wherein the one or more ophthalmic articles comprises an internal structure for associating around one or more haptics of the IOL. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure is the same as a shape of the one or more haptics. In some embodiments, the one or more ophthalmic articles comprises an internal structure for securing around a notched region of the one or more haptics. In some embodiments, the one or more ophthalmic articles comprises an outer diameter of at most 1.5 mm. In some embodiments, the internal structure comprises a diameter of at most 0.7 mm. In some embodiments, the one or more ophthalmic articles is compressively associated to an outward surface of the one or more haptics. In some embodiments, the one or more ophthalmic articles is associated to the one or more haptics of the IOL. In some embodiments, the compressing comprises folding the IOL having the one or more ophthalmic articles associated thereto into a tubular shape through the IOL injector that comprises the injector tip inner diameter from about 0.5 mm to 3 mm. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 μg to 800 μg of the one or more active agents and/or diagnostic agents.

In another aspect, the present disclosure provides a method of administering an active agent or diagnostic agent. In one embodiment, the method comprises (a) combining one or more active agents or diagnostic agents with a biocompatible matrix, thereby generating one or more ophthalmic articles; (b) associating the one or more ophthalmic articles to one or more haptics of at least one intraocular lens, thereby generating at least one agent-releasing intraocular lens; (c) compressing the at least one agent-releasing intraocular lens through an intraocular lens injector comprising an injector tip inner diameter from about 0.5 mm to 3 mm; and (d) implanting the at least one agent-releasing intraocular lens into an eye of a subject in need thereof for sustained intraocular active agent or diagnostic agent delivery. In some embodiments, about one of the one or more ophthalmic articles is associated with the one or more haptics. In some embodiments, about two of the one or more ophthalmic articles are associated with the one or more haptics. In some embodiments, about 3, 4, 5, 6, 7, 8, 9, or 10 of the one or more ophthalmic articles are associated with the one or more haptics. In some embodiments, about one of the one or more ophthalmic articles is associated with one of the one or more haptics. In some embodiments, about two of the one or more ophthalmic articles are associated with one of the one or more haptics. In some embodiments, about 3, 4, 5, 6, 7, 8, 9, or 10 of the one or more ophthalmic articles are associated with one of the one or more haptics. In some embodiments, the biocompatible matrix comprises a copolymer derived from about 20 wt % to about 60 wt % of a caprolactone monomer and from about 40 wt % to 80 wt % of at least one other monomer. In some embodiments, the biocompatible matrix comprises a copolymer derived from about 40 wt % of the caprolactone monomer and about 60 wt % of the at least one other monomer. In some embodiments, the at least one other monomer is lactide, glycolide, or trimethylene carbonate. In some embodiments, the copolymer is a random copolymer, a block copolymer, or a gradient copolymer. In some embodiments, the copolymer is a random copolymer. In some embodiments, the biocompatible matrix is biodegradable. In some embodiments, the one or more ophthalmic article has a tensile strength of at least about 0.5 megapascal (MPa). In some embodiments, the one or more ophthalmic article has a tensile strength from about 25 MPa to 35 MPa. In some embodiments, the one or more ophthalmic article has a glass transition temperature of at most about 24° C. as measured by differential scanning calorimetry. In some embodiments, the one or more ophthalmic article has a glass transition temperature from about −20° C. to 24° C. as measured by differential scanning calorimetry. In some embodiments, the one or more ophthalmic article has an elasticity modulus of at most about 3 MPa. In some embodiments, the one or more ophthalmic article has an elasticity modulus from about 0.5 MPa to 3 MPa. In some embodiments, the one or more ophthalmic article has an elongation at break of at least about 100% as measured by tensile testing. In some embodiments, the one or more ophthalmic article has an elongation at break from about 500% to 1500% at from about 18° C. to 24° C. In some embodiments, a shape of the one or more ophthalmic article is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the associating comprises indirect association between the one or more ophthalmic articles and the one or more haptics. In some embodiments, the one or more ophthalmic articles comprises an internal structure for associating around the one or more haptics. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure is the same as a shape of the one or more haptics. In some embodiments, the one or more ophthalmic articles comprises an internal structure for securing around a notched region of the one or more haptics. In some embodiments, the one or more ophthalmic articles comprises an outer diameter of at most 1.5 mm. In some embodiments, the one or more ophthalmic articles comprises an inner diameter of at most 0.7 mm. In some embodiments, the one or more ophthalmic articles is configured such that the active agent or diagnostic agent is released from the biocompatible copolymer matrix. In some embodiments, the one or more active agents or diagnostic agents is released from the biocompatible matrix over at least about 7 days. In some embodiments, the one or more active agents or diagnostic agents is released from the biocompatible matrix over from about 5-30 days, 5-21 days, 5-14 days, 5-10 days, 7-30 days, 7-21 days, 7-14 days, or 7-10 days. In some embodiments, the one or more active agents or diagnostic agents is released from the biocompatible matrix through degradation of the biocompatible copolymer matrix. In some embodiments, the biocompatible matrix is sufficiently compressible such that it is compatible with injection through an IOL injector that comprises an injector tip inner diameter from about 0.5 mm to 3 mm. In some embodiments, the biocompatible matrix is sufficiently flexible such that it is compatible with injection through an IOL injector that comprises an injector tip inner diameter from about 0.5 mm to 3 mm. In some embodiments, the biocompatible matrix is sufficiently elastic such that it recovers its original shape after injection through an IOL injector that comprises an injector tip inner diameter from about 0.5 mm to 3 mm. In some embodiments, the one or more ophthalmic articles is compressively associated to an outward surface of the one or more haptics. In some embodiments, the compressing comprises folding the at least one agent-releasing intraocular lens into a tubular shape through the IOL injector that comprises the injector tip inner diameter from about 0.5 mm to 3 mm. In some embodiments, the subject is concurrently undergoing or has undergone ophthalmic surgery. In some embodiments, the subject is concurrently undergoing or has undergone cataract surgery. In some embodiments, the associating comprises direct association between the one or more ophthalmic articles and the one or more haptics through a chemical bond, physical bond, compressive forces, or contractile forces. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 μg to 800 μg of the one or more active agents and/or diagnostic agents.

In another aspect, the present disclosure provides an ophthalmic drug delivery system. In one embodiment, the ophthalmic drug delivery system comprises (a) one or more ophthalmic articles comprising (1) one or more active agents or diagnostic agents, and (2) a biocompatible copolymer matrix derived from about 40 wt % of a caprolactone monomer and 60 wt % of a lactide monomer, which biocompatible copolymer matrix comprises at least one of the following characteristics: (i) the biocompatible copolymer matrix comprises a random copolymer; (ii) the one or more ophthalmic articles has a tensile strength from about 25 Megapascal (MPa) to 35 MPa; (iii) the one or more ophthalmic articles has a glass transition temperature of at most about 24° C. as measured by differential scanning calorimetry; (iv) the one or more ophthalmic articles has an elasticity modulus from about 0.5 MPa to 3 MPa; (v) the one or more ophthalmic articles has an elongation at break from about 500% to 1500% at from about 18° C. to 24° C.; and (b) one or more intraocular lenses (IOLs) comprising one or more haptics; wherein the one or more ophthalmic articles comprises an outer diameter of at most 1.5 mm and is configured to associate to an outward surface of the one or more haptics of the one or more IOLs to secure the one or more ophthalmic articles to the one or more haptics of the one or more IOLs. In some embodiments, about one of the one or more ophthalmic articles are associated with the one or more haptics. In some embodiments, about two of the one or more ophthalmic articles are associated with the one or more haptics. In some embodiments, about 3, 4, 5, 6, 7, 8, 9, or 10 of the one or more ophthalmic articles are associated with the one or more haptics. In some embodiments, about one of the one or more ophthalmic articles is associated with one of the one or more haptics of the IOL. In some embodiments, about two of the one or more ophthalmic articles are associated with one of the one or more haptics of the IOL. In some embodiments, about 3, 4, 5, 6, 7, 8, 9, or 10 of the one or more ophthalmic articles are associated with one of the one or more haptics of the IOL. In some embodiments, the biocompatible copolymer matrix is biodegradable. In some embodiments, a shape of the one or more ophthalmic articles is an annulus, an extruded annulus, a torus, or a prism with a hole in the center. In some embodiments, the prism is a round prism, rectangular prism, a prism with three or more sides, or a prism with another shape. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the one or more ophthalmic articles comprises an internal structure for associating around the one or more haptics. In some embodiments, a perimeter or widest dimension of the internal structure is less than or equal to a perimeter or widest dimension of the one or more haptics. In some embodiments, a perimeter of the internal structure is less than or equal to a perimeter of the one or more haptics. In some embodiments, a widest dimension of the internal structure is less than or equal to a widest dimension of the one or more haptics. In some embodiments, the one or more ophthalmic articles extends no more than about 0.32 mm beyond the one or more haptics once the one or more ophthalmic articles is associated to the one or more haptics. In some embodiments, a shape of the internal structure of the one or more ophthalmic articles is the same as a shape of the one or more haptic. In some embodiments, the one or more ophthalmic articles comprises an internal structure for securing around a notched region of the one or more haptics. In some embodiments, the one or more ophthalmic articles comprises an inner diameter of at most 0.7 mm. In some embodiments, the one or more ophthalmic articles is configured such that the active agent or diagnostic agent is released from the biocompatible copolymer matrix. In some embodiments, the active agent or diagnostic agent is released from the biocompatible copolymer matrix over at least about 7 days. In some embodiments, the active agent or diagnostic agent is released from the biocompatible copolymer matrix over from about 5-30 days, 5-21 days, 5-14 days, 5-10 days, 7-30 days, 7-21 days, 7-14 days, or 7-10 days. In some embodiments, the active agent or diagnostic agent is released from the biocompatible copolymer matrix through degradation of the biocompatible copolymer matrix. In some embodiments, the biocompatible copolymer matrix is sufficiently compressible such that it is compatible with injection through an IOL injector that comprises an injector tip inner diameter from about 0.5 mm to 3 mm. In some embodiments, the biocompatible copolymer matrix is sufficiently flexible such that it is compatible with injection through an IOL injector that comprises an injector tip inner diameter from about 0.5 mm to 3 mm. In some embodiments, the biocompatible copolymer matrix is sufficiently elastic such that it recovers its original shape after injection through an IOL injector that comprises an injector tip inner diameter from about 0.5 mm to 3 mm. In some embodiments, the biocompatible copolymer matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agents.

In another aspect, the present disclosure provides an ophthalmic article. In one embodiment, the ophthalmic article comprises (a) a biocompatible copolymer matrix derived from about 40 wt % of a caprolactone monomer and 60 wt % of a lactide monomer, which biocompatible copolymer matrix comprises at least one of the following characteristics: (i) the biocompatible copolymer matrix comprises a random copolymer; (ii) the ophthalmic article has a tensile strength from about 25 Megapascal (MPa) to 35 MPa; (iii) the ophthalmic article has a glass transition temperature of at most about 24° C. as measured by differential scanning calorimetry; (iv) the ophthalmic article has an elasticity modulus from about 0.5 MPa to 3 MPa; (v) the ophthalmic article has an elongation at break from about 500% to 1500% at 18-24° C.; and (b) an active agent or diagnostic agent; wherein the ophthalmic article comprises an outer diameter of at most 1.5 mm and is configured to associate to an outward surface of a haptic of an intraocular lens (IOL) to secure the ophthalmic article to the haptic of the IOL. In some embodiments, the biocompatible copolymer matrix is biodegradable. In some embodiments, a shape of the ophthalmic article is an annulus, an extruded annulus, a torus, or a prism with a hole in the center, which may be round, rectangular or other another shape. In some embodiments, the prism is a round prism, rectangular prism, a prism with three or more sides, or a prism with another shape. In some embodiments, the ophthalmic article comprises an internal structure for associating around the outward surface of the haptic of the IOL. In some embodiments, a perimeter or widest dimension of the internal structure is less than or equal to a perimeter or widest dimension of the haptic of the IOL. In some embodiments, a perimeter of the internal structure is less than or equal to a perimeter of the haptic of the IOL. In some embodiments, a widest dimension of the internal structure is less than or equal to a widest dimension of the haptic of the IOL. In some embodiments, the ophthalmic article extends no more than about 0.32 mm beyond the haptic of the IOL once the ophthalmic article is associated to the haptic of the IOL. In some embodiments, a shape of the internal structure is the same as a shape of the haptic of the IOL. In some embodiments, the ophthalmic article comprises an internal structure for securing around a notched region of the haptic of the IOL. In some embodiments, the ophthalmic article comprises an internal hole with a diameter of at most 0.7 mm. In some embodiments, the active agent is an interocular pressure (IOP) lowering agent, corticosteroid, non-steroidal anti-inflammatory drug, antibiotic, antiviral, antimetabolite, antifungal, antifibrotic agent, or angiogenesis inhibitor. In some embodiments, the active agent is dexamethasone, ketorolac, diclofenac, moxifloxacin, travoprost, 5-fluorouracil, or methotrexate. In some embodiments, the ophthalmic article is configured such that the active agent or the diagnostic agent is released from the biocompatible copolymer matrix. In some embodiments, the active agent or diagnostic agent is released from the biocompatible copolymer matrix over at least about 7 days. In some embodiments, the active agent or diagnostic agent is released from the biocompatible copolymer matrix over from about 5-30 days, 5-21 days, 5-14 days, 5-10 days, 7-30 days, 7-21 days, 7-14 days, or 7-10 days. In some embodiments, the active agent or diagnostic agent is released from the biocompatible copolymer matrix through degradation of the biocompatible copolymer matrix. In some embodiments, the biocompatible copolymer matrix is sufficiently compressible such that it is compatible with injection through an IOL injector that comprises an injector tip inner diameter from about 0.5 mm to 3 mm. In some embodiments, the biocompatible copolymer matrix is sufficiently flexible such that it is compatible with injection through an IOL injector that comprises an injector tip inner diameter from about 0.5 mm to 3 mm. In some embodiments, the biocompatible copolymer matrix is sufficiently elastic such that it recovers its original shape after injection through an IOL injector that comprises an injector tip inner diameter from about 0.5 mm to 3 mm. In some embodiments, the biocompatible matrix is sufficiently elastic such that the ophthalmic article recovers its shape once implanted inside an eye. In some embodiments, the ophthalmic article is sufficiently physically stable in a physiologic environment such that it does not significantly change shape within at least 7 days after implantation of the ophthalmic article in an eye of a subject. In some embodiments, the ophthalmic article comprises from about 1 µg to 800 µg of the one or more active agents and/or diagnostic agent.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A illustrates a plan view of an annulus shaped ophthalmic article, in accordance with many embodiments;

FIG. 2B illustrates a cross-sectional view of the annulus shaped ophthalmic article, in accordance with many embodiments;

FIG. 2C illustrates a plan view of a toroid shaped ophthalmic article, in accordance with many embodiments;

FIG. 2D illustrates a cross-sectional view of the toroid shaped ophthalmic article, in accordance with many embodiments;

FIG. 2E illustrates a plan view of a square shaped ophthalmic article, in accordance with many embodiments;

FIG. 2F illustrates a cross-sectional view of a square shaped ophthalmic article, in accordance with many embodiments;

FIG. 2G illustrates a plan view of an octagon shaped ophthalmic article, in accordance with many embodiments;

FIG. 2H illustrates a cross-sectional view of an octagon shaped ophthalmic article, in accordance with many embodiments;

FIG. 3A illustrates a plan view of an intraocular lens with an ophthalmic article, in accordance with many embodiments;

FIG. 3B illustrates a side view of an intraocular lens (IOL) with an ophthalmic article, in accordance with many embodiments;

FIG. 5B schematically illustrates an example of an implanting method, in accordance with many embodiments;

FIG. 5C schematically illustrates another example of an intraocular lens with an ophthalmic article associated thereto;

FIG. 7A illustrates an example of an ophthalmic article;

FIG. 7B illustrates an example of an ophthalmic article placed on an ocular device;

FIG. 8A illustrates an example of an ophthalmic article positioned on a haptic of an IOL;

FIG. 8B schematically illustrates an ophthalmic article;

FIG. 9A illustrates a pre-stretched state of an ophthalmic article;

FIG. 9B illustrates a stretched state of the ophthalmic article;

FIG. 9C illustrates a recovered state of the ophthalmic article;

FIG. 15A shows an exemplary appearance of the ophthalmic article and IOL before an in vitro IOL injection was performed;

FIG. 15B shows the exemplary appearance of the ophthalmic article and IOL after the in vitro IOL injection was performed;

FIG. 16A shows an exemplary appearance of the ophthalmic article and IOL before an in vitro IOL injection was performed;

FIG. 16B shows the exemplary appearance of the ophthalmic article and IOL after the in vitro IOL injection was performed;

FIG. 17A shows an exemplary appearance of the ophthalmic article and IOL before an in vitro IOL injection was performed;

FIG. 17B shows the appearance of ophthalmic article and IOL after the in vitro IOL injection is performed;

FIGS. 18A, 18C and 18E show the appearances of coated IOLs before in vitro IOL injections are performed;

FIGS. 18B, 18D and 18F show the appearances of the coated IOL after in vitro IOL injections are performed;

FIGS. 19A, 19C and 19E show the appearances of coated IOLs before in vitro IOL injections are performed;

FIGS. 19B, 19D and 19F show the appearances of the coated IOL after in vitro IOL injections are performed;

FIGS. 20A-20F show an example of a qualitative testing of a copolymer;

FIGS. 36A-F illustrates digital planar photographs associated with the ocular examination of rabbit's eyes in one group;

FIGS. 36G-L illustrates digital planar photographs associated with the ocular examination of rabbit's eyes in another group;

FIGS. 39A-38D shows representative images of histopathology sections of the eyes of the animals in another group;

FIGS. 50A-50D illustrate a loading process of an IOL with an associated ophthalmic article into an IOL injector cartridge;

DETAILED DESCRIPTION

Figure 1B:
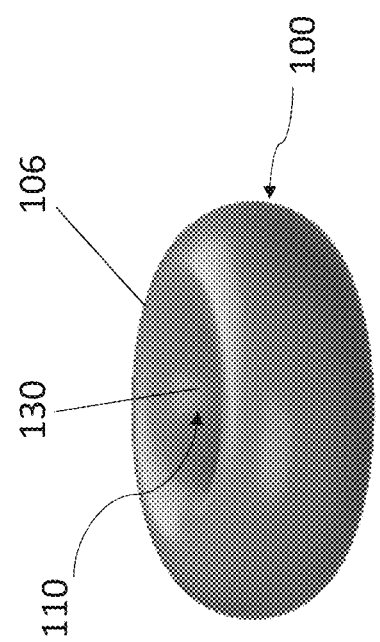
FIG. 1B illustrates another perspective view of an ophthalmic article, in accordance with many embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular forms "a," "an," and "the" include plural references unless the context clearly dictates otherwise. Any reference to "or" herein is intended to encompass "and/or" unless otherwise stated.

As used herein, "substantial" or "substantially" can refer to the complete or nearly complete extent or degree of an action, characteristic, property, state, structure, item, or result. For example, an object that is substantially enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "effective amount" refers to an amount of an ingredient which, when included in a composition, is sufficient to achieve an intended compositional or physiological effect. Thus, a "therapeutically effective amount" refers to a substantially non-toxic, but sufficient amount of an active agent, to achieve therapeutic results in treating or preventing a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. However, the determination of an effective amount may be within the ordinary skill in the art of pharmaceutical and nutritional sciences as well as medicine.

As used herein, "reshape" can refer to the act of reducing the overall dimensions of an object (e.g., an ophthalmic article), for instance by bending, folding, rolling or otherwise collapsing the object to a desired configuration (shape), physically or chemically. To that end, the terms, "collapsing", "bending", "folding", "rolling" can refer to the reshaping of the ophthalmic article and/or ocular device of the present invention to allow the ophthalmic article to fit in an intraocular injector tip's inner diameter that is smaller in at least one dimension than that of the ophthalmic article in its original shape (e.g. prior to reshaping).

As used herein, "subject" refers to a mammal that may benefit from the administration of a composition or method as recited herein. Examples of subjects include humans, and can also include other animals such as horses, pigs, cattle, dogs, cats, rabbits, or aquatic mammals.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "at most", "no more than," "up to," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Cataract surgery has evolved significantly over the past 30 to 40 years. The advent of new biomaterials (e.g., soft acrylic polymers) has enabled development of deformable, elastic IOLs with capacity to be folded, rolled or otherwise deformed into narrower profiles for injection through smaller incisions. Advancements in surgical instruments (e.g., IOL injector cartridges and injectors) have improved the efficiency of IOL folding and rolling with greater consistency and reliability than traditional methods (e.g., IOL forceps). Such innovations have reduced the invasiveness and duration of cataract surgery resulting in fewer complications, better refractive outcomes and faster recovery for patients.

In designing an ophthalmic article (e.g., drug delivery device) intended for implantation inside the eye, the ophthalmic article's physical, chemical and/or biologic properties may affect its safety profile. The ophthalmic article can be sufficiently soft and/or flexible so as not to deform, abrade, pierce, occlude or otherwise physically injure internal structures of an eye. The inactive materials that comprise the drug delivery device, and any degradants thereof, may be biocompatible and not cause untoward effects within the eye. The active agents (e.g., active ingredients) and/or diagnostic agents that comprise the ophthalmic article may be present in quantities sufficient to achieve their intended function but not exceed levels known to cause toxicity within the eye.

Surgical procedures may be optimized to achieve the maximum benefit to a subject (e.g., patient) with the lowest possible risk of complications. Any modifications to the standard surgical technique may alter the risk benefit-ratio for subjects (e.g., patients). In designing an ophthalmic article (e.g., drug delivery device) for association to an ocular device (e.g., an intraocular lens), the ocular device with the ophthalmic article attached thereto may be compatible with standard surgical technique for surgery (e.g., cataract surgery). Furthermore, the usability and human factors aspects of the ocular device with the ophthalmic article attached thereto may be comparable to that of an ocular device alone.

The present disclosure provides articles, methods, systems, and kits for delivery or administration of active agents and/or diagnostic agents from an ocular device to an eye. The present disclosure also provides articles, methods, systems, and kits for diagnosis and/or treatment of a disease, condition, or complication. For example, the present disclosure provides articles, methods, devices, systems, and kits for delivery of active agents (e.g., medications) from an intraocular lens (IOL) to an eye. In some embodiments, articles, systems, and associated methods of the present disclosure can be positioned within an anterior segment of the eye (e.g. within the lens capsule) of a subject to deliver an active agent and/or diagnostic agent to the posterior segment of an eye of the subject. Non-limiting examples of ocular regions found within the posterior segment of the eye can include at least one of vitreous humor, the choroid, and the retina. In addition to delivering the active agent and/or diagnostic agent to the posterior segment of the eye, the active agent and/or diagnostic agent can also be delivered to the anterior segment of the eye. The anterior segment of the eye can include at least one of the aqueous humor, the iris, and the lens capsule. The delivery may provide sustained release of the active agents and/or diagnostic agents over a period of time (e.g., with continuous release kinetics). The ophthalmic article for delivery or administration of the active agent and/or diagnostic agent to the eye can comprise a polymeric material (e.g., biocompatible polymer matrix), a non polymeric material, and/or an agent (e.g., active agent and/or diagnostic agent, a variety or combination of different active agents and/or diagnostic agents). The ophthalmic article (e.g., a drug delivery device) as described herein can be associated with to the ocular device (e.g., intraocular device) and can provide active agent and/or diagnostic agent delivery by alleviating the methods of multiple injections or complex eyedrop regimens. This allows for automatic active agent delivery to the eye and can eliminate the issue of patient non-compliance.

In an aspect, the present disclosure provides an ophthalmic article. The ophthalmic article may comprise a biocompatible material (e.g., biocompatible matrix). The biocompatible material may comprise a polymeric material comprising one or more polymers. The polymer may be a copolymer derived from one or more monomers. In some embodiments, the polymer may be a copolymer derived from a caprolactone monomer and at least one other monomer. In some embodiments, the one or more ophthalmic article may comprise at least one active agent and/or diagnostic agent.

In another aspect, the present disclosure provides an ophthalmic article. The ophthalmic article may comprise a biocompatible material (e.g., a biocompatible matrix). The ophthalmic article may also comprise an active agent and/or a diagnostic agent. The ophthalmic article can comprise an equivalent elasticity, compressibility, tensile strength, shape recovery, or reshapability to another article comprising a biocompatible matrix comprising a copolymer derived from a caprolactone monomer and a lactide monomer. In some embodiments, the ophthalmic article can comprise an equivalent elasticity, compressibility, tensile strength, shape recovery, or reshapability to an article comprising a biocompatible matrix comprising a copolymer derived from about 40 wt % of a caprolactone monomer and about 60 wt % of a lactide monomer. The ophthalmic article may be configured to associate to a portion of an ocular device (e.g., a haptic of an intraocular lens).

In another aspect, the present disclosure provides an ophthalmic system. The ophthalmic system may comprise one or more ophthalmic articles. The one or more ophthalmic articles may comprise a biocompatible material (e.g., polymer matrix) comprising at least a polymer. The polymer may be a copolymer. The copolymer may be derived from one or more monomers. In some embodiments, the one or more monomers may be lactide, glycolide, caprolactone, ethylene glycol, trimethylene carbonate, or combinations thereof. In some embodiments, the polymer may be a copolymer derived from a caprolactone monomer and at least one other monomer. In some embodiments, the one or more ophthalmic article may comprise at least one active agent and/or diagnostic agent. The ophthalmic system may also comprise one or more ocular devices (e.g., an intraocular lens). The one or more ocular devices may be associated to the one or more ophthalmic articles.

In any of the various aspects, the one or more ophthalmic articles described herein are engineered in composition, size, shape, and combinations thereof, to provide maximal approximation of the ophthalmic article to a subject's eye. In some embodiments, the one or more ophthalmic articles may comprise a material. The material may be a biocompatible material (e.g., a biocompatible matrix). The biocompatible matrix may be a polymeric matrix. The material may comprise a polymeric material (e.g., a polymeric matrix) and/or a non-polymeric material. Non-polymeric materials can comprise glass (silica), soda-lime glass, alkali aluminosilicate glass, borosilicate glass, alkali-free glass, crystal glass quartz glass, metals and metal alloys (steel, aluminum, silver, gold, tantalum, titanium, copper, nickel, palladium platinum, zinc tin, antimony, bismuth, zinc, manganese, antimony, molybdenum, vanadium), crystalline materials (diamond, sapphire, graphene), carbon fiber, fiberglass, silicon carbide, alumina, graphite, aluminum oxide, aluminum oxide with chrome, brown fused aluminum oxide (ALOX), low titanium dioxide brown fused aluminum oxide (ALOX), zirconia-alumina, hydrated alumina, ceramic aluminum oxide (ALOX), green silicon carbide, black silicon carbide, boron carbide, cubic boron nitride, and diamond.

Biocompatible materials may comprise substances that do not elicit an adverse reaction when placed in a biologic environment. Biocompatible materials can be natural or synthetic in origin.

In some embodiments, the polymeric material can comprise a biocompatible polymer and/or a biodegradable polymer. For example, the polymeric materials or compositions for use in the ophthalmic article may comprise materials which are compatible (e.g., biocompatible) with the eye so as to cause no substantial interference with the functioning or physiology of the eye. Such polymeric materials may also be biodegradable and/or bioerodible. A biodegradable polymer can refer to one or more polymers, which can erode or degrade (e.g., in vivo) under physiological conditions over time due, at least in part, to contact with substances found in the surrounding tissue fluids, or by cellular function. The release of the active agent and/or diagnostic agent can occur concurrent with, or subsequent to, the degradation of a biodegradable polymer over time.

In some embodiments, the polymeric material may comprise homopolymers (e.g., polymers comprising one type of monomeric repeating unit), copolymers (e.g., polymer comprising two or more types of monomeric repeating units), or a polymer comprising more than two different polymeric units. In some embodiments, the polymeric material (e.g., polymer matrix) can comprise a homogeneous mixture of polymers. For example, the homogeneous mixture of polymers may not include a mixture wherein one portion thereof is different from another portion, (e.g., by ingredient or density). In some embodiments, the polymeric material (e.g., polymer matrix) can comprise a heterogeneous mixture of polymers. In some embodiments, the polymeric material may comprise a mixture of polymers of the same type (e.g. two different polylactic acid polymers) or of different types (e.g. polylactic acid polymers combined with polycaprolactone polymers). In some embodiments, the polymeric material may comprise a copolymer. In other embodiments, the copolymer may comprise one or more of a block copolymer (by way of illustration represented by PPPP-HHHH; wherein P and H are each illustrative monomeric units), alternating copolymer (by way of illustration represented by PHPHPHPH; wherein P and H are each illustrative monomeric units), statistical or random copolymer (by way of illustration represented by PHPPHPHH; wherein P and H are each illustrative monomeric units), a star copolymer, a brush copolymer, a gradient copolymer, or a graft copolymer. In some embodiments, the copolymer may be a random copolymer.

In some embodiments, the polymeric materials may comprise poly(L-lactide-co-caprolactone) (e.g., different ratios of L-lactide to caprolactone content), poly(D-lactide-co-caprolactone), poly(D,L-lactide-co-caprolactone), poly-(D-lactic acid) (PDLA), poly-(L-lactic acid) (PLLA), poly(D,L-lactic acid) (PLA), polycaprolactone (PCL), polyvinyl alcohol (PVA), poly(ethylene glycol) (PEG), poly(glycolic acid) (PGA), poly(L-lactide-co-glycolide), poly(D-lactide-co-glycolide), poly(D,L-lactide-co-glycolide) (PLGA), poly (L-lactide-co-trimethylene carbonate), poly(D-lactide-co-trimethylene carbonate), poly(D,L-lactide-co-trimethylene carbonate), poly(trimethylene carbonate-co-ε-caprolactone), poly(caprolactone-co-glycolide), polyorthoesters, polyanhydrides, polyesters, polyamides, polyesteramides, polycarbonates, polyethylene, polypropylene, polygalactic acid, polyacrylamide, polystyrene, polyurethane, silicone, hydroxypropylmethylcellulose (HPMC), hydroxypropylcellulose (HPC), polyglycolic acid-polyvinyl alcohol copolymers, polycaprolactone-polyethylene glycol copolymers, collagen, croscarmellose collagen, hyaluronic acid, elastin, polyhydroxybutyrate, polyalkaneanhydrides, gelatin, cellulose, oxidized cellulose, polyphosphazene, poly(sebacic acid), poly(ricenolic acid), poly(fumaric acid), chitin, chitosan, polyvinylpyrrolidone (PVP), synthetic cellulose esters, polyacrylic acids, polybutyric acid; triblock copolymers (e.g., PLGA-PEG-PLGA, PEG-PLGA-PEG), poly(N-isopropylacrylamide, poly(ethylene oxide)-poly(propylene oxide)-poly(ethylene oxide) tri-block copolymers (PEO-PPO-PEO), poly valeric acid, poly(valerolactone), polyhydroxyalkylcellulose; siloxane, polysiloxane; dimethylsiloxane/-methylvinylsiloxane copolymer; poly (dimethylsiloxane/-methylvinylsiloxane/-methylhydrogensiloxane) dimethylvinyl or trimethyl copolymer, polypeptides, poly(amino acids), poly(dioxanones), poly(alkylene alkylates), hydrophobic polyethers, polyetheresters, polyacetals, polycyanoacrylates, polyacrylates, polymethylmethacrylates, polysiloxanes, poly(oxyethylene)/poly(oxypropylene) copolymers, polyketals, polyphosphates, polyhydroxyvalerates, polyalkylene oxalates, polyalkylene succinates, poly(maleic acid), as well as copolymers thereof or derivatives thereof including oxidized, reduced, mono substituted, disubstituted, multi-substituted derivatives, or any combinations thereof. In some embodiments, the polymeric materials may comprise one or more elements as described by, for example, Abraham J. Domb et al., Biodegradable Polymers in Clinical Use and Clinical Development (2011), (ISBN 978-1-118-01580-3), which is incorporated by reference herein in its entirety. In some embodiments, the polymeric material may comprise polymers (e.g., polylactic acid, polycaprolactone, poly(lactide-co-caprolactone) and/or poly(L-lactide-co-caprolactone)) that can provide sustained-release of the active agent and/or diagnostic agent into the eye over time. In some embodiments, the polymeric material can comprise polylactic acid. In other embodiments, the polymeric material can comprise polycaprolactone. In other embodiments, the polymeric material can comprise poly(lactide-co-caprolactone). In other embodiments, the polymeric material can comprise poly(L-lactide-co-caprolactone).

In some embodiments, the polymeric material includes mixtures of a copolymer with another homopolymer or another copolymer. In some embodiment, the polymer may include a mixture of poly(lactide-co-caprolactone) (PLCL) with another homopolymer or another copolymer. In some embodiment, the polymer may include a mixture of poly(L-lactide-co-caprolactone) with another homopolymer or another copolymer. In some embodiment, the polymer may include a mixture of poly(L-lactide-co-caprolactone) with a PLA. In some embodiment, the polymer may include a mixture of poly(L-lactide-co-caprolactone) with a PGA. In some embodiment, the polymer may include a mixture of poly(L-lactide-co-caprolactone) with a PLGA. In some embodiment, the polymer may include a mixture of poly(L-lactide-co-caprolactone) with a PGA and/or PLGA.

In some embodiments, examples of polymeric materials comprise materials derived from and/or including organic esters and/or organic ethers, which when degraded results in physiologically acceptable degradation products. In some embodiments, the polymeric materials can comprise materials derived from and/or including, anhydrides, amides, esters, orthoesters and the like, alone or in combination with other monomers. The polymeric materials may be addition or condensation polymers. The polymeric materials may be cross-linked or non-cross-linked.

In some embodiments, besides carbon and hydrogen, the polymers may include at least one of oxygen and/or nitrogen. The oxygen may be present as oxy (e.g. hydroxy or ether), carbonyl (e.g., non-oxo carbonyl, carboxylic acid, carboxylic acid ester, amide and the like). The nitrogen may be present as part of an amide, cyano, or amino (including substituted amino) moieties. In some embodiments, polymers of hydroxyaliphatic carboxylic acids, polymers of hydroxalkanoates, either homopolymers or copolymers, and polysaccharides can be used in the ophthalmic articles. In some embodiments, polyesters can also be used in ophthalmic articles and can comprise polymers of D-lactic acid, L-lactic acid, racemic lactic acid (D,L-lactic acid), caproic acid, hydroxybutyric acid, glycolic acid, caprolactone, valerolactone, polymers and co-polymers thereof in any ratios, or combinations thereof.

Some characteristics of the polymers or polymeric materials for use in embodiments of the present disclosure may comprise biocompatibility, compatibility with the active agents and/or diagnostic agents, ease of use of the polymer in making the active agent and/or diagnostic agent delivery systems described herein, a desired half-life in the physiological environment, and hydrophilicity.

In some embodiments, the polymer matrix used to manufacture the ophthalmic article may be a synthetic aliphatic polyester, for example, a polymer of lactic acid and/or caproic acid, which can comprise poly-(D,L-lactide) (PLA), poly-(D-lactide), poly-(L-lactide), polycaprolactone (PCL), poly(L-lactide-co-caprolactone), poly(D-lactide-co-caprolactone), or mixtures, or copolymers thereof.

These polymers can degrade via backbone hydrolysis (bulk erosion) and the final degradation products of PLCL are lactic acid (e.g., L-lactic acid) and caproic acid, which are non-toxic and considered natural metabolic compounds. Lactic acid (e.g., L-lactic acid) and caproic acid are eliminated safely via the Krebs cycle by conversion to carbon dioxide and water. The ophthalmic article and/or the biocompatible material can degrade (e.g., non-enzymatic hydrolysis of its ester linkages throughout the polymer matrix, in the presence of water in the surrounding tissues) homogenously at a constant rate throughout the polymer matrix thereby enabling diffusion of the active agent and/or diagnostic agent from the matrix into the surrounding environment. This contrasts with other polymer-drug release systems that degrade through "surface erosion" whereby degradation of the polymer only occurs at outwardly exposure surfaces.

In bulk erosion, degradation of the matrix occurs throughout the matrix simultaneously with solubilization of oligomers in the surrounding media and drug release occurs by diffusion, which is a concentration-dependent phenomenon. On the other hand, surface erosion occurs from the front of the device, which continuously moves to the core of the device. As these types of polymers are made up of very hydrophobic monomers they do not allow aqueous media to penetrate the core; moreover, the oligomers usually deposit on the device itself and further hinder the release of entrapped bioactives. As a particular volume of the device is exposed to the environment, release occurs in zero-order fashion. These surface-eroding polymers have very labile hydrolytic bonds, thus may not be suitable for sustaining the release in nanoscopic carriers.

In some embodiments, poly(lactide-co-caprolactone) (PLCL) may be synthesized through random ring-opening co-polymerization of D,L-lactide and ε-caprolactone. Successive monomeric units of D,L-lactide or ε-caprolactone can be linked together by ester linkages. The ratio of lactide to caprolactone can be varied, altering the biodegradation characteristics of the product. By altering the ratio it may be possible to tailor the polymer degradation time. Drug release characteristics can be affected by the rate of biodegradation, molecular weight or molecular mass, and degree of crystallinity in drug delivery systems. By altering and customizing the biodegradable polymer matrix, the drug delivery profile can be changed.

In some embodiments, poly(L-lactide-co-caprolactone) may be synthesized through random ring-opening co-polymerization of L-lactide and ε-caprolactone. Successive monomeric units of L-lactide or ε-caprolactone are linked together by ester linkages. The ratio of L-lactide to ε-caprolactone can be varied, altering the biodegradation characteristics of the product. By altering the ratio it may be possible to tailor the polymer degradation time. Drug release characteristics can be affected by the rate of biodegradation, molecular weight or molecular mass, and degree of crystallinity in drug delivery systems. By altering and customizing the biodegradable polymer matrix, the drug delivery profile can be changed.

Alternatively, the synthesis of various molecular weights or molecular mass of PLCL with various D,L-lactide-caprolactone ratios may be possible. For example, the synthesis of various molecular weights or molecular mass of poly(L-lactide-co-caprolactone) with various L-lactide-caprolactone ratios is possible. The polymers used to form the ophthalmic articles of the disclosure have independent properties associated with them that when combined provide the properties needed to provide sustained release of an effective amount (e.g., therapeutically effective amount) of an active agent and/or diagnostic agent. A few of the primary polymer characteristics that control active agent and/or diagnostic agent release rates can be the molecular weight distribution or molecular mass distribution, polymer end group (i.e., carboxylic acid or ester), and the ratio of monomers within a copolymer, and/or the ratio of polymers and/or copolymers in the polymer matrix. The present disclosure provides an example of a polymer matrix that possess desirable active agent and/or diagnostic agent release characteristics by manipulating one or more of the aforementioned properties to develop a suitable ophthalmic article.

Some polymeric materials can be subject to enzymatic or hydrolytic instability. Water soluble polymers may be cross-linked with hydrolytic or biodegradable unstable cross-links to provide useful water insoluble polymers. Thus, the degree of stability can vary, depending upon the choice of one or more monomers, whether a homopolymer or copolymer is employed, employing mixtures of polymers, and whether the polymer includes terminal acid groups.

Another factor for controlling the biodegradation of the polymer matrix and hence the extended release profile of the ophthalmic article is the relative average molecular weight or molecular mass of the polymeric composition employed in the ophthalmic article. Different molecular weights or molecular mass of the same or different polymeric compositions may modulate the release profile (e.g., extended release, non-extended release, linear release) of the at least one active agent and/or diagnostic agent. In some embodiments, the polymeric material may be selected from biodegradable polymers, disclosed herein, that do not substantially swell when in the presence of the aqueous humor. For example, PLGA polymers swell when used as the matrix material of drug delivery implants whereas PLA based polymer blends do not appreciably swell in the presence of the aqueous humor.

Example polymers used in various embodiments of the disclosure may comprise variation in the mole ratio of a first monomer (e.g., L-lactide) to a second monomer (e.g., ε-caprolactone) from approximately 50:50 to approximately 85:15, including, but not limited to, 50:50, 51:49, 52:48, 53:47, 54:46, 55:45, 54:46, 53:47, 52:48, 51:49, 60:40, 61:39, 62:38, 63:37, 64:35, 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 90:10, or 95:5. In some embodiments, the mole ratio of the first monomer (e.g., L-lactide) to the second monomer may be a ratio aside from 50:50 (e.g., ε-caprolactone). In some embodiments, the mole ratio of the first monomer (e.g., L-lactide) to the second monomer (e.g., ε-caprolactone) may be 60:40.

Example polymers used in various embodiments of the disclosure may comprise variation in the weight ratio of a first monomer (e.g., L-lactide) to a second monomer (e.g., ε-caprolactone) from approximately 50:50 to approximately 85:15, including, but not limited to, about 5:95, about 10:90, about 15:85, about 20:80, about 25:75, about 30:70, about 35:65, about 40:60, about 45:55, about 50:50, about 51:49, about 52:48, about 53:47, about 54:46, about 55:45, about 54:46, about 53:47, about 52:48, about 51:49, about 60:40, about 61:39, about 62:38, about 63:37, about 64:35, about 65:35, about 66:34, about 67:33, about 68:32, about 69:31, about 70:30, about 71:29, about 72:28, about 73:27, about 74:26, about 75:25, about 76:24, about 77:23, about 78:22, about 79:21, about 80:20, about 81:19, about 82:18, about 83:17, about 84:16, about 85:15, about 90:10, or about 90:15. In some embodiments, the ratio of the first monomer (e.g., L-lactide) to the second monomer may be a ratio aside from 50:50. In some embodiments, the mole ratio of the first monomer (e.g., L-lactide) to the second monomer (e.g., ε-caprolactone) may be 60:40.

In one example, the polymeric material can comprise poly(lactide-co-caprolactone) having a copolymer ratio from 10:90 to 90:10 and in another case from 52:48 to 90:10. In yet other examples, the copolymer ratio can be from about 60:40 to about 40:60, or from about 55:45 to about 45:55. In some embodiments, the copolymer ratio can be about 60:40. In some embodiments, the copolymer ratio can be about 50:50. In some embodiments, the copolymer ratio can be a ratio aside from about 50:50. In some embodiments, the copolymer ratio can be 52-78:48-22 and in another specific example from 60-90:40-10.

In one example, the polymeric material can comprise poly(L-lactide-co-caprolactone) having a copolymer ratio from 10:90 to 90:10 and in another case from 52:48 to 90:10. In yet other examples, the copolymer ratio can be from about 60:40 to about 40:60, or from about 55:45 to about 45:55. In some embodiments, the copolymer ratio can be about 60:40. In some embodiments, the copolymer ratio can be about 50:50. In some embodiments, the copolymer ratio can be a ratio aside from about 50:50. In some embodiments, the copolymer ratio can be 52-78:48-22 and in another specific example from 60-90:40-10. Although degradation rates can be dependent on such proportions, additional alternative approaches can also be useful such as device coatings, particle encapsulation, and the like.

In one example, the polymeric material can comprise poly(L-lactide-co-caprolactone) having a copolymer ratio from 10:90 to 90:10 and in another case from 52:48 to 90:10. In yet other examples, the copolymer ratio can be from about 60:40 to about 40:60, or from about 55:45 to about 45:55. In some embodiments, the copolymer ratio can be about 60:40. In some embodiments, the copolymer ratio can be about 50:50. In some embodiments, the copolymer ratio can be a ratio aside from about 50:50. In some embodiments, the copolymer ratio can be 52-78:48-22 and in another specific example from 60-90:40-10.

In some embodiments, the polymeric material (e.g., biocompatible copolymer matrix) may be derived from about 20 wt % to about 60 wt % of a caprolactone monomer and from about 40 wt % to 80 wt % of at least one other monomer. In some embodiments, the polymeric material (e.g., biocompatible copolymer matrix) may be derived from about 40 wt % of the caprolactone monomer and about 60 wt % of the at least one other monomer. In some embodiments, the at least one other monomer may be lactide, glycolide, caprolactone, ethylene glycol, trimethylene carbonate, or combinations thereof. In some embodiments, the at least one other monomer is lactide.

In some embodiments, the polymeric material (e.g., biocompatible matrix) may be derived from about 20 wt % to about 60 wt % of a caprolactone monomer and from about 40 wt % to 80 wt % of lactide. In some embodiments, the polymeric material (e.g., biocompatible matrix) may be derived from about 40 wt % of the caprolactone monomer and about 60 wt % of lactide.

In some embodiments, the polymeric material (e.g., biocompatible matrix) may be derived from about 20 wt % to about 60 wt % of a caprolactone monomer and from about 40 wt % to 80 wt % of L-lactide. In some embodiments, the polymeric material (e.g., biocompatible matrix) may be derived from about 40 wt % of the caprolactone monomer and about 60 wt % of L-lactide.

In some embodiments, the ophthalmic article can contain at least about 50 wt % polymeric material and/or at least about 50 wt % active agent and/or diagnostic agent. In some embodiments, the ophthalmic article can contain at least about 55 wt % polymeric material and/or at least about 45 wt % active agent and/or diagnostic agent. In some embodiments, the ophthalmic article can contain at least about 60 wt % polymeric material and/or at least about 40 wt % active agent and/or diagnostic agent. In some embodiments, the ophthalmic article can contain at least about 65 wt % polymeric material and/or at least about 35 wt % active agent and/or diagnostic agent. In some embodiments, the ophthalmic article can contain at least about 70 wt % polymeric material and/or at least about 30 wt % active agent and/or diagnostic agent. In some embodiments, the ophthalmic article can contain at least about 75 wt % polymeric material and/or at least about 25 wt % active agent and/or diagnostic agent. In some embodiments, the ophthalmic article can contain at least about 80 wt % polymeric material and/or at least about 20 wt % active agent and/or diagnostic agent. In some embodiments, the ophthalmic article can contain at least about 85 wt % polymeric material and/or at least about 15 wt % active agent and/or diagnostic agent. In some embodiments, the ophthalmic article can contain at least about 90 wt % polymeric material and/or at least about 10 wt % active agent and/or diagnostic agent. In some embodiments, the ophthalmic article can contain at least about 95 wt % polymeric material and/or at least about 5 wt % active agent and/or diagnostic agent.

In some embodiments, the ophthalmic article can contain at most about 50 wt % polymeric material and/or at most about 50 wt % active agent and/or diagnostic agent. In some embodiments, the ophthalmic article can contain at most about 55 wt % polymeric material and/or at most about 45 wt % active agent and/or diagnostic agent. In some embodiments, the ophthalmic article can contain at most about 60 wt % polymeric material and/or at most about 40 wt % active agent and/or diagnostic agent. In some embodiments, the ophthalmic article can contain at most about 65 wt % polymeric material and/or at most about 35 wt % active agent and/or diagnostic agent. In some embodiments, the ophthalmic article can contain at most about 70 wt % polymeric material and/or at most about 30 wt % active agent and/or diagnostic agent. In some embodiments, the ophthalmic article can contain at most about 75 wt % polymeric material and/or at most about 25 wt % active agent and/or diagnostic agent. In some embodiments, the ophthalmic article can contain at most about 80 wt % polymeric material and/or at most about 20 wt % active agent and/or diagnostic agent. In some embodiments, the ophthalmic article can contain at most about 85 wt % polymeric material and/or at most about 15 wt % active agent and/or diagnostic agent. In some embodiments, the ophthalmic article can contain at most about 90 wt % polymeric material and/or at most about 10 wt % active agent and/or diagnostic agent. In some embodiments, the ophthalmic article can contain at most about 95 wt % polymeric material and/or at most about 5 wt % active agent and/or diagnostic agent.

In some embodiments, the ophthalmic article can contain about 50 wt % to about 55 wt % polymeric material and/or about 45 wt % to about 50 wt % active agent and/or diagnostic agent. In some embodiments, the ophthalmic article can contain about 55 wt % to about 60 wt % polymeric material and/or about 40 wt % to about 45 wt % active agent and/or diagnostic agent. In some embodiments, the ophthalmic article can contain about 60 wt % to about 65 wt % polymeric material and/or about 35 wt % to about 40 wt % active agent and/or diagnostic agent. In some embodiments, the ophthalmic article can contain about 65 wt % to about 70 wt % polymeric material and/or about 30 wt % to about 35 wt % active agent and/or diagnostic agent. In some embodiments, the ophthalmic article can contain about 70 wt % to about 75 wt % polymeric material and/or about 25 wt % to about 30 wt % active agent and/or diagnostic agent. In some embodiments, the ophthalmic article can contain about 75 wt % to about 80 wt % polymeric material and/or about 20 wt % to about 25 wt % active agent and/or diagnostic agent. In some embodiments, the ophthalmic article can contain about 80 wt % to about 85 wt % polymeric material and/or about 15 wt % to about 20 wt % active agent and/or diagnostic agent. In some embodiments, the ophthalmic article can contain about 85 wt % to about 90 wt % polymeric material and/or about 10 wt % to about 15 wt % active agent and/or diagnostic agent. In some embodiments, the ophthalmic article can contain about 90 wt % to about 95 wt % polymeric material and/or about 5 wt % to about 10 wt % active agent and/or diagnostic agent.

In some embodiments, the ophthalmic article can contain at least about 50 wt % polymeric material, at least about 10 wt % active agent and/or diagnostic agent and/or at least about 40 wt % pharmaceutically acceptable excipient. In some embodiments, the ophthalmic article can contain at least about 55 wt % polymeric material, at least about 10 wt % active agent and/or diagnostic agent and/or at least about 35 wt % pharmaceutically acceptable excipient. In some embodiments, the ophthalmic article can contain at least about 60 wt % polymeric material, at least about 10 wt % active agent and/or diagnostic agent and/or at least about 30 wt % pharmaceutically acceptable excipient. In some embodiments, the ophthalmic article can contain at least about 65 wt % polymeric material, at least about 10 wt % active agent and/or diagnostic agent and/or at least about 25 wt % pharmaceutically acceptable excipient. In some embodiments, the ophthalmic article can contain at least about 70 wt % polymeric material, at least about 10 wt % active agent and/or diagnostic agent and/or at least about 20 wt % pharmaceutically acceptable excipient. In some embodiments, the ophthalmic article can contain at least about 75 wt % polymeric material, at least about 10 wt % active agent and/or diagnostic agent and/or at least about 15 wt % pharmaceutically acceptable excipient. In some embodiments, the ophthalmic article can contain at least about 80 wt % polymeric material, at least about 10 wt % active agent and/or diagnostic agent and/or at least about 10 wt % pharmaceutically acceptable excipient. In some embodiments, the ophthalmic article can contain at least about 85 wt % polymeric material, at least about 10 wt % active agent and/or diagnostic agent and/or at least about 5 wt % pharmaceutically acceptable excipient.

In some embodiments, the ophthalmic article can contain at least about 50 wt % polymeric material, at least about 20 wt % active agent and/or diagnostic agent and/or at least about 30 wt % pharmaceutically acceptable excipient. In some embodiments, the ophthalmic article can contain at least about 55 wt % polymeric material, at least about 20 wt % active agent and/or diagnostic agent and/or at least about 25 wt % pharmaceutically acceptable excipient. In some embodiments, the ophthalmic article can contain at least about 60 wt % polymeric material, at least about 20 wt % active agent and/or diagnostic agent and/or at least about 20 wt % pharmaceutically acceptable excipient. In some embodiments, the ophthalmic article can contain at least about 65 wt % polymeric material, at least about 20 wt % active agent and/or diagnostic agent and/or at least about 15 wt % pharmaceutically acceptable excipient. In some embodiments, the ophthalmic article can contain at least about 70 wt % polymeric material, at least about 20 wt % active agent and/or diagnostic agent and/or at least about 10 wt % pharmaceutically acceptable excipient. In some embodiments, the ophthalmic article can contain at least about 75 wt % polymeric material, at least about 20 wt % active agent and/or diagnostic agent and/or at least about 5 wt % pharmaceutically acceptable excipient.

In some embodiments, the ophthalmic article can contain at most about 50 wt % polymeric material, at most about 10 wt % active agent and/or diagnostic agent and/or at most about 40 wt % pharmaceutically acceptable excipient. In some embodiments, the ophthalmic article can contain at most about 55 wt % polymeric material, at most about 10 wt % active agent and/or diagnostic agent and/or at most about 35 wt % pharmaceutically acceptable excipient. In some embodiments, the ophthalmic article can contain at most about 60 wt % polymeric material, at most about 10 wt % active agent and/or diagnostic agent and/or at most about 30 wt % pharmaceutically acceptable excipient. In some embodiments, the ophthalmic article can contain at most about 65 wt % polymeric material, at most about 10 wt % active agent and/or diagnostic agent and/or at most about 25 wt % pharmaceutically acceptable excipient. In some embodiments, the ophthalmic article can contain at most about 70 wt % polymeric material, at most about 10 wt % active agent and/or diagnostic agent and/or at most about 20 wt % pharmaceutically acceptable excipient. In some embodiments, the ophthalmic article can contain at most about 75 wt % polymeric material, at most about 10 wt % active agent and/or diagnostic agent and/or at most about 15 wt % pharmaceutically acceptable excipient. In some embodiments, the ophthalmic article can contain at most about 80 wt % polymeric material, at most about 10 wt % active agent and/or diagnostic agent and/or at most about 10 wt % pharmaceutically acceptable excipient. In some embodiments, the ophthalmic article can contain at most about 85 wt % polymeric material, at most about 10 wt % active agent and/or diagnostic agent and/or at most about 5 wt % pharmaceutically acceptable excipient.

In some embodiments, the ophthalmic article can contain at most about 50 wt % polymeric material, at most about 20 wt % active agent and/or diagnostic agent and/or at most about 30 wt % pharmaceutically acceptable excipient. In some embodiments, the ophthalmic article can contain at most about 55 wt % polymeric material, at most about 20 wt % active agent and/or diagnostic agent and/or at most about 25 wt % pharmaceutically acceptable excipient. In some embodiments, the ophthalmic article can contain at most about 60 wt % polymeric material, at most about 20 wt % active agent and/or diagnostic agent and/or at most about 20 wt % pharmaceutically acceptable excipient. In some embodiments, the ophthalmic article can contain at most about 65 wt % polymeric material, at most about 20 wt % active agent and/or diagnostic agent and/or at most about 15 wt % pharmaceutically acceptable excipient. In some embodiments, the ophthalmic article can contain at most about 70 wt % polymeric material, at most about 20 wt % active agent and/or diagnostic agent and/or at most about 10 wt % pharmaceutically acceptable excipient. In some embodiments, the ophthalmic article can contain at most about 75 wt % polymeric material, at most about 20 wt % active agent and/or diagnostic agent and/or at most about 5 wt % pharmaceutically acceptable excipient.

In some embodiments, at least a first monomer (e.g., first monomer) can be present in the ophthalmic article at a concentration of from about 5 wt % to about 95 wt %, or from about 5 wt % to about 90 wt %, or from about 5 wt % to about 85 wt %, or from about 5 wt % to about 75 wt %, or from about 5 wt % to about 70 wt %, or from about 5 wt % to about 65 wt %, or from about 5 wt % to about 60 wt %, or from about 5 wt % to about 55 wt %, or from about 5 wt % to about 50 wt %, or from about 5 wt % to about 45 wt %, or from about 5 wt % to about 40 wt %, or from about 5 wt % to about 35 wt %, or from about 5 wt % to about 30 wt %, or from about 5 wt % to about 25 wt %, or from about 5 wt % to about 20 wt %, or from about 5 wt % to about 15 wt %, or from about 5 wt % to about 10 wt %, or from about 10 wt % to about 90 wt %, or from about 10 wt % to about 85 wt %, or from about 10 wt % to about 75 wt %, or from about 10 wt % to about 70%, or from about 10 wt % to at most about 65 wt %, or from about 10 wt % to at most about 60 wt %, or from about 10 wt % to about 55 wt %, or from about 10 wt % to about 50 wt %, or from about 10 wt % to about 45 wt %, or from about 10 wt % to about 40 wt %, or from about 10 wt % to about 35 wt %, or from about 10 wt % to about 30 wt %, or from about 10 wt % to about 25 wt %, or from 10 wt % to about 20 wt % or from about 10 wt % to about 15 wt %.

In some embodiments, at least a second monomer (e.g., second monomer) can be present in the ophthalmic article at a concentration of from about 5 wt % to about 95 wt %, or from about 5 wt % to about 90 wt %, or from about 5 wt % to about 85 wt %, or from about 5 wt % to about 75 wt %, or from about 5 wt % to about 70 wt %, or from about 5 wt % to about 65 wt %, or from about 5 wt % to about 60 wt %, or from about 5 wt % to about 55 wt %, or from about 5 wt % to about 50 wt %, or from about 5 wt % to about 45 wt %, or from about 5 wt % to about 40 wt %, or from about 5 wt % to about 35 wt %, or from about 5 wt % to about 30 wt %, or from about 5 wt % to about 25 wt %, or from about 5 wt % to about 20 wt %, or from about 5 wt % to about 15 wt %, or from about 5 wt % to about 10 wt %, or from about 10 wt % to about 90 wt %, or from about 10 wt % to about 85 wt %, or from about 10 wt % to about 75 wt %, or from about 10 wt % to about 70 wt %, or from about 10 wt % to about 65 wt %, or from about 10 wt % to about 60 wt %, or from about 10 wt % to about 55 wt %, or from about 10 wt % to about 50 wt %, or from about 10 wt % to about 45 wt %, or from about 10 wt % to about 40 wt %, or from about 10 wt % to about 35 wt %, or from about 10 wt % to about 30 wt %, or from about 10 wt % to about 25 wt %, or from about 10 wt % to about 20 wt % or from about 10 wt % to about 15 wt %.

Molecular weight (e.g., polymer molecular weight) or molecular mass can be expressed in different ways such as number average molecular weight ($M_n$) or molecular mass, weight average molecular weight ($M_w$) or molecular mass, viscosity average molecular weight (Mv) or molecular mass and/or higher average molecular weight ($M_z$, $Mz_{+1}$) or molecular mass. Molecular weight or molecular mass can be measured by any method known in the art. By way of illustration, the average molecular weight or molecular mass may be measured by end group analysis ($M_n$). In another embodiment, the average molecular weight or molecular mass can be determined by Ebullioscopy (boiling point elevation) or Cryoscopy (freezing point depression ($M_n$). In another embodiment, the average molecular weight or molecular mass can be determined by osmometry ($M_n$). In another embodiment, the average molecular weight or molecular mass can be determined by gel permeation chromatography (GPC). In another embodiment, the average molecular weight or molecular mass can be determined by light scattering techniques ($M_w$). In another embodiment, the average molecular weight or molecular mass can be determined by sedimentation equilibrium (Mw, Mz). In another embodiment, the average molecular weight or molecular mass can be determined by viscometry (Mη).

In some embodiments, the active agent and/or drug release profile can be controlled by varying the molecular weight or molecular mass of the ophthalmic article's material (e.g., PLCL). For example, PLCL-co-caprolactone) may have an average molecular weight or molecular mass between 1 kilodalton (kDa) and 200 kDa. In some embodiments, the ophthalmic article's material can comprise poly (lactide-co-caprolactone) (50:50) with a numerical average molecular weight ($M_n$) or molecular mass from about 75 kDa to about 85 kDa. In some embodiments, the ophthalmic article's material can comprise poly(lactide-co-caprolactone) (60:40) with a numerical average molecular weight ($M_n$) or molecular mass from about 75 kDa to 85 kDa. In some embodiments, the ophthalmic article's material can comprise poly(lactide-co-caprolactone) (50:50) with a weight average molecular weight ($M_w$) or molecular mass from about 75 kDa to about 85 kDa. In some embodiments, the ophthalmic article's material can comprise poly(lactide-co-caprolactone) (60:40) with a weight average molecular weight ($M_w$) or molecular mass from about 75 kDa to 85 kDa.

In some embodiments, the active agent and/or drug release profile can be controlled by varying the molecular weight or molecular mass of the ophthalmic article's material which is exemplarily poly(L-lactide-co-caprolactone). For example, poly(L-lactide-co-caprolactone) may have an average molecular weight or molecular mass between 1 kilodalton (kDa) and 200 kDa. In some embodiments, the ophthalmic article's material can comprise poly(L-lactide-co-caprolactone) (50:50) with a numerical average molecular weight ($M_n$) or molecular mass from about 75 kDa to about 85 kDa. In some embodiments, the ophthalmic article's material can comprise poly(L-lactide-co-caprolactone) (60:40) with a numerical average molecular weight ($M_n$) or molecular mass from about 75 kDa to 85 kDa. In some embodiments, the ophthalmic article's material can comprise poly(L-lactide-co-caprolactone) (50:50) with a weight average molecular weight ($M_w$) or molecular mass from about 75 kDa to about 85 kDa. In some embodiments, the ophthalmic article's material can comprise poly(L-lactide-co-caprolactone) (60:40) with a weight average molecular weight ($M_w$) or molecular mass from about 75 kDa to 85 kDa.

In some embodiments, the ophthalmic article's material can have an average molecular weight or average molecular mass (e.g., a number average molecular mass) of at least about 1 kDa, at least about 2 kDa, at least about 3 kDa, at least about 4 kDa, at least about 5 kDa, at least about 6 kDa, at least about 7 kDa, at least about 8 kDa, at least about 9 kDa, at least about 10 kDa, at least about 11 kDa, at least about 12 kDa, at least about 13 kDa, at least about 14 kDa, at least about 15 kDa, at least about 16 kDa, at least about 17 kDa, at least about 18 kDa, at least about 19 kDa, at least about 20 kDa, at least about 21 kDa, at least about 22 kDa, at least about 23 kDa, at least about 24 kDa, at least about 25 kDa, at least about 26 kDa, at least about 27 kDa, at least about 28 kDa, at least about 29 kDa, at least about 30 kDa, at least about 31 kDa, at least about 32 kDa, at least about 33 kDa, at least about 34 kDa, at least about 35 kDa, at least about 36 kDa, at least about 37 kDa, at least about 38 kDa, at least about 39 kDa, at least about 40 kDa, at least about 41 kDa, at least about 42 kDa, at least about 43 kDa, at least about 44 kDa, at least about 45 kDa, at least about 46 kDa, at least about 47 kDa, at least about 48 kDa, at least about 49 kDa, at least about 50 kDa, at least about 51 kDa, at least about 52 kDa, at least about 53 kDa, at least about 54 kDa, at least about 55 kDa, at least about 56 kDa, at least about 57 kDa, at least about 58 kDa, at least about 59 kDa, at least about 60 kDa, at least about 65 kDa, at least about 70 kDa, at least about 75 kDa, at least about 80 kDa, at least about 85 kDa, at least about 90 kDa, at least about 95 kDa, at least about 100 kDa, at least about 110 kDa, at least about 120 kDa, at least about 130 kDa, at least about 140 kDa, at least about 150 kDa, at least about 160 kDa, at least about 170 kDa, at least about 180 kDa, at least about 190 kDa, at least about 200 kDa, at least about 250 kDa, at least about 300 kDa, at least about 350 kDa, or at least about 400 kDa. In any of the above possibilities, molecular weight or molecular mass may be determined by any of the methods described herein.

In some embodiments, the ophthalmic article's material can have an average molecular weight or average molecular mass (e.g., a number average molecular mass) of at most about 1 kDa, at most about 2 kDa, at most about 3 kDa, at most about 4 kDa, at most about 5 kDa, at most about 6 kDa, at most about 7 kDa, at most about 8 kDa, at most about 9 kDa, at most about 10 kDa, at most about 11 kDa, at most about 12 kDa, at most about 13 kDa, at most about 14 kDa, at most about 15 kDa, at most about 16 kDa, at most about 17 kDa, at most about 18 kDa, at most about 19 kDa, at most about 20 kDa, at most about 21 kDa, at most about 22 kDa, at most about 23 kDa, at most about 24 kDa, at most about 25 kDa, at most about 26 kDa, at most about 27 kDa, at most about 28 kDa, at most about 29 kDa, at most about 30 kDa, at most about 31 kDa, at most about 32 kDa, at most about 33 kDa, at most about 34 kDa, at most about 35 kDa, at most about 36 kDa, at most about 37 kDa, at most about 38 kDa, at most about 39 kDa, at most about 40 kDa, at most about 41 kDa, at most about 42 kDa, at most about 43 kDa, at most about 44 kDa, at most about 45 kDa, at most about 46 kDa, at most about 47 kDa, at most about 48 kDa, at most about 49 kDa, at most about 50 kDa, at most about 51 kDa, at most about 52 kDa, at most about 53 kDa, at most about 54 kDa, at most about 55 kDa, at most about 56 kDa, at most about 57 kDa, at most about 58 kDa, at most about 59 kDa, at most about 60 kDa, at most about 65 kDa, at most about 70 kDa, at most about 75 kDa, at most about 80 kDa, at most about 85 kDa, at most about 90 kDa, at most about 95 kDa, at most about 100 kDa, at most about 110 kDa, at most about 120 kDa, at most about 130 kDa, at most about 140 kDa, at most about 150 kDa, at most about 160 kDa, at most about 170 kDa, at most about 180 kDa, at most about 190 kDa, at most about 200 kDa, at most about 250 kDa, at most about 300 kDa, at most about 350 kDa, or at most about 400 kDa. In any of the above possibilities, molecular weight or molecular mass may be determined by any of the methods described herein.

In some embodiments, the ophthalmic article's material can have an average molecular weight or average molecular mass (e.g., a number average molecular mass) of about 1 kDa, about 2 kDa, about 3 kDa, about 4 kDa, about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 36 kDa, about 37 kDa, about 38 kDa, about 39 kDa, about 40 kDa, about 41 kDa, about 42 kDa, about 43 kDa, about 44 kDa, about 45 kDa, about 46 kDa, about 47 kDa, about 48 kDa, about 49 kDa, about 50 kDa, about 51 kDa, about 52 kDa, about 53 kDa, about 54 kDa, about 55 kDa, about 56 kDa, about 57 kDa, about 58 kDa, about 59 kDa, about 60 kDa, about 65 kDa, about 70 kDa, about 75 kDa, about 80 kDa, about 85 kDa, about 90 kDa, about 95 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 250 kDa, about 300 kDa, about 350 kDa, or about 400 kDa. In any of the above possibilities, molecular weight or molecular mass may be determined by any of the methods described herein.

In some embodiments, the ophthalmic article's material can have an average molecular weight or average molecular mass of about 50 kDa to about 400 kDa. In some embodiments, the ophthalmic article's material can have a number average molecular weight or average molecular mass of about 50 kDa to about 55 kDa, about 50 kDa to about 60 kDa, about 50 kDa to about 80 kDa, about 50 kDa to about 100 kDa, about 50 kDa to about 120 kDa, about 50 kDa to about 150 kDa, about 50 kDa to about 200 kDa, about 50 kDa to about 300 kDa, about 50 kDa to about 400 kDa, about 55 kDa to about 60 kDa, about 55 kDa to about 80 kDa, about 55 kDa to about 100 kDa, about 55 kDa to about 120 kDa, about 55 kDa to about 150 kDa, about 55 kDa to about 200 kDa, about 55 kDa to about 300 kDa, about 55 kDa to about 400 kDa, about 60 kDa to about 80 kDa, about 60 kDa to about 100 kDa, about 60 kDa to about 120 kDa, about 60 kDa to about 150 kDa, about 60 kDa to about 200 kDa, about 60 kDa to about 300 kDa, about 60 kDa to about 400 kDa, about 80 kDa to about 100 kDa, about 80 kDa to about 120 kDa, about 80 kDa to about 150 kDa, about 80 kDa to about 200 kDa, about 80 kDa to about 300 kDa, about 80 kDa to about 400 kDa, about 100 kDa to about 120 kDa, about 100 kDa to about 150 kDa, about 100 kDa to about 200 kDa, about 100 kDa to about 300 kDa, about 100 kDa to about 400 kDa, about 120 kDa to about 150 kDa, about 120 kDa to about 200 kDa, about 120 kDa to about 300 kDa, about 120 kDa to about 400 kDa, about 150 kDa to about 200 kDa, about 150 kDa to about 300 kDa, about 150 kDa to about 400 kDa, about 200 kDa to about 300 kDa, about 200 kDa to about 400 kDa, or about 300 kDa to about 400 kDa.

In some embodiments, the ophthalmic article can comprise one or more active agents and/or diagnostic agents in an amount to deliver an effective amount (e.g., therapeutically effective amount) or effective dose (e.g., therapeutically effective dose) of the one or more active agents and/or diagnostic agents to the eye (e.g., posterior segment of the eye) from the lens capsule. An effective amount or effective dose can vary depending on the particular active agent and/or diagnostic being employed in the polymeric material (e.g., biodegradable polymer matrix). Further, the effective amount or effective dose can vary depending on the severity of the condition or complication being treated. Nonetheless, the active agent and/or diagnostic agent can be present in an amount to facilitate delivery of the active agent and/or diagnostic agent (e.g., from the anterior segment of the eye (e.g. from the lens capsule) to the posterior segment of the eye.

In any of the various aspects, the at least one active agent and/or diagnostic described herein for use in various embodiments of the disclosure may be (e.g., found in the Orange Book published by the Food and Drug Administration) used for the diagnosis and/or treatment or prevention of infection, inflammation (e.g., postoperative inflammation), macular edema, neovascularization, age-related macular degeneration (neovascular form or atrophic form), glaucoma, diabetic retinopathy, retinopathy of prematurity, uveitis, corneal transplant rejection, fibrosis (e.g., capsular fibrosis), posterior capsule opacification, retinal vein occlusions, infections, and the like. For example, the ophthalmic article, for delivery or administration of the active agent to the eye, can comprise active ingredients for treatment or prevention of complications associated with cataract surgery. The function of the active agent (e.g., active ingredients) may be to impart pharmacologic properties upon release from the ophthalmic article. Active agent may be an agent or substance that has measurable specified or selected physiologic activity when administered to a subject in a significant or effective amount. The active agent may be a therapeutic agent. Diagnostic agents may be substances used to examine the body in order to detect impairment of its normal functions. In some cases, diagnostic agents may be pharmacological and non-pharmacological agents with a functional purpose, such as for use in the detection of ocular deformities, ailments, and pathophysiological aspects. For example, the diagnostic agent may be an important and effective diagnostic adjuvant, such as a dye (e.g., fluorescein dye, indocyanine green, trypan blue, a dark quencher such as a cyanine dye, an azo dye, an acridine, a fluorone, an oxazine, a phenanthridine, a naphthalimide, a rhodamine, a benzopyrone, a perylene, a benzanthrone, pra benzoxanthrone), to aid in visualization of ocular tissues. The diagnostic agent may comprise paramagnetic molecules, fluorescent compounds, magnetic molecules, radionuclides, x-ray imaging agents, and/or contrast media. In some embodiments, a diagnostic agent may include radiopharmaceuticals, contrast agents for use in imaging techniques, allergen extracts, activated charcoal, different testing strips (e.g., cholesterol, ethanol, and glucose), pregnancy test, breath test with urea $^{13}$C, and various stains/markers. In some embodiments, the labelling moiety is a fluorescent dye or a dark quencher, selected from the group consisting of a coumarin, a cyanine dye, an azo dye, an acridine, a fluorone, an oxazine, a phenanthridine, a naphthalimide, a rhodamine, a benzopyrone, a perylene, a benzanthrone, and a benzoxanthrone. In particular non-limiting embodiments, the fluorescent dye is or is the residue of a compound selected from the group consisting of Coumarin, Fluorescein, Cyanine 3 (Cy3), Cyanine 5 (Cy5), Cyanine 7 (Cy7), Alexa dyes, bodipy derivatives, (E)-2-(4-(phenyldiazenyl)phenoxy)acetic acid, 3-(3',3'-dimethyl-6-nitrospiro[chromene-2,2'-indolin]-1'-yl)propanoate (Spiropyran), 3,5-dihydroxybenzoate and (E)-2-(4-(phenyldiazenyl)phenoxy)acetic acid, or combinations thereof.

As used herein, the phrase "radionuclides" encompasses any chemical compound or moiety that includes one or more radioactive isotopes. A radioactive isotope is an element which emits radiation. Examples include α-radiation emitters, β-radiation emitters or γ-radiation emitters. Suitable radionuclides for use as radioactive agents include, but are not limited to, Carbon-11, Fluorine-18, Bromine-76, or Iodine-123, and Iodine-124 and metallic radionuclides include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175. Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+ 191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-6, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, or Zirconium-95. In certain embodiments the radionuclide is selected from for example 99mTechnetium, 201Thalium, 111Indium, 67Gallium, 90Yttrium, 177Lutetium, or 123Iodine.

Numerous active agents are known for the treatment or prophylaxis of various eye conditions or complications, such as infection, inflammation (e.g., postoperative inflammation), macular edema, neovascularization, age related macular degeneration (neovascular form or atrophic form), glaucoma, diabetic retinopathy, retinopathy of prematurity, uveitis, corneal transplant rejection, fibrosis (e.g., capsular fibrosis), posterior capsule opacification, retinal vein occlusions, infections, and the like.

Categories of active agents that may be utilized for incorporation into the polymeric material can comprise anti-inflammatory agents, anti-vaso-proliferative agents, corticosteroids, non-steroidal anti-inflammatory drugs (NSAIDs), interocular pressure (IOP) lowering agents, anti-infective drugs, antibiotics, anti-mitotic agents, antivirals, antifungals, antimetabolites, antifibrotic agents, glaucoma medications, anti-neovascular agents, integrins, integrin antagonists, complement antagonists, cytokines, cytokine inhibitors, antibody-blocking agents, angiogenesis inhibitors, vaccines, immunomodulatory agents, anticoagulants, anti-neoplastic agents, anesthetics, analgesics, adrenergic agonists or antagonists, cholinergic agonists or antagonists, enzymes, enzyme inhibitors, neuroprotective agents, cytoprotective agents, regenerative agents, antisense oligonucleotides, aptamers, antibodies, or combinations thereof.

The active agents may be comprised of proteins, peptides, lipids, carbohydrates, hormones, metals, radioactive elements and compounds, or combinations thereof.

In some embodiments, corticosteroids can comprise hydrocortisone, loteprednol, cortisol, cortisone, prednisolone, methylprednisolone, dexamethasone, betamethasone, triamcinolone, aldosterone or fludrocortisone.

In some embodiments, NSAIDs can comprise diclofenac (e.g., diclofenac sodium), flubiprofen (e.g., flubiprofen sodium), ketorolac (e.g., ketorolac tromethamine), bromfenac, or nepafenac.

In some embodiments, IOP lowering agents and/or glaucoma medications can comprise prostaglandin analogs (e.g., bimatoprost, latanoprost, travoprost, or latanoprostene bunod), rho kinase inhibitor (e.g., netarsudil), adrenergic agonists (epinepherine or dipivefrin), beta-adrenergic antagonists also known as beta blockers (e.g., timolol, levobunolol, metipranolol, carteolol, or betaxolol), alpha2-adrenergic agonists (e.g., apraclonidine, brimonidine, or brimonidine tartrate), carbonic anhydrase inhibitors (e.g., brinzolamide, dichlorphenamide, methazolamide acetazolamide, acetazolamide, or dorzolamide), pilocarpine, echothiophate, demercarium, physostigmine, and/or isofluorophate.

In some embodiments, anti-infective can comprise antibiotics comprising ciprofloxacin, tobramycin, erythromycin, ofloxacin, gentamicin, fluoroquinolone antibiotics, moxifloxacin, and/or gatifloxacin; antivirals comprising ganciclovir, idoxuridine, vidarabine, and/or trifluridine; and/or antifungals comprising amphotericin B, natamycin, voriconazole, fluconazole, miconazole, clotrimazole, ketoconazole, posaconazole, echinocandin, caspofungin, and/or micafungin.

In some embodiments, antimetabolites can comprise methotrexate, mycophenolate, or azathioprine.

In some embodiments, antifibrotic agents can comprise maitomycin C or 5-fluorouracil.

In some embodiments, angiogenesis inhibitors can comprise anti-VEGF agents (e.g., aflibercept, ranibizumab, bevacizumab), PDGF-B inhibitors (e.g., Fovista®), complement antagonists (e.g., eculizumab), tyrosine kinase inhibitors (e.g. sunitinib, axitinib), and/or integrin antagonists (e.g., natalizumab and vedolizumab).

In some embodiments, cytoprotective agents can comprise ebselen, sulforaphane, oltipraz or dimethyl fumarate.

In some embodiments, neuroprotective agents can comprise ursodiol, memantine or acetylcysteine.

In some embodiments, anesthetic agents can comprise lidocaine, proparacaine or bupivacaine.

In some embodiments, the active agent can be dexamethasone, ketorolac, diclofenac, vancomycin, moxifloxacin, gatifloxicin, besifloxacin, travoprost, 5-fluorouracil, methotrexate, mitomycin C, prednisolone, bevacizumab (Avastin®), ranibizumab (Lucentis®), sunitinib, pegaptanib (Macugen®), timolol, latanoprost, brimonidine, nepafenac, bromfenac, triamcinolone, difluprednate, fluocinolide, aflibercept, or combinations thereof. In some embodiments, the active agent may be dexamethasone, ketorolac, diclofenac, moxifloxacin, travoprost, 5-fluorouracil, or methotrexate. In some embodiments, the active agent is dexamethasone. In some embodiments, the active agent is ketorolac. In some embodiments, the active ingredient is dexamethasone.

In some embodiments, the ophthalmic article may comprise inactive agents (e.g., polymers). The function of the inactive ingredients may be to impart certain physical properties to the ophthalmic article, such as bulk, adhesion, firmness, flexibility, conformity, erosion, color and opacity, as well as to affect the rate of release of the inactive agents (e.g., inactive ingredients). Various inactive ingredients can be used with the ophthalmic article and in approved active agents (e.g., drug products) and may be biocompatible. In some embodiments, the ophthalmic article may also comprise a pigment to aid visualization by the surgeon.

In some embodiments, the ophthalmic article may also comprise one or more excipients and/or disintegrants. Excipients may be comprise preservatives, penetration enhancers, plasticizers, lubricants, emulsifying agents, solubilizing agents, suspending agents, stiffening agents, thickening agents, buffering agents, acidifying agents, alkalinizing agents, viscosity-increasing agents, colorants, release-modifying agents, controlled-release agents, opacifiers, stabilizing agents, gelling agents, antioxidants, dispersing agents, hydroxypropylcellulose, sodium carboxymethylcellulose, croscarmellose sodium, hyaluronic acid, and/or albumin. Excipient may comprise one or more described by, for example, Raymond C. Rowe et al., Handbook of Pharmaceutical Excipients ($6^{th}$ Edition, 2009), which is incorporated by reference herein in its entirety.

Distintegrant can be a superdistintegrant. Non-limiting examples of suitable disintegrants can include crosslinked celluloses (e.g. croscarmellose, Ac-Di-Sol, Nymce ZSX, Primellose, SoluTab, VIVASOL), microcrystalline cellulose, alginates, crosslinked PVP (e.g. Crosspovidone, Kollidon, Polyplasdone), crosslinked starch, soy polysaccharides, calcium silicate, salts thereof, or the like.

For example, an excipient and/or disintegrant can be from 3 weight percentage (wt %) to 25 wt %, and in one case from 3 wt % to 20 wt % of the ophthalmic article. A disintegrant at greater than about 25 wt % can be useful for delivery times less than about 1 week, while less than about 3% can be useful for extended delivery times of greater than 6 to 9 months.

In some embodiments, the ophthalmic article may comprise from at least or up to about 0.1 wt % to 50 wt % of the excipient and/or disintegrant. In some embodiments, the ophthalmic article may comprise from about 0.5 wt % to 50 wt % of the excipient and/or disintegrant. In some embodiments, the ophthalmic article may comprise from about 1.0 wt % to 50 wt % of the excipient and/or disintegrant. In some embodiments, the ophthalmic article may comprise from about 5 wt % to 50 wt % of the excipient and/or disintegrant. In some embodiments, the ophthalmic article may comprise from about 10 wt % to 50 wt % of the excipient and/or disintegrant. In some embodiments, the ophthalmic article may comprise from about 15 wt % to 50 wt % of the excipient and/or disintegrant. In some embodiments, the ophthalmic article may comprise from about 20 wt % to 50 wt % of the excipient and/or disintegrant. In some embodiments, the ophthalmic article may comprise from 25 wt % to 50 wt % of the excipient and/or disintegrant. In some embodiments, the ophthalmic article may comprise from about 30 wt % to 50 wt % of the excipient and/or disintegrant. In some embodiments, the ophthalmic article may comprise from about 35 wt % to 50 wt % of the excipient and/or disintegrant. In some embodiments, the ophthalmic article may comprise from about 45 wt % to 50 wt % of the excipient and/or disintegrant. In some embodiments, the ophthalmic article may comprise from about 5 wt % to 40 wt % of the excipient and/or disintegrant. In some embodiments, the ophthalmic article may comprise from about 5 wt % to 35 wt % of the excipient and/or disintegrant. In some embodiments, the ophthalmic article may comprise from about 5 wt % to 30 wt % of the excipient and/or disintegrant. In some embodiments, the ophthalmic article may comprise from about 5 wt % to 25 wt % of the excipient and/or disintegrant. In some embodiments, the ophthalmic article may comprise from about 5 wt % to 20 wt % of the excipient and/or disintegrant. In some embodiments, the ophthalmic article may comprise from about 5 wt % to 15 wt % of the excipient and/or disintegrant. In some embodiments, the ophthalmic article may comprise from about 5 wt % to 10 wt % of the excipient and/or disintegrant.

In some embodiments, the ophthalmic article can be formed, for example, by mixing a polymeric material with a loading amount of active agent and/or diagnostic agent to form a matrix dispersion or solution. In some embodiments, the ophthalmic article can be formed using a biodegradable matrix and/or non-biodegradable materials.

In some embodiments, non-biodegradable materials may comprise methacrylates, acrylates and/or co-polymers thereof, silicone, and/or polymers and/or co-polymers of vinyl acetates, vinyl pyrrolidone and/or vinyl alcohol. Methacrylates may comprise poly(methyl acrylate) (PMA) or poly(methyl methacrylate) (PMMA). Vinyl acetates include vinyl acetate or ethylene vinyl acetate (EVA).

The active agent and/or diagnostic agent can be homogeneously dispersed as a solid, dissolved uniformly, or partially dissolved as long as uniformity and homogeneity is maintained. Thus, in some examples, the active agent and/or diagnostic agent can be homogenously combined with the polymer matrix such that the at least a portion (e.g., the entire) ophthalmic article is homogenous or substantially homogenous. For example, the homogeneity can extend throughout the entire ophthalmic article such that the ophthalmic article consists essentially of the homogeneously mixed matrix and active agent and/or diagnostic agent along with optional additives. The loading amount can be chosen to correspond to the desired dosage during diffusion. In some cases, the loading amount can take into consideration diffusion characteristics of the polymeric material and active agent and/or diagnostic agent, residual active agent and/or diagnostic agent, delivery time, and the like. The matrix dispersion can then be formed into the device shape using any suitable technique. For example, the matrix dispersion can be cast, sprayed and dried, extruded, stamped, or the like.

In some embodiments, the ophthalmic article (e.g., biocompatible and/or biodegradable matrix) can be configured to biodegrade or bioerode to provide release (e.g., controlled release) of the active agent (e.g., therapeutic agent) and/or diagnostic agent from the material (e.g., polymeric material). In some embodiments, the ophthalmic article (e.g., biocompatible and/or biodegradable matrix) can be configured to biodegrade or bioerode to provide release of the effective amount (e.g., therapeutically effective amount) of the active agent (e.g., therapeutic agent) and/or diagnostic agent from the polymeric material (e.g., polymer matrix) over a period of days, weeks, or months.

In some embodiments, the ophthalmic article for active agent (e.g., drug delivery) and/or diagnostic agent delivery to the eye may comprise bioerodible polymers, which may be any natural or synthetic polymers that spontaneously degrade when placed into a biologic environment. Mechanisms of bioerosion include ester hydrolysis, enzymatic degradation or reduction of a disulfide bond. Examples of bioerodible polymers may comprise polylactides, polyglycolides, polycaprolactone, poly(trimethylene carbonate), chitosan, polyethylene glycol, poly-beta-amino esters, poly-L-malic acid, hyaluronic acid, peptides, nucleic acids, or dextran-based polymers.

In some embodiments, the article for drug delivery to the eye can be designed to release drug over a short period of time (e.g. the first 24 to 48 hours after surgery). "Burst release" may be desirable to prevent immediate infection or inflammation following surgery. In other embodiments, the article for drug delivery to the eye might be designed to release drug over a longer period of time (e.g., many days to weeks or even months after surgery). Such sustained release would be desirable to treat more chronic conditions like glaucoma, posterior capsular opacification, or macular edema. In some embodiments, the ophthalmic article, described herein, can be targeted for a relatively short delivery duration, such as less than eight weeks. In some examples, the active agent and/or diagnostic agent has a delivery duration of from about one week to about six or eight weeks. In some examples, the active agent and/or diagnostic agent has a delivery duration of from about two weeks to about six or eight weeks. In some examples, the active agent and/or diagnostic agent has a delivery duration of from about three weeks to about six or eight weeks. In some examples, the active agent and/or diagnostic agent has a delivery duration of from about four weeks to about six or eight weeks. In some examples, the active agent and/or diagnostic agent has a delivery duration of from about one week to about 2 weeks. In some examples, the active agent and/or diagnostic agent has a delivery duration of from about one week to about 3 weeks. In some examples, the active agent and/or diagnostic agent has a delivery duration of from about one week to about 4 weeks. In some examples, the active agent and/or diagnostic agent has a delivery duration of from about one week to about 5 weeks. In some examples, the active agent and/or diagnostic agent has a delivery duration of from about one week to about 6 weeks.

In some examples, the active agent and/or diagnostic agent has a delivery duration of from about one week to about 7 weeks. In some examples, the active agent and/or diagnostic agent has a delivery duration of from about one week to about 8 weeks.

In some embodiments, the material (e.g., biocompatible matrix) and the active agent (e.g., drug) and/or diagnostic agent may be selected to provide release for more than 7 days. In some embodiments, the active agent and/or diagnostic agent can be released from the biocompatible polymer matrix (e.g., the biocompatible copolymer matrix) over at least about 7 days. In some embodiments, the active agent and/or diagnostic agent is released from the biocompatible material (e.g., biocompatible polymer matrix) over from about 5-30 days, 5-21 days, 5-14 days, 5-10 days, 7-30 days, 7-21 days, 7-14 days, or 7-10 days.

In some embodiments, the active agent and/or diagnostic agent can be released from the biocompatible polymer matrix (e.g., the biocompatible copolymer matrix) over about 1 day up to about 36 months. In some embodiments, the active agent and/or diagnostic agent can be released from the biocompatible polymer matrix (e.g., the biocompatible copolymer matrix) over at least about 34 months, at least about 32 months, at least about 30 months, at least about 28 months, at least about 26 months, at least about 24 months, at least about 22 months, at least about 20 months, at least about 18 months, at least about 16 months, at least about 14 months, at least about 12 months, at least about 10 months, at least about 8 months, at least about 6 months, at least about 4 months, at least about 2 months, at least about 1 month, at least about 3 weeks, at least about 2 weeks, at least about 1 week, at least about 6 days, at least about 5 days, at least about 4 days, at least about 3 days, at least about 2 day, or at least about 1 day. In some embodiments, the active agent and/or diagnostic agent can be released from the biocompatible polymer matrix (e.g., the biocompatible copolymer matrix) over at least about 7 days. In some embodiments, the active agent and/or diagnostic agent can be released from the biocompatible polymer matrix (e.g., the biocompatible copolymer matrix) over at least about 14 days. In some embodiments, the active agent and/or diagnostic agent can be released from the biocompatible polymer matrix (e.g., the biocompatible copolymer matrix) over at least about 45 days. In some embodiments, the active agent and/or diagnostic agent can be released from the biocompatible polymer matrix (e.g., the biocompatible copolymer matrix) over at least about 90 days.

In some embodiments, the active agent and/or diagnostic agent can be released from the biocompatible polymer matrix (e.g., the biocompatible copolymer matrix) over about 1 day up to about 36 months. In some embodiments, the active agent and/or diagnostic agent can be released from the biocompatible polymer matrix (e.g., the biocompatible copolymer matrix) over at most about 34 months, at most about 32 months, at most about 30 months, at most about 28 months, at most about 26 months, at most about 24 months, at most about 22 months, at most about 20 months, at most about 18 months, at most about 16 months, at most about 14 months, at most about 12 months, at most about 10 months, at most about 8 months, at most about 6 months, at most about 4 months, at most about 2 months, at most about 1 month, at most about 3 weeks, at most about 2 weeks, at most about 1 week, at most about 6 days, at most about 5 days, at most about 4 days, at most about 3 days, at most about 2 day, or at most about 1 day. In some embodiments, the active agent and/or diagnostic agent can be released from the biocompatible polymer matrix (e.g., the biocompatible copolymer matrix) over at most about 7 days. In some embodiments, the active agent and/or diagnostic agent can be released from the biocompatible polymer matrix (e.g., the biocompatible copolymer matrix) over at most about 14 days. In some embodiments, the active agent and/or diagnostic agent can be released from the biocompatible polymer matrix (e.g., the biocompatible copolymer matrix) over at most about 45 days. In some embodiments, the active agent and/or diagnostic agent can be released from the biocompatible polymer matrix (e.g., the biocompatible copolymer matrix) over at most about 90 days.

In some embodiments, the active agent and/or diagnostic agent can be released from the biocompatible polymer matrix (e.g., the biocompatible copolymer matrix) over about 1 week to about 36 months, about 1 week to about 34 months, about 1 week to about 32 months, about 1 week to about 30 months, about 1 week to about 30 months, about 1 week to about 28 months, about 1 week to about 26 months, about 1 week to about 24 months, about 1 week to about 22 months, about 1 week to about 20 months, about 1 week to about 18 months, about 1 week to about 16 months, about 1 week to about 14 months, about 1 week to about 12 months, about 1 week to about 10 months, about 1 week to about 8 months, about 1 week to about 6 months, about 1 week to about 4 months, about 1 week to about 2 months, about 1 week to about 1 month, about 1 week to about 3 weeks, or about 1 week to about 2 weeks. In some embodiments, the active agent and/or diagnostic agent can be released from the biocompatible polymer matrix (e.g., the biocompatible copolymer matrix) over about 1 day to about 7 days. In some embodiments, the active agent and/or diagnostic agent can be released from the biocompatible polymer matrix (e.g., the biocompatible copolymer matrix) over about 1 day to about 14 days. In some embodiments, the active agent and/or diagnostic agent can be released from the biocompatible polymer matrix (e.g., the biocompatible copolymer matrix) over about 1 day to about 45 days.

In an example, the therapeutically effective amount can be released over a period ranging from about 1 day to about 10 weeks. In other examples, the therapeutically effective amount can be released over a period ranging from about 1 day to about 3 weeks, from about 2 weeks to about 6 weeks, or from about 5 weeks to about 8 weeks. In some embodiments, the therapeutically effective amount can be released over at least about 1 day up to about 36 months.

In some embodiments, the therapeutically effective amount can be released over at least about 34 months, at least about 32 months, at least about 30 months, at least about 28 months, at least about 26 months, at least about 24 months, at least about 22 months, at least about 20 months, at least about 18 months, at least about 16 months, at least about 14 months, at least about 12 months, at least about 10 months, at least about 8 months, at least about 6 months, at least about 4 months, at least about 2 months, at least about 1 month, at least about 3 weeks, at least about 2 weeks, at least about 1 week, at least about 6 days, at least about 5 days, at least about 4 days, at least about 3 days, at least about 2 day, or at least about 1 day. In some embodiments, the therapeutically effective amount can be released over at least about 7 days. In some embodiments, the therapeutically effective amount can be released over at least about 14 days. In some embodiments, the therapeutically effective amount can be released over at least about 45 days. In some embodiments, the therapeutically effective amount can be released over at least about 90 days.

In some embodiments, the therapeutically effective amount can be released over at most about 34 months, at most about 32 months, at most about 30 months, at most about 28 months, at most about 26 months, at most about 24 months, at most about 22 months, at most about 20 months, at most about 18 months, at most about 16 months, at most about 14 months, at most about 12 months, at most about 10 months, at most about 8 months, at most about 6 months, at most about 4 months, at most about 2 months, at most about 1 month, at most about 3 weeks, at most about 2 weeks, at most about 1 week, at most about 6 days, at most about 5 days, at most about 4 days, at most about 3 days, at most about 2 day, or at most about 1 day. In some embodiments, the therapeutically effective amount can be released over at most about 7 days. In some embodiments, the therapeutically effective amount can be released over at most about 14 days. In some embodiments, the therapeutically effective amount can be released over at most about 45 days. In some embodiments, the therapeutically effective amount can be released over at most about 90 days.

In some embodiments, the therapeutically effective amount can be released over about 1 week to about 36 months, about 1 week to about 34 months, about 1 week to about 32 months, about 1 week to about 30 months, about 1 week to about 30 months, about 1 week to about 28 months, about 1 week to about 26 months, about 1 week to about 24 months, about 1 week to about 22 months, about 1 week to about 20 months, about 1 week to about 18 months, about 1 week to about 16 months, about 1 week to about 14 months, about 1 week to about 12 months, about 1 week to about 10 months, about 1 week to about 8 months, about 1 week to about 6 months, about 1 week to about 4 months, about 1 week to about 2 months, about 1 week to about 1 month, about 1 week to about 3 weeks, or about 1 week to about 2 weeks. In some embodiments, the therapeutically effective amount can be released over about 1 day to about 7 days. In some embodiments, the therapeutically effective amount can be released over about 1 day to about 14 days. In some embodiments, the therapeutically effective amount can be released over about 1 day to about 45 days. In some embodiments, the therapeutically effective amount can be released over about 1 day to about 90 days.

The effective amount (e.g., therapeutically effective amount) or effective dose (e.g., therapeutically effective dose) can range from about 1 micrograms (μg) to about 10 milligrams (mg). The effective amount or effective dose can depend on the active agent and/or diagnostic agent being employed and the severity of the condition or complication. In some embodiments, the effective amount or effective dose can range from about 50 μg to about 800 μg. In some embodiments, the effective amount or effective dose can range from about 50 μg to about 100 μg, from about 50 μg to about 150 μg, from about 50 μg to about 200 μg, from about 50 μg to about 250 μg, from about 50 μg to about 300 μg, from about 50 μg to about 350 μg, from about 50 μg to about 400 μg, from about 50 μg to about 450 μg, from about 50 μg to about 500 μg, from about 50 μg to about 550 μg, from about 50 μg to about 600 μg, from about 50 μg to about 650 μg, from about 50 μg to about 700 μg, from about 50 μg to about 750 μg, from about 50 μg to about 800 μg, from about 100 μg to about 150 μg, from about 100 μg to about 200 μg, from about 100 μg to about 250 μg, from about 100 μg to about 300 μg, from about 100 μg to about 350 μg, from about 100 μg to about 400 μg, from about 100 μg to about 450 μg, from about 100 μg to about 500 μg, from about 100 μg to about 550 μg, from about 100 μg to about 600 μg, from about 100 μg to about 650 μg, from about 100 μg to about 700 μg, from about 100 μg to about 750 μg, from about 100 μg to about 800 μg, from about 150 μg to about 200 μg, from about 150 μg to about 250 μg, from about 150 μg to about 300 μg, from about 150 μg to about 350 μg, from about 150 μg to about 400 μg, from about 150 μg to about 450 μg, from about 150 μg to about 500 μg, from about 150 μg to about 550 μg, from about 150 μg to about 600 μg, from about 150 μg to about 650 μg, from about 150 μg to about 700 μg, from about 150 μg to about 750 μg, from about 150 μg to about 800 μg, from about 200 μg to about 250 μg, from about 200 μg to about 300 μg, from about 200 μg to about 350 μg, from about 200 μg to about 400 μg, from about 200 μg to about 450 μg, from about 200 μg to about 500 μg, from about 200 μg to about 550 μg, from about 200 μg to about 600 μg, from about 200 μg to about 650 μg, from about 200 μg to about 700 μg, from about 200 μg to about 750 μg, from about 200 μg to about 800 μg, from about 250 μg to about 300 μg, from about 250 μg to about 350 μg, from about 250 μg to about 400 μg, from about 250 μg to about 450 μg, from about 250 μg to about 500 μg, from about 250 μg to about 550 μg, from about 250 μg to about 600 μg, from about 250 μg to about 650 μg, from about 250 μg to about 700 μg, from about 250 μg to about 750 μg, from about 250 μg to about 800 μg, from about 300 μg to about 350 μg, from about 300 μg to about 400 μg, from about 300 μg to about 450 μg, from about 300 μg to about 500 μg, from about 300 μg to about 550 μg, from about 300 μg to about 600 μg, from about 300 μg to about 650 μg, from about 300 μg to about 700 μg, from about 300 μg to about 750 μg, from about 300 μg to about 800 μg, from about 350 μg to about 400 μg, from about 350 μg to about 450 μg, from about 350 μg to about 500 μg, from about 350 μg to about 550 μg, from about 350 μg to about 600 μg, from about 350 μg to about 650 μg, from about 350 μg to about 700 μg, from about 350 μg to about 750 μg, from about 350 μg to about 800 μg, from about 400 μg to about 450 μg, from about 400 μg to about 500 μg, from about 400 μg to about 550 μg, from about 400 μg to about 600 μg, from about 400 μg to about 650 μg, from about 400 μg to about 700 μg, from about 400 μg to about 750 μg, from about 400 μg to about 800 μg, from about 450 μg to about 500 μg, from about 450 μg to about 550 μg, from about 450 μg to about 600 μg, from about 450 μg to about 650 μg, from about 450 μg to about 700 μg, from about 450 μg to about 750 μg, from about 500 μg to about 550 μg, from about 500 μg to about 600 μg, from about 500 μg to about 650 μg, from about 500 μg to about 700 μg, from about 500 μg to about 750 μg, from about 500 μg to about 800 μg, from about 550 μg to about 600 μg, from about 550 μg to about 650 μg, from about 550 μg to about 700 μg, from about 550 μg to about 750 μg, from about 550 μg to about 800 μg, from about 600 μg to about 650 μg, from about 600 μg to about 700 μg, from about 600 μg to about 750 μg, from about 650 μg to about 700 μg, from about 650 μg to about 750 μg, from about 600 μg to about 800 μg, from about 700 μg to about 750 μg, from about 700 μg to about 800 μg, or from about 750 μg to about 800 μg. In some embodiments, the effective amount or effective dose can range from about 50 μg to about 200 μg. In some embodiments, the effective amount or effective dose can range from about 50 μg to about 400 μg. In some embodiments, the effective amount or effective dose can range from about 50 μg to about 700 μg.

In some embodiments, the effective amount or effective dose can be at least about 50 μg, at least about 60 μg, at least about 70 μg, at least about 80 μg, at least about 90 μg, at least about 100 μg, at least about 150 μg, at least about 200 μg, at least about 250 μg, at least about 300 μg, at least about 350 μg, at least about 400 μg, at least about 450 μg, at least about 500 μg, at least about 600 μg, at least about 650 μg, at least about 700 μg, at least about 750 μg, at least about 800 μg, at least about 850 µg, at least about 900 µg, at least about 1 mg, at least about 2 mg, at least about 3 mg, at least about 4 mg, at least about 5 mg, at least about 6 mg, at least about 7 mg, at least about 8 mg, at least about 9 mg, or at least about 10 mg. In some embodiments, the effective amount or effective dose can be at least about 150 µg. In some embodiments, the effective amount or effective dose can be at least about 300 µg. In some embodiments, the effective amount or effective dose can be at least about 600 µg.

In some embodiments, the effective amount or effective dose can be at most about 50 µg, at most about 60 µg, at most about 70 µg, at most about 80 µg, at most about 90 µg, at most about 100 µg, at most about 150 µg, at most about 200 µg, at most about 250 µg, at most about 300 µg, at most about 350 µg, at most about 400 µg, at most about 450 µg, at most about 500 µg, at most about 600 µg, at most about 650 µg, at most about 700 µg, at most about 750 µg, at most about 800 µg, at most about 850 µg, at most about 900 µg, at most about 1 mg, at most about 2 mg, at most about 3 mg, at most about 4 mg, at most about 5 mg, at most about 6 mg, at most about 7 mg, at most about 8 mg, at most about 9 mg, or at most about 10 mg. In some embodiments, the effective amount or effective dose can be at most about 150 µg. In some embodiments, the effective amount or effective dose can be at most about 300 µg. In some embodiments, the effective amount or effective dose can be at most about 600 µg.

In some embodiments, the effective amount or effective dose can be about 50 µg, about 60 µg, about 70 µg, about 80 µg, about 90 µg, about 100 µg, about 150 µg, about 200 µg, about 250 µg, about 300 µg, about 350 µg, about 400 µg, about 450 µg, about 500 µg, about 600 µg, about 650 µg, about 700 µg, about 750 µg, about 800 µg, about 850 µg, about 900 µg, about 1 mg, about 2 mg, about 3 mg, about 4 mg, about 5 mg, about 6 mg, about 7 mg, about 8 mg, about 9 mg, or about 10 mg. In some embodiments, the effective amount or effective dose can be about 150 µg. In some embodiments, the effective amount or effective dose can be about 300 µg. In some embodiments, the effective amount or effective dose can be about 600 µg.

In some examples, the ophthalmic article can release from about 1 µg to about 10 mg of active agent and/or diagnostic agent over a period of from about 1 week to about 36 months. In some additional examples, the ophthalmic article can release from about 1 µg to about 500 µg of active agent and/or diagnostic agent over a period of from about 1 week to about 12 weeks.

In some additional examples, the ophthalmic article can release from about 1 µg to about 500 µg of active agent and/or diagnostic agent over a period of from about 1 week to about 6 months. In some additional examples, the ophthalmic article can release from about 1 µg to about 500 µg of active agent and/or diagnostic agent over a period of from about 1 week to about 8 months. In some additional examples, the ophthalmic article can release from about 1 µg to about 500 µg of active agent and/or diagnostic agent over a period of from about 1 week to about 10 months. In some additional examples, the ophthalmic article can release from about 1 µg to about 500 µg of active agent and/or diagnostic agent over a period of from about 1 week to about 12 months. In some additional examples, the ophthalmic article can release from about 1 µg to about 500 µg of active agent and/or diagnostic agent over a period of from about 1 week to about 14 months. In some additional examples, the ophthalmic article can release from about 1 µg to about 500 µg of active agent and/or diagnostic agent over a period of from about 1 week to about 16 months. In some additional examples, the ophthalmic article can release from about 1 µg to about 500 µg of active agent and/or diagnostic agent over a period of from about 1 week to about 18 months. In some additional examples, the ophthalmic article can release from about 1 µg to about 500 µg of active agent and/or diagnostic agent over a period of from about 1 week to about 20 months. In some additional examples, the ophthalmic article can release from about 1 µg to about 500 µg of active agent and/or diagnostic agent over a period of from about 1 week to about 22 months. In some additional examples, the ophthalmic article can release from about 1 µg to about 500 µg of active agent and/or diagnostic agent over a period of from about 1 week to about 24 months. In some additional examples, the ophthalmic article can release from about 1 µg to about 500 µg of active agent and/or diagnostic agent over a period of from about 1 week to about 26 months. In some additional examples, the ophthalmic article can release from about 1 µg to about 500 µg of active agent and/or diagnostic agent over a period of from about 1 week to about 28 months. In some additional examples, the ophthalmic article can release from about 1 µg to about 500 µg of active agent and/or diagnostic agent over a period of from about 1 week to about 30 months. In some additional examples, the ophthalmic article can release from about 1 µg to about 500 µg of active agent and/or diagnostic agent over a period of from about 1 week to about 32 months. In some additional examples, the ophthalmic article can release from about 1 µg to about 500 µg of active agent and/or diagnostic agent over a period of from about 1 week to about 34 months. In some additional examples, the ophthalmic article can release from about 1 µg to about 500 µg of active agent and/or diagnostic agent over a period of from about 1 week to about 36 months.

In yet other examples, the ophthalmic article can release from about 100 µg to about 1000 µg of active agent and/or diagnostic agent over a period of from about 2 weeks to about 8 weeks. In still other examples, the ophthalmic article can release from about 100 µg to about 500 µg, or from about 200 µg to about 1000 µg of active agent and/or diagnostic agent over a period of from about 2 weeks to about 8 weeks. In another example, the ophthalmic article can release about 1 µg to about 300 µg over 2-3 weeks. In another example, the ophthalmic article can release 100 µg to about 600 µg over 6-8 weeks.

In some additional examples, the ophthalmic article can release from about 100 µg to about 500 µg, or from about 200 µg to about 1000 µg of active agent and/or diagnostic agent over a period of from about 1 week to about 6 months. In some additional examples, the ophthalmic article can release from about 100 µg to about 500 µg, or from about 200 µg to about 1000 µg of active agent and/or diagnostic agent over a period of from about 1 week to about 8 months. In some additional examples, the ophthalmic article can release from about 100 µg to about 500 µg, or from about 200 µg to about 1000 µg of active agent and/or diagnostic agent over a period of from about 1 week to about 10 months. In some additional examples, the ophthalmic article can release from about 100 µg to about 500 µg, or from about 200 µg to about 1000 µg of active agent and/or diagnostic agent over a period of from about 1 week to about 12 months. In some additional examples, the ophthalmic article can release from about 100 µg to about 500 µg, or from about 200 µg to about 1000 µg of active agent and/or diagnostic agent over a period of from about 1 week to about 14 months. In some additional examples, the ophthalmic article can release from about 100 µg to about 500 µg, or from about 200 µg to about 1000 µg of active agent and/or diagnostic agent over a period of from about 1 week to about 16 months. In some additional examples, the ophthalmic article can release from about 100 µg to about 500 µg, or from about 200 µg to about 1000 µg of active agent and/or diagnostic agent over a period of from about 1 week to about 18 months. In some additional examples, the ophthalmic article can release from about 100 µg to about 500 µg, or from about 200 µg to about 1000 µg of active agent and/or diagnostic agent over a period of from about 1 week to about 20 months. In some additional examples, the ophthalmic article can release from about 100 µg to about 500 µg, or from about 200 µg to about 1000 µg of active agent and/or diagnostic agent over a period of from about 1 week to about 22 months. In some additional examples, the ophthalmic article can release from about 100 µg to about 500 µg, or from about 200 µg to about 1000 µg of active agent and/or diagnostic agent over a period of from about 1 week to about 24 months. In some additional examples, the ophthalmic article can release from about 100 µg to about 500 µg, or from about 200 µg to about 1000 µg of active agent and/or diagnostic agent over a period of from about 1 week to about 26 months. In some additional examples, the ophthalmic article can release from about 100 µg to about 500 µg, or from about 200 µg to about 1000 µg of active agent and/or diagnostic agent over a period of from about 1 week to about 28 months. In some additional examples, the ophthalmic article can release from about 100 µg to about 500 µg, or from about 200 µg to about 1000 µg of active agent and/or diagnostic agent over a period of from about 1 week to about 30 months. In some additional examples, the ophthalmic article can release from about 100 µg to about 500 µg, or from about 200 µg to about 1000 µg of active agent and/or diagnostic agent over a period of from about 1 week to about 32 months. In some additional examples, the ophthalmic article can release from about 100 µg to about 500 µg, or from about 200 µg to about 1000 µg of active agent and/or diagnostic agent over a period of from about 1 week to about 34 months. In some additional examples, the ophthalmic article can release from about 100 µg to about 500 µg, or from about 200 µg to about 1000 µg of active agent and/or diagnostic agent over a period of from about 1 week to about 36 months.

In some examples, the ophthalmic article can deliver an average of from about 0.1 µg to about 1 µg per day of the active agent and/or diagnostic agent during a release period. In other examples, the ophthalmic article can deliver an average of from about 1 µg to about 10 µg per day of the active agent and/or diagnostic agent during a release period. In yet other examples, the ophthalmic article can deliver an average of from about 10 µg to about 50 µg per day of the active agent and/or diagnostic agent during a release period.

In yet other examples, the ophthalmic article can deliver an average of from about 10 µg to about 100 µg per day of the active agent and/or diagnostic agent during a release period. In yet other examples, the ophthalmic article can deliver an average of from about 10 µg to about 150 µg per day of the active agent and/or diagnostic agent during a release period. In yet other examples, the ophthalmic article can deliver an average of from about 10 µg to about 200 µg per day of the active agent and/or diagnostic agent during a release period. In yet other examples, the ophthalmic article can deliver an average of from about 10 µg to about 250 µg per day of the active agent and/or diagnostic agent during a release period. In yet other examples, the ophthalmic article can deliver an average of from about 10 µg to about 300 µg per day of the active agent and/or diagnostic agent during a release period. In yet other examples, the ophthalmic article can deliver an average of from about 10 µg to about 350 µg per day of the active agent and/or diagnostic agent during a release period. In yet other examples, the ophthalmic article can deliver an average of from about 10 µg to about 400 µg per day of the active agent and/or diagnostic agent during a release period. In yet other examples, the ophthalmic article can deliver an average of from about 10 µg to about 450 µg per day of the active agent and/or diagnostic agent during a release period. In yet other examples, the ophthalmic article can deliver an average of from about 10 µg to about 500 µg per day of the active agent and/or diagnostic agent during a release period. In yet other examples, the ophthalmic article can deliver an average of from about 10 µg to about 550 µg per day of the active agent and/or diagnostic agent during a release period. In yet other examples, the ophthalmic article can deliver an average of from about 10 µg to about 600 µg per day of the active agent and/or diagnostic agent during a release period. In yet other examples, the ophthalmic article can deliver an average of from about 10 µg to about 650 µg per day of the active agent and/or diagnostic agent during a release period. In yet other examples, the ophthalmic article can deliver an average of from about 10 µg to about 700 µg per day of the active agent and/or diagnostic agent during a release period. In yet other examples, the ophthalmic article can deliver an average of from about 10 µg to about 750 µg per day of the active agent and/or diagnostic agent during a release period. In yet other examples, the ophthalmic article can deliver an average of from about 10 µg to about 800 µg per day of the active agent and/or diagnostic agent during a release period. In yet other examples, the ophthalmic article can deliver an average of from about 10 µg to about 850 µg per day of the active agent and/or diagnostic agent during a release period. In yet other examples, the ophthalmic article can deliver an average of from about 10 µg to about 900 µg per day of the active agent and/or diagnostic agent during a release period. In yet other examples, the ophthalmic article can deliver an average of from about 10 µg to about 950 µg per day of the active agent and/or diagnostic agent during a release period. In yet other examples, the ophthalmic article can deliver an average of about 1 µg per day of the active agent and/or diagnostic agent during a release period. In yet other examples, the ophthalmic article can deliver an average of about 5 µg per day of the active agent and/or diagnostic agent during a release period. In yet other examples, the ophthalmic article can deliver an average of about 10 µg per day of the active agent and/or diagnostic agent during a release period. In yet other examples, the ophthalmic article can deliver an average of about 50 µg per day of the active agent and/or diagnostic agent during a release period. In yet other examples, the ophthalmic article can deliver an average of about 100 µg per day of the active agent and/or diagnostic agent during a release period. In yet other examples, the ophthalmic article can deliver an average of about 200 µg per day of the active agent and/or diagnostic agent during a release period. In yet other examples, the ophthalmic article can deliver an average of about 300 µg per day of the active agent and/or diagnostic agent during a release period. In yet other examples, the ophthalmic article can deliver an average of about 400 µg per day of the active agent and/or diagnostic agent during a release period. In yet other examples, the ophthalmic article can deliver an average of about 500 µg per day of the active agent and/or diagnostic agent during a release period. In yet other examples, the ophthalmic article can deliver an average of about 600 µg per day of the active agent and/or diagnostic agent during a release period. In yet other examples, the ophthalmic article can deliver an average of about 700 µg per day of the active agent and/or diagnostic agent during a release period. In yet other examples, the ophthalmic article can deliver an average of about 800 µg per day of the active agent and/or diagnostic agent during a release period. In yet other examples, the ophthalmic article can deliver an average of about 900 µg per day of the active agent and/or diagnostic agent during a release period. In yet other examples, the ophthalmic article can deliver an average of about 1,000 µg per day of the active agent and/or diagnostic agent during a release period.

In some embodiments, the active agent and/or diagnostic agent can be present in the ophthalmic article at a concentration of from about 5 weight percentage (wt %) to about 50 wt %. In some embodiments, the active agent and/or diagnostic agent can be present in the ophthalmic article at a concentration of from about 5 wt % to about 10 wt %, from about 5 wt % to about 15 wt %, from about 5 wt % to about 20 wt %, from about 5 wt % to about 25 wt %, from about 5 wt % to about 30 wt %, from about 5 wt % to about 35 wt %, from about 5 wt % to about 40 wt %, from about 5 wt % to about 45 wt %, from about 10 wt % to about 15 wt %, from about 10 wt % to about 20 wt %, from about 10 wt % to about 25 wt %, from about 10 wt % to about 30 wt %, from about 10 wt % to about 35 wt %, from about 10 wt % to about 40 wt %, from about 10 wt % to about 45 wt %, from about 10 wt % to about 50 wt %, from about 15 wt % to about 20 wt %, from about 15 wt % to about 25 wt %, from about 15 wt % to about 30 wt %, from about 15 wt % to about 35 wt %, from about 15 wt % to about 40 wt %, from about 15 wt % to about 45 wt %, from about 15 wt % to about 50 wt %, from about 20 wt % to about 25 wt %, from about 20 wt % to about 30 wt %, from about 20 wt % to about 35 wt %, from about 20 wt % to about 40 wt %, from about 20 wt % to about 45 wt %, from about 20 wt % to about 50 wt %, from about 25 wt % to about 30 wt %, from about 25 wt % to about 35 wt %, from about 25 wt % to about 40 wt %, from about 25 wt % to about 45 wt %, from about 25 wt % to about 50 wt %, from about 30 wt % to about 35 wt %, from about 30 wt % to about 40 wt %, from about 30 wt % to about 45 wt %, from about 30 wt % to about 50 wt %, from about 35 wt % to about 40 wt %, from about 35 wt % to about 45 wt %, from about 35 wt % to about 50 wt %, from about 40 wt % to about 45 wt %, from about 40 wt % to about 50 wt %, or from about 45 wt % to about 50 wt %. In some embodiments, the active agent and/or diagnostic agent can be present in the ophthalmic article at a concentration of from about 5 wt % to about 25 wt %. In some embodiments, the active agent and/or diagnostic agent can be present in the ophthalmic article at a concentration of from about 5 wt % to about 15 wt %. %. In some embodiments, the active agent and/or diagnostic agent can be present in the ophthalmic article at a concentration of at least about 5 wt %. In some embodiments, the active agent and/or diagnostic agent can be present in the ophthalmic article at a concentration of at least about 10 wt %. In some embodiments, the active agent and/or diagnostic agent can be present in the ophthalmic article at a concentration of at least about 20 wt %.

In some embodiments, the active agent and/or diagnostic agent can be present in the ophthalmic article at a concentration of at least about 5 wt %, at least about 10 wt %, at least about 15 wt %, at least about 20 wt %, at least about 25 wt %, at least about 30 wt %, at least about 35 wt %, at least about 40 wt %, at least about 45 wt %, at least about, or at least about 50 wt %.

In some embodiments, the active agent and/or diagnostic agent can be present in the ophthalmic article at a concentration of at most about 5 wt %, at most about 10 wt %, at most about 15 wt %, at most about 20 wt %, at most about 25 wt %, at most about 30 wt %, at most about 35 wt %, at most about 40 wt %, at most about 45 wt %, at most about, or at most about 50 wt %. In some embodiments, the active agent and/or diagnostic agent can be present in the ophthalmic article at a concentration of at most about 5 wt %. In some embodiments, the active agent and/or diagnostic agent can be present in the ophthalmic article at a concentration of at most about 10 wt %. In some embodiments, the active agent and/or diagnostic agent can be present in the ophthalmic article at a concentration of at most about 20 wt %.

In some embodiments, the active agent and/or diagnostic agent can be present in the ophthalmic article at a concentration of about 5 wt %, about 10 wt %, about 15 wt %, about 20 wt %, about 25 wt %, about 30 wt %, about 35 wt %, about 40 wt %, about 45 wt %, about, or about 50 wt %.

In some embodiments, the molecular weight, molecular mass, or molecular size of the active agent and/or diagnostic agent can affect delivery of the active agent and/or diagnostic agent to the eye (e.g., posterior segment of the eye). Thus, in some examples, the active agent and/or diagnostic agent can have a molecular weight or molecular mass of 250,000 daltons (Da) or less. In yet additional examples, the active agent and/or diagnostic agent can have a molecular weight or molecular mass of 200,000 Da or less. In yet additional examples, the active agent and/or diagnostic agent can have a molecular weight or molecular mass of 190,000 Da or less. In yet additional examples, the active agent and/or diagnostic agent can have a molecular weight or molecular mass of 180,000 Da or less. In yet other examples, the active agent and/or diagnostic agent can have a molecular weight or molecular mass of 170,000 Da or less. In yet other examples, the active agent and/or diagnostic agent can have a molecular weight or molecular mass of 160,000 Da or less. In yet other examples, the active agent and/or diagnostic agent can have a molecular weight or molecular mass of 150,000 Da or less. In yet other examples, the active agent and/or diagnostic agent can have a molecular weight or molecular mass of 140,000 Da or less. In yet other examples, the active agent and/or diagnostic agent can have a molecular weight or molecular mass of 130,000 Da or less. In yet other examples, the active agent and/or diagnostic agent can have a molecular weight or molecular mass of 120,000 Da or less. In yet other examples, the active agent and/or diagnostic agent can have a molecular weight or molecular mass of 110,000 Da or less. In yet other examples, the active agent and/or diagnostic agent can have a molecular weight or molecular mass of 100,000 Da or less. In yet other examples, the active agent and/or diagnostic agent can have a molecular weight or molecular mass of 90,000 Da or less. In yet other examples, the active agent and/or diagnostic agent can have a molecular weight or molecular mass of 80,000 Da or less. In yet other examples, the active agent and/or diagnostic agent can have a molecular weight or molecular mass of 70,000 Da or less. In yet other examples, the active agent and/or diagnostic agent can have a molecular weight or molecular mass of 60,000 Da or less. In yet other examples, the active agent and/or diagnostic agent can have a molecular weight or molecular mass of 50,000 Da or less. In yet other examples, the active agent and/or diagnostic agent can have a molecular weight or molecular mass of 40,000 Da or less. In yet other examples, the active agent and/or diagnostic agent can have a molecular weight or molecular mass of 30,000 Da or less. In yet other examples, the active agent and/or diagnostic agent can have a molecular weight or molecular mass of 20,000 Da or less. In yet other examples, the active agent and/or diagnostic agent can have a molecular weight or molecular mass of 10,000 Da or less. In yet other examples, the active agent and/or diagnostic agent can have a molecular weight or molecular mass of 5,000 Da or less. In yet other examples, the active agent and/or diagnostic agent can have a molecular weight or molecular mass of 1,000 Da or less. In yet additional examples, the active agent and/or diagnostic agent can have a molecular weight or molecular mass of 500 Da or less. In yet other examples, the active agent and/or diagnostic agent can have a molecular weight or molecular mass of 400 Da or less. In yet other examples, the active agent and/or diagnostic agent can have a molecular weight or molecular mass of 300 Da or less. In yet other examples, the active agent and/or diagnostic agent can have a molecular weight or molecular mass of 200 Da or less. In yet other examples, the active agent and/or diagnostic agent can have a molecular weight or molecular mass of 100 Da or less.

In some embodiments, one, two or more ophthalmic articles can be introduced or implanted per eye to achieve an effective amount (e.g., therapeutically effective amount) and/or an effective dose (e.g., therapeutically effective dose). In some embodiments, at least about 1, 2, 3, 4, 5, 6, 7, 8, 9, or 10, or more ophthalmic articles can be introduced or implanted per eye. In some embodiments, at most about 10, 9, 8, 7, 6, 5, 4, 3, 2, or 1 ophthalmic articles can be introduced or implanted per eye. In some embodiments, at least about 1 ophthalmic articles can be introduced or implanted per eye. In some embodiments, at least about 2 ophthalmic articles can be introduced or implanted per eye. In some embodiments, at least about 3 ophthalmic articles can be introduced or implanted per eye. In some embodiments, at least about 4 ophthalmic articles can be introduced or implanted per eye. In some embodiments, at least about 5 ophthalmic articles can be introduced or implanted per eye.

In some embodiments, at most about 1 ophthalmic articles can be introduced or implanted per eye. In some embodiments, at most about 2 ophthalmic articles can be introduced or implanted per eye. In some embodiments, at most about 3 ophthalmic articles can be introduced or implanted per eye. In some embodiments, at most about 4 ophthalmic articles can be introduced or implanted per eye. In some embodiments, at most about 5 ophthalmic articles can be introduced or implanted per eye.

In some embodiments, about 1 ophthalmic articles can be introduced or implanted per eye. In some embodiments, about 2 ophthalmic articles can be introduced or implanted per eye. In some embodiments, about 3 ophthalmic articles can be introduced or implanted per eye. In some embodiments, about 4 ophthalmic articles can be introduced or implanted per eye. In some embodiments, about 5 ophthalmic articles can be introduced or implanted per eye In any of the various aspects, the one or more ophthalmic articles described herein are engineered in size and/or shape, to provide maximal approximation of the ophthalmic article to a subject's eye. The shape and/or size of ophthalmic articles (e.g., homogenous active agent and/or diagnostic agent delivery devices) for delivery or administration of the active agent and/or diagnostic agent to the eye can play an important role in the amount and rate of delivery of the active agent and/or diagnostic agent. For example, the shape and/or size of the ophthalmic articles (e.g., homogenous active agent and/or diagnostic agent delivery devices) can be designed to accommodate faster and/or slower release rates; and greater or smaller amounts of active agents and/or diagnostic agents released by the ophthalmic articles (e.g., homogenous active agent and/or diagnostic agent delivery devices) while maintaining suitable compositional parameters for a desired release profile.

In some embodiments, the shape of the ophthalmic article can be a prism with an open internal structure (e.g., a hole in the center) In some embodiments, the prism may be an extruded prism. The prism may be a round prism, a rectangular prism, a square prism, quadrilateral prism, pentagon prism, hexagon prism, heptagon prism, octagon prism, nonagon prism, decagon prism, undecagon prism, dodecagon prism, or a prism of another shape. In some embodiments, the prism may be a polyhedron. In some embodiments, the ophthalmic article may be an annulus, an extruded annulus, a torus, an extruded square, extruded quadrilateral, an extruded rectangle, extruded pentagon, an extruded hexagon, extruded heptagon, extruded octagon, extruded nonagon, extruded decagon, extruded undecagon, extruded dodecagon, an extruded polygon with an open internal structure (e.g., a hole in the center). In some embodiments, the polygon may comprise 3, 4, 5, 6, 7, 8, 9, or 10 sides.

In some embodiments, the shape of ophthalmic article may be disc, cylinder, nail-like-plug, rod, tablet, sphere, truncated cone with a bended axis, polymer wire rolled around a portion of an ocular device, and polymer sheet wrapped around a portion of an ocular device.

In some embodiments, the ophthalmic article may comprise an internal structure for associating with a portion of an ocular device. The internal structure may be a hole. For example, an ophthalmic article of any of the shapes disclosed herein may comprise a hole in the center for associating with an intraocular lens. In some embodiments, a shape of the ophthalmic article and/or internal structure may be the same as a shape of a portion of the ocular device (e.g., intraocular device) to which the ophthalmic article is associated. For example, the shape of the ophthalmic article and/or internal structure may be the same as a shape of a haptic of an intraocular lens. In some embodiments, a shape of the ophthalmic article and/or internal structure may be different from a shape of a portion of the ocular device (e.g., intraocular device) to which the ophthalmic article is associated. For example, the shape of the ophthalmic article and/or internal structure may be different than a shape of a haptic of an intraocular lens.

In some embodiments, the shape of the ophthalmic article can be manipulated to prevent obstruction of a line of sight in the eye. For example, in some cases, the ophthalmic article can have a crescent shape, an ellipsoid shape (e.g. a disc shape, a football shape, an egg shape, or the like), a rod shape, or the like, to allow the size to increase to a greater extent along one axis relative to a perpendicular axis so as to not obstruct a line of sight in the eye.

In some embodiments, where a polymeric material (e.g., biodegradable polymer matrix) is employed in the ophthalmic articles (e.g., homogenous active agent and/or diagnostic agent delivery devices), the polymeric material (e.g., biodegradable polymer matrix) can accommodate various amounts of active agents and/or diagnostic agents while maintaining a desirable biodegradation profile. The amount of active agents and/or diagnostic agents that a biodegradable matrix can release (e.g., controllably release) within a particular biodegradation profile may depend on both the composition of the polymeric matrix and the one or more active agents and/or diagnostic agents.

In some embodiments, a small or a large amount of an active agent and/or diagnostic agent can be required to provide an effective amount (e.g., therapeutically effective amount) to a subject to treat or diagnose a particular condition. The overall size of the ophthalmic article can be increased to accommodate a large amount of active agent and/or diagnostic agent. Conversely, as another example, the size of the ophthalmic article can be reduced where lesser amounts of the active agent and/or diagnostic agent are needed.

In some embodiments, the ophthalmic article may comprise an internal structure (e.g., a hole) for associating (e.g., attaching) around a portion of an ocular device (e.g., intraocular device). For example, the ophthalmic article may comprise a hole for associating around a geometric shape of a haptic of an intraocular lens. The hole may be round and the haptic can be circular or rectangular.

In some embodiments, a dimension or parameter of the internal structure (e.g., hole) may be less than, equal to, or greater than a corresponding dimension or parameter of a portion of the ocular device (e.g., intraocular device) to which the ophthalmic article associates. In some embodiments, a perimeter of the internal structure (e.g., hole) of the ophthalmic article may be less than or equal to a perimeter of a portion of the ocular device (e.g., intraocular device) to which the ophthalmic article associates. In some cases, a perimeter of the hole of the ophthalmic article may be less than or equal to a perimeter of the haptic on the intraocular lens to which the ophthalmic article associates. For example, when cross-sectional dimensions of a haptic of an IOL (e.g., Aurovue) is about 1.00 mm×0.32 mm wide, the perimeter of the hole of the ophthalmic article can be less than or equal to 2.64 mm. In some embodiments, the perimeter of the hole of the ophthalmic article can be about 1.57 mm. In another example, when cross-sectional dimensions of a haptic of an IOL (e.g., by Johnson & Johnson Surgical Vision foldable acrylic IOL Tecnis 1-piece) can be a rectangle about 0.72× 0.46 mm wide, the perimeter of the hole of the ophthalmic article can be less than or equal to 2.36 mm.

In some embodiments, the perimeter of the hole of the ophthalmic article may be about 0.5 mm to about 6 mm. In some embodiments, the perimeter of the hole of the ophthalmic article may be about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about 0.5 mm to about 5.5 mm, about 0.5 mm to about 6 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1 mm to about 4.5 mm, about 1 mm to about 5 mm, about 1 mm to about 5.5 mm, about 1 mm to about 6 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 1.5 mm to about 4.5 mm, about 1.5 mm to about 5 mm, about 1.5 mm to about 5.5 mm, about 1.5 mm to about 6 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 5.5 mm, about 2 mm to about 6 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 5.5 mm, about 2.5 mm to about 6 mm, about 3 mm to about 3.5 mm, about 3 mm to about 4 mm, about 3 mm to about 4.5 mm, about 3 mm to about 5 mm, about 3 mm to about 5.5 mm, about 3 mm to about 6 mm, about 3.5 mm to about 4 mm, about 3.5 mm to about 4.5 mm, about 3.5 mm to about 5 mm, about 3.5 mm to about 5.5 mm, about 3.5 mm to about 6 mm, about 4 mm to about 4.5 mm, about 4 mm to about 5 mm, about 4 mm to about 5.5 mm, about 4 mm to about 6 mm, about 4.5 mm to about 5 mm, about 4.5 mm to about 5.5 mm, about 4.5 mm to about 6 mm, about 5 mm to about 5.5 mm, about 5 mm to about 6 mm, or about 5.5 mm to about 6 mm.

In some embodiments, the perimeter of the hole of the ophthalmic article may be at least about 0.5 mm, at least about 1 mm, at least about 1.2 mm, at least about 1.3 mm, at least about 1.4 mm, at least about 1.5 mm, at least about 1.6 mm, at least about 1.7 mm, at least about 1.8 mm, at least about 1.9 mm, at least about 2 mm, at least about 2.1 mm, at least about 2.2 mm, at least about 2.3 mm, at least about 2.4 mm, at least about 2.5 mm, at least about 2.6 mm, at least about 2.7 mm, at least about 2.8 mm, at least about 2.9 mm, at least about 3 mm, at least about 3.2 mm, at least about 3.4 mm, at least about 3.6 mm, at least about 3.8 mm, at least about 4 mm, at least about 4.2 mm, at least about 4.4 mm, at least about 4.6 mm, at least about 4.8 mm, at least about 5 mm, at least about 5.2 mm, at least about 5.4 mm, at least about 5.6 mm, at least about 5.8 mm, at least about 6 mm, at least about 6.2 mm, at least about 6.4 mm, at least about 6.6 mm, at least about 6.8 mm, or at least about 7 mm.

In some embodiments, the perimeter of the hole of the ophthalmic article may be at most about 0.5 mm, at most about 1 mm, at most about 1.2 mm, at most about 1.3 mm, at most about 1.4 mm, at most about 1.5 mm, at most about 1.6 mm, at most about 1.7 mm, at most about 1.8 mm, at most about 1.9 mm, at most about 2 mm, at most about 2.1 mm, at most about 2.2 mm, at most about 2.3 mm, at most about 2.4 mm, at most about 2.5 mm, at most about 2.6 mm, at most about 2.7 mm, at most about 2.8 mm, at most about 2.9 mm, at most about 3 mm, at most about 3.2 mm, at most about 3.4 mm, at most about 3.6 mm, at most about 3.8 mm, at most about 4 mm, at most about 4.2 mm, at most about 4.4 mm, at most about 4.6 mm, at most about 4.8 mm, at most about 5 mm, at most about 5.2 mm, at most about 5.4 mm, at most about 5.6 mm, at most about 5.8 mm, at most about 6 mm, at most about 6.2 mm, at most about 6.4 mm, at most about 6.6 mm, at most about 6.8 mm, or at most about 7 mm.

In some embodiments, a widest dimension of the internal structure of the ophthalmic device may be less than or equal to a widest dimension of a portion of the ocular device (e.g., intraocular device) to which the ophthalmic article associates. For example, a widest dimension of the internal structure of the ophthalmic device may be less than or equal to a widest dimension of a haptic of the intraocular lens to which the ophthalmic article associates. The widest dimension of the haptic of a 1-piece foldable acrylic IOL may be around 0.7 mm to 1.0 mm, and the widest dimension of the haptic of a 3-piece foldable IOL may be around 0.1 mm to 0.2 mm. In some embodiments, a diameter of the internal structure of the ophthalmic device may be less than or equal to a diameter of a portion of the ocular device (e.g., intraocular device) to which the ophthalmic article associates. For example, a diameter of the internal structure of the ophthalmic device may be less than, equal to, or greater than a diameter of a haptic of the intraocular lens to which the ophthalmic article associates.

In some embodiments, the widest dimension of the haptic of any of the IOL herein may be about 0.01 mm to about 10 mm. In some embodiments, the widest dimension of the haptic of any of the IOL herein may be about 0.01 mm to about 0.05 mm, about 0.01 mm to about 0.1 mm, about 0.01 mm to about 0.5 mm, about 0.01 mm to about 1 mm, about 0.01 mm to about 1.5 mm, about 0.01 mm to about 2 mm, about 0.01 mm to about 3 mm, about 0.01 mm to about 4 mm, about 0.01 mm to about 5 mm, about 0.01 mm to about 10 mm, about 0.05 mm to about 0.1 mm, about 0.05 mm to about 0.5 mm, about 0.05 mm to about 1 mm, about 0.05 mm to about 1.5 mm, about 0.05 mm to about 2 mm, about 0.05 mm to about 3 mm, about 0.05 mm to about 4 mm, about 0.05 mm to about 5 mm, about 0.05 mm to about 10 mm, about 0.1 mm to about 0.5 mm, about 0.1 mm to about 1 mm, about 0.1 mm to about 1.5 mm, about 0.1 mm to about 2 mm, about 0.1 mm to about 3 mm, about 0.1 mm to about 4 mm, about 0.1 mm to about 5 mm, about 0.1 mm to about 10 mm, about 0.5 mm to about 1 mm, about 0.5 mm to about 1.5 mm, about 0.5 mm to about 2 mm, about 0.5 mm to about 3 mm, about 0.5 mm to about 4 mm, about 0.5 mm to about 5 mm, about 0.5 mm to about 10 mm, about 1 mm to about 1.5 mm, about 1 mm to about 2 mm, about 1 mm to about 3 mm, about 1 mm to about 4 mm, about 1 mm to about 5 mm, about 1 mm to about 10 mm, about 1.5 mm to about 2 mm, about 1.5 mm to about 3 mm, about 1.5 mm to about 4 mm, about 1.5 mm to about 5 mm, about 1.5 mm to about 10 mm, about 2 mm to about 3 mm, about 2 mm to about 4 mm, about 2 mm to about 5 mm, about 2 mm to about 10 mm, about 3 mm to about 4 mm, about 3 mm to about 5 mm, about 3 mm to about 10 mm, about 4 mm to about 5 mm, about 4 mm to about 10 mm, or about 5 mm to about 10 mm.

In some embodiments, the widest dimension of the haptic of any of the IOL herein may be at least about 0.01 mm, at least about 0.05 mm, at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1 mm, at least about 1.1 mm, at least about 1.2 mm, at least about 1.3 mm, at least about 1.4 mm, at least about 1.5 mm, at least about 1.6 mm, at least about 1.7 mm, at least about 1.8 mm, at least about 1.9 mm, at least about 2 mm, at least about 3 mm, at least about 4 mm, at least about 5 mm, at least about 6 mm, at least about 7 mm, at least about 8 mm, at least about 9 mm, or at least about 10. In some embodiments, the widest dimension of the haptic of any of the IOL herein may be at least about 0.5 mm. In some embodiments, the widest dimension of the haptic of any of the IOL herein may be at least about 0.07 mm. In some embodiments, the widest dimension of the haptic of any of the IOL herein may be at least about 1 mm.

In some embodiments, the widest dimension of the haptic of any of the IOL herein may be at most about 0.01 mm, at most about 0.05 mm, at most about 0.1 mm, at most about 0.2 mm, at most about 0.3 mm, at most about 0.4 mm, at most about 0.5 mm, at most about 0.6 mm, at most about 0.7 mm, at most about 0.8 mm, at most about 0.9 mm, at most about 1 mm, at most about 1.1 mm, at most about 1.2 mm, at most about 1.3 mm, at most about 1.4 mm, at most about 1.5 mm, at most about 1.6 mm, at most about 1.7 mm, at most about 1.8 mm, at most about 1.9 mm, at most about 2 mm, at most about 3 mm, at most about 4 mm, at most about 5 mm, at most about 6 mm, at most about 7 mm, at most about 8 mm, at most about 9 mm, or at most about 10. In some embodiments, the widest dimension of the haptic of any of the IOL herein may be at most about 1.5 mm. In some embodiments, the widest dimension of the haptic of any of the IOL herein may be at most about 1 mm. In some embodiments, the widest dimension of the haptic of any of the IOL herein may be at most about 0.5 mm.

In some embodiments, a diameter of the internal structure of the ophthalmic device may be about 0.1 mm to 2.3 mm. In some embodiments, a diameter of the internal structure of the ophthalmic device may be about 0.1 mm to about 0.3 mm, about 0.1 mm to about 0.5 mm, about 0.1 mm to about 0.7 mm, about 0.1 mm to about 0.9 mm, about 0.1 mm to about 1.1 mm, about 0.1 mm to about 1.3 mm, about 0.1 mm to about 1.5 mm, about 0.1 mm to about 1.7 mm, about 0.1 mm to about 1.9 mm, about 0.1 mm to about 2.1 mm, about 0.1 mm to about 2.3 mm, about 0.3 mm to about 0.5 mm, about 0.3 mm to about 0.7 mm, about 0.3 mm to about 0.9 mm, about 0.3 mm to about 1.1 mm, about 0.3 mm to about 1.3 mm, about 0.3 mm to about 1.5 mm, about 0.3 mm to about 1.7 mm, about 0.3 mm to about 1.9 mm, about 0.3 mm to about 2.1 mm, about 0.3 mm to about 2.3 mm, about 0.5 mm to about 0.7 mm, about 0.5 mm to about 0.9 mm, about 0.5 mm to about 1.1 mm, about 0.5 mm to about 1.3 mm, about 0.5 mm to about 1.5 mm, about 0.5 mm to about 1.7 mm, about 0.5 mm to about 1.9 mm, about 0.5 mm to about 2.1 mm, about 0.5 mm to about 2.3 mm, about 0.7 mm to about 0.9 mm, about 0.7 mm to about 1.1 mm, about 0.7 mm to about 1.3 mm, about 0.7 mm to about 1.5 mm, about 0.7 mm to about 1.7 mm, about 0.7 mm to about 1.9 mm, about 0.7 mm to about 2.1 mm, about 0.7 mm to about 2.3 mm, about 0.9 mm to about 1.1 mm, about 0.9 mm to about 1.3 mm, about 0.9 mm to about 1.5 mm, about 0.9 mm to about 1.7 mm, about 0.9 mm to about 1.9 mm, about 0.9 mm to about 2.1 mm, about 0.9 mm to about 2.3 mm, about 1.1 mm to about 1.3 mm, about 1.1 mm to about 1.5 mm, about 1.1 mm to about 1.7 mm, about 1.1 mm to about 1.9 mm, about 1.1 mm to about 2.1 mm, about 1.1 mm to about 2.3 mm, about 1.3 mm to about 1.5 mm, about 1.3 mm to about 1.7 mm, about 1.3 mm to about 1.9 mm, about 1.3 mm to about 2.1 mm, about 1.3 mm to about 2.3 mm, about 1.5 mm to about 1.7 mm, about 1.5 mm to about 1.9 mm, about 1.5 mm to about 2.1 mm, about 1.5 mm to about 2.3 mm, about 1.7 mm to about 1.9 mm, about 1.7 mm to about 2.1 mm, about 1.7 mm to about 2.3 mm, about 1.9 mm to about 2.1 mm, about 1.9 mm to about 2.3 mm, or about 2.1 mm to about 2.3 mm. In some embodiments, a diameter of the internal structure of the ophthalmic device may be about 0.1 mm to about 1 mm. In some embodiments, a diameter of the internal structure of the ophthalmic device may be about 0.1 mm to about 0.7 mm.

In some embodiments, a diameter of the internal structure of the ophthalmic device may be at least about 0.1 mm, at least about 0.2 mm, at least about 0.25 mm, at least about 0.3 mm, at least about 0.35 mm, at least about 0.4 mm, at least about 0.45 mm, at least about 0.5 mm, at least about 0.55 mm, at least about 0.6 mm, at least about 0.65 mm, at least about 0.7 mm, at least about 0.75 mm, at least about 0.8 mm, at least about 0.85 mm, at least about 0.9 mm, at least about 0.95 mm, at least about 1 mm, at least about 1.05 mm, at least about 1.1 mm, at least about 1.15 mm, at least about 1.2 mm, at least about 1.25 mm, at least about 1.3 mm, at least about 1.35 mm, at least about 1.4 mm, at least about 1.45 mm, at least about 1.5 mm, at least about 1.55 mm, at least about 1.6 mm, at least about 1.65 mm, at least about 1.7 mm, at least about 1.75 mm, at least about 1.8 mm, at least about 1.85 mm, at least about 1.9 mm, at least about 1.95 mm, at least about 2 mm, at least about 2.05 mm, at least about 2.1 mm, at least about 2.15 mm, at least about 2.2 mm, at least about 2.25 mm, or at least about 2.3. In some embodiments, a diameter of the internal structure of the ophthalmic device may be at least about 0.1 mm. In some embodiments, a diameter of the internal structure of the ophthalmic device may be at least about 0.5 mm.

In some embodiments, a diameter of the internal structure of the ophthalmic device may be at most about 0.1 mm, at most about 0.2 mm, at most about 0.25 mm, at most about 0.3 mm, at most about 0.35 mm, at most about 0.4 mm, at most about 0.45 mm, at most about 0.5 mm, at most about 0.55 mm, at most about 0.6 mm, at most about 0.65 mm, at most about 0.7 mm, at most about 0.75 mm, at most about 0.8 mm, at most about 0.85 mm, at most about 0.9 mm, at most about 0.95 mm, at most about 1 mm, at most about 1.05 mm, at most about 1.1 mm, at most about 1.15 mm, at most about 1.2 mm, at most about 1.25 mm, at most about 1.3 mm, at most about 1.35 mm, at most about 1.4 mm, at most about 1.45 mm, at most about 1.5 mm, at most about 1.55 mm, at most about 1.6 mm, at most about 1.65 mm, at most about 1.7 mm, at most about 1.75 mm, at most about 1.8 mm, at most about 1.85 mm, at most about 1.9 mm, at most about 1.95 mm, at most about 2 mm, at most about 2.05 mm, at most about 2.1 mm, at most about 2.15 mm, at most about 2.2 mm, at most about 2.25 mm, or at most about 2.3. In some embodiments, a diameter of the internal structure of the ophthalmic device may be at most about 0.5 mm. In some embodiments, a diameter of the internal structure of the ophthalmic device may be at most about 1 mm. In some embodiments, a diameter of the internal structure of the ophthalmic device may be at most about 1.5 mm.

In some embodiments, a diameter of the internal structure of the ophthalmic device may be about 0.1 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1 mm, about 1.05 mm, about 1.1 mm, about 1.15 mm, about 1.2 mm, about 1.25 mm, about 1.3 mm, about 1.35 mm, about 1.4 mm, about 1.45 mm, about 1.5 mm, about 1.55 mm, about 1.6 mm, about 1.65 mm, about 1.7 mm, about 1.75 mm, about 1.8 mm, about 1.85 mm, about 1.9 mm, about 1.95 mm, about 2 mm, about 2.05 mm, about 2.1 mm, about 2.15 mm, about 2.2 mm, about 2.25 mm, or about 2.3. In some embodiments, a diameter of the internal structure of the ophthalmic device may be about 0.5 mm.

Figure 1A:
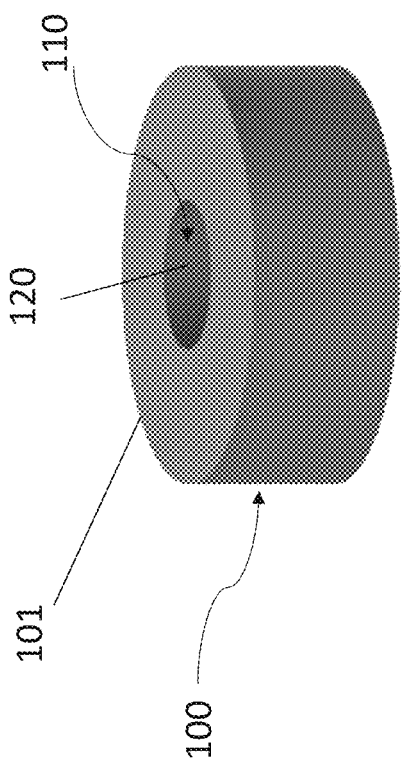
FIG. 1A illustrates a perspective view of an ophthalmic article, in accordance with many embodiments.

FIG. 1A and FIG. 1B schematically illustrate examples of various shaped ophthalmic articles (e.g., active agent and/or diagnostic agent delivery devices) 100. The ophthalmic article 100 may comprise an internal structure (e.g., a hole) 110. In some figures, the ophthalmic article 100 may be an annulus (e.g., extruded annulus) shaped ophthalmic article 101 and/or a toroid shaped ophthalmic article 106. FIG. 1A illustrates a perspective view of an annulus (e.g., extruded annulus) shaped ophthalmic article 101. FIG. 1B illustrates a perspective view of a toroid shaped ophthalmic article 106. In some figures, the internal structure (e.g., a hole) 110 may be a circular hole 120 of the annulus (e.g., extruded annulus) shaped ophthalmic article 101. In some figures, the internal structure (e.g., a hole) 110 may be a circular hole 130 of the toroid shaped ophthalmic article 106.

FIG. 2A, FIG. 2B, FIG. 2C, FIG. 2D, FIG. 2E, FIG. 2F, FIG. 2G, and FIG. 2H schematically illustrate other views (e.g., plan view, cross-sectional view) of examples of various shaped ophthalmic articles (e.g., active agent and/or diagnostic agent delivery devices) 100. The ophthalmic article 100 may comprise an internal structure (e.g., hole) 110 with an inner diameter or side edge 240. The ophthalmic article 100 may also comprise an outer diameter or outer edge 230, cross-sectional thickness 250, and/or a wall thickness 260.

FIG. 2A illustrates a plan view of an annulus (e.g., extruded annulus) shaped ophthalmic article 101. FIG. 2B illustrates a cross-sectional view of the annulus shaped ophthalmic article 101. The annulus shaped ophthalmic article 101 comprises an internal structure 110 which is a circular hole 120. The internal structure 110 comprises an inner diameter or side edge 240. The inner diameter or side edge 240 may be inner diameter 204. The annulus shaped ophthalmic article 101 may also comprise an outer diameter or outer edge 230, a cross-sectional thickness 250, and/or a wall thickness 260. The outer diameter or outer edge 230 may be outer diameter 203. The cross-sectional thickness 250 may be cross-sectional thickness 205. The wall thickness 260 may be wall thickness 216.

FIG. 2C illustrates a plan view of a toroid shaped ophthalmic article 106. FIG. 2D illustrates a cross-sectional view of the toroid shaped ophthalmic article 106. The toroid shaped ophthalmic article 106 comprises an internal structure 110 which is a circular hole 130. The internal structure 110 comprises an inner diameter or side edge 240. The inner diameter or side edge 240 may be inner diameter 209. The toroid shaped ophthalmic article 106 may also comprise an outer diameter or outer edge 230, a cross-sectional thickness 250, and/or a wall thickness 260. The outer diameter or outer edge 230 may be outer diameter 208. The cross-sectional thickness 250 may be cross-sectional thickness 210. The wall thickness 260 may be wall thickness 217.

In some figures, the ophthalmic article 100 may be a square shaped (e.g., extruded square shaped) ophthalmic article 211. FIG. 2E illustrates a plan view of a square shaped (e.g., extruded square shaped) ophthalmic article 211. FIG. 2F illustrates a cross-sectional view of a square shaped (e.g., extruded square shaped) ophthalmic article 211. The square shaped (e.g., extruded square shaped) ophthalmic article 211 may comprise an internal structure (e.g., a hole) 110 that can be a square hole 255. The internal structure 110 comprises an inner diameter or side edge 240. The inner diameter or side edge 240 may be side edge 214. The square shaped ophthalmic article 211 may also comprise an outer diameter or outer edge 230, cross-sectional thickness 250, and/or a wall thickness 260. The outer diameter or outer edge 230 may be outer edge 213. The cross-sectional thickness 250 may be cross-sectional thickness 215. The wall thickness 260 may be wall thickness 218.

In some figures, the ophthalmic article 100 may be an octagon shaped ophthalmic article 270. FIG. 2G illustrates a plan view of an octagon shaped ophthalmic article 270. FIG. 2H illustrates a cross-sectional view of an octagon shaped ophthalmic article 270. The octagon shaped ophthalmic article 270 may comprise an internal structure (e.g., a hole) 110 that can be an octagon shaped hole 272. The internal structure 110 comprises an inner diameter or side edge 240. The inner diameter or side edge 240 may be an inner diameter 274. The octagon shaped ophthalmic article 270 may also comprise an outer diameter or outer edge 230, cross-sectional thickness 250, and/or a wall thickness 260. The outer diameter or outer edge 230 may be outer edge 276. The cross-sectional thickness 250 may be cross-sectional thickness 278. The wall thickness 260 may be wall thickness 280.

In some embodiments, the inner diameter 240 (e.g., inner diameter 204, inner diameter 209, inner diameter 274) or an inner side length 240 (e.g., inner diameter 214) may be from about 0.05 millimeters (mm) to 6 mm.

In some embodiments, the inner diameter 240 or an inner side length 240 may be from about 0.05 mm to 6 mm. In some embodiments, the inner diameter 240 or an inner side length 240 may be about 0.05 mm to about 0.5 mm, about 0.05 mm to about 0.1 mm, about 0.05 mm to about 1.5 mm, about 0.05 mm to about 2 mm, about 0.05 mm to about 2.5 mm, about 0.05 mm to about 3 mm, about 0.05 mm to about 3.5 mm, about 0.05 mm to about 4 mm, about 0.05 mm to about 4.5 mm, about 0.05 mm to about 5 mm, about 0.05 mm to about 5.5 mm, about 0.05 mm to about 6 mm, about 0.5 mm to about 0.1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about 0.5 mm to about 5.5 mm, about 0.5 mm to about 6 mm, about 0.1 mm to about 1.5 mm, about 0.1 mm to about 2 mm, about 0.1 mm to about 2.5 mm, about 0.1 mm to about 3 mm, about 0.1 mm to about 3.5 mm, about 0.1 mm to about 4 mm, about 0.1 mm to about 4.5 mm, about 0.1 mm to about 5 mm, about 0.1 mm to about 5.5 mm, about 1 mm to about 6 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 1.5 mm to about 4.5 mm, about 1.5 mm to about 5 mm, about 1.5 mm to about 5.5 mm, about 1.5 mm to about 6 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 5.5 mm, about 2 mm to about 6 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 5.5 mm, about 2.5 mm to about 6 mm, about 3 mm to about 3.5 mm, about 3 mm to about 4 mm, about 3 mm to about 4.5 mm, about 3 mm to about 5 mm, about 3 mm to about 5.5 mm, about 3 mm to about 6 mm, about 3.5 mm to about 4 mm, about 3.5 mm to about 4.5 mm, about 3.5 mm to about 5 mm, about 3.5 mm to about 5.5 mm, about 3.5 mm to about 6 mm, about 4 mm to about 4.5 mm, about 4 mm to about 5 mm, about 4 mm to about 5.5 mm, about 4.5 mm to about 5 mm, about 4.5 mm to about 5.5 mm, about 4.5 mm to about 6 mm, about 5 mm to about 5.5 mm, about 5 mm to about 6 mm, or about 5.5 mm to about 6 mm.

In some embodiments, the inner diameter 240 or an inner side length 240 of the ophthalmic device may be at least about 0.05 mm, at least about 0.1 mm, at least about 0.15 mm, at least about 0.2 mm, at least about 0.25 mm, at least about 0.3 mm, at least about 0.35 mm, at least about 0.4 mm, at least about 0.45 mm, at least about 0.5 mm, at least about 0.55 mm, at least about 0.6 mm, at least about 0.65 mm, at least about 0.7 mm, at least about 0.75 mm, at least about 0.8 mm, at least about 0.85 mm, at least about 0.9 mm, at least about 0.95 mm, at least about 1 mm, at least about 1.05 mm, at least about 1.1 mm, at least about 1.15 mm, at least about 1.2 mm, at least about 1.25 mm, at least about 1.3 mm, at least about 1.35 mm, at least about 1.4 mm, at least about 1.45 mm, at least about 1.5 mm, at least about 1.55 mm, at least about 1.6 mm, at least about 1.65 mm, at least about 1.7 mm, at least about 1.75 mm, at least about 1.8 mm, at least about 1.85 mm, at least about 1.9 mm, at least about 1.95 mm, at least about 2 mm, at least about 2.05 mm, at least about 2.1 mm, at least about 2.15 mm, at least about 2.2 mm, at least about 2.25 mm, at least about 2.3 mm, at least about 2.4 mm, at least about 2.5 mm, at least about 2.6 mm, at least about 2.7 mm, at least about 2.8 mm, at least about 2.9 mm, at least about 3 mm, at least about 3.5 mm, at least about 4 mm, at least about 4.5 mm, at least about 5 mm, at least about 5.5 mm, or at least about 6 mm. In some embodiments, the inner diameter 240 or an inner side length 240 of the ophthalmic device may be at least about 0.1 mm. In some embodiments, the inner diameter 240 or an inner side length 240 of the ophthalmic device may be at least about 0.5 mm.

In some embodiments, the inner diameter 240 or an inner side length 240 of the ophthalmic device may be at most about 0.05 mm, at most about 0.1 mm, at most about 0.15 mm, at most about 0.2 mm, at most about 0.25 mm, at most about 0.3 mm, at most about 0.35 mm, at most about 0.4 mm, at most about 0.45 mm, at most about 0.5 mm, at most about 0.55 mm, at most about 0.6 mm, at most about 0.65 mm, at most about 0.7 mm, at most about 0.75 mm, at most about 0.8 mm, at most about 0.85 mm, at most about 0.9 mm, at most about 0.95 mm, at most about 1 mm, at most about 1.05 mm, at most about 1.1 mm, at most about 1.15 mm, at most about 1.2 mm, at most about 1.25 mm, at most about 1.3 mm, at most about 1.35 mm, at most about 1.4 mm, at most about 1.45 mm, at most about 1.5 mm, at most about 1.55 mm, at most about 1.6 mm, at most about 1.65 mm, at most about 1.7 mm, at most about 1.75 mm, at most about 1.8 mm, at most about 1.85 mm, at most about 1.9 mm, at most about 1.95 mm, at most about 2 mm, at most about 2.05 mm, at most about 2.1 mm, at most about 2.15 mm, at most about 2.2 mm, at most about 2.25 mm, at most about 2.3 mm, at most about 2.4 mm, at most about 2.5 mm, at most about 2.6 mm, at most about 2.7 mm, at most about 2.8 mm, at most about 2.9 mm, at most about 3 mm, at most about 3.5 mm, at most about 4 mm, at most about 4.5 mm, at most about 5 mm, at most about 5.5 mm, or at most about 6 mm. In some embodiments, the inner diameter 240 or an inner side length 240 of the ophthalmic device may be at most about 0.5 mm. In some embodiments, the inner diameter 240 or an inner side length 240 of the ophthalmic device may be at most about 1 mm. In some embodiments, the inner diameter 240 or an inner side length 240 of the ophthalmic device may be at most about 1.5 mm.

In some embodiments, the inner diameter 240 or an inner side length 240 of the ophthalmic device may be about 0.05 mm, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1 mm, about 1.05 mm, about 1.1 mm, about 1.15 mm, about 1.2 mm, about 1.25 mm, about 1.3 mm, about 1.35 mm, about 1.4 mm, about 1.45 mm, about 1.5 mm, about 1.55 mm, about 1.6 mm, about 1.65 mm, about 1.7 mm, about 1.75 mm, about 1.8 mm, about 1.85 mm, about 1.9 mm, about 1.95 mm, about 2 mm, about 2.05 mm, about 2.1 mm, about 2.15 mm, about 2.2 mm, about 2.25 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, about 5 mm, about 5.1 mm, about 5.2 mm, about 5.3 mm, about 5.4 mm, about 5.5 mm, about 5.6 mm, about 5.7 mm, about 5.8 mm, about 5.9 mm, or about 6 mm. In some embodiments, the inner diameter 240 or an inner side length 240 of the ophthalmic device may be about 0.5 mm.

In some embodiments, a wall thickness 260 (e.g., wall thickness 216, wall thickness 217, wall thickness 218, wall thickness 280) of the ophthalmic article may be from about 0.001 mm to 3 mm. In some embodiments, a wall thickness of the ophthalmic article may be about 0.001 mm to about 0.01 mm, about 0.001 mm to about 0.1 mm, about 0.001 mm to about 0.2 mm, about 0.001 mm to about 0.3 mm, about 0.001 mm to about 0.4 mm, about 0.001 mm to about 0.5 mm, about 0.001 mm to about 1 mm, about 0.001 mm to about 1.5 mm, about 0.001 mm to about 2 mm, about 0.001 mm to about 2.5 mm, about 0.001 mm to about 3 mm, about 0.01 mm to about 0.1 mm, about 0.01 mm to about 0.2 mm, about 0.01 mm to about 0.3 mm, about 0.01 mm to about 0.4 mm, about 0.01 mm to about 0.5 mm, about 0.01 mm to about 1 mm, about 0.01 mm to about 1.5 mm, about 0.01 mm to about 2 mm, about 0.01 mm to about 2.5 mm, about 0.01 mm to about 3 mm, about 0.1 mm to about 0.2 mm, about 0.1 mm to about 0.3 mm, about 0.1 mm to about 0.4 mm, about 0.1 mm to about 0.5 mm, about 0.1 mm to about 1 mm, about 0.1 mm to about 1.5 mm, about 0.1 mm to about 2 mm, about 0.1 mm to about 2.5 mm, about 0.1 mm to about 3 mm, about 0.2 mm to about 0.3 mm, about 0.2 mm to about 0.4 mm, about 0.2 mm to about 0.5 mm, about 0.2 mm to about 1 mm, about 0.2 mm to about 1.5 mm, about 0.2 mm to about 2 mm, about 0.2 mm to about 2.5 mm, about 0.2 mm to about 3 mm, about 0.3 mm to about 0.4 mm, about 0.3 mm to about 0.5 mm, about 0.3 mm to about 1 mm, about 0.3 mm to about 1.5 mm, about 0.3 mm to about 2 mm, about 0.3 mm to about 2.5 mm, about 0.3 mm to about 3 mm, about 0.4 mm to about 0.5 mm, about 0.4 mm to about 1 mm, about 0.4 mm to about 1.5 mm, about 0.4 mm to about 2 mm, about 0.4 mm to about 2.5 mm, about 0.4 mm to about 3 mm, about 0.5 mm to about 1 mm, about 0.5 mm to about 1.5 mm, about 0.5 mm to about 2 mm, about 0.5 mm to about 2.5 mm, about 0.5 mm to about 3 mm, about 1 mm to about 1.5 mm, about 1 mm to about 2 mm, about 1 mm to about 2.5 mm, about 1 mm to about 3 mm, about 1.5 mm to about 2 mm, about 1.5 mm to about 2.5 mm, about 1.5 mm to about 3 mm, about 2 mm to about 2.5 mm, about 2 mm to about 3 mm, or about 2.5 mm to about 3 mm. In some embodiments, a wall thickness of the ophthalmic article may be about 0.1 mm to about 1 mm. In some embodiments, a wall thickness of the ophthalmic article may be about 0.1 mm to about 1.5 mm.

In some embodiments, a wall thickness of the ophthalmic article may be at least about 0.001 mm, at least about 0.005 mm, at least about 0.01 mm, at least about 0.02 mm, at least about 0.03 mm, at least about 0.04 mm, at least about 0.05 mm, at least about 0.06 mm, at least about 0.07 mm, at least about 0.08 mm, at least about 0.09 mm, at least about 0.1 mm, at least about 0.15 mm, at least about 0.2 mm, at least about 0.25 mm, at least about 0.3 mm, at least about 0.35 mm, at least about 0.4 mm, at least about 0.45 mm, at least about 0.5 mm, at least about 0.55 mm, at least about 0.6 mm, at least about 0.65 mm, at least about 0.7 mm, at least about 0.75 mm, at least about 0.8 mm, at least about 0.85 mm, at least about 0.9 mm, at least about 0.95 mm, at least about 1 mm, at least about 1.2 mm, at least about 1.4 mm, at least about 1.6 mm, at least about 1.8 mm, at least about 2 mm, at least about 2.2 mm, at least about 2.4 mm, at least about 2.6 mm, at least about 2.8 mm, or at least about 3 mm. In some embodiments, a wall thickness of the ophthalmic article may be at least about 0.1 mm. In some embodiments, a wall thickness of the ophthalmic article may be at least about 0.5 mm. In some embodiments, a wall thickness of the ophthalmic article may be at least about 1 mm.

In some embodiments, a wall thickness of the ophthalmic article may be at most about 0.001 mm, at most about 0.005 mm, at most about 0.01 mm, at most about 0.02 mm, at most about 0.03 mm, at most about 0.04 mm, at most about 0.05 mm, at most about 0.06 mm, at most about 0.07 mm, at most about 0.08 mm, at most about 0.09 mm, at most about 0.1 mm, at most about 0.15 mm, at most about 0.2 mm, at most about 0.25 mm, at most about 0.3 mm, at most about 0.35 mm, at most about 0.4 mm, at most about 0.45 mm, at most about 0.5 mm, at most about 0.55 mm, at most about 0.6 mm, at most about 0.65 mm, at most about 0.7 mm, at most about 0.75 mm, at most about 0.8 mm, at most about 0.85 mm, at most about 0.9 mm, at most about 0.95 mm, at most about 1 mm, at most about 1.2 mm, at most about 1.4 mm, at most about 1.6 mm, at most about 1.8 mm, at most about 2 mm, at most about 2.2 mm, at most about 2.4 mm, at most about 2.6 mm, at most about 2.8 mm, or at most about 3 mm. In some embodiments, a wall thickness of the ophthalmic article may be at most about 0.5 mm. In some embodiments, a wall thickness of the ophthalmic article may be at most about 1 mm. In some embodiments, a wall thickness of the ophthalmic article may be at most about 1.5 mm.

In some embodiments, a wall thickness of the ophthalmic article may be about 0.001 mm, about 0.005 mm, about 0.01 mm, about 0.02 mm, about 0.03 mm, about 0.04 mm, about 0.05 mm, about 0.06 mm, about 0.07 mm, about 0.08 mm, about 0.09 mm, about 0.1 mm, about 0.11 mm, about 0.12 mm, about 0.13 mm, about 0.14 mm, about 0.15 mm, about 0.16 mm, about 0.17 mm, about 0.18 mm, about 0.19 mm, about 0.2 mm, about 0.21 mm, about 0.22 mm, about 0.23 mm, about 0.24 mm, about 0.25 mm, about 0.26 mm, about 0.27 mm, about 0.28 mm, about 0.29 mm, about 0.3 mm, about 0.31 mm, about 0.32 mm, about 0.33 mm, about 0.34 mm, about 0.35 mm, about 0.36 mm, about 0.37 mm, about 0.38 mm, about 0.39 mm, about 0.4 mm, about 0.41 mm, about 0.42 mm, about 0.43 mm, about 0.44 mm, about 0.45 mm, about 0.46 mm, about 0.47 mm, about 0.48 mm, about 0.49 mm, about 0.5 mm, about 0.51 mm, about 0.52 mm, about 0.53 mm, about 0.54 mm, about 0.55 mm, about 0.56 mm, about 0.57 mm, about 0.58 mm, about 0.59 mm, about 0.6 mm, about 0.61 mm, about 0.62 mm, about 0.63 mm, about 0.64 mm, about 0.65 mm, about 0.66 mm, about 0.67 mm, about 0.68 mm, about 0.69 mm, about 0.7 mm, about 0.71 mm, about 0.72 mm, about 0.73 mm, about 0.74 mm, about 0.75 mm, about 0.76 mm, about 0.77 mm, about 0.78 mm, about 0.79 mm, about 0.8 mm, about 0.81 mm, about 0.82 mm, about 0.83 mm, about 0.84 mm, about 0.85 mm, about 0.86 mm, about 0.87 mm, about 0.88 mm, about 0.89 mm, about 0.9 mm, about 0.91 mm, about 0.92 mm, about 0.93 mm, about 0.94 mm, about 0.95 mm, about 0.96 mm, about 0.97 mm, about 0.98 mm, about 0.99 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm. In some embodiments, a wall thickness of the ophthalmic article may be about 0.7 mm.

In some embodiments, the ophthalmic article extends no more than about 0.32 mm beyond a portion of the ocular device (e.g., the haptic of an IOL) once the ophthalmic article is associated (e.g., attached) with the portion of the ocular device (e.g., the haptic of an IOL). In some embodiments, the ophthalmic article extends beyond a portion of the ocular device (e.g., the haptic of an IOL), once the ophthalmic article is associated (e.g., attached) with the portion (e.g., haptic) of the ocular device (e.g., IOL), of at most about 3 mm, 2.9 mm, 2.8 mm, 2.7 mm, 2.6 mm, 2.5 mm, 2.4 mm, 2.3 mm, 2.2 mm, 2.1 mm, 2 mm, 1.9 mm, 1.8 mm, 1.7 mm, 1.6 mm, 1.5 mm, 1.4 mm, 1.3 mm, 1.2 mm, 1.1 mm, 1 mm, 0.9 mm, 0.8 mm, 0.7 mm, 0.6 mm, 0.5 mm, 0.4 mm, 0.3 mm, 0.2 mm, 0.1 mm, or less.

In some embodiments, the ophthalmic article extends beyond a portion (e.g., haptic) of the ocular device (e.g., IOL), once the ophthalmic article is associated (e.g., attached) with the portion (e.g., haptic) of the ocular device (e.g., IOL), of at least about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, or more.

In some embodiments, the ophthalmic article extends beyond a portion (e.g., haptic) of the ocular device (e.g., IOL), once the ophthalmic article is associated (e.g., attached) with the portion (e.g., haptic) of the ocular device (e.g., IOL), of about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm.

In some embodiments, a cross-sectional thickness 250 (e.g., cross-sectional thickness 205, cross-sectional thickness 210, cross-sectional thickness 215, cross-sectional thickness 278) of the ophthalmic article may be from about 0.05 mm to 3 mm.

In some embodiments, the cross-sectional thickness of the ophthalmic article may be about 0.01 mm to about 4 mm. In some embodiments, the cross-sectional thickness of the ophthalmic article may be about 0.01 mm to about 0.05 mm, about 0.01 mm to about 0.1 mm, about 0.01 mm to about 0.5 mm, about 0.01 mm to about 1 mm, about 0.01 mm to about 1.5 mm, about 0.01 mm to about 2 mm, about 0.01 mm to about 2.5 mm, about 0.01 mm to about 3 mm, about 0.01 mm to about 3.5 mm, about 0.01 mm to about 4 mm, about 0.05 mm to about 0.1 mm, about 0.05 mm to about 0.5 mm, about 0.05 mm to about 1 mm, about 0.05 mm to about 1.5 mm, about 0.05 mm to about 2 mm, about 0.05 mm to about 2.5 mm, about 0.05 mm to about 3 mm, about 0.05 mm to about 3.5 mm, about 0.05 mm to about 4 mm, about 0.1 mm to about 0.5 mm, about 0.1 mm to about 1 mm, about 0.1 mm to about 1.5 mm, about 0.1 mm to about 2 mm, about 0.1 mm to about 2.5 mm, about 0.1 mm to about 3 mm, about 0.1 mm to about 3.5 mm, about 0.1 mm to about 4 mm, about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 2 mm to about 2.5 mm, about 2 mm to about 3 mm, about 2 mm to about 3.5 mm, about 2 mm to about 4 mm, about 2.5 mm to about 3 mm, about 2.5 mm to about 3.5 mm, about 2.5 mm to about 4 mm, about 3 mm to about 3.5 mm, about 3 mm to about 4 mm, or about 3.5 mm to about 4 mm. In some embodiments, the cross-sectional thickness of the ophthalmic article may be about 0.1 mm to about 1 mm.

In some embodiments, the cross-sectional thickness of the ophthalmic article may be at least about 0.01 mm, at least about 0.05 mm, at least about 0.1 mm, at least about 0.5 mm, at least about 1 mm, at least about 1.5 mm, at least about 2 mm, at least about 2.5 mm, at least about 3 mm, at least about 3.5 mm, or at least about 4 mm. In some embodiments, the cross-sectional thickness of the ophthalmic article may be at least about 0.1 mm. In some embodiments, the cross-sectional thickness of the ophthalmic article may be at least about 0.5 mm.

In some embodiments, the cross-sectional thickness of the ophthalmic article may be at most about 0.01 mm, at most about 0.05 mm, at most about 0.1 mm, at most about 0.5 mm, at most about 1 mm, at most about 1.5 mm, at most about 2 mm, at most about 2.5 mm, at most about 3 mm, at most about 3.5 mm, or at most about 4 mm. In some embodiments, the cross-sectional thickness of the ophthalmic article may be at most about 1 mm. In some embodiments, the cross-sectional thickness of the ophthalmic article may be at most about 1.5 mm.

In some embodiments, the outer diameter 230 (e.g., outer diameter 203, outer diameter 208, outer diameter 276) or an outer edge 230 (e.g., outer diameter 213) of may be from about 0.1 millimeters (mm) to 6 mm. In some embodiments, the outer diameter or an outer edge of the ophthalmic article may be about 0.1 mm to about 1.5 mm, about 0.1 mm to about 2 mm, about 0.1 mm to about 2.5 mm, about 0.1 mm to about 3 mm, about 0.1 mm to about 3.5 mm, about 0.1 mm to about 4 mm, about 0.1 mm to about 4.5 mm, about 0.1 mm to about 5 mm, about 0.1 mm to about 5.5 mm, about 1 mm to about 6 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 1.5 mm to about 4.5 mm, about 1.5 mm to about 5 mm, about 1.5 mm to about 5.5 mm, about 1.5 mm to about 6 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 5.5 mm, about 2 mm to about 6 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 5.5 mm, about 2.5 mm to about 6 mm, about 3 mm to about 3.5 mm, about 3 mm to about 4 mm, about 3 mm to about 4.5 mm, about 3 mm to about 5 mm, about 3 mm to about 5.5 mm, about 3 mm to about 6 mm, about 3.5 mm to about 4 mm, about 3.5 mm to about 4.5 mm, about 3.5 mm to about 5 mm, about 3.5 mm to about 5.5 mm, about 3.5 mm to about 6 mm, about 4 mm to about 4.5 mm, about 4 mm to about 5 mm, about 4 mm to about 5.5 mm, about 4.5 mm to about 5 mm, about 4.5 mm to about 5.5 mm, about 4.5 mm to about 6 mm, about 5 mm to about 5.5 mm, about 5 mm to about 6 mm, or about 5.5 mm to about 6 mm. In some embodiments, the outer diameter or an outer edge of the ophthalmic article may be about 0.1 mm to about 1.5 mm. In some embodiments, the outer diameter or an outer edge of the ophthalmic article may be about 0.5 mm to about 1.5 mm. In some embodiments, the outer diameter or an outer edge of the ophthalmic article may be about 0.5 mm to about 2 mm.

In some embodiments, the outer diameter or an outer edge of the ophthalmic article may be at least about 0.1 mm, at least about 0.15 mm, at least about 0.2 mm, at least about 0.25 mm, at least about 0.3 mm, at least about 0.35 mm, at least about 0.4 mm, at least about 0.45 mm, at least about 0.5 mm, at least about 0.55 mm, at least about 0.6 mm, at least about 0.65 mm, at least about 0.7 mm, at least about 0.75 mm, at least about 0.8 mm, at least about 0.85 mm, at least about 0.9 mm, at least about 0.95 mm, at least about 1 mm, at least about 1.05 mm, at least about 1.1 mm, at least about 1.15 mm, at least about 1.2 mm, at least about 1.25 mm, at least about 1.3 mm, at least about 1.35 mm, at least about 1.4 mm, at least about 1.45 mm, at least about 1.5 mm, at least about 1.55 mm, at least about 1.6 mm, at least about 1.65 mm, at least about 1.7 mm, at least about 1.75 mm, at least about 1.8 mm, at least about 1.85 mm, at least about 1.9 mm, at least about 1.95 mm, at least about 2 mm, at least about 2.05 mm, at least about 2.1 mm, at least about 2.15 mm, at least about 2.2 mm, at least about 2.25 mm, at least about 2.3 mm, at least about 2.4 mm, at least about 2.5 mm, at least about 2.6 mm, at least about 2.7 mm, at least about 2.8 mm, at least about 2.9 mm, at least about 3 mm, at least about 3.5 mm, at least about 4 mm, at least about 4.5 mm, at least about 5 mm, at least about 5.5 mm, or at least about 6 mm. In some embodiments, the outer diameter or an outer edge of the ophthalmic article may be at least about 0.5 mm. In some embodiments, the outer diameter or an outer edge of the ophthalmic article may be at least about 1 mm. In some embodiments, the outer diameter or an outer edge of the ophthalmic article may be at least about 1.5 mm.

In some embodiments, the outer diameter or an outer edge of the ophthalmic article may be at most about 0.1 mm, at most about 0.15 mm, at most about 0.2 mm, at most about 0.25 mm, at most about 0.3 mm, at most about 0.35 mm, at most about 0.4 mm, at most about 0.45 mm, at most about 0.5 mm, at most about 0.55 mm, at most about 0.6 mm, at most about 0.65 mm, at most about 0.7 mm, at most about 0.75 mm, at most about 0.8 mm, at most about 0.85 mm, at most about 0.9 mm, at most about 0.95 mm, at most about 1 mm, at most about 1.05 mm, at most about 1.1 mm, at most about 1.15 mm, at most about 1.2 mm, at most about 1.25 mm, at most about 1.3 mm, at most about 1.35 mm, at most about 1.4 mm, at most about 1.45 mm, at most about 1.5 mm, at most about 1.55 mm, at most about 1.6 mm, at most about 1.65 mm, at most about 1.7 mm, at most about 1.75 mm, at most about 1.8 mm, at most about 1.85 mm, at most about 1.9 mm, at most about 1.95 mm, at most about 2 mm, at most about 2.05 mm, at most about 2.1 mm, at most about 2.15 mm, at most about 2.2 mm, at most about 2.25 mm, at most about 2.3 mm, at most about 2.4 mm, at most about 2.5 mm, at most about 2.6 mm, at most about 2.7 mm, at most about 2.8 mm, at most about 2.9 mm, at most about 3 mm, at most about 3.5 mm, at most about 4 mm, at most about 4.5 mm, at most about 5 mm, at most about 5.5 mm, or at most about 6 mm. In some embodiments, the outer diameter or an outer edge of the ophthalmic article may be at most about 2 mm. In some embodiments, the outer diameter or an outer edge of the ophthalmic article may be at most about 1 mm.

In some embodiments, the outer diameter or an outer edge of the ophthalmic article may be about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1 mm, about 1.05 mm, about 1.1 mm, about 1.15 mm, about 1.2 mm, about 1.25 mm, about 1.3 mm, about 1.35 mm, about 1.4 mm, about 1.45 mm, about 1.5 mm, about 1.55 mm, about 1.6 mm, about 1.65 mm, about 1.7 mm, about 1.75 mm, about 1.8 mm, about 1.85 mm, about 1.9 mm, about 1.95 mm, about 2 mm, about 2.05 mm, about 2.1 mm, about 2.15 mm, about 2.2 mm, about 2.25 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, about 5 mm, about 5.1 mm, about 5.2 mm, about 5.3 mm, about 5.4 mm, about 5.5 mm, about 5.6 mm, about 5.7 mm, about 5.8 mm, about 5.9 mm, or about 6 mm. In some embodiments, the outer diameter or an outer edge of the ophthalmic article may be about 1.5 mm. In some embodiments, the outer diameter or an outer edge of the ophthalmic article may be about 1.3 mm.

In some embodiments, the shape of the ophthalmic article can also affect the active agent and/or diagnostic agent release rate for the homogenous delivery device. For example, in some cases, a thinner homogenous delivery device can biodegrade more quickly than a thicker homogenous delivery device, resulting in a faster active agent and/or diagnostic agent release profile. Additionally, in some examples, the perimeter edges or other sections of the ophthalmic article can be made thinner and/or rougher than other parts of the ophthalmic article to provide an initial burst of active agent and/or diagnostic agent followed by a near zero order release profile. Further, in some examples, the overall geometrical shape alone of the homogenous delivery device can affect the release rate of the active agent and/or diagnostic agent. For example, exposed surface area to volume ratio can be increased to increase release rate and degradation.

In one example, efficacy can be provided for treatment of uveitis and post-operative cataract surgery inflammation. For example, dexamethasone can be dispersed within a biodegradable polymeric matrix. Although dexamethasone dosage amounts can vary, generally from about 100 µg to about 1000 µg can be effective. In some cases, a subject may be categorized as low risk while another subject can be categorized as high risk due to various factors such as age, secondary complications, pre-existing conditions. A low risk patient can benefit from a low dosage of about 100 µg to about 500 µg. In contrast, a high risk individual can be administered a high dosage of about 500 µg to about 1000 µg. The ophthalmic articles can be specifically designed and tested for the various conditions and treatments (e.g., treatment of postoperative surgery inflammation) disclosed herein, and can deliver an active agent (e.g., pharmaceutical active agent) up to or about 2 weeks or more. In other examples, other ophthalmic articles (e.g., biodegradable active agent delivery devices) can be designed and tested for the treatment of postoperative surgery inflammation and uveitis and can deliver active agent up to or about 4 weeks or more. In some examples, depending on the severity of the condition (e.g., inflammation), one, two, more implants (e.g., ophthalmic article and/or ocular device) can be administered per eye during surgery.

In some embodiments, each eye may be administered with at least about 1 implant, at least about 2 implants, at least about 3 implants, at least about 4 implants, at least about 5 implants, at least about 6 implants, at least about 7 implants, at least about 8 implants, at least about 9 implants, or at least about 10 implants. In some embodiments, depending on the severity of the condition, each eye may be administered with at most about 1 implant, at most about 2 implants, at most about 3 implants, at most about 4 implants, at most about 5 implants, at most about 6 implants, at most about 7 implants, at most about 8 implants, at most about 9 implants, or at most about 10 implants. In some embodiments, each eye may be administered with a plurality of implants (e.g., two or more implants), and the plurality of implants may be administered to the eye simultaneously or sequentially. The plurality of implants may be administered to the same location within eye or to different locations within the eye.

In any of the various aspects, the one or more ophthalmic articles and/or ocular device (e.g., intraocular device) can comprise a material (e.g., a polymeric material) described herein, with a tensile strength, glass transition temperature, elasticity modulus (e.g., Young's modulus), and/or elongation at break, suitable for maximal approximation of the ophthalmic article and/or ocular device to a subject's eye.

The ophthalmic articles, ophthalmic articles associated with at least a portion of an ocular device, and/or biocompatible matrix as described herein, may be deformable so that it can fit through a small incision (e.g., about 1.8 mm to 2.5 mm) in a subject's eye. The tensile strength of a material may be a suitable amount so that the ophthalmic articles, ophthalmic articles associated with at least a portion of an ocular device, and/or biocompatible matrix can resist deformation after implantation. For example, if the material is too soft and did not comprise the appropriate tensile strength then the ophthalmic articles and/or ophthalmic articles associated with at least a portion of an ocular device may collapse after implantation.

In some embodiments, the ophthalmic articles, ophthalmic articles associated with at least a portion of an ocular device, and/or biocompatible matrix can have a tensile strength from about 25 MPa to 35 MPa. In some embodiments, the ophthalmic articles, ophthalmic articles associated with at least a portion of an ocular device, and/or biocompatible matrix can have a tensile strength from about 25 MPa to about 26 MPa, about 25 MPa to about 27 MPa, about 25 MPa to about 28 MPa, about 25 MPa to about 29 MPa, about 25 MPa to about 30 MPa, about 25 MPa to about 31 MPa, about 25 MPa to about 32 MPa, about 25 MPa to about 33 MPa, about 25 MPa to about 34 MPa, about 25 MPa to about 35 MPa, about 26 MPa to about 27 MPa, about 26 MPa to about 28 MPa, about 26 MPa to about 29 MPa, about 26 MPa to about 30 MPa, about 26 MPa to about 31 MPa, about 26 MPa to about 32 MPa, about 26 MPa to about 33 MPa, about 26 MPa to about 34 MPa, about 26 MPa to about 35 MPa, about 27 MPa to about 28 MPa, about 27 MPa to about 29 MPa, about 27 MPa to about 30 MPa, about 27 MPa to about 31 MPa, about 27 MPa to about 32 MPa, about 27 MPa to about 33 MPa, about 27 MPa to about 34 MPa, about 27 MPa to about 35 MPa, about 28 MPa to about 29 MPa, about 28 MPa to about 30 MPa, about 28 MPa to about 31 MPa, about 28 MPa to about 32 MPa, about 28 MPa to about 33 MPa, about 28 MPa to about 34 MPa, about 28 MPa to about 35 MPa, about 29 MPa to about 30 MPa, about 29 MPa to about 31 MPa, about 29 MPa to about 32 MPa, about 29 MPa to about 33 MPa, about 29 MPa to about 34 MPa, about 29 MPa to about 35 MPa, about 30 MPa to about 31 MPa, about 30 MPa to about 32 MPa, about 30 MPa to about 33 MPa, about 30 MPa to about 34 MPa, about 30 MPa to about 35 MPa, about 31 MPa to about 32 MPa, about 31 MPa to about 33 MPa, about 31 MPa to about 34 MPa, about 31 MPa to about 35 MPa, about 32 MPa to about 33 MPa, about 32 MPa to about 34 MPa, about 32 MPa to about 35 MPa, about 33 MPa to about 34 MPa, about 33 MPa to about 35 MPa, or about 34 MPa to about 35 MPa.

In some embodiments, the ophthalmic articles, ophthalmic articles associated with at least a portion of an ocular device, and/or biocompatible matrix can have a tensile strength of at least about 25 MPa, at least about 26 MPa, at least about 27 MPa, at least about 28 MPa, at least about 29 MPa, at least about 30 MPa, at least about 31 MPa, at least about 32 MPa, at least about 33 MPa, at least about 34 MPa, or at least about 35 MPa.

In some embodiments, the ophthalmic articles, ophthalmic articles associated with at least a portion of an ocular device, and/or biocompatible matrix can have a tensile strength of at most about 25 MPa, at most about 26 MPa, at most about 27 MPa, at most about 28 MPa, at most about 29 MPa, at most about 30 MPa, at most about 31 MPa, at most about 32 MPa, at most about 33 MPa, at most about 34 MPa, or at most about 35 MPa.

In some embodiments, ophthalmic articles, ophthalmic articles associated with at least a portion of an ocular device, and/or biocompatible matrix can have a tensile strength of about 25 MPa, about 26 MPa, about 27 MPa, about 28 MPa, about 29 MPa, about 30 MPa, about 31 MPa, about 32 MPa, about 33 MPa, about 34 MPa, or about 35 MPa.

In some embodiments, the tensile strength of the ophthalmic articles, ophthalmic articles associated with at least a portion of an ocular device, and/or biocompatible matrix may be about 0.5 MPa to about 50 MPa. In some embodiments, the tensile strength of the ophthalmic articles, ophthalmic articles associated with at least a portion of an ocular device, and/or biocompatible matrix may be about 0.5 MPa to about 1 MPa, about 0.5 MPa to about 5 MPa, about 0.5 MPa to about 10 MPa, about 0.5 MPa to about 15 MPa, about 0.5 MPa to about 20 MPa, about 0.5 MPa to about 25 MPa, about 0.5 MPa to about 30 MPa, about 0.5 MPa to about 35 MPa, about 0.5 MPa to about 40 MPa, about 0.5 MPa to about 45 MPa, about 0.5 MPa to about 50 MPa, about 1 MPa to about 5 MPa, about 1 MPa to about 10 MPa, about 1 MPa to about 15 MPa, about 1 MPa to about 20 MPa, about 1 MPa to about 25 MPa, about 1 MPa to about 30 MPa, about 1 MPa to about 35 MPa, about 1 MPa to about 40 MPa, about 1 MPa to about 45 MPa, about 1 MPa to about 50 MPa, about 5 MPa to about 10 MPa, about 5 MPa to about 15 MPa, about 5 MPa to about 20 MPa, about 5 MPa to about 25 MPa, about 5 MPa to about 30 MPa, about 5 MPa to about 35 MPa, about 5 MPa to about 40 MPa, about 5 MPa to about 45 MPa, about 5 MPa to about 50 MPa, about 10 MPa to about 15 MPa, about 10 MPa to about 20 MPa, about 10 MPa to about 25 MPa, about 10 MPa to about 30 MPa, about 10 MPa to about 35 MPa, about 10 MPa to about 40 MPa, about 10 MPa to about 45 MPa, about 10 MPa to about 50 MPa, about 15 MPa to about 20 MPa, about 15 MPa to about 25 MPa, about 15 MPa to about 30 MPa, about 15 MPa to about 35 MPa, about 15 MPa to about 40 MPa, about 15 MPa to about 45 MPa, about 15 MPa to about 50 MPa, about 20 MPa to about 25 MPa, about 20 MPa to about 30 MPa, about 20 MPa to about 35 MPa, about 20 MPa to about 40 MPa, about 20 MPa to about 45 MPa, about 20 MPa to about 50 MPa, about 25 MPa to about 30 MPa, about 25 MPa to about 35 MPa, about 25 MPa to about 40 MPa, about 25 MPa to about 45 MPa, about 25 MPa to about 50 MPa, about 30 MPa to about 35 MPa, about 30 MPa to about 40 MPa, about 30 MPa to about 45 MPa, about 30 MPa to about 50 MPa, about 35 MPa to about 40 MPa, about 35 MPa to about 45 MPa, about 35 MPa to about 50 MPa, about 40 MPa to about 45 MPa, about 40 MPa to about 50 MPa, or about 45 MPa to about 50 MPa. In some embodiments, the tensile strength of the ophthalmic articles, ophthalmic articles associated with at least a portion of an ocular device, and/or biocompatible matrix may be at least about 0.5 MPa, at least about 1 MPa, at least about 5 MPa, at least about 10 MPa, at least about 15 MPa, at least about 20 MPa, at least about 25 MPa, at least about 30 MPa, at least about 35 MPa, at least about 40 MPa, at least about 45 MPa, or at least about 50 MPa. In some embodiments, the tensile strength of the ophthalmic article and/or the polymeric material may be at most about 0.5 MPa, at most about 1 MPa, at most about 5 MPa, at most about 10 MPa, at most about 15 MPa, at most about 20 MPa, at most about 25 MPa, at most about 30 MPa, at most about 35 MPa, at most about 40 MPa, at most about 45 MPa, or at most about 50 MPa.

In some embodiments, tensile strength may be measured or determined by tensile testing (e.g., uniaxial tensile testing, biaxial tensile testing).

The glass transition temperature may be the temperature that a polymeric material transitions from a hard, glassy material to a soft, rubbery material. Such a parameter may be important for determining where the ophthalmic articles, ophthalmic articles associated with at least a portion of an ocular device, and/or biocompatible matrix is flexible at room temperature and for use in various operating room temperatures. The ophthalmic article should be soft when implanted inside of an eye, otherwise if it is rigid, it may not unfold once implanted into the eye. Furthermore, an ophthalmic article, ocular device, and/or biocompatible matrix comprising a material that can be deformable (e.g., soft and compliant with the surrounding tissue) is advantageous for reducing harm to the eye (e.g., rubbing or inflaming the iris).

In some embodiments, the ophthalmic article and/or biocompatible matrix may be at least as soft as the ocular device (e.g., IOL). If the ophthalmic article and/or biocompatible matrix is more rigid than the ocular device, then when implanted into an eye, the ophthalmic article and/or biocompatible matrix can cut or create ridges and/or marks in the ocular device that would affect its optical or mechanical properties.

In some embodiments, the glass transition temperature may be sufficiently lower than that of a room (e.g., operating room) where the ophthalmic article is associated to a portion of the ocular device (e.g., IOL). In some embodiments, the ophthalmic article, ocular device, and/or biocompatible matrix can have a glass transition temperature from about −50° C. to 50° C. as measured by differential scanning calorimetry. In some embodiments, the ophthalmic article, ocular device, and/or biocompatible matrix has a glass transition temperature of at most about 24° C. as measured by differential scanning calorimetry.

In some embodiments, the ophthalmic article, ocular device, and/or biocompatible matrix can have a glass transition temperature from about −15° C. to about −10° C., about −15° C. to about −5° C., about −15° C. to about 0° C., about −15° C. to about 5° C., about −15° C. to about 10° C., about −15° C. to about 15° C., about −15° C. to about 20° C., about −15° C. to about 25° C., about −15° C. to about 30° C., about −15° C. to about 35° C., about −15° C. to about 40° C., about −10° C. to about −5° C., about −10° C. to about 0° C., about −10° C. to about 5° C., about −10° C. to about 10° C., about −10° C. to about 15° C., about −10° C. to about 20° C., about −10° C. to about 25° C., about −10° C. to about 30° C., about −10° C. to about 35° C., about −10° C. to about 40° C., about −5° C. to about 0° C., about −5° C. to about 5° C., about −5° C. to about 10° C., about −5° C. to about 15° C., about −5° C. to about 20° C., about −5° C. to about 25° C., about −5° C. to about 30° C., about −5° C. to about 35° C., about −5° C. to about 40° C., about 0° C. to about 5° C., about 0° C. to about 10° C., about 0° C. to about 15° C., about 0° C. to about 20° C., about 0° C. to about 25° C., about 0° C. to about 30° C., about 0° C. to about 35° C., about 0° C. to about 40° C., about 5° C. to about 10° C., about 5° C. to about 15° C., about 5° C. to about 20° C., about 5° C. to about 25° C., about 5° C. to about 30° C., about 5° C. to about 35° C., about 5° C. to about 40° C., about 10° C. to about 15° C., about 10° C. to about 20° C., about 10° C. to about 25° C., about 10° C. to about 30° C., about 10° C. to about 35° C., about 10° C. to about 40° C., about 15° C. to about 20° C., about 15° C. to about 25° C., about 15° C. to about 30° C., about 15° C. to about 35° C., about 15° C. to about 40° C., about 20° C. to about 25° C., about 20° C. to about 30° C., about 20° C. to about 35° C., about 20° C. to about 40° C., about 25° C. to about 30° C., about 25° C. to about 35° C., about 25° C. to about 40° C., about 30° C. to about 35° C., about 30° C. to about 40° C., or about 35° C. to about 40° C. The glass transition temperature may be measured by differential scanning calorimetry. In some embodiments, the glass transition temperature may be measured by differential scanning calorimetry, thermal mechanical analysis, and/or dynamic mechanical analysis.

In some embodiments, the ophthalmic article and/or the polymeric material (e.g., biocompatible polymer matrix) can have a glass transition temperature of at least or up to at least or up to about −15° C., at least or up to at least or up to about −10° C., at least or up to about −5° C., at least or up to about 0° C., at least or up to about 5° C., at least or up to about 10° C., at least or up to about 14° C., at least or up to about 15° C., at least or up to about 16° C., at least or up to about 18° C., at least or up to about 20° C., at least or up to about 22° C., at least or up to about 24° C., at least or up to about 25° C., at least or up to about 26° C., at least or up to about 28° C., at least or up to about 30° C., at least or up to about 32° C., at least or up to about 35° C., or at least or up to about 40° C. The glass transition temperature may be measured by differential scanning calorimetry. In some embodiments, the glass transition temperature may be measured by differential scanning calorimetry, thermal mechanical analysis, and/or dynamic mechanical analysis.

In some embodiments, ophthalmic article, ocular device, and/or biocompatible matrix can have a glass transition temperature of about −15° C., about −10° C., about −5° C., about 0° C., about 5° C., about 10° C., about 14° C., about 15° C., about 16° C., about 18° C., about 20° C., about 22° C., about 24° C., about 25° C., about 26° C., about 28° C., about 30° C., about 32° C., about 35° C., or about 40° C. The glass transition temperature may be measured by differential scanning calorimetry. In some embodiments, the glass transition temperature may be measured by differential scanning calorimetry, thermal mechanical analysis, and/or dynamic mechanical analysis.

In some embodiments, the glass transition temperature of the ophthalmic article, ocular device, and/or biocompatible matrix may be about −50° C. to about 50° C. In some embodiments, the glass transition temperature of the ophthalmic article and/or the polymeric material may be about −50° C. to about −40° C., about −50° C. to about −30° C., about −50° C. to about −20° C., about −50° C. to about −10° C., about −50° C. to about 0° C., about −50° C. to about 10° C., about −50° C. to about 20° C., about −50° C. to about 30° C., about −50° C. to about 40° C., about −50° C. to about 50° C., about −40° C. to about −30° C., about −40° C. to about −20° C., about −40° C. to about −10° C., about −40° C. to about 0° C., about −40° C. to about 10° C., about −40° C. to about 20° C., about −40° C. to about 30° C., about −40° C. to about 40° C., about −40° C. to about 50° C., about −30° C. to about −20° C., about −30° C. to about −10° C., about −30° C. to about 0° C., about −30° C. to about 10° C., about −30° C. to about 20° C., about −30° C. to about 30° C., about −30° C. to about 40° C., about −30° C. to about 50° C., about −20° C. to about −10° C., about −20° C. to about 0° C., about −20° C. to about 10° C., about −20° C. to about 20° C., about −20° C. to about 30° C., about −20° C. to about 40° C., about −20° C. to about 50° C., about −10° C. to about 0° C., about −10° C. to about 10° C., about −10° C. to about 20° C., about −10° C. to about 30° C., about −10° C. to about 40° C., about −10° C. to about 50° C., about 0° C. to about 10° C., about 0° C. to about 20° C., about 0° C. to about 30° C., about 0°

C. to about 40° C., about 0° C. to about 50° C., about 10° C. to about 20° C., about 10° C. to about 30° C., about 10° C. to about 40° C., about 10° C. to about 50° C., about 20° C. to about 30° C., about 20° C. to about 40° C., about 20° C. to about 50° C., about 30° C. to about 40° C., about 30° C. to about 50° C., or about 40° C. to about 50° C. In some embodiments, the glass transition temperature of the ophthalmic article and/or the polymeric material may be about −20° C. to about 24° C. In some embodiments, the glass transition temperature of the ophthalmic article and/or the polymeric material may be about −20° C. to about −10° C.

In some embodiments, the glass transition temperature of the ophthalmic article, ocular device, and/or biocompatible matrix may be at least about −50° C., at least about −45° C., at least about −40° C., at least about −35° C., at least about −30° C., at least about −25° C., at least about −20° C., at least about −15° C., at least about −10° C., at least about −5° C., at least about 0° C., at least about 5° C., at least about 10° C., at least about 15° C., at least about 20° C., at least about 25° C., at least about 30° C., at least about 35° C., at least about 40° C., at least about 45° C., or at least about 50° C. In some embodiments, the glass transition temperature of the ophthalmic article, ocular device, and/or biocompatible matrix may be at least about −20° C.

In some embodiments, the glass transition temperature of the ophthalmic article, ocular device, and/or biocompatible matrix may be at most about −50° C., at most about −45° C., at most about −40° C., at most about −35° C., at most about −30° C., at most about −25° C., at most about −20° C., at most about −15° C., at most about −10° C., at most about −5° C., at most about 0° C., at most about 5° C., at most about 10° C., at most about 15° C., at most about 20° C., at most about 25° C., at most about 30° C., at most about 35° C., at most about 40° C., at most about 45° C., or at most about 50° C. In some embodiments, the glass transition temperature of the ophthalmic article, ocular device, and/or biocompatible matrix may be at most about −10° C. In some embodiments, the glass transition temperature of the ophthalmic article, ocular device, and/or biocompatible matrix may be at most about 0° C. In some embodiments, the glass transition temperature of the ophthalmic article, ocular device, and/or biocompatible matrix may be at most about 25° C. In some embodiments, the glass transition temperature of the ophthalmic article, ocular device, and/or biocompatible matrix may be at most about 20° C. The glass transition temperature may be measured by differential scanning calorimetry. In some embodiments, the glass transition temperature may be measured by differential scanning calorimetry, thermal mechanical analysis, and/or dynamic mechanical analysis.

The elasticity modulus or Young's modulus may be a quantity that measures an object or substance's resistance to being deformed elastically (i.e., non-permanently) when a stress is applied to it. Elasticity modulus or "Young's modulus" may be a measure of the stiffness of a given material. This can be experimentally determined from the slope of a stress-strain curve created during tensile tests conducted on a sample of the material. Young's modulus measurements can be made, for example, by dynamic mechanical analysis (DMA) testing.

In some embodiments, the ophthalmic article, ocular device, and/or biocompatible matrix has an elasticity modulus, storage modulus, and/or loss modulus from about 0.5 MPa to 3 MPa. In some embodiments, the ophthalmic article, ocular device, and/or biocompatible matrix has an elasticity modulus, storage modulus, and/or loss modulus of at most about 3 MPa. In some embodiments, the ophthalmic article, ocular device, and/or biocompatible matrix has an elasticity modulus, storage modulus, and/or loss modulus from about 0.5 MPa to 10 MPa. In some embodiments, the elasticity modulus, storage modulus, and/or loss modulus of the ophthalmic article and/or the polymeric material may be about 0.1 MPa to about 3 MPa. In some embodiments, the elasticity modulus, storage modulus, and/or loss modulus of the ophthalmic article and/or the polymeric material may be about 0.1 MPa to about 1 MPa.

In some embodiments, the elasticity modulus, storage modulus, and/or loss modulus of the ophthalmic article, ocular device, and/or biocompatible matrix may be about 0.5 MPa to about 10 MPa. In some embodiments, the elasticity modulus, storage modulus, and/or loss modulus of the ophthalmic article and/or the polymeric material may be about 0.5 MPa to about 1 MPa, about 0.5 MPa to about 1.5 MPa, about 0.5 MPa to about 2 MPa, about 0.5 MPa to about 3 MPa, about 0.5 MPa to about 4 MPa, about 0.5 MPa to about 5 MPa, about 0.5 MPa to about 6 MPa, about 0.5 MPa to about 7 MPa, about 0.5 MPa to about 8 MPa, about 0.5 MPa to about 9 MPa, about 0.5 MPa to about 10 MPa, about 1 MPa to about 1.5 MPa, about 1 MPa to about 2 MPa, about 1 MPa to about 3 MPa, about 1 MPa to about 4 MPa, about 1 MPa to about 5 MPa, about 1 MPa to about 6 MPa, about 1 MPa to about 7 MPa, about 1 MPa to about 8 MPa, about 1 MPa to about 9 MPa, about 1 MPa to about 10 MPa, about 1.5 MPa to about 2 MPa, about 1.5 MPa to about 3 MPa, about 1.5 MPa to about 4 MPa, about 1.5 MPa to about 5 MPa, about 1.5 MPa to about 6 MPa, about 1.5 MPa to about 7 MPa, about 1.5 MPa to about 8 MPa, about 1.5 MPa to about 9 MPa, about 1.5 MPa to about 10 MPa, about 2 MPa to about 3 MPa, about 2 MPa to about 4 MPa, about 2 MPa to about 5 MPa, about 2 MPa to about 6 MPa, about 2 MPa to about 7 MPa, about 2 MPa to about 8 MPa, about 2 MPa to about 9 MPa, about 2 MPa to about 10 MPa, about 3 MPa to about 4 MPa, about 3 MPa to about 5 MPa, about 3 MPa to about 6 MPa, about 3 MPa to about 7 MPa, about 3 MPa to about 8 MPa, about 3 MPa to about 9 MPa, about 3 MPa to about 10 MPa, about 4 MPa to about 5 MPa, about 4 MPa to about 6 MPa, about 4 MPa to about 7 MPa, about 4 MPa to about 8 MPa, about 4 MPa to about 9 MPa, about 4 MPa to about 10 MPa, about 5 MPa to about 6 MPa, about 5 MPa to about 7 MPa, about 5 MPa to about 8 MPa, about 5 MPa to about 9 MPa, about 5 MPa to about 10 MPa, about 6 MPa to about 7 MPa, about 6 MPa to about 8 MPa, about 6 MPa to about 9 MPa, about 6 MPa to about 10 MPa, about 7 MPa to about 8 MPa, about 7 MPa to about 9 MPa, about 7 MPa to about 10 MPa, about 8 MPa to about 9 MPa, about 8 MPa to about 10 MPa, or about 9 MPa to about 10 MPa.

In some embodiments, the elasticity modulus, storage modulus, and/or loss modulus of the ophthalmic article and/or the polymeric material may be at least about 0.5 MPa, at least about 0.6 MPa, at least about 0.7 MPa, at least about 0.8 MPa, at least about 0.9 MPa, at least about 1 MPa, at least about 1.1 MPa, at least about 1.2 MPa, at least about 1.3 MPa, at least about 1.4 MPa, at least about 1.5 MPa, at least about 1.6 MPa, at least about 1.7 MPa, at least about 1.8 MPa, at least about 1.9 MPa, at least about 2 MPa, at least about 2.5 MPa, at least about 3 MPa, at least about 3.5 MPa, at least about 4 MPa, at least about 4.5 MPa, at least about 5 MPa, at least about 5.5 MPa, at least about 6 MPa, at least about 6.5 MPa, at least about 7 MPa, at least about 7.5 MPa, at least about 8 MPa, at least about 8.5 MPa, at least about 9 MPa, at least about 9.5 MPa, or at least about 10 MPa. In some embodiments, the elasticity modulus, storage modulus, and/or loss modulus of the ophthalmic article and/or the polymeric material may be at least about 0.1 MPa. In some embodiments, the elasticity modulus, storage modulus, and/or loss modulus of the ophthalmic article and/or the polymeric material may be at least about 0.5 MPa. In some embodiments, the elasticity modulus, storage modulus, and/or loss modulus of the ophthalmic article and/or the polymeric material may be at least about 1 MPa. In some embodiments, the elasticity modulus, storage modulus, and/or loss modulus of the ophthalmic article and/or the polymeric material may be at least about 1.5 MPa. In some embodiments, the elasticity modulus, storage modulus, and/or loss modulus of the ophthalmic article and/or the polymeric material may be at least about 2 MPa. In some embodiments, the elasticity modulus, storage modulus, and/or loss modulus of the ophthalmic article and/or the polymeric material may be at least about 3 MPa.

In some embodiments, the elasticity modulus, storage modulus, and/or loss modulus of the ophthalmic article, ocular device, and/or biocompatible matrix may be at most about 0.5 MPa, at most about 0.6 MPa, at most about 0.7 MPa, at most about 0.8 MPa, at most about 0.9 MPa, at most about 1 MPa, at most about 1.1 MPa, at most about 1.2 MPa, at most about 1.3 MPa, at most about 1.4 MPa, at most about 1.5 MPa, at most about 1.6 MPa, at most about 1.7 MPa, at most about 1.8 MPa, at most about 1.9 MPa, at most about 2 MPa, at most about 2.5 MPa, at most about 3 MPa, at most about 3.5 MPa, at most about 4 MPa, at most about 4.5 MPa, at most about 5 MPa, at most about 5.5 MPa, at most about 6 MPa, at most about 6.5 MPa, at most about 7 MPa, at most about 7.5 MPa, at most about 8 MPa, at most about 8.5 MPa, at most about 9 MPa, at most about 9.5 MPa, or at most about 10 MPa. In some embodiments, the elasticity modulus, storage modulus, and/or loss modulus of the ophthalmic article, ocular device, and/or biocompatible matrix may be at most about 4 MPa. In some embodiments, the elasticity modulus, storage modulus, and/or loss modulus of the ophthalmic article, ocular device, and/or biocompatible matrix may be at most about 3 MPa. In some embodiments, the elasticity modulus, storage modulus, and/or loss modulus of the ophthalmic article, ocular device, and/or biocompatible matrix may be at most about 2 MPa. In some embodiments, the elasticity modulus, storage modulus, and/or loss modulus of the ophthalmic article, ocular device, and/or biocompatible matrix may be at most about 1 MPa.

Flexibility of the ophthalmic article's material may be important so that the material can comprise the ability to stretch (e.g., elongation at break). Furthermore, elastic memory is an important material property because the ophthalmic article, ocular device, and/or biocompatible matrix can fold and/or unfold in a way that doesn't damage a subject's eye. For example, if the material is too springy, once the ophthalmic article, ocular device, and/or biocompatible matrix is implanted into the eye, it may jump out of the intraocular injector and shift its position.

In some embodiments, the ophthalmic article, ocular device, and/or biocompatible matrix has an elongation at break of at least about 100% as measured by tensile testing. In some embodiments, the ophthalmic article, ocular device, and/or biocompatible matrix has an elongation at break from about 100% to 2000% at 18-24° C.

In some embodiments, ophthalmic article, ocular device, and/or biocompatible matrix has an elongation at break range from about 100% to about 200%, about 100% to about 300%, about 100% to about 400%, about 100% to about 500%, about 100% to about 600%, about 100% to about 700%, about 100% to about 800%, about 100% to about 900%, about 100% to about 1,000%, about 100% to about 1,100%, about 100% to about 1,200%, about 200% to about 300%, about 200% to about 400%, about 200% to about 500%, about 200% to about 600%, about 200% to about 700%, about 200% to about 800%, about 200% to about 900%, about 200% to about 1,000%, about 200% to about 1,100%, about 200% to about 1,200%, about 300% to about 400%, about 300% to about 500%, about 300% to about 600%, about 300% to about 700%, about 300% to about 800%, about 300% to about 900%, about 300% to about 1,000%, about 300% to about 1,100%, about 300% to about 1,200%, about 400% to about 500%, about 400% to about 600%, about 400% to about 700%, about 400% to about 800%, about 400% to about 900%, about 400% to about 1,000%, about 400% to about 1,100%, about 400% to about 1,200%, about 500% to about 600%, about 500% to about 700%, about 500% to about 800%, about 500% to about 900%, about 500% to about 1,000%, about 500% to about 1,100%, about 500% to about 1,200%, about 600% to about 700%, about 600% to about 800%, about 600% to about 900%, about 600% to about 1,000%, about 600% to about 1,100%, about 600% to about 1,200%, about 700% to about 800%, about 700% to about 900%, about 700% to about 1,000%, about 700% to about 1,100%, about 700% to about 1,200%, about 800% to about 900%, about 800% to about 1,000%, about 800% to about 1,100%, about 800% to about 1,200%, about 900% to about 1,000%, about 900% to about 1,100%, about 900% to about 1,200%, about 1,000% to about 1,100%, about 1,000% to about 1,200%, or about 1,100% to about 1,200%. In some embodiments, ophthalmic article, ocular device, and/or biocompatible matrix has an elongation at break range from about 100% to about 800%. In some embodiments, ophthalmic article, ocular device, and/or biocompatible matrix has an elongation at break range from about 500% to about 1000%. The elongation at break may be determined at 18-24° C.

In some embodiments, the ophthalmic article, ocular device, and/or biocompatible matrix has an elongation at break of at least about 100%, at least about 200%, at least about 300%, at least about 400%, at least about 500%, at least about 600%, at least about 700%, at least about 800%, at least about 900%, at least about 1,000%, at least about 1,100%, or at least about 1,200%. In some embodiments, the ophthalmic article, ocular device, and/or biocompatible matrix has an elongation at break of at least about 100%. In some embodiments, the ophthalmic article, ocular device, and/or biocompatible matrix has an elongation at break of at least about 500%. The elongation at break may be determined at 18-24° C.

In some embodiments, the ophthalmic article, ocular device, and/or biocompatible matrix has an elongation at break of at most about 100%, at most about 200%, at most about 300%, at most about 400%, at most about 500%, at most about 600%, at most about 700%, at most about 800%, at most about 900%, at most about 1,000%, at most about 1,100%, or at most about 1,200%. In some embodiments, the ophthalmic article, ocular device, and/or biocompatible matrix has an elongation at break of at most about 1000%. In some embodiments, the ophthalmic article, ocular device, and/or biocompatible matrix has an elongation at break of at most about 1500%. In some embodiments, the ophthalmic article, ocular device, and/or biocompatible matrix has an elongation at break of at most about 500%. The elongation at break may be determined at 18-24° C.

In some embodiments, the ophthalmic article, ocular device, and/or biocompatible matrix has an elongation at break of about 100%, about 150%, about 200%, about 250%, about 300%, about 350%, about 400%, about 450%, about 500%, about 550%, about 600%, about 650%, about 700%, about 750%, about 800%, about 850%, about 900%, about 950%, about 1,000%, about 1,100%, or about 1,200%. In some embodiments, the ophthalmic article, ocular device, and/or biocompatible matrix has an elongation at break of about 100%. The elongation at break may be determined at 18-24° C.

In some embodiments, elongation at break may be measured or determined by pulling an object (e.g., ophthalmic article or ophthalmic article, biocompatible matrix) in tension until fracture.

In some embodiments, the ophthalmic article, ocular device, and/or biocompatible matrix can recover to its original shape in at most about 30 seconds (sec), 29 sec, 28 sec, 27 sec, 26 sec, 25 sec, 24 sec, 23 sec, 22 sec, 21 sec, 20 sec, 19 sec, 18 sec, 17 sec, 16 sec, 15 sec, 14 sec, 13 sec, 12 sec, 11 sec, 10 sec, 9 sec, 8 sec, 7 sec, 6 sec, 5 sec, 4 sec, 3 sec, or less.

In some embodiments, the ophthalmic article, ocular device, and/or biocompatible matrix can recover to its original shape in at least about 3 sec, 4 sec, 5 sec, 6 sec, 7 sec, 8 sec, 9 sec, 10 sec, 11 sec, 12 sec, 13 sec, 14 sec, 15 sec, 16 sec, 17 sec, 18 sec, 19 sec, 20 sec, 21 sec, 22 sec, 23 sec, 24 sec, 25 sec, 26 sec, 27 sec, 28 sec, 29 sec, 30 sec, or more.

In some embodiments, the ophthalmic article, ocular device, and/or biocompatible matrix can recover to its original shape in at about 30 seconds (sec), about 29 sec, about 28 sec, about 27 sec, about 26 sec, about 25 sec, about 24 sec, about 23 sec, about 22 sec, about 21 sec, about 20 sec, about 19 sec, about 18 sec, about 17 sec, about 16 sec, about 15 sec, about 14 sec, about 13 sec, about 12 sec, about 11 sec, about 10 sec, about 9 sec, about 8 sec, about 7 sec, about 6 sec, about 5 sec, about 4 sec, or about 3 sec.

In some embodiments, the ophthalmic article, ocular device, and/or biocompatible matrix may be sufficiently soft, flexible and compressible to not cut or pierce the lens capsule once implanted. In some embodiments, the ophthalmic article, ocular device, and/or biocompatible matrix may be sufficiently soft, flexible and compressible to not adversely affect the natural contraction of the lens capsule around the ocular device (e.g., IOL). In some embodiments, the ophthalmic article, ocular device, and/or biocompatible matrix may be sufficiently soft, flexible and compressible to not abrade the iris if direct contact occurs inside the eye or indirectly through the lens capsule. In some embodiments, the ophthalmic article, ocular device, and/or biocompatible matrix may be sufficiently soft, flexible and compressible to not displace or deflect the iris anterior to an extent that causes angle closure and/or IOP elevation.

In any of the various aspects, positioning of the one or more ophthalmic articles at one or more locations on the ocular device (e.g., intraocular lens) can provide suitable delivery of the one or more active agents and/or diagnostic agents to various locations inside the eye closer to one or more target tissues. For example, the intracapsular positioning of the ophthalmic article within a lens capsule can affect delivery of the active agent and/or diagnostic agent to various locations inside the eye closer to one or more target tissues. The ophthalmic articles, described herein, can associate (e.g., attach) to one or more portions of ocular devices (e.g., intraocular lenses) of varying sizes, shapes and refractive powers or material. In some embodiments, the one or more portions of the ocular device may be an appendage of the ocular device. For example, the appendage may be one or more haptics of an intraocular lens. An ocular device as described herein can be a device (e.g., intraocular lens) which can be implanted inside, outside, or in close proximity to an eye of a subject.

In some embodiments, the ocular device may be an intraocular device. In some embodiments, the ocular device may be an extraocular device. In some embodiments, the ocular device can be an intraocular lens, capsular tension ring, minimally invasive glaucoma surgery device, glaucoma drainage device, drug delivery system, intraocular pressure sensor, retisert implant, port delivery system (e.g., ranibizumab port delivery system), scleral buckle, surgical fixation device, prosthesis, and/or a device that can be implanted inside, outside or in close proximity to an eye for therapeutic and/or diagnostic purposes. In some embodiments, the ocular device is an intraocular lens (IOL). The IOL may be a lens that can be implanted into an eye to provide improved vision and can be combined with one or more of many surgical procedures and apparatus (e.g., cataract surgery and intra-ocular lens inserters). The IOL can be a lens implanted in the eye of a subject as part of a treatment for various eye conditions, as described herein, such as cataracts or myopia. The most common type of IOL is the pseudophakic IOL. These are implanted during cataract surgery, after the cloudy eye's natural lens (e.g., a cataract) has been removed. Usually an IOL replaces the existing crystalline lens, for example because it has been clouded over by a cataract. Alternatively, an intraocular lens may be implanted in addition to the existing crystalline lens. This type of IOL is also referred to as intraocular contact lens or implantable contact lens and is a small corrective lens that is surgically placed in the eye's posterior chamber behind the iris and in front of the lens to correct higher amounts of myopia and hyperopia.

IOLs can comprise a lens (e.g., plastic lens) with one or more side struts (e.g., plastic side struts), called haptics, to hold the lens in place in the capsular bag inside the eye. The haptic can comprise the "optic-haptic" junction, which is a region where the haptic portion of the IOL may be connected to the optic portion of the IOL. In some cases, the haptic and optic-haptic junction may be non-optic portions of the IOL. A haptic may be any size and/or geometry. In some embodiments, the haptic may be linear. In other embodiments, the haptic may be curved. Insertion of an intraocular lens may be the most commonly performed eye surgical procedure; cataracts are the most common eye disease. The procedure can be done under local anesthesia with the patient awake throughout the operation which usually takes less than 30 minutes in the hands of an experienced ophthalmologist. There are foldable intraocular lenses made of acrylic or silicone which can be rolled up and inserted through a tube with a very small incision not requiring any stitches; inflexible lenses (typically made of PMMA (polymethyl methacrylate)) require a larger incision.

FIG. 3A and FIG. 3B schematically illustrate an example of an intraocular lens (IOL) 300 with an ophthalmic article 100 for delivery of an active agent and/or diagnostic agent. FIG. 3A illustrates a plan view of the IOL 300 with an ophthalmic article. FIG. 3B illustrates a side view of the IOL 300 with an ophthalmic article. The IOL 300 comprises a central optic portion 301 with a first haptic 302 attached to the optic portion 301 at a first location 303. A second haptic 304 may be attached to the optic portion 301 at a second location 305. The IOL 300 may also comprise a length 306, a cross sectional length 307, a thickness 308, and an optical diameter 309. The ophthalmic article 100 for delivery of an active agent and/or diagnostic agent may be positioned on the first haptic 302. For example, the ophthalmic article 100 for delivery of the active agent and/or diagnostic agent to the eye may comprise an internal structure 110 with a diameter and circumference sized to accommodate placement onto the first haptic 302 of the IOL 300. In some embodiments, inner diameter or side edge 240 in FIGS. 2A-2H of the hole in the ophthalmic article may be sized to associate or approximate the cross-sectional length 307 and/or a thickness 308 of FIG. 3A and FIG. 3B.

Figure 4B:
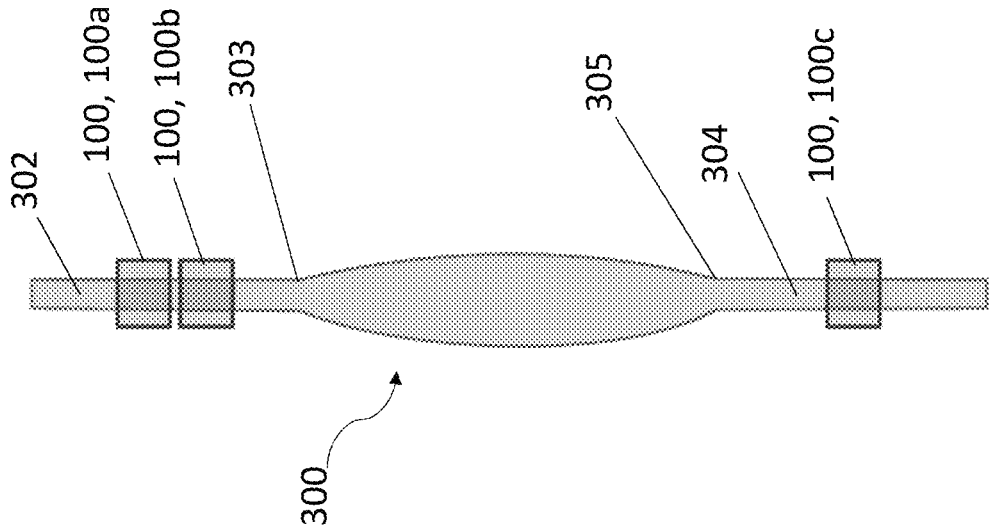
FIG. 4B illustrates a side view of an IOL with ophthalmic articles, in accordance with many embodiments.
Figure 4A:
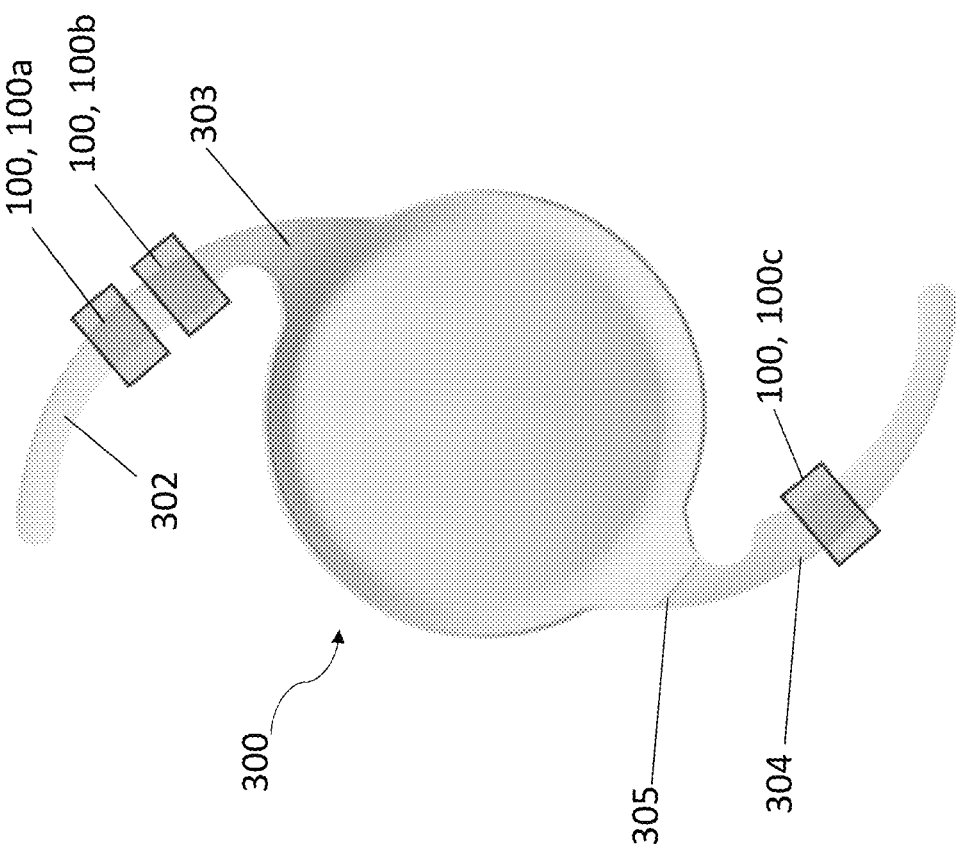
FIG. 4A illustrates a plan view of an IOL with ophthalmic articles, in accordance with many embodiments.

FIG. 4A and FIG. 4B schematically illustrate an example of an intraocular lens (IOL) 300 with several ophthalmic articles 100. FIG. 4A and FIG. 4B schematically illustrate an example of an intraocular lens (IOL) 300 with a first ophthalmic article 100*a*, a second ophthalmic article 100*b*, and a third ophthalmic article 100*c* for delivery of an active agent and/or diagnostic agent into a subject's eye. FIG. 4A illustrates a plan view of the IOL 300 with a first ophthalmic article 100*a*, a second ophthalmic article 100*b*, and a third ophthalmic article 100*c*. FIG. 4B illustrates a side view of the IOL 300 with a first ophthalmic article 100*a*, a second ophthalmic article 100*b*, and a third ophthalmic article 100*c*. The IOL 300 comprises a first haptic 302 associated with the first ophthalmic article 100*a* and the second ophthalmic article 100*b*. The IOL 300 also comprises a second haptic 304 associated with the third ophthalmic article 100*c*.

In some embodiments, at least about 1, 2, 3, 4, 5, 6, 7, 8, 9, 10, 11, 12, 13, 14, 15, 16, 17, 18, 19, 20 or more of the one or more ophthalmic articles may be associated with one or more portions of an ocular device (e.g., haptics of an IOL). In some embodiments, at most about 20, 19, 18, 17, 16, 15, 14, 13, 12, 11, 10, 9, 8, 7, 6, 5, 4, 3, 2, or 1 of the one or more ophthalmic articles may be associated with one or more portions of an ocular device (e.g., haptics of an IOL). In some embodiments, one of the one or more ophthalmic articles may be associated with one or more portions of an ocular device (e.g., haptics of an IOL). In some embodiments, two of the one or more ophthalmic articles may be associated with one or more portions of an ocular device (e.g., haptics of an IOL).

In some embodiments, at least about 1, 2, 3, 4, 5, 6, 7, 8, 9, 10, 11, 12, 13, 14, 15, 16, 17, 18, 19, 20 or more of one or more ophthalmic articles may be associated with one of the one or more portions (e.g., haptics) of an ocular device (e.g., IOL). In some embodiments, at most about 20, 19, 18, 17, 16, 15, 14, 13, 12, 11, 10, 9, 8, 7, 6, 5, 4, 3, 2, or 1 of the one or more ophthalmic articles may be associated with one of the one or more portions (e.g., haptics) of an ocular device (e.g., IOL). In some embodiments, one of the one or more ophthalmic articles may be associated with one of the one or more portions (e.g., haptics) of an ocular device (e.g., IOL). In some embodiments, two of the one or more ophthalmic articles may be associated with one of the one or more portions (e.g., haptics) of an ocular device (e.g., IOL).

In some embodiments, the IOL (e.g., used for cataract surgery in humans) may comprise a length (e.g., length 306) of about 13 mm. In some embodiments, the IOL (e.g., used for cataract surgery in humans) may comprise a length (e.g., length 306) of about 10 mm to about 10.5 mm, about 10 mm to about 11 mm, about 10 mm to about 11.5 mm, about 10 mm to about 12 mm, about 10 mm to about 12.5 mm, about 10 mm to about 13 mm, about 10 mm to about 13.5 mm, about 10 mm to about 14 mm, about 10.5 mm to about 11 mm, about 10.5 mm to about 11.5 mm, about 10.5 mm to about 12 mm, about 10.5 mm to about 12.5 mm, about 10.5 mm to about 13 mm, about 10.5 mm to about 13.5 mm, about 10.5 mm to about 14 mm, about 11 mm to about 11.5 mm, about 11 mm to about 12 mm, about 11 mm to about 12.5 mm, about 11 mm to about 13 mm, about 11 mm to about 13.5 mm, about 11 mm to about 14 mm, about 11.5 mm to about 12 mm, about 11.5 mm to about 12.5 mm, about 11.5 mm to about 13 mm, about 11.5 mm to about 13.5 mm, about 11.5 mm to about 14 mm, about 12 mm to about 12.5 mm, about 12 mm to about 13 mm, about 12 mm to about 13.5 mm, about 12 mm to about 14 mm, about 12.5 mm to about 13 mm, about 12.5 mm to about 13.5 mm, about 12.5 mm to about 14 mm, about 13 mm to about 13.5 mm, about 13 mm to about 14 mm, or about 13.5 mm to about 14 mm.

In some embodiments, the IOL (e.g., used for cataract surgery in humans) may comprise a length (e.g., length 306) of at least about 10 mm, at least about 10.5 mm, at least about 11 mm, at least about 11.5 mm, at least about 12 mm, at least about 12.5 mm, at least about 13 mm, at least about 13.5 mm, or at least about 14 mm.

In some embodiments, the IOL (e.g., used for cataract surgery in humans) may comprise a length (e.g., length 306) of at most about 10 mm, at most about 10.5 mm, at most about 11 mm, at most about 11.5 mm, at most about 12 mm, at most about 12.5 mm, at most about 13 mm, at most about 13.5 mm, or at most about 14 mm.

In some embodiments, the IOL (e.g., used for cataract surgery in humans) may comprise a length (e.g., length 306) of about 10 mm, about 10.5 mm, about 11 mm, about 11.5 mm, about 12 mm, about 12.5 mm, about 13 mm, about 13.5 mm, or about 14 mm.

In some embodiments, the IOL (e.g., used for cataract surgery in humans) may comprise an optic diameter (e.g., optic diameter 309) from about 4 mm to 7 mm.

In some embodiments, the IOL (e.g., used for cataract surgery in humans) may comprise an optic diameter (e.g., optic diameter 309) of about 4 mm to about 4.25 mm, about 4 mm to about 4.5 mm, about 4 mm to about 4.75 mm, about 4 mm to about 5 mm, about 4 mm to about 5.25 mm, about 4 mm to about 5.5 mm, about 4 mm to about 5.75 mm, about 4 mm to about 6 mm, about 4 mm to about 6.25 mm, about 4 mm to about 6.5 mm, about 4 mm to about 6.75 mm, about 4 mm to about 7 mm, about 4.25 mm to about 4.5 mm, about 4.25 mm to about 4.75 mm, about 4.25 mm to about 5 mm, about 4.25 mm to about 5.25 mm, about 4.25 mm to about 5.5 mm, about 4.25 mm to about 5.75 mm, about 4.25 mm to about 6 mm, about 4.25 mm to about 6.25 mm, about 4.25 mm to about 6.5 mm, about 4.25 mm to about 6.75 mm, about 4.25 mm to about 7 mm, about 4.5 mm to about 4.75 mm, about 4.5 mm to about 5 mm, about 4.5 mm to about 5.25 mm, about 4.5 mm to about 5.5 mm, about 4.5 mm to about 5.75 mm, about 4.5 mm to about 6 mm, about 4.5 mm to about 6.25 mm, about 4.5 mm to about 6.5 mm, about 4.5 mm to about 6.75 mm, about 4.5 mm to about 7 mm, about 4.75 mm to about 5 mm, about 4.75 mm to about 5.25 mm, about 4.75 mm to about 5.5 mm, about 4.75 mm to about 5.75 mm, about 4.75 mm to about 6 mm, about 4.75 mm to about 6.25 mm, about 4.75 mm to about 6.5 mm, about 4.75 mm to about 6.75 mm, about 4.75 mm to about 7 mm, about 5 mm to about 5.25 mm, about 5 mm to about 5.5 mm, about 5 mm to about 5.75 mm, about 5 mm to about 6 mm, about 5 mm to about 6.25 mm, about 5 mm to about 6.5 mm, about 5 mm to about 6.75 mm, about 5 mm to about 7 mm, about 5.25 mm to about 5.5 mm, about 5.25 mm to about 5.75 mm, about 5.25 mm to about 6 mm, about 5.25 mm to about 6.25 mm, about 5.25 mm to about 6.5 mm, about 5.25 mm to about 6.75 mm, about 5.25 mm to about 7 mm, about 5.5 mm to about 5.75 mm, about 5.5 mm to about 6 mm, about 5.5 mm to about 6.25 mm, about 5.5 mm to about 6.5 mm, about 5.5 mm to about 6.75 mm, about 5.5 mm to about 7 mm, about 5.75 mm to about 6 mm, about 5.75 mm to about 6.25 mm, about 5.75 mm to about 6.5 mm, about 5.75 mm to about 6.75 mm, about 5.75 mm to about 7 mm, about 6 mm to about 6.25 mm, about 6 mm to about 6.5 mm, about 6 mm to about 6.75 mm, about 6 mm to about 7 mm, about 6.25 mm to about 6.5 mm, about 6.25 mm to about 6.75 mm, about 6.25 mm to about 7 mm, about 6.5 mm to about 6.75 mm, about 6.5 mm to about 7 mm, or about 6.75 mm to about 7 mm.

In some embodiments, the IOL (e.g., used for cataract surgery in humans) may comprise an optic diameter (e.g., optic diameter 309) of at least about 4 mm, 4.25 mm, at least about 4.5 mm, at least about 4.75 mm, at least about 5 mm, at least about 5.25 mm, at least about 5.5 mm, at least about 5.75 mm, at least about 6 mm, at least about 6.25 mm, at least about 6.5 mm, at least about 6.75 mm, or at least about 7 mm. In some embodiments, the IOL (e.g., used for cataract surgery in humans) may comprise an optic diameter (e.g., optic diameter 309) of at most about 4 mm, 4.25 mm, at most about 4.5 mm, at most about 4.75 mm, at most about 5 mm, at most about 5.25 mm, at most about 5.5 mm, at most about 5.75 mm, at most about 6 mm, at most about 6.25 mm, at most about 6.5 mm, at most about 6.75 mm, or at most about 7 mm.

In some embodiments, the IOL (e.g., used for cataract surgery in humans) may comprise an optic diameter (e.g., optic diameter 309) of about 4 mm, 4.25 mm, about 4.5 mm, about 4.75 mm, about 5 mm, about 5.25 mm, about 5.5 mm, about 5.75 mm, about 6 mm, about 6.25 mm, about 6.5 mm, about 6.75 mm, or about 7 mm.

In some embodiments, the IOL haptics may comprise a cross-sectional length (e.g., cross-sectional length 307) from about 0.1 mm to 1.0 mm.

In some embodiments, the IOL haptics may comprise a cross-sectional length (e.g., cross-sectional length 307) of about 0.1 mm to about 0.2 mm, about 0.1 mm to about 0.3 mm, about 0.1 mm to about 0.4 mm, about 0.1 mm to about 0.5 mm, about 0.1 mm to about 0.6 mm, about 0.1 mm to about 0.7 mm, about 0.1 mm to about 0.8 mm, about 0.1 mm to about 0.9 mm, about 0.1 mm to about 1 mm, about 0.2 mm to about 0.3 mm, about 0.2 mm to about 0.4 mm, about 0.2 mm to about 0.5 mm, about 0.2 mm to about 0.6 mm, about 0.2 mm to about 0.7 mm, about 0.2 mm to about 0.8 mm, about 0.2 mm to about 0.9 mm, about 0.2 mm to about 1 mm, about 0.3 mm to about 0.4 mm, about 0.3 mm to about 0.5 mm, about 0.3 mm to about 0.6 mm, about 0.3 mm to about 0.7 mm, about 0.3 mm to about 0.8 mm, about 0.3 mm to about 0.9 mm, about 0.3 mm to about 1 mm, about 0.4 mm to about 0.5 mm, about 0.4 mm to about 0.6 mm, about 0.4 mm to about 0.7 mm, about 0.4 mm to about 0.8 mm, about 0.4 mm to about 0.9 mm, about 0.4 mm to about 1 mm, about 0.5 mm to about 0.6 mm, about 0.5 mm to about 0.7 mm, about 0.5 mm to about 0.8 mm, about 0.5 mm to about 0.9 mm, about 0.5 mm to about 1 mm, about 0.6 mm to about 0.7 mm, about 0.6 mm to about 0.8 mm, about 0.6 mm to about 0.9 mm, about 0.6 mm to about 1 mm, about 0.7 mm to about 0.8 mm, about 0.7 mm to about 0.9 mm, about 0.7 mm to about 1 mm, about 0.8 mm to about 0.9 mm, about 0.8 mm to about 1 mm, or about 0.9 mm to about 1 mm.

In some embodiments, the IOL haptics may comprise a cross-sectional length (e.g., cross-sectional length 307) of at least about 0.1 mm, at least about 0.15 mm, at least about 0.2 mm, at least about 0.25 mm, at least about 0.3 mm, at least about 0.35 mm, at least about 0.4 mm, at least about 0.45 mm, at least about 0.5 mm, at least about 0.55 mm, at least about 0.6 mm, at least about 0.65 mm, at least about 0.7 mm, at least about 0.75 mm, at least about 0.8 mm, at least about 0.85 mm, at least about 0.9 mm, at least about 0.95 mm, or at least about 1 mm. In some embodiments, the IOL haptics may comprise a cross-sectional length (e.g., cross-sectional length 307) of at most about 0.1 mm, at most about 0.15 mm, at most about 0.2 mm, at most about 0.25 mm, at most about 0.3 mm, at most about 0.35 mm, at most about 0.4 mm, at most about 0.45 mm, at most about 0.5 mm, at most about 0.55 mm, at most about 0.6 mm, at most about 0.65 mm, at most about 0.7 mm, at most about 0.75 mm, at most about 0.8 mm, at most about 0.85 mm, at most about 0.9 mm, at most about 0.95 mm, or at most about 1 mm.

In some embodiments, the IOL haptics may comprise a cross-sectional length (e.g., cross-sectional length 307) of about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, or about 1 mm.

In some embodiments, the IOL haptics may comprise a thickness 308 or widest dimension of from about 0.1 mm to 1 mm. In some embodiments, the IOL haptics may comprise a thickness 308 of from about 0.1 mm to about 0.2 mm, about 0.1 mm to about 0.3 mm, about 0.1 mm to about 0.4 mm, about 0.1 mm to about 0.5 mm, about 0.1 mm to about 0.6 mm, about 0.1 mm to about 0.7 mm, about 0.1 mm to about 0.8 mm, about 0.1 mm to about 0.9 mm, about 0.1 mm to about 1 mm, about 0.2 mm to about 0.3 mm, about 0.2 mm to about 0.4 mm, about 0.2 mm to about 0.5 mm, about 0.2 mm to about 0.6 mm, about 0.2 mm to about 0.7 mm, about 0.2 mm to about 0.8 mm, about 0.2 mm to about 0.9 mm, about 0.2 mm to about 1 mm, about 0.3 mm to about 0.4 mm, about 0.3 mm to about 0.5 mm, about 0.3 mm to about 0.6 mm, about 0.3 mm to about 0.7 mm, about 0.3 mm to about 0.8 mm, about 0.3 mm to about 0.9 mm, about 0.3 mm to about 1 mm, about 0.4 mm to about 0.5 mm, about 0.4 mm to about 0.6 mm, about 0.4 mm to about 0.7 mm, about 0.4 mm to about 0.8 mm, about 0.4 mm to about 0.9 mm, about 0.4 mm to about 1 mm, about 0.5 mm to about 0.6 mm, about 0.5 mm to about 0.7 mm, about 0.5 mm to about 0.8 mm, about 0.5 mm to about 0.9 mm, about 0.5 mm to about 1 mm, about 0.6 mm to about 0.7 mm, about 0.6 mm to about 0.8 mm, about 0.6 mm to about 0.9 mm, about 0.6 mm to about 1 mm, about 0.7 mm to about 0.8 mm, about 0.7 mm to about 0.9 mm, about 0.7 mm to about 1 mm, about 0.8 mm to about 0.9 mm, about 0.8 mm to about 1 mm, or about 0.9 mm to about 1 mm.

In some embodiments, the IOL haptics may comprise a thickness 308 or widest dimension of about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, or about 1 mm.

In some embodiments, the IOL haptics may comprise a thickness 308 or widest dimension of at least about 0.1 mm, at least about 0.15 mm, at least about 0.2 mm, at least about 0.25 mm, at least about 0.3 mm, at least about 0.35 mm, at least about 0.4 mm, at least about 0.45 mm, at least about 0.5 mm, at least about 0.55 mm, at least about 0.6 mm, at least about 0.65 mm, at least about 0.7 mm, at least about 0.75 mm, at least about 0.8 mm, at least about 0.85 mm, at least about 0.9 mm, at least about 0.95 mm, or at least about 1 mm. In some embodiments, the IOL haptics may comprise a thickness 308 or widest dimension of at most about 0.1 mm, at most about 0.15 mm, at most about 0.2 mm, at most about 0.25 mm, at most about 0.3 mm, at most about 0.35 mm, at most about 0.4 mm, at most about 0.45 mm, at most about 0.5 mm, at most about 0.55 mm, at most about 0.6 mm, at most about 0.65 mm, at most about 0.7 mm, at most about 0.75 mm, at most about 0.8 mm, at most about 0.85 mm, at most about 0.9 mm, at most about 0.95 mm, or at most about 1 mm In some embodiments, the one or more ophthalmic articles may be associated with ocular devices having portions of any type, such as size, shape, and/or configuration to which the ophthalmic article may be associated with. The manner of association between the ophthalmic article and the ocular device may depend on the size and shape of an internal structure of the ophthalmic article. In some embodiments, the manner of association between the ophthalmic article and the ocular device may depend on the size and shape of a portion of the ocular device (e.g., a haptic on the IOL). In some embodiments, the one or more ophthalmic articles may be associated with intraocular lenses (IOLS) having haptics of any type, such as size, shape, configuration and/or haptics comprising outer surfaces of any type, such as size, shape, texture. For example, the ophthalmic article can be designed, as described herein, to accommodate positioning on one or more portions of the ocular device (e.g., one or more haptics of the intraocular lens). In some embodiments, the ophthalmic article can comprise an internal structure (e.g., a hole) of various shapes and sizes, as disclosed herein, to accommodate placement on the ocular device (e.g., one or more haptics of the intraocular lens).

During the association, a connection (e.g., physical connection) may exist between the ocular device (e.g., one or more haptics of an intraocular lens) and the one or more ophthalmic articles. In some embodiments, the associating comprises indirect association between the one or more ophthalmic articles and one or more portions of the ocular device (e.g., haptics of an intraocular lens). For example, the one or more ophthalmic articles may be indirectly associated to one or more haptics through a barrier layer. In another example, the one ophthalmic article may indirectly associate with the haptic in which the ophthalmic article can rotate or move within a groove or an indent along the haptic, without detaching from the haptic. In some embodiments, associating comprises direct association between the ophthalmic article and the haptics through a chemical bond, physical bond, compressive forces, and/or contractile forces.

In some embodiments, the ophthalmic article may comprise an internal structure that is sized to accommodate placement on a portion of an ocular device. For example, the ophthalmic article may comprise an internal structure (e.g., a hole) that is sized to accommodate placement around a haptic (e.g., haptics with different shapes, sizes, and configurations) of an IOL. In some embodiments, the internal structure (e.g., hole) of the ophthalmic article is sized exactly to fit the cross-sectional dimensions of a portion of an ocular device (e.g., a haptic of an IOL). In other embodiments, the internal structure (e.g., hole) of the ophthalmic article is undersized for the cross-sectional dimensions of the portion of the ocular device (e.g., the haptic of an IOL). In such cases, elasticity of the ophthalmic article and/or at least the portion of the ocular device (e.g., the haptic of an IOL) can allow for application of the ophthalmic article onto the portion of the ocular device without fracturing or permanently distorting a shape of either the ophthalmic article and/or at least the portion of the ocular device. In some embodiments, the portion (e.g., haptic) of the ocular device may comprise one or more regions with a different perimeter (e.g., cross-sectional perimeter) than at least another region of the portion (e.g., haptic) of the ocular device (e.g., IOL).

In some embodiments, the ophthalmic article can stretch beyond the largest perimeter (e.g., cross-sectional perimeter) of the portion (e.g., haptic) of the ocular device (e.g., IOL). In such a case, the movement of the ophthalmic article may be limited by its position at a narrower part of the portion (e.g., haptic) of the ocular device than adjacent regions (e.g. a notch or valley).

One benefit of positioning an undersized ophthalmic article (e.g., undersized internal structure of the ophthalmic article) comprised of a polymeric material (e.g., an elastic polymeric material) on the portion of the ocular device (e.g., the haptic of an IOL) is that the stress and/or strain induced by this arrangement promotes the adherence of the ophthalmic article to the portion of the ocular device (e.g., the haptic of an IOL). Such adherence may be advantageous for preventing displacement of the ophthalmic article from the portion of the ocular device (e.g., the haptic of an IOL) during injection through a narrow aperture during surgery (e.g., cataract surgery). This may be advantageous over other techniques.

In some embodiments, the ophthalmic article may comprise an internal structure (e.g., a hole) that is shaped to accommodate placement around a portion of an ocular device (e.g., portions of the ocular device with different shapes, sizes, and configurations). For example, the ophthalmic article may comprise an internal structure (e.g., a hole) that is shaped to accommodate placement around a haptic (e.g., haptics with different shapes, sizes, and configurations) of an IOL. In some embodiments, the portion of the ocular device (e.g., haptic of an IOL) may be uniformly flat along its outer surface. In other embodiments, the portion of the ocular device (e.g., haptic of an IOL) may comprise at least one indent or groove along its outer surface. The indent or groove may comprise a structure for receiving the circumference of the inner structure of the ophthalmic article. In other embodiments, the portion of the ocular device (e.g., haptic of an IOL) may comprise at least one protrusion along its outer surface. In any of the embodiments, a size and/or shape of the ophthalmic article may be designed, as described herein, so that the ophthalmic article may associate with the portion of the ocular device (e.g., haptic of an IOL).

In some embodiments, the ophthalmic article may be configured to compressively associate to a surface (e.g., an outward surface) of a portion of the ocular device (e.g., haptic of an IOL) to secure the ophthalmic article to the portion of the ocular device. In one example, if an elastic ophthalmic article is associated (e.g., attached) to a hard and/or rigid portion of the ocular device (e.g., haptic of the IOL), the hard and/or rigid portion may not deform in response to a compressive force of the ophthalmic article, but friction resulting from the compressive force may prevent movement between the ophthalmic article and the hard and/or rigid portion. Friction (e.g., coefficient of friction) may be a function of normal force and intrinsic properties of the ophthalmic article and materials of at least a portion of the ocular device. The normal force may be proportional to the stretch on the ophthalmic article and can be a function of the inner circumference of the ophthalmic article relative to the perimeter of, for example, the haptic around which it is stretched.

In another example, if an elastic annulus ophthalmic article is associated (e.g., attached) to a soft haptic, the haptic will narrow in response to the compressive force of the ophthalmic article. Friction resulting from the compressive force may contribute to resistance against movement as well as from the inward contraction of the ophthalmic article into the valley of the haptic.

In some embodiments, the ophthalmic article may be configured to associate with the surface (e.g., an outward surface) of the portion of the ocular device (e.g., haptic of an IOL) through an indent, groove, narrowing, or protrusion along the surface of the portion of the ocular device. For example, the ophthalmic article may comprise an internal structure for securing around a notched region of the haptic of an IOL. In this case, the elastic annulus ophthalmic article can be applied to a notched haptic, such that it is first stretched to an inner circumference at least as large as the outer perimeter of the haptic distal to the notch. Next, the elastic annulus ophthalmic article may be advanced over the notch and allowed to constrict around the narrow portion of the haptic. In this case, friction is less relevant and the sides of the notch secure the ophthalmic article and may prevent dislocation of the ophthalmic article. The ophthalmic article can be hooked in the notch and can freely move or rotate within the notch. Alternatively, the ophthalmic article may be hooked in the notch with restricted movement or rotation within the notch. In another example, the ophthalmic article may be hooked in the notch so that it can compressively associate (e.g., attach) to a surface of the haptic within the notch.

In some embodiments, the association between the ophthalmic article and the ocular device (e.g., one or more haptics of an intraocular lens) is such that handling (e.g., routine handling) of the device prior to implantation and wearing the device after implantation do not lead to a detachment of the ophthalmic article from the ocular device (e.g., one or more haptics of an intraocular lens). In some embodiments, the ophthalmic article is associated in manner so that vision is not impaired. In some embodiments, association may be such that a movement of the ophthalmic article relative to the ocular device (e.g., one or more haptics of an intraocular lens) is not possible. Alternatively, association may be such that the ophthalmic article can be moved relative to the ocular device (e.g., one or more haptics of an intraocular lens).

In some embodiments, the one or more ophthalmic articles may be positioned on one or more portions of an ocular device (e.g., one or more haptics of the IOL). In some embodiments, at least about 1, 2, 3, 4, 5, 9, 10, or more ophthalmic articles may be positioned on one or more portions of an ocular device (e.g., one or more haptics of the IOL). In some embodiments, about 1, 2, 3, 4, 5, 6, 7, 8, 9, or 10 ophthalmic articles may be positioned on one or more portions of an ocular device (e.g., one or more haptics of the IOL). In some embodiments, at most about 10, 9, 8, 7, 6, 5, 4, 3, 2, or 1 ophthalmic articles may be positioned on one portion of an ocular device (e.g., a haptic of the IOL). In some embodiments, the one or more ophthalmic articles may be positioned on one portion of an ocular device (e.g., a haptic of the IOL). In some embodiments, at least about 1, 2, 3, 5, 6, 7, 8, 9, 10, or more ophthalmic articles may be positioned on one portion of an ocular device (e.g., a haptic of the IOL). In some embodiments, about 1, 2, 3, 4, 5, 6, 7, 8, 9, or 10 ophthalmic articles may be positioned on one portion of an ocular device (e.g., a haptic of the IOL). In some embodiments, at most about 10, 9, 8, 7, 6, 5, 4, 3, 2, or 1 ophthalmic articles may be positioned on one portion of an ocular device (e.g., a haptic of the IOL). In some embodiments, at least about 1, 2, 3, 4, 5, 6, 7, 8, 9, 10, or more ophthalmic articles may be associated with an ocular device (e.g., IOL). In some embodiments, at most about 10, 9, 8, 7, 6, 5, 4, 3, 2, or 1 ophthalmic articles may be associated with an ocular device (e.g., IOL). In some embodiments, about 1, 2, 3, 4, 5, 6, 7, 8, 9, or 10 ophthalmic articles may be associated with an ocular device (e.g., IOL).

In some embodiments, one or more ophthalmic articles may be desirable for delivery of either larger quantities of the same active agent and/or diagnostic agent or different active agents and/or diagnostic agents from the same ocular device (e.g., IOL).

Different types of ocular devices can be paired with one or more ophthalmic articles described herein. For example, there are different manufacturers of IOLs, each promoting IOLs with different designs for various clinical conditions. One difference among IOLs is the configuration of the haptics. Some haptics are thicker and wider than others, with sizes ranging from approximately 0.1 to 10 mm in the widest dimension. In some embodiments, the widest dimension of the haptics may be about 0.1 mm to about 20 mm. In some embodiments, the widest dimension of the haptics may be about 0.1 mm to about 0.5 mm, about 0.1 mm to about 1 mm, about 0.1 mm to about 1.5 mm, about 0.1 mm to about 2 mm, about 0.1 mm to about 5 mm, about 0.1 mm to about 10 mm, about 0.1 mm to about 20 mm, about 0.5 mm to about 1 mm, about 0.5 mm to about 1.5 mm, about 0.5 mm to about 2 mm, about 0.5 mm to about 5 mm, about 0.5 mm to about 10 mm, about 0.5 mm to about 20 mm, about 1 mm to about 1.5 mm, about 1 mm to about 2 mm, about 1 mm to about 5 mm, about 1 mm to about 10 mm, about 1 mm to about 20 mm, about 1.5 mm to about 2 mm, about 1.5 mm to about 5 mm, about 1.5 mm to about 10 mm, about 1.5 mm to about 20 mm, about 2 mm to about 5 mm, about 2 mm to about 10 mm, about 2 mm to about 20 mm, about 5 mm to about 10 mm, about 5 mm to about 20 mm, or about 10 mm to about 20 mm. In some embodiments, the widest dimension of the haptics may be at least about 0.1 mm, at least about 0.5 mm, at least about 1 mm, at least about 1.5 mm, at least about 2 mm, at least about 5 mm, at least about 10 mm, or at least about 20 mm. In some embodiments, the widest dimension of the haptics may be at most about 0.1 mm, at most about 0.5 mm, at most about 1 mm, at most about 1.5 mm, at most about 2 mm, at most about 5 mm, at most about 10 mm, or at most about 20 mm. In some embodiments, when the haptic is curved, this dimension can refer to the length of the curve.

The ophthalmic articles, described herein, may accommodate one or more portions of an ocular device. The portions may comprise of different sizes, shapes, and configurations (e.g., notched haptic, groove haptic, haptic with one or more protrusions, rigid haptic, soft haptic) among different ocular devices. In some embodiments, the ophthalmic articles, described herein, may accommodate haptics of different sizes, shapes, and configurations (e.g., notched haptic, groove haptic, haptic with one or more protrusions, rigid haptic, soft haptic). Because of the elasticity and flexibility of the materials and designs, disclosed herein, for the ophthalmic articles, one advantage is that the ophthalmic article may not need to be sized exactly to fit a given ocular device (e.g., IOL) and could be used interchangeably with multiple types of ocular devices (e.g., brands and models that have slightly different sized haptics). The ophthalmic articles, disclosed herein, may also be designed and produced in categorical size ranges (e.g. small, medium, large) to be used with portions of ocular devices (e.g., IOLs with haptics) of varying size ranges (e.g., 0.1 to 0.2 mm, 0.3 to 0.4 mm and 0.5 to 0.6).

It is desirable for cataract surgeons to have flexibility to select IOLs of different sizes, shapes and refractive power for different clinical conditions. In various embodiments of the invention, the drug delivery article is manufactured and supplied separately from the IOL to allow physicians to use it with different types of IOLs. In other embodiments, the drug delivery article and IOL are manufactured and/or supplied to the surgeon as a single product.

In one or more embodiments, the intraocular lens is selected from a range of refractive powers (e.g. 5 to 30 D in increments of 0.5 D). In some embodiments, the refractive power of the intraocular lens may be at least about 5, at least about 5.5, at least about 6, at least about 6.5, at least about 7, at least about 7.5, at least about 8, at least about 8.5, at least about 9, at least about 9.5, at least about 10, at least about 10.5, at least about 11, at least about 11.5, at least about 12, at least about 12.5, at least about 13, at least about 13.5, at least about 14, at least about 14.5, at least about 15, at least about 15.5, at least about 16, at least about 16.5, at least about 17, at least about 17.5, at least about 18, at least about 18.5, at least about 19, at least about 19.5, at least about 20, at least about 20.5, at least about 21, at least about 21.5, at least about 22, at least about 22.5, at least about 23, at least about 23.5, at least about 24, at least about 24.5, at least about 25, at least about 25.5, at least about 26, at least about 26.5, at least about 27, at least about 27.5, at least about 28, at least about 28.5, at least about 29, at least about 29.5, or at least about 30. In some embodiments, the refractive power of the intraocular lens may be at most about 5, at most about 5.5, at most about 6, at most about 6.5, at most about 7, at most about 7.5, at most about 8, at most about 8.5, at most about 9, at most about 9.5, at most about 10, at most about 10.5, at most about 11, at most about 11.5, at most about 12, at most about 12.5, at most about 13, at most about 13.5, at most about 14, at most about 14.5, at most about 15, at most about 15.5, at most about 16, at most about 16.5, at most about 17, at most about 17.5, at most about 18, at most about 18.5, at most about 19, at most about 19.5, at most about 20, at most about 20.5, at most about 21, at most about 21.5, at most about 22, at most about 22.5, at most about 23, at most about 23.5, at most about 24, at most about 24.5, at most about 25, at most about 25.5, at most about 26, at most about 26.5, at most about 27, at most about 27.5, at most about 28, at most about 28.5, at most about 29, at most about 29.5, or at most about 30.

In some embodiments, the ophthalmic article's and/or ocular device's size, shape, and material properties can aid in its compressibility, flexibility, and/or elasticity when fitting through an intraocular injector and an incision size (e.g., 2.2 mm) suitable for ocular surgery. In some embodiments, the material (e.g., biocompatible polymer) may be sufficiently compressible and flexible such that it is compatible with injection through an IOL injector designed for a small corneal incision. In some embodiments, the material (e.g., biocompatible copolymer matrix) may be sufficiently compressible, such that it is compatible with injection through an IOL injector that comprises an injector tip inner diameter from about 0.5 to 3 mm (e.g., from about 1.2 mm to 1.8 mm). In some embodiments, the material (e.g., biocompatible copolymer matrix) may be sufficiently flexible such that it is compatible with injection through an IOL injector that comprises an injector tip inner diameter from about 0.5 to 3 mm (e.g., from about 1.2 mm to 1.8 mm). In some embodiments, the material (e.g., biocompatible polymer) may be sufficiently elastic such it recovers its original shape after injection through an IOL injector designed for a small corneal incision. In some embodiments, the material (e.g., biocompatible copolymer matrix) may be sufficiently elastic such that it recovers its original shape after injection through an IOL injector that comprises an injector tip inner diameter from about 0.5 to 3 mm (e.g., from about 1.2 mm to 1.8 mm).

In another aspect, the present disclosure provides an ophthalmic article. In some embodiments, the ophthalmic article comprises a biocompatible copolymer matrix derived from about 40 wt % of a caprolactone monomer and 60 wt % of a lactide monomer. In some embodiments, the ophthalmic article comprises an active agent and/or a diagnostic agent. In some embodiments, the ophthalmic article comprises at least one of the following characteristics: (i) the biocompatible copolymer matrix comprises a random copolymer; (ii) the ophthalmic article has a tensile strength from about 25 Megapascal (MPa) to 35 MPa; (iii) the ophthalmic article has a glass transition temperature of at most about 24° C. as measured by differential scanning calorimetry; (iv) the ophthalmic article has an elasticity modulus of at most about 3 MPa; (v) the ophthalmic article has an elongation at break from about 500% to 1500% at 18-24° C.; and (vi) the ophthalmic article comprises an outer diameter of at most 1.5 mm. In some embodiments, the ophthalmic article is configured to associate (e.g., attach) to a haptic of an intraocular lens (IOL).

In another aspect, the present disclosure provides an ophthalmic drug delivery system. The ophthalmic drug delivery system may comprise one or more ophthalmic articles comprising (1) one or more therapeutic agents, and (2) a biocompatible copolymer matrix derived from about 40 wt % of a caprolactone monomer and 60 wt % of a lactide monomer. In some embodiments, the one or more ophthalmic articles comprises at least one of the following characteristics: (i) biocompatible copolymer matrix comprises a random copolymer; (ii) the one or more ophthalmic articles has a tensile strength from about 25 Megapascal (MPa) to 35 MPa; (iii) the one or more ophthalmic articles has a glass transition temperature of at most about 24° C. as measured by differential scanning calorimetry; (iv) the one or more ophthalmic articles has an elasticity modulus of at most about 3 MPa; (v) the one or more ophthalmic articles has an elongation at break from about 500% to 1500% at 18-24° C. The ophthalmic drug delivery system may also comprise one or more intraocular lenses (IOLs) comprising one or more haptics. In some embodiments, the one or more ophthalmic articles comprises an outer diameter of at most 1.5 mm and is configured to associate (e.g., attach) to the one or more haptics of the one or more IOLs.

In another aspect, the present disclosure provides a kit. The kit may comprise a container comprising one or more ophthalmic articles (e.g., drug delivery articles). The ophthalmic article may comprise a material (e.g., a biocompatible matrix). The biocompatible matrix may comprise a copolymer derived from a first monomer (e.g., caprolactone monomer) and at least one other monomer. The ophthalmic article may also comprise one or more active agents and/or diagnostic agents. In some embodiments, the kit can comprise instructions for use.

In another aspect, the present disclosure provides a kit. The kit may comprise a first container comprising one or more ophthalmic articles (e.g., drug delivery articles). The ophthalmic article may comprise a material (e.g., a biocompatible matrix). The biocompatible matrix may comprise a copolymer derived from a first monomer (e.g., caprolactone monomer) and at least one other monomer. The ophthalmic article may also comprise one or more active agents and/or diagnostic agents. The kit may also comprise a second container comprising one or more ocular devices (e.g., intraocular lenses with one or more haptics) comprising one or more portions for associating with the one or more ophthalmic articles. The kit may also comprise instructions for use.

The kit may comprise one or more elements disclosed herein in relation to any of the various aspects, in any combination. Materials in a kit may be contained in any suitable container and may be in an immediately usable form or require combination with other materials in the kit or materials supplied by a user. The kit may provide one or more tools for handling and one or more ophthalmic article disclosed herein. In some embodiments, the kit may provide an applicator tool for facilitating association of the ophthalmic article to the ocular device. The kit may provide one or more tools for handling and compressing an ocular device with one or more ophthalmic article associated thereto and disclosed herein. In some embodiments, the one or more tools may be forceps.

The system and/or kit may provide one or more ocular device injectors (e.g., intraocular lens injectors).

In some embodiments, the system and/or kits may comprise materials for performing cataract surgery. In some embodiments, the system and/or kits may comprise drapes (e.g., sterile drapes), gloves (e.g., sterile gloves), disinfectant, topical anesthetic, dilating agents, knives, blades, postoperative medications (separate from active agents and/or diagnostic agents provided in the ophthalmic article), surgical viscoelastic substance, sutures, gauze, tape, and/or eye patches.

In some embodiments, a delivery tool may be used to implant the ocular device with the one or more ophthalmic articles into the eye of a subject. Suitable delivery tools may comprise a needle or needle-like applicator.

The delivery tool may be an injector or a syringe with an appropriately sized needle or may be a injector-like tool or syringe-like tool with a needle-like applicator. In some embodiments, the delivery tool may have an injector tip inner diameter from about 1.2 mm to 1.7 mm.

In some embodiments, the delivery tool may have an injector tip inner diameter of about 1.2 mm to about 1.25 mm, about 1.2 mm to about 1.3 mm, about 1.2 mm to about 1.35 mm, about 1.2 mm to about 1.4 mm, about 1.2 mm to about 1.45 mm, about 1.2 mm to about 1.5 mm, about 1.2 mm to about 1.55 mm, about 1.2 mm to about 1.6 mm, about 1.2 mm to about 1.65 mm, about 1.2 mm to about 1.7 mm, about 1.25 mm to about 1.3 mm, about 1.25 mm to about 1.35 mm, about 1.25 mm to about 1.4 mm, about 1.25 mm to about 1.45 mm, about 1.25 mm to about 1.5 mm, about 1.25 mm to about 1.55 mm, about 1.25 mm to about 1.6 mm, about 1.25 mm to about 1.65 mm, about 1.25 mm to about 1.7 mm, about 1.3 mm to about 1.35 mm, about 1.3 mm to about 1.4 mm, about 1.3 mm to about 1.45 mm, about 1.3 mm to about 1.5 mm, about 1.3 mm to about 1.55 mm, about 1.3 mm to about 1.6 mm, about 1.3 mm to about 1.65 mm, about 1.3 mm to about 1.7 mm, about 1.35 mm to about 1.4 mm, about 1.35 mm to about 1.45 mm, about 1.35 mm to about 1.5 mm, about 1.35 mm to about 1.55 mm, about 1.35 mm to about 1.6 mm, about 1.35 mm to about 1.65 mm, about 1.35 mm to about 1.7 mm, about 1.4 mm to about 1.45 mm, about 1.4 mm to about 1.5 mm, about 1.4 mm to about 1.55 mm, about 1.4 mm to about 1.6 mm, about 1.4 mm to about 1.65 mm, about 1.4 mm to about 1.7 mm, about 1.45 mm to about 1.5 mm, about 1.45 mm to about 1.55 mm, about 1.45 mm to about 1.6 mm, about 1.45 mm to about 1.65 mm, about 1.45 mm to about 1.7 mm, about 1.5 mm to about 1.55 mm, about 1.5 mm to about 1.6 mm, about 1.5 mm to about 1.65 mm, about 1.5 mm to about 1.7 mm, about 1.55 mm to about 1.6 mm, about 1.55 mm to about 1.65 mm, about 1.55 mm to about 1.7 mm, about 1.6 mm to about 1.65 mm, about 1.6 mm to about 1.7 mm, or about 1.65 mm to about 1.7 mm.

In some embodiments, the delivery tool may have an injector tip inner diameter of at least about 1.2 mm, at least about 1.25 mm, at least about 1.3 mm, at least about 1.35 mm, at least about 1.4 mm, at least about 1.45 mm, at least about 1.5 mm, at least about 1.55 mm, at least about 1.6 mm, at least about 1.65 mm, or at least about 1.7 mm. In some embodiments, the delivery tool may have an injector tip inner diameter of about 1.2 mm, about 1.25 mm, about 1.3 mm, about 1.35 mm, about 1.4 mm, about 1.45 mm, about 1.5 mm, about 1.55 mm, about 1.6 mm, about 1.65 mm, or about 1.7 mm. In some embodiments, the delivery tool may have an injector tip inner diameter of at most about 1.2 mm, at most about 1.25 mm, at most about 1.3 mm, at most about 1.35 mm, at most about 1.4 mm, at most about 1.45 mm, at most about 1.5 mm, at most about 1.55 mm, at most about 1.6 mm, at most about 1.65 mm, or at most about 1.7 mm.

In some embodiments, the delivery tool may have the injector tip inner diameter of about 0.5 mm to about 3 mm. In some embodiments, the delivery tool may have the injector tip inner diameter of about 0.5 mm to about 1 mm, about 0.5 mm to about 1.5 mm, about 0.5 mm to about 2 mm, about 0.5 mm to about 2.5 mm, about 0.5 mm to about 3 mm, about 1 mm to about 1.5 mm, about 1 mm to about 2 mm, about 1 mm to about 2.5 mm, about 1 mm to about 3 mm, about 1.5 mm to about 2 mm, about 1.5 mm to about 2.5 mm, about 1.5 mm to about 3 mm, about 2 mm to about 2.5 mm, about 2 mm to about 3 mm, or about 2.5 mm to about 3 mm. In some embodiments, the delivery tool may have the injector tip inner diameter of at least about 0.5 mm, at least about 1 mm, at least about 1.5 mm, at least about 2 mm, at least about 2.5 mm, or at least about 3 mm. In some embodiments, the delivery tool may have the injector tip inner diameter of at most about 0.5 mm, at most about 1 mm, at most about 1.5 mm, at most about 2 mm, at most about 2.5 mm, or at most about 3 mm. In some embodiments, the delivery tool may have the injector tip inner diameter of about 1 mm to about 2 mm. In some embodiments, the delivery tool may have the injector tip inner diameter of about 1.2 mm to about 1.7 mm. In some embodiments, the delivery tool may have the injector tip inner diameter of at most about 2 mm. In some embodiments, the delivery tool may have the injector tip inner diameter of at least about 1 mm.

In some embodiments, the ocular device with the one or more ophthalmic articles may be loaded into the delivery tool prior to packaging. In this example, once the kit is opened, the delivery implant may be ready for use. In some embodiments, the kit components may be sterilized individually and combined into the kit. In some embodiments, the kit components may be sterilized after being combined into the kit.

Methods

In another aspect, the present disclosure provides a method for preparing at least one drug-releasing ocular device (e.g., a drug-releasing intraocular lens). In some embodiments, one or more active agents and/or diagnostic agents may be combined with a material (e.g., biocompatible matrix) to generate one or more ophthalmic articles. The biocompatible matrix may comprise a copolymer derived from a first monomer (e.g., caprolactone monomer) and at least a second monomer. The one or more ophthalmic articles may then be associated to one or more portions of an ocular device (e.g., haptics of an intraocular lens).

In another aspect, the present disclosure provides a method for treating or preventing a disease, condition, and/or complication. One or more active agents and/or diagnostic agents may be combined with a biocompatible matrix (e.g., a biocompatible copolymer matrix) to generate one or more ophthalmic articles. The one or more ophthalmic articles may be associated to one or more portions of an ocular device (e.g., haptics of an intraocular lens), thereby generating at least one active agent and/or diagnostic agent releasing ocular device (e.g., active agent and/or diagnostic agent releasing intraocular lens). The active agent and/or diagnostic agent releasing ocular device may be an ocular device associated to an ophthalmic article that comprises one or more active agents and/or diagnostic agents. The at least one active agent and/or diagnostic agent releasing ocular device may be implanted into an eye of a subject in need thereof for sustained intraocular active agent and/or diagnostic agent delivery. In some embodiments, within 7 days after implantation the one or more ophthalmic articles releases the one or more active agents and/or diagnostic agents and results in an inflammation score of at most 1 (e.g., as measured by an anterior chamber cell score using slit lamp biomicroscopy) and/or absence of eye pain.

In another aspect, the present disclosure provides a method of treating or preventing a disease, condition, and/or complication. One or more ophthalmic articles may be associated to one or more portions of an ocular device (e.g., haptics of at least one intraocular lens), thereby generating at least one active agent and/or diagnostic agent releasing ocular device (e.g., active agent and/or diagnostic agent releasing intraocular lens). The at least one active agent and/or diagnostic agent releasing ocular device may be implanted into an eye of a subject in need thereof for sustained intraocular active agent and/or diagnostic agent delivery. In some embodiments, within 7 days after implantation, the one or more ophthalmic articles releases the one or more active agents and/or diagnostic agents and results in an inflammation score of at most 1 (e.g., as measured by an anterior chamber cell score using slit lamp biomicroscopy) and/or absence of eye pain (e.g., as measure by a 10-point visual analog scale).

In another aspect, the present disclosure provides a method of treating or preventing a disease, condition, or a complication. In some embodiments, one or more ophthalmic articles may be implanted into an eye of a subject in need thereof for sustained intraocular drug delivery. In some embodiments, one or more ocular devices (e.g., an intraocular lens) may be implanted into an eye of a subject in need thereof for sustained intraocular drug delivery. The IOL having one or more drug release articles associated thereto, wherein said one or more drug release articles comprises one or more active agents (e.g., therapeutic agents), wherein within 7 days after implantation said one or more drug release articles releases said one or more therapeutic agents and results in an inflammation score of at most 1 (e.g., as measured by an anterior chamber cell score using slit lamp biomicroscopy) and/or absence of eye pain (e.g., as measure by a 10-point visual analog scale).

In another aspect, the present disclosure provides a method of administering an active or diagnostic agent. One or more active agents and/or diagnostic agents may be combined with a biocompatible matrix (e.g., biocompatible copolymer matrix), thereby generating one or more ophthalmic articles. One or more ophthalmic articles may be associated to one or more portions of one or more ocular devices (e.g., haptics of an intraocular lens), thereby generating at least one active agent and/or diagnostic agent releasing ocular device (e.g., active agent and/or diagnostic agent releasing intraocular lens). Then, the at least one active agent and/or diagnostic agent releasing ocular device may be compressed through an ocular device injector (e.g., intraocular lens injector). In some embodiments, the ocular device injector may comprise an injector tip inner diameter from about 0.5 mm to 3 mm (e.g., about 1.2 to 1.7 mm). Next, the at least one active agent and/or diagnostic agent releasing ocular device (e.g., active agent and/or diagnostic agent releasing intraocular lens) may be implanted into an eye of a subject in need thereof for sustained intraocular active agent and/or diagnostic agent delivery.

In another aspect, the present disclosure provides a method of administering an active and/or diagnostic agent. One or more ocular devices (e.g., intraocular lens) having one or more ophthalmic articles associated thereto may be compressed through an ocular device injector (intraocular injector), thereby generating a compressed ocular device (e.g., intraocular lens) having one or more ophthalmic articles associated thereto. The ocular device injector (e.g., an intraocular device injector) may comprise an injector tip. The injector tip may comprise an inner diameter from about 1.2 to 1.7 mm. The compressed ocular device (e.g., intraocular lens) having one or more ophthalmic articles associated thereto may be implanted into an eye of a subject in need thereof for sustained ocular active agent and/or diagnostic agent delivery.

In another aspect, the present disclosure provides a method of active agent (e.g., drug) and/or diagnostic agent delivery. The method may comprise providing an article (e.g., ophthalmic article) for delivery of an active agent (e.g., drug) and/or diagnostic agent to an eye, as described herein. The method may also comprise associating (e.g., positioning) the article (e.g., ophthalmic article) on one or more haptics of an intraocular lens.

In another aspect, the present disclosure provides a method of diagnosing a disease or condition of an eye of a subject. The method may comprise administering into an eye of a subject in need thereof one or more ocular devices (e.g., an intraocular lens) for delivery of one or more diagnostic agents to the eye of the subject. The one or more ocular devices may comprise one or more ophthalmic articles associated thereto. The one or more ophthalmic article may comprise one or more diagnostic agents selected from the group consisting of paramagnetic molecules, fluorescent compounds, magnetic molecules, radionuclides, x-ray imaging agents, and contrast media.

Figure 6:
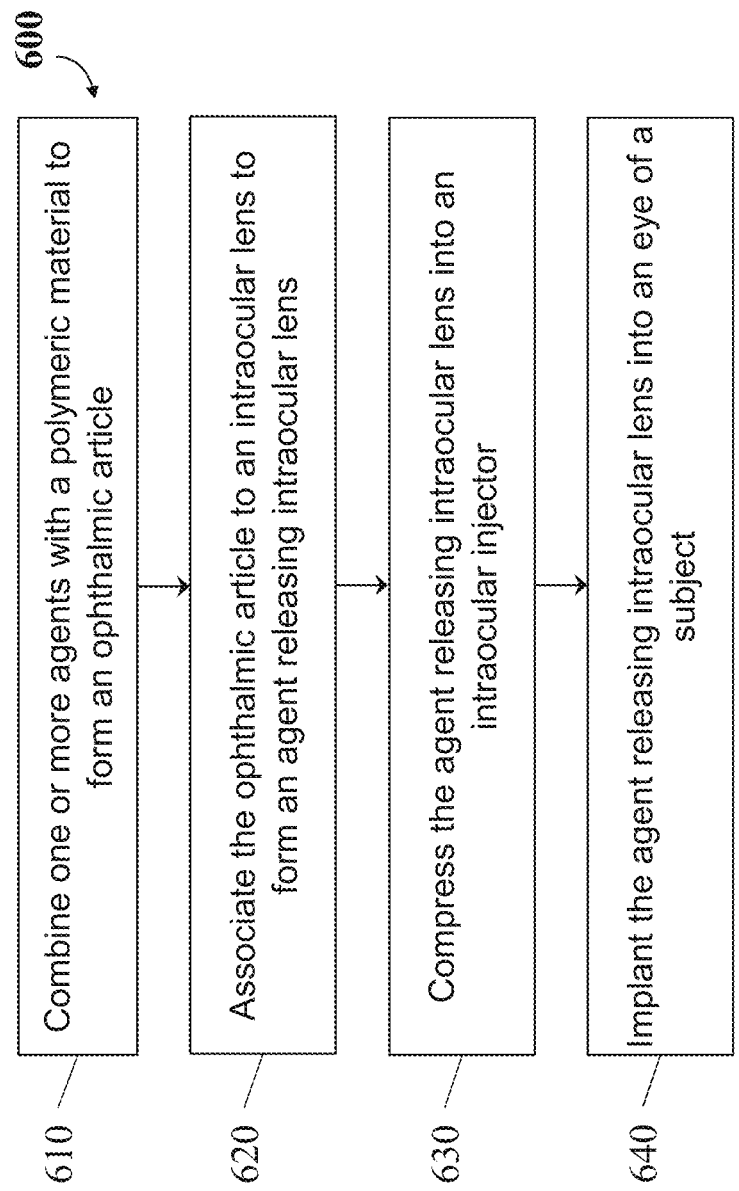
FIG. 6 schematically illustrates an example of an administration, treatment, and/or diagnosis method, in accordance with many embodiments.

FIG. 6 schematically illustrates an example of an administration, treatment, and/or diagnosis method ("method") 600. The method comprises combining one or more active agents and/or diagnostic agents with a polymeric material (e.g., biocompatible polymer matrix), thereby generating one or more ophthalmic articles (process 610). Next, the method comprises associating the one or more ophthalmic articles to one or more haptics of at least one intraocular lens, thereby generating at least one active agent and/or diagnostic agent releasing intraocular lens (process 620). The ophthalmic article comprises one or more components, as provided herein. In an example, the ophthalmic article may be an embodiment of the aforementioned ophthalmic article as illustrated in, for example, FIG. 1A, FIG. 1B, FIGS. 2A-2H, FIG. 3A, FIG. 3B, FIG. 4A, and/or FIG. 4B. The intraocular lens may also comprise one or more components, as provided herein. In another example, the intraocular lens may be an embodiment of the intraocular lens as illustrated in FIG. 3A, FIG. 3B, FIG. 4A, and/or FIG. 4B. Referring to FIG. 6, the method further comprises compressing the at least one active agent and/or diagnostic agent releasing intraocular lens through an intraocular lens injector (e.g., an intraocular lens injector comprising an injector tip inner diameter from about 0.5 mm to 3 mm, such as 1.2 mm to 1.7 mm) (process 630). The method may then comprise implanting (e.g., using standard microsurgical cataract surgery technique) the at least one active agent and/or diagnostic agent releasing intraocular lens into an eye of a subject in need thereof for sustained intraocular active agent and/or diagnostic agent delivery (process 640).

In any of the various aspects, the method can also comprise compressing or shaping the ocular device having one or more ophthalmic articles associated thereto prior to implanting it into an eye. In order to accommodate delivery through the ocular device (e.g., IOL injector device), whose tips can have inner diameters of 0.5 mm to 3 mm (e.g., 1.2 to 1.7 mm), foldable ocular device having one or more ophthalmic articles associated thereto may be manufactured from compressible, flexible materials, as disclosed herein, with sufficient elasticity to facilitate rapid unfolding inside the eye with retention of the original device size, shape and optical properties.

Eye surgeons may be able to use an ocular device (e.g., an injector device) with one or more ophthalmic articles associated thereto in the same manner as a conventional IOL. In some embodiments, surgery (e.g., cataract surgery) can involve insertion of one or more ocular devices with one or more ophthalmic articles associated (e.g., attached) thereto using an injector device. In some embodiments, the condition may be a condition arising from or aggravated by implantation of an ocular device. In some embodiments, the condition may be a condition present prior to implantation. In some cases, the condition may not link directly to the condition being treated by surgery. In some embodiments, one ocular device may be delivered (e.g., implanted) into, in proximity, or around an eye of a subject. In some embodiments, two ocular devices may be delivered (e.g., implanted) into, in proximity, or around an eye of a subject. In some embodiments, 2, 3, 4, 5, 6, 7 ocular devices may be delivered (e.g., implanted) into, in proximity, or around an eye of a subject. In some embodiments, the ophthalmic article can include a polymeric material (e.g., a biodegradable copolymer matrix) that is formulated to provide sustained release of an effective amount (e.g., a therapeutically effective amount) of the active agent and/or diagnostic agent during a release period. Where the ophthalmic article includes a biodegradable polymeric matrix, the biodegradable polymeric matrix can be allowed to biodegrade to provide sustained release of the active agent and/or diagnostic agent to the eye during a release period.

Prior to injection into the eye, the ocular device (with one or more ophthalmic articles associated thereto) may be folded or compressed (e.g., in a cassette) and/or loaded into the injector device (e.g., intraocular lens injector) comprising an injector tip inner diameter from about 0.5 mm to 3 mm (e.g., about 1.2 to 1.7 mm). In some embodiments, compressing may comprise folding the intraocular lens with the ophthalmic article associated thereto into a tubular shape through the injector device (e.g., IOL injector that comprises an injector tip inner diameter from about 0.5 mm to 3 mm, such as about 1.2 to 1.7 mm).

In some embodiments, folding tools (e.g., forceps) may be used to fold an ocular device (e.g., intraocular device) in half for insertion through an incision size from about 1.5 mm to 3 mm. In other embodiments, folding tools (e.g., forceps) may be used to roll an ocular device for insertion through an incision size from about 1.5 mm to 3 mm.

In some embodiments, folding tools may be used to roll the ocular device for insertion through an incision size from about 0.1 mm to about 5 mm. In some embodiments, folding tools may be used to roll the ocular device for insertion through an incision size from about 1.5 mm to about 2.5 mm. In some embodiments, folding tools may be used to roll the ocular device for insertion through an incision size from about 0.1 mm to about 0.5 mm, about 0.1 mm to about 1 mm, about 0.1 mm to about 1.5 mm, about 0.1 mm to about 2 mm, about 0.1 mm to about 2.5 mm, about 0.1 mm to about 3 mm, about 0.1 mm to about 3.5 mm, about 0.1 mm to about 4 mm, about 0.1 mm to about 4.5 mm, about 0.1 mm to about 5 mm, about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1 mm to about 4.5 mm, about 1 mm to about 5 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 1.5 mm to about 4.5 mm, about 1.5 mm to about 5 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 3 mm to about 3.5 mm, about 3 mm to about 4 mm, about 3 mm to about 4.5 mm, about 3 mm to about 5 mm, about 3.5 mm to about 4 mm, about 3.5 mm to about 4.5 mm, about 3.5 mm to about 5 mm, about 4 mm to about 4.5 mm, about 4 mm to about 5 mm, or about 4.5 mm to about 5 mm.

In some embodiments, folding tools may be used to roll the ocular device for insertion through an incision size of at least about 0.1 mm, at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, or at least about 5 mm. In some embodiments, folding tools may be used to roll the ocular device for insertion through an incision size of at least about 1.5 mm. In some embodiments, folding tools may be used to roll the ocular device for insertion through an incision size of at least about 1.8 mm.

In some embodiments, folding tools may be used to roll the ocular device for insertion through an incision size of at most about 0.1 mm, at most about 0.5 mm, at most about 1 mm, at most about 1.5 mm, at most about 2 mm, at most about 2.5 mm, at most about 3 mm, at most about 3.5 mm, at most about 4 mm, at most about 4.5 mm, or at most about 5 mm. In some embodiments, folding tools may be used to roll the ocular device for insertion through an incision size of at most about 2 mm. In some embodiments, folding tools may be used to roll the ocular device for insertion through an incision size of at most about 3 mm.

In some embodiments, the method comprises introducing an ocular device (e.g., intraocular lens) containing the ophthalmic article into the eye by ejecting the ocular device from an ocular device injector (e.g., intraocular injector). For example, the method can comprise inserting the ocular device (e.g., IOL) with one or more ophthalmic articles associated thereto into the eye (e.g., lens capsule or ciliary sulcus of an eye) to deliver an active agent and/or diagnostic agent to the eye of a subject. The ocular device with the one or more ophthalmic articles associated thereto may be able to be folded, loaded and inserted into an eye through incisions consistent with current standard of care.

In some embodiments, the ophthalmic article for active agent and/or diagnostic agent delivery to the eye may comprise a compressible, flexible and/or elastic polymer that, when positioned on a portion of the ocular device (e.g., haptic of an IOL), does not interfere with injection of the ocular device and the ophthalmic article through a standard injector device or unfolding of the IOL inside the eye following injection.

In some embodiments, the biocompatible matrix and/or the ophthalmic article is sufficiently compressible such that it is compatible with injection through an intraocular injector (e.g., IOL injector) that comprises an injector tip inner diameter from about 0.5 mm to 3 mm (e.g., about 1.2 to 1.7 mm). In some embodiments, the biocompatible matrix and/or the ophthalmic article is sufficiently flexible such that it is compatible with injection through an intraocular injector (e.g., IOL injector) that comprises an injector tip inner diameter from about 0.5 mm to 3 mm (e.g., about 1.2 to 1.7 mm). In some embodiments, the biocompatible matrix and/or the ophthalmic article is sufficiently elastic such that it recovers its original shape after injection through intraocular injector (e.g., IOL injector) that comprises an injector tip inner diameter from about 0.5 mm to 3 mm (e.g., about 1.2 to 1.7 mm).

Figure 5A:
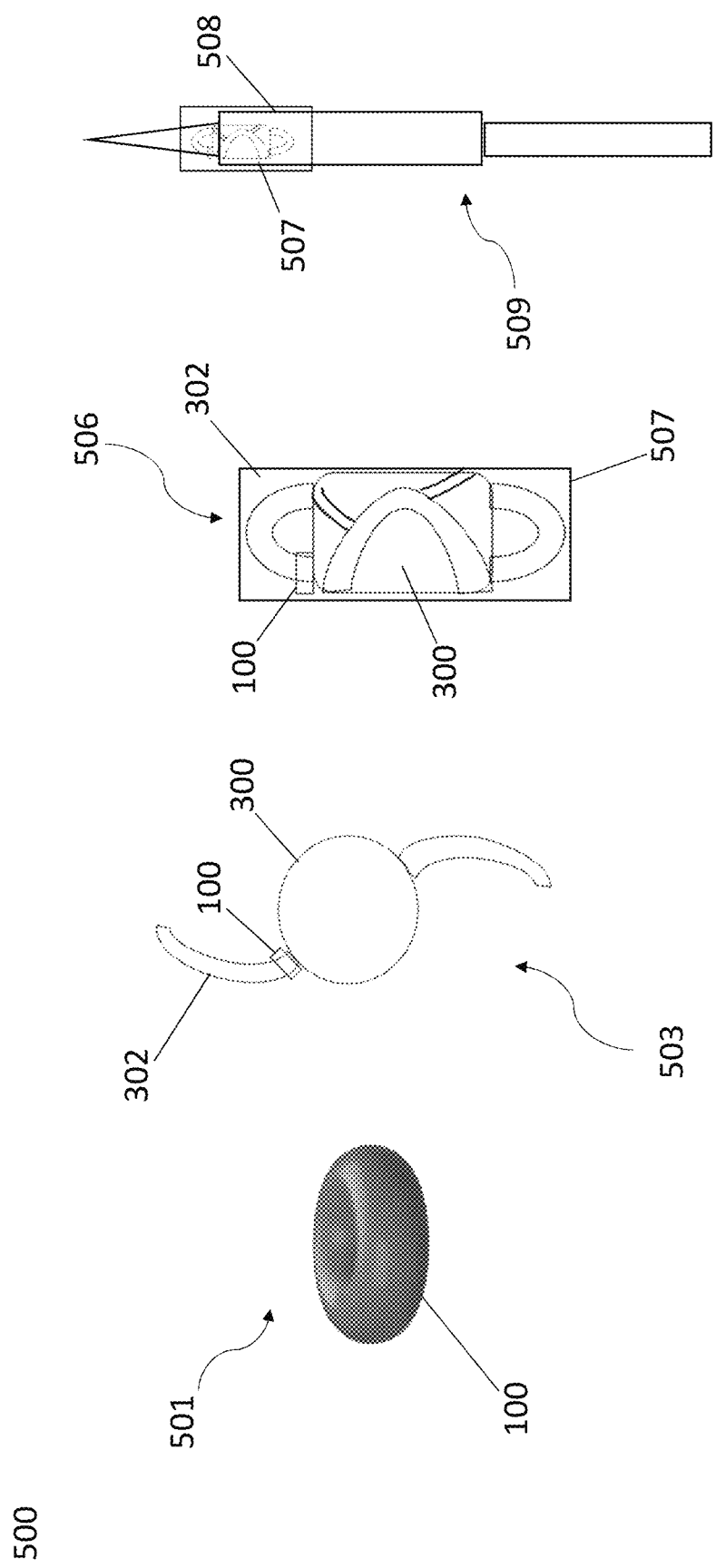
FIG. 5A schematically illustrates an example of a loading method, in accordance with many embodiments.

FIG. 5A schematically illustrates an example of a loading method ("the method") 500 for loading an ocular device (e.g., intraocular device) with one or more ophthalmic articles associated thereto into an injector device. In this example, the loading method may be an embodiment for a method for treating or preventing a disease, condition, and/or complication. The loading method may also be an embodiment for a method for administering an active agent and/or a diagnostic agent. The method comprises providing an ophthalmic article (process 501). The ophthalmic article comprises one or more components of the ophthalmic article, as disclosed herein. For example, the ophthalmic article can comprise a polymeric material (e.g., a biocompatible copolymer matrix) and an active agent and/or diagnostic agent. In another example, the ophthalmic article may be an embodiment of the aforementioned ophthalmic article as illustrated in, for example, FIG. 1A, FIG. 1B, FIGS. 2A-2H, FIG. 3A, FIG. 3B. FIG. 4A, and/or FIG. 4B. Referring to FIG. 5A, the method comprises associating ophthalmic article 100 onto a haptic 302 of the intraocular lens 300 (process 503). The intraocular lens comprises one or more components of the intraocular lens, as disclosed herein. In an example, the intraocular lens may be an embodiment of the aforementioned intraocular lens as illustrated in FIG. 3A, FIG. 3B, FIG. 4A, and/or FIG. 4B. Referring to FIG. 5A, the method also comprises compressing the intraocular lens 300 with the ophthalmic article 100 associated thereto into a cassette 507 (process 506). The method may then comprises loading the cassette 507 comprising intraocular lens 300 with an ophthalmic article associated 100 thereto into the intraocular lens injector 508 (process 509).

In some examples, the method may comprise performing surgery (e.g., a cataract removal surgery) on the eye of the subject. FIG. 5B schematically illustrates an example of an implanting method ("the method") 510 for implanting an intraocular lens comprising an ophthalmic article associated thereto. In this example, the implanting method may be an embodiment for a method for treating or preventing a disease, condition, and/or complication. The implanting method may also be an embodiment for a method for administering an active agent and/or a diagnostic agent. The implanting method can comprise making an incision 513 in the side of the cornea in preparation for implanting an intraocular lens 300 with an ophthalmic article 100 associated thereto (process 511). The ophthalmic article 100 may comprise one or more components of the ophthalmic article, as disclosed herein. For example, the ophthalmic article can comprise a polymeric material (e.g., a biocompatible copolymer matrix) and an active agent or diagnostic agent. In another example, the ophthalmic article may be an embodiment of the aforementioned ophthalmic article as illustrated in FIG. 1A, FIG. 1B, FIGS. 2A-2H, FIG. 3A, FIG. 3B. FIG. 4A, and/or FIG. 4B. The intraocular lens comprises one or more components of the intraocular lens, as disclosed herein. In an example, the intraocular lens may be an embodiment of the aforementioned intraocular lens as illustrated in FIG. 3A, FIG. 3B, FIG. 4A, and/or FIG. 4B. Referring to FIG. 5B, the method comprises removing an existing lens 515 (e.g., a diseased lens) from the eye of the subject using a surgical tool 520 (process 514), implanting an intraocular lens using the loaded intraocular lens injector 508 into the eye of the subject (process 516), and placing the intraocular lens 300 with the ophthalmic article 100 associated thereto within the capsular bag (process 518). Other delivery routes of the ophthalmic article can comprise punctal, intravitreal, subconjunctival, lens, intrascleral, fornix, anterior sub-Tenon's, suprachoroidal, posterior sub-Tenon's, subretinal, anterior chamber, and posterior chamber. In some embodiments, the subject is concurrently undergoing or has undergone ophthalmic surgery. In some embodiments, the subject is concurrently undergoing or has undergone cataract surgery. FIG. 5C schematically illustrates an example of an intraocular lens 300 with an ophthalmic article 100 associated thereto in which the ophthalmic article does not interfere with placement of the intraocular lens in the desired position, location and orientation within the capsular bag 519 of the eye. The ophthalmic article can be associated to the intraocular lens by actual contact or sufficient proximity while allowing effective diffusion of an active agent and/or diagnostic agent to target areas of the eye. The active agent and/or diagnostic agent may be released from the ophthalmic article's polymeric material (e.g., biocompatible copolymer matrix) through degradation of the polymeric material, as disclosed herein.

Over the course of release, the polymeric material (e.g., biodegradable polymer matrix) can degrade releasing the active agent and/or diagnostic agent. In some embodiments, the polymeric material can be configured to biodegrade or bioerode to provide controlled release of an effective amount (e.g., therapeutically effective amount) of the active agent and/or diagnostic agent over a period of days, weeks, or months. Once the active agent and/or diagnostic agent has been completely released, the polymer matrix is expected to be gone. In some embodiments, complete polymer matrix degradation may take longer than the complete release of the active agent and/or the diagnostic agent. In some embodiments, polymer matrix degradation may occur at the same rate as the release of the active agent and/or the diagnostic agent.

For example, the ophthalmic article may be designed to release an effective amount of the active agent and/or the diagnostic agent for about 1 day to about 12 months from the polymeric material (e.g., biocompatible copolymer matrix). In some embodiments, the active agent and/or the diagnostic agent is released from the polymeric material (e.g., biocompatible copolymer matrix) over at least about 7 days. In some embodiments, the active agent and/or the diagnostic agent is released from the polymeric material (e.g., biocompatible copolymer matrix) over a period ranging from about 5-30 days, 5-21 days, 5-14 days, 5-10 days, 7-30 days, 7-21 days, 7-14 days, or 7-10 days.

In some embodiments, the active agent and/or the diagnostic agent may be released from the polymeric material over a period of about 1 day to about 365 days. In some embodiments, the active agent and/or the diagnostic agent may be released from the polymeric material over a period of about 1 day to about 5 days, about 1 day to about 10 days, about 1 day to about 15 days, about 1 day to about 20 days, about 1 day to about 30 days, about 1 day to about 40 days, about 1 day to about 50 days, about 1 day to about 100 days, about 1 day to about 200 days, about 1 day to about 300 days, about 1 day to about 365 days, about 5 days to about 10 days, about 5 days to about 15 days, about 5 days to about 20 days, about 5 days to about 30 days, about 5 days to about 40 days, about 5 days to about 50 days, about 5 days to about 100 days, about 5 days to about 200 days, about 5 days to about 300 days, about 5 days to about 365 days, about 10 days to about 15 days, about 10 days to about 20 days, about 10 days to about 30 days, about 10 days to about 40 days, about 10 days to about 50 days, about 10 days to about 100 days, about 10 days to about 200 days, about 10 days to about 300 days, about 10 days to about 365 days, about 15 days to about 20 days, about 15 days to about 30 days, about 15 days to about 40 days, about 15 days to about 50 days, about 15 days to about 100 days, about 15 days to about 200 days, about 15 days to about 300 days, about 15 days to about 365 days, about 20 days to about 30 days, about 20 days to about 40 days, about 20 days to about 50 days, about 20 days to about 100 days, about 20 days to about 200 days, about 20 days to about 300 days, about 20 days to about 365 days, about 30 days to about 40 days, about 30 days to about 50 days, about 30 days to about 100 days, about 30 days to about 200 days, about 30 days to about 300 days, about 30 days to about 365 days, about 40 days to about 50 days, about 40 days to about 100 days, about 40 days to about 200 days, about 40 days to about 300 days, about 40 days to about 365 days, about 50 days to about 100 days, about 50 days to about 200 days, about 50 days to about 300 days, about 50 days to about 365 days, about 100 days to about 200 days, about 100 days to about 300 days, about 100 days to about 365 days, about 200 days to about 300 days, about 200 days to about 365 days, or about 300 days to about 365 days. In some embodiments, the active agent and/or the diagnostic agent may be released from the polymeric material over a period of at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In some embodiments, the active agent and/or the diagnostic agent may be released from the polymeric material over a period of at most about 1 day, at most about 2 days, at most about 3 days, at most about 4 days, at most about 5 days, at most about 6 days, at most about 7 days, at most about 2 weeks, at most about 3 weeks, at most about 4 weeks, at most about 1 month, at most about 2 months, at most about 3 months, at most about 4 months, at most about 5 months, at most about 6 months, at most about 7 months, at most about 8 months, at most about 9 months, at most about 10 months, at most about 11 months, or at most about 12 months.

In some examples, the effective amount (e.g., therapeutically effective amount) can be released over a period ranging from about 1 week to about 12 weeks. In other examples, the effective amount can be released over a period ranging from about 1 week to about 3 weeks, from about 2 weeks to about 6 weeks, or from about 5 weeks to about 8 weeks. In cases such as retinal vein/artery occlusion, diabetic retinopathy, macular edema or retinal degenerations, the period can often range from 2 months to 12 months, and in some cases from 2.5 months to 5 months. For example, bioerodible lipid polymers and/or bioerodible polycaprolactone can be used as an extended release matrix material.

In some examples, the effective amount (e.g., therapeutically effective amount) can be released over a period ranging from about 1 week to about 2 weeks, about 1 week to about 3 weeks, about 1 week to about 4 weeks, about 1 week to about 5 weeks, about 1 week to about 6 weeks, about 1 week to about 7 weeks, about 1 week to about 8 weeks, about 1 week to about 9 weeks, about 1 week to about 10 weeks, about 1 week to about 11 weeks, about 1 week to about 12 weeks, about 2 weeks to about 3 weeks, about 2 weeks to about 4 weeks, about 2 weeks to about 5 weeks, about 2 weeks to about 6 weeks, about 2 weeks to about 7 weeks, about 2 weeks to about 8 weeks, about 2 weeks to about 9 weeks, about 2 weeks to about 10 weeks, about 2 weeks to about 11 weeks, about 2 weeks to about 12 weeks, about 3 weeks to about 4 weeks, about 3 weeks to about 5 weeks, about 3 weeks to about 6 weeks, about 3 weeks to about 7 weeks, about 3 weeks to about 8 weeks, about 3 weeks to about 9 weeks, about 3 weeks to about 10 weeks, about 3 weeks to about 11 weeks, about 3 weeks to about 12 weeks, about 4 weeks to about 5 weeks, about 4 weeks to about 6 weeks, about 4 weeks to about 7 weeks, about 4 weeks to about 8 weeks, about 4 weeks to about 9 weeks, about 4 weeks to about 10 weeks, about 4 weeks to about 11 weeks, about 4 weeks to about 12 weeks, about 5 weeks to about 6 weeks, about 5 weeks to about 7 weeks, about 5 weeks to about 8 weeks, about 5 weeks to about 9 weeks, about 5 weeks to about 10 weeks, about 5 weeks to about 11 weeks, about 5 weeks to about 12 weeks, about 6 weeks to about 7 weeks, about 6 weeks to about 8 weeks, about 6 weeks to about 9 weeks, about 6 weeks to about 10 weeks, about 6 weeks to about 11 weeks, about 6 weeks to about 12 weeks, about 7 weeks to about 8 weeks, about 7 weeks to about 9 weeks, about 7 weeks to about 10 weeks, about 7 weeks to about 11 weeks, about 7 weeks to about 12 weeks, about 8 weeks to about 9 weeks, about 8 weeks to about 10 weeks, about 8 weeks to about 11 weeks, about 8 weeks to about 12 weeks, about 9 weeks to about 10 weeks, about 9 weeks to about 11 weeks, about 9 weeks to about 12 weeks, about 10 weeks to about 11 weeks, about 10 weeks to about 12 weeks, or about 11 weeks to about 12 weeks.

In some examples, the effective amount (e.g., therapeutically effective amount) can be released over a period of at least or up to about 1 week, at least or up to about 2 weeks, at least or up to about 3 weeks, at least or up to about 4 weeks, at least or up to about 5 weeks, at least or up to about 6 weeks, at least or up to about 7 weeks, at least or up to about 8 weeks, at least or up to about 9 weeks, at least or up to about 10 weeks, at least or up to about 11 weeks, or at least or up to about 12 weeks. In some examples, the effective amount (e.g., therapeutically effective amount) can be released over a period of about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks.

In some examples, the effective amount (e.g., therapeutically effective amount) can be released over a period of about 2 months to about 3 months, about 2 months to about 4 months, about 2 months to about 5 months, about 2 months to about 6 months, about 2 months to about 7 months, about 2 months to about 8 months, about 2 months to about 9 months, about 2 months to about 10 months, about 2 months to about 11 months, about 2 months to about 12 months, about 3 months to about 4 months, about 3 months to about 5 months, about 3 months to about 6 months, about 3 months to about 7 months, about 3 months to about 8 months, about 3 months to about 9 months, about 3 months to about 10 months, about 3 months to about 11 months, about 3 months to about 12 months, about 4 months to about 5 months, about 4 months to about 6 months, about 4 months to about 7 months, about 4 months to about 8 months, about 4 months to about 9 months, about 4 months to about 10 months, about 4 months to about 11 months, about 4 months to about 12 months, about 5 months to about 6 months, about 5 months to about 7 months, about 5 months to about 8 months, about 5 months to about 9 months, about 5 months to about 10 months, about 5 months to about 11 months, about 5 months to about 12 months, about 6 months to about 7 months, about 6 months to about 8 months, about 6 months to about 9 months, about 6 months to about 10 months, about 6 months to about 11 months, about 6 months to about 12 months, about 7 months to about 8 months, about 7 months to about 9 months, about 7 months to about 10 months, about 7 months to about 11 months, about 7 months to about 12 months, about 8 months to about 9 months, about 8 months to about 10 months, about 8 months to about 11 months, about 8 months to about 12 months, about 9 months to about 10 months, about 9 months to about 11 months, about 9 months to about 12 months, about 10 months to about 11 months, about 10 months to about 12 months, or about 11 months to about 12 months.

In some examples, the effective amount (e.g., therapeutically effective amount) can be released over a period of at least about 2 months, at least about 3 months, at least about 4 months, at least about 5 months, at least about 6 months, at least about 7 months, at least about 8 months, at least about 9 months, at least about 10 months, at least about 11 months, or at least about 12 months. from at least at least about 2 months, at least about 3 months, at least about 4 months, at least about 5 months, at least about 6 months, at least about 7 months, at least about 8 months, at least about 9 months, at least about 10 months, or at least about 11 months.

In some examples, the effective amount (e.g., therapeutically effective amount) can be released over a period of at most about 2 months, at most about 3 months, at most about 4 months, at most about 5 months, at most about 6 months, at most about 7 months, at most about 8 months, at most about 9 months, at most about 10 months, at most about 11 months, or at most about 12 months. from at least at most about 2 months, at most about 3 months, at most about 4 months, at most about 5 months, at most about 6 months, at most about 7 months, at most about 8 months, at most about 9 months, at most about 10 months, or at most about 11 months.

In some examples, the effective amount (e.g., therapeutically effective amount) can be released over a period of about 2 months, about 3 months, about 4 months, about 5 months, about 6 months, about 7 months, about 8 months, about 9 months, about 10 months, about 11 months, or about 12 months. from at least about 2 months, about 3 months, about 4 months, about 5 months, about 6 months, about 7 months, about 8 months, about 9 months, about 10 months, or about 11 months.

In some examples, the effective amount (e.g., therapeutically effective amount) can be released over a period of at least about 1 day, at least about 2 days, at least about 3 days, at least about 4 days, at least about 5 days, at least about 6 days, or at least about 7 days. In some examples, the effective amount (e.g., therapeutically effective amount) can be released over a period of at most about 1 day, at most about 2 days, at most about 3 days, at most about 4 days, at most about 5 days, at most about 6 days, or at most about 7 days.

A biodegradable system can have substantial value in routine cataract surgery to provide short-term/time-limited delivery of postoperative medicines while minimizing or eliminating the need for eyedrop usage by the patient. The lens that is removed can be the original natural lens of the eye, or it can be a lens that was previously inserted into the eye as a result of a prior procedure. Once implanted, the ocular device (e.g., intraocular device) and one or more ophthalmic articles associated thereto may then spontaneously unfold and can be positioned into place and adjusted by the surgeon (e.g., using small instruments inserted into the eye). In some embodiments, the ophthalmic article does not disintegrate or fracture under the stress of injection through an intraocular (e.g., IOL) injector device.

Decentration or angulation of an ocular device (e.g., intraocular device) within the lens capsule can adversely affect the optical power of an IOL leading to refractive errors and patient dissatisfaction. In some embodiments, the ophthalmic article, when positioned on a portion of an ocular device (e.g., the haptic of an IOL), may not interfere with placement of the ocular device in the desired position, location and orientation with proper visual outcomes.

Intraoperative, the surgeon may be able to insert the ocular device (e.g., intraocular device) with the ophthalmic article associated thereto inside the eye and further manipulate it into the correct axis and plane to achieve proper centration and lack of tilt. In some embodiments, the ocular device (e.g., intraocular device) may remain in the proper position and orientation during the postoperative period during which time the ocular device (e.g., IOL) can contract and the lens capsule may shift in response to changes in body position. In some embodiments, the ocular device (e.g., IOL) may remain capable of being positioned by the surgeon using various surgical techniques (e.g., micro incision surgical technique).

A procedure to implant an ocular device (e.g., intraocular device) in a subject's eye can cause complications such as irritation and inflammation. In order to evaluate an extent of inflammation and/or other complications caused by the procedure, an ocular examination can be performed using a slit lamp biomicroscope and/or indirect ophthalmoscope. The ocular examination may include evaluating an ocular surface morphology, an anterior and/or posterior segment inflammation, or a capsular fibrosis. A score can be generated using a grading system (e.g., a Hackett and McDonald ocular grading system or a modified Hackett and McDonald ocular grading system with additional scoring parameters for the ocular posterior segment) to quantify an outcome of the ocular examination. The modified Hackett and McDonald system is most commonly used for ocular testing in animal models of eye disease. In human subjects, other standardized scales (e.g. the grading system developed by the Standardization of Uveitis Nomenclature Working Group) may be used to quantify the outcomes of ocular examinations.

In some embodiments, an anterior chamber cell score of a subject as measured by a grading system (e.g., Standardization of Uveitis Nomenclature Working Group) is at most 1+, or 6-15 cells per field, where the field is defined by a slit lamp beam measuring 1×1 mm. In some embodiments, the anterior chamber cell score of the subject may be about 0 to about 2. In some embodiments, the anterior chamber cell score of the subject may be about 0 to about 0.5, about 0 to about 1, about 0 to about 2, about 0.5 to about 1, about 0.5 to about 2, or about 1 to about 2. In some embodiments, the anterior chamber cell score of the subject may be about 0, about 0.5, about 1, or about 2. In some embodiments, the anterior chamber cell score of the subject may be at least about 0, at least about 0.5, at least about 1, or at least about 2. In some embodiments, the anterior chamber cell score of the subject may be at most about 0, at most about 0.5, at most about 1, or at most about 2.

In some embodiments, the anterior chamber cell score may be characterized by having about 0 cells per field to about 30 cells per field. In some embodiments, the anterior chamber cell score may be characterized by having about 0 cells per field to about 1 cell per field, about 0 cells per field to about 2 cells per field, about 0 cells per field to about 4 cells per field, about 0 cells per field to about 6 cells per field, about 0 cells per field to about 8 cells per field, about 0 cells per field to about 10 cells per field, about 0 cells per field to about 12 cells per field, about 0 cells per field to about 14 cells per field, about 0 cells per field to about 16 cells per field, about 0 cells per field to about 20 cells per field, about 0 cells per field to about 30 cells per field, about 1 cell per field to about 2 cells per field, about 1 cell per field to about 4 cells per field, about 1 cell per field to about 6 cells per field, about 1 cell per field to about 8 cells per field, about 1 cell per field to about 10 cells per field, about 1 cell per field to about 12 cells per field, about 1 cell per field to about 14 cells per field, about 1 cell per field to about 16 cells per field, about 1 cell per field to about 20 cells per field, about 1 cell per field to about 30 cells per field, about 2 cells per field to about 4 cells per field, about 2 cells per field to about 6 cells per field, about 2 cells per field to about 8 cells per field, about 2 cells per field to about 10 cells per field, about 2 cells per field to about 12 cells per field, about 2 cells per field to about 14 cells per field, about 2 cells per field to about 16 cells per field, about 2 cells per field to about 20 cells per field, about 2 cells per field to about 30 cells per field, about 4 cells per field to about 6 cells per field, about 4 cells per field to about 8 cells per field, about 4 cells per field to about 10 cells per field, about 4 cells per field to about 12 cells per field, about 4 cells per field to about 14 cells per field, about 4 cells per field to about 16 cells per field, about 4 cells per field to about 20 cells per field, about 4 cells per field to about 30 cells per field, about 6 cells per field to about 8 cells per field, about 6 cells per field to about 10 cells per field, about 6 cells per field to about 12 cells per field, about 6 cells per field to about 14 cells per field, about 6 cells per field to about 16 cells per field, about 6 cells per field to about 20 cells per field, about 6 cells per field to about 30 cells per field, about 8 cells per field to about 10 cells per field, about 8 cells per field to about 12 cells per field, about 8 cells per field to about 14 cells per field, about 8 cells per field to about 16 cells per field, about 8 cells per field to about 20 cells per field, about 8 cells per field to about 30 cells per field, about 10 cells per field to about 12 cells per field, about 10 cells per field to about 14 cells per field, about 10 cells per field to about 16 cells per field, about 10 cells per field to about 20 cells per field, about 10 cells per field to about 30 cells per field, about 12 cells per field to about 14 cells per field, about 12 cells per field to about 16 cells per field, about 12 cells per field to about 20 cells per field, about 12 cells per field to about 30 cells per field, about 14 cells per field to about 16 cells per field, about 14 cells per field to about 20 cells per field, about 14 cells per field to about 30 cells per field, about 16 cells per field to about 20 cells per field, about 16 cells per field to about 30 cells per field, or about 20 cells per field to about 30 cells per field. In some embodiments, the anterior chamber cell score may be characterized by having about 0 cells per field, about 1 cell per field, about 2 cells per field, about 4 cells per field, about 6 cells per field, about 8 cells per field, about 10 cells per field, about 12 cells per field, about 14 cells per field, about 16 cells per field, about 20 cells per field, or about 30 cells per field. In some embodiments, the anterior chamber cell score may be characterized by having at least about 0 cells per field, at least about 1 cell per field, at least about 2 cells per field, at least about 4 cells per field, at least about 6 cells per field, at least about 8 cells per field, at least about 10 cells per field, at least about 12 cells per field, at least about 14 cells per field, at least about 16 cells per field, at least about 20 cells per field, or at least about 30 cells per field. In some embodiments, the anterior chamber cell score may be characterized by having at most about 0 cells per field, at most about 1 cell per field, at most about 2 cells per field, at most about 4 cells per field, at most about 6 cells per field, at most about 8 cells per field, at most about 10 cells per field, at most about 12 cells per field, at most about 14 cells per field, at most about 16 cells per field, at most about 20 cells per field, or at most about 30 cells per field.

In some embodiments, an anterior chamber cell score of a subject is at most one, 20 days to 100 days after the implantation of an ocular device (e.g., intraocular device). In some embodiments, the anterior chamber cell score of the subject may be at most one, following implantation of the ocular device for about 5 days to about 200 days. In some embodiments, the anterior chamber cell score of the subject may be at most one, following implantation of the ocular device for about 5 days to about 10 days, about 5 days to about 15 days, about 5 days to about 20 days, about 5 days to about 30 days, about 5 days to about 40 days, about 5 days to about 50 days, about 5 days to about 60 days, about 5 days to about 80 days, about 5 days to about 100 days, about 5 days to about 150 days, about 5 days to about 200 days, about 10 days to about 15 days, about 10 days to about 20 days, about 10 days to about 30 days, about 10 days to about 40 days, about 10 days to about 50 days, about 10 days to about 60 days, about 10 days to about 80 days, about 10 days to about 100 days, about 10 days to about 150 days, about 10 days to about 200 days, about 15 days to about 20 days, about 15 days to about 30 days, about 15 days to about 40 days, about 15 days to about 50 days, about 15 days to about 60 days, about 15 days to about 80 days, about 15 days to about 100 days, about 15 days to about 150 days, about 15 days to about 200 days, about 20 days to about 30 days, about 20 days to about 40 days, about 20 days to about 50 days, about 20 days to about 60 days, about 20 days to about 80 days, about 20 days to about 100 days, about 20 days to about 150 days, about 20 days to about 200 days, about 30 days to about 40 days, about 30 days to about 50 days, about 30 days to about 60 days, about 30 days to about 80 days, about 30 days to about 100 days, about 30 days to about 150 days, about 30 days to about 200 days, about 40 days to about 50 days, about 40 days to about 60 days, about 40 days to about 80 days, about 40 days to about 100 days, about 40 days to about 150 days, about 40 days to about 200 days, about 50 days to about 60 days, about 50 days to about 80 days, about 50 days to about 100 days, about 50 days to about 150 days, about 50 days to about 200 days, about 60 days to about 80 days, about 60 days to about 100 days, about 60 days to about 150 days, about 60 days to about 200 days, about 80 days to about 100 days, about 80 days to about 150 days, about 80 days to about 200 days, about 100 days to about 150 days, about 100 days to about 200 days, or about 150 days to about 200 days. In some embodiments, the anterior chamber cell score of the subject may be at most one, following implantation of the ocular device for about 5 days, about 10 days, about 15 days, about 20 days, about 30 days, about 40 days, about 50 days, about 60 days, about 80 days, about 100 days, about 150 days, or about 200 days. In some embodiments, the anterior chamber cell score of the subject may be at most one, following implantation of the ocular device for at least about 5 days, at least about 10 days, at least about 15 days, at least about 20 days, at least about 30 days, at least about 40 days, at least about 50 days, at least about 60 days, at least about 80 days, at least about 100 days, at least about 150 days, or at least about 200 days. In some embodiments, the anterior chamber cell score of the subject may be at most one, following implantation of the ocular device for at most about 5 days, at most about 10 days, at most about 15 days, at most about 20 days, at most about 30 days, at most about 40 days, at most about 50 days, at most about 60 days, at most about 80 days, at most about 100 days, at most about 150 days, or at most about 200 days.

In some embodiments, an active agent (e.g., dexamethasone, moxifloxacin, ketorolac) concentration in an aqueous humor of a subject implanted with the ophthalmic article is at least 80 ng/mL on day 28 following surgery (e.g., 2,500 ng/mL on day 3; 2.5 ng/mL on day 14). In some embodiments, following the surgery (e.g., on day 28 following surgery), the drug concentration in the aqueous humor of the subject implanted with the ophthalmic article may be about 1 ng/mL to about 2,000 ng/mL. In some embodiments, following the surgery, the drug concentration in the aqueous humor of the subject implanted with the ophthalmic article may be about 1 ng/mL to about 5 ng/mL, about 1 ng/mL to about 10 ng/mL, about 1 ng/mL to about 15 ng/mL, about 1 ng/mL to about 20 ng/mL, about 1 ng/mL to about 40 ng/mL, about 1 ng/mL to about 80 ng/mL, about 1 ng/mL to about 100 ng/mL, about 1 ng/mL to about 200 ng/mL, about 1 ng/mL to about 500 ng/mL, about 1 ng/mL to about 1,000 ng/mL, about 1 ng/mL to about 2,000 ng/mL, about 5 ng/mL to about 10 ng/mL, about 5 ng/mL to about 15 ng/mL, about 5 ng/mL to about 20 ng/mL, about 5 ng/mL to about 40 ng/mL, about 5 ng/mL to about 80 ng/mL, about 5 ng/mL to about 100 ng/mL, about 5 ng/mL to about 200 ng/mL, about 5 ng/mL to about 500 ng/mL, about 5 ng/mL to about 1,000 ng/mL, about 5 ng/mL to about 2,000 ng/mL, about 10 ng/mL to about 15 ng/mL, about 10 ng/mL to about 20 ng/mL, about 10 ng/mL to about 40 ng/mL, about 10 ng/mL to about 80 ng/mL, about 10 ng/mL to about 100 ng/mL, about 10 ng/mL to about 200 ng/mL, about 10 ng/mL to about 500 ng/mL, about 10 ng/mL to about 1,000 ng/mL, about 10 ng/mL to about 2,000 ng/mL, about 15 ng/mL to about 20 ng/mL, about 15 ng/mL to about 40 ng/mL, about 15 ng/mL to about 80 ng/mL, about 15 ng/mL to about 100 ng/mL, about 15 ng/mL to about 200 ng/mL, about 15 ng/mL to about 500 ng/mL, about 15 ng/mL to about 1,000 ng/mL, about 15 ng/mL to about 2,000 ng/mL, about 20 ng/mL to about 40 ng/mL, about 20 ng/mL to about 80 ng/mL, about 20 ng/mL to about 100 ng/mL, about 20 ng/mL to about 200 ng/mL, about 20 ng/mL to about 500 ng/mL, about 20 ng/mL to about 1,000 ng/mL, about 20 ng/mL to about 2,000 ng/mL, about 40 ng/mL to about 80 ng/mL, about 40 ng/mL to about 100 ng/mL, about 40 ng/mL to about 200 ng/mL, about 40 ng/mL to about 500 ng/mL, about 40 ng/mL to about 1,000 ng/mL, about 40 ng/mL to about 2,000 ng/mL, about 80 ng/mL to about 100 ng/mL, about 80 ng/mL to about 200 ng/mL, about 80 ng/mL to about 500 ng/mL, about 80 ng/mL to about 1,000 ng/mL, about 80 ng/mL to about 2,000 ng/mL, about 100 ng/mL to about 200 ng/mL, about 100 ng/mL to about 500 ng/mL, about 100 ng/mL to about 1,000 ng/mL, about 100 ng/mL to about 2,000 ng/mL, about 200 ng/mL to about 500 ng/mL, about 200 ng/mL to about 1,000 ng/mL, about 200 ng/mL to about 2,000 ng/mL, about 500 ng/mL to about 1,000 ng/mL, about 500 ng/mL to about 2,000 ng/mL, or about 1,000 ng/mL to about 2,000 ng/mL. In some embodiments, following the surgery, the drug concentration in the aqueous humor of the subject implanted with the ophthalmic article may be about 1 ng/mL, about 5 ng/mL, about 10 ng/mL, about 15 ng/mL, about 20 ng/mL, about 40 ng/mL, about 80 ng/mL, about 100 ng/mL, about 200 ng/mL, about 500 ng/mL, about 1,000 ng/mL, or about 2,000 ng/mL. In some embodiments, following the surgery, the drug concentration in the aqueous humor of the subject implanted with the ophthalmic article may be at least about 1 ng/mL, at least about 5 ng/mL, at least about 10 ng/mL, at least about 15 ng/mL, at least about 20 ng/mL, at least about 40 ng/mL, at least about 80 ng/mL, at least about 100 ng/mL, at least about 200 ng/mL, at least about 500 ng/mL, at least about 1,000 ng/mL, or at least about 2,000 ng/mL. In some embodiments, following the surgery, the drug concentration in the aqueous humor of the subject implanted with the ophthalmic article may be at most about 1 ng/mL, at most about 5 ng/mL, at most about 10 ng/mL, at most about 15 ng/mL, at most about 20 ng/mL, at most about 40 ng/mL, at most about 80 ng/mL, at most about 100 ng/mL, at most about 200 ng/mL, at most about 500 ng/mL, at most about 1,000 ng/mL, or at most about 2,000 ng/mL.

In some embodiments, a drug (e.g., dexamethasone, moxifloxacin, ketorolac) concentration in a plasma sample from a subject implanted with the ophthalmic article is at most 1 ng/mL. In some embodiments, the drug concentration in the plasma sample from the subject implanted with the ophthalmic article may be about 0.01 ng/mL to about 100 ng/mL. In some embodiments, the drug concentration in the plasma sample from the subject implanted with the ophthalmic article may be about 0.01 ng/mL to about 0.05 ng/mL, about 0.01 ng/mL to about 0.1 ng/mL, about 0.01 ng/mL to about 0.5 ng/mL, about 0.01 ng/mL to about 1 ng/mL, about 0.01 ng/mL to about 5 ng/mL, about 0.01 ng/mL to about 10 ng/mL, about 0.01 ng/mL to about 50 ng/mL, about 0.01 ng/mL to about 100 ng/mL, about 0.05 ng/mL to about 0.1 ng/mL, about 0.05 ng/mL to about 0.5 ng/mL, about 0.05 ng/mL to about 1 ng/mL, about 0.05 ng/mL to about 5 ng/mL, about 0.05 ng/mL to about 10 ng/mL, about 0.05 ng/mL to about 50 ng/mL, about 0.05 ng/mL to about 100 ng/mL, about 0.1 ng/mL to about 0.5 ng/mL, about 0.1 ng/mL to about 1 ng/mL, about 0.1 ng/mL to about 5 ng/mL, about 0.1 ng/mL to about 10 ng/mL, about 0.1 ng/mL to about 50 ng/mL, about 0.1 ng/mL to about 100 ng/mL, about 0.5 ng/mL to about 1 ng/mL, about 0.5 ng/mL to about 5 ng/mL, about 0.5 ng/mL to about 10 ng/mL, about 0.5 ng/mL to about 50 ng/mL, about 0.5 ng/mL to about 100 ng/mL, about 1 ng/mL to about 5 ng/mL, about 1 ng/mL to about 10 ng/mL, about 1 ng/mL to about 50 ng/mL, about 1 ng/mL to about 100 ng/mL, about 5 ng/mL to about 10 ng/mL, about 5 ng/mL to about 50 ng/mL, about 5 ng/mL to about 100 ng/mL, about 10 ng/mL to about 50 ng/mL, about 10 ng/mL to about 100 ng/mL, or about 50 ng/mL to about 100 ng/mL. In some embodiments, the drug concentration in the plasma sample from the subject implanted with the ophthalmic article may be about 0.01 ng/mL, about 0.05 ng/mL, about 0.1 ng/mL, about 0.5 ng/mL, about 1 ng/mL, about 5 ng/mL, about 10 ng/mL, about 50 ng/mL, or about 100 ng/mL. In some embodiments, the drug concentration in the plasma sample from the subject implanted with the ophthalmic article may be at least about 0.01 ng/mL, at least about 0.05 ng/mL, at least about 0.1 ng/mL, at least about 0.5 ng/mL, at least about 1 ng/mL, at least about 5 ng/mL, at least about 10 ng/mL, at least about 50 ng/mL, or at least about 100 ng/mL. In some embodiments, the drug concentration in the plasma sample from the subject implanted with the ophthalmic article may be at most about 0.01 ng/mL, at most about 0.05 ng/mL, at most about 0.1 ng/mL, at most about 0.5 ng/mL, at most about 1 ng/mL, at most about 5 ng/mL, at most about 10 ng/mL, at most about 50 ng/mL, or at most about 100 ng/mL.

For safety purposes, it may be desirable for the plasma drug concentration in subject implanted with an ophthalmic article to be as low as possible. For every drug there is plasma concentration below which no adverse effects are expected (e.g., the no-observed-adverse-effect level (NO-AEL)). A margin of safety can be estimated as the ratio between NOAEL and the observed plasma concentration in the subject dosed with the ophthalmic article. When considering the pharmacokinetic properties of a drug released from an implanted ophthalmic article, the concentration of the drug in the medium surrounding the ophthalmic article (e.g. the aqueous humor) may be relatively high compared to the plasma concentration, because volume of distribution within the eye is significantly smaller than the volume of distribution for the plasma.

Histopathology of a sample from a subject implanted with the ophthalmic article can include histopathology of anterior segment of an eye (e.g., Cornea, Anterior chamber, iris, ciliary body), posterior segment of an eye (vitreous, retina, choroid, optic nerve), and lens regrowth.

Intraocular pressure (IOP) may be in the range of 11 to 21 mmHg, though transient fluctuations may occur during the early postoperative period. An abnormally high IOP might indicate adverse effects of the intraocular article due to, among other things, the pharmacology of the active ingredient, accumulation polymer degradants that block aqueous outflow, impingement of the article on the iris in manner that restricts aqueous outflow, or an inflammatory response to the ophthalmic article resulting in secondary glaucoma. The absence of abnormal IOP is an important safety indicator for the ophthalmic article.

In some embodiments, the IOP may be about 11 mmHg to about 21 mmHg. In some embodiments, the IOP may be about 11 mmHg to about 12 mmHg, about 11 mmHg to about 13 mmHg, about 11 mmHg to about 14 mmHg, about 11 mmHg to about 15 mmHg, about 11 mmHg to about 16 mmHg, about 11 mmHg to about 17 mmHg, about 11 mmHg to about 18 mmHg, about 11 mmHg to about 19 mmHg, about 11 mmHg to about 20 mmHg, about 11 mmHg to about 21 mmHg, about 12 mmHg to about 13 mmHg, about 12 mmHg to about 14 mmHg, about 12 mmHg to about 15 mmHg, about 12 mmHg to about 16 mmHg, about 12 mmHg to about 17 mmHg, about 12 mmHg to about 18 mmHg, about 12 mmHg to about 19 mmHg, about 12 mmHg to about 20 mmHg, about 12 mmHg to about 21 mmHg, about 13 mmHg to about 14 mmHg, about 13 mmHg to about 15 mmHg, about 13 mmHg to about 16 mmHg, about 13 mmHg to about 17 mmHg, about 13 mmHg to about 18 mmHg, about 13 mmHg to about 19 mmHg, about 13 mmHg to about 20 mmHg, about 13 mmHg to about 21 mmHg, about 14 mmHg to about 15 mmHg, about 14 mmHg to about 16 mmHg, about 14 mmHg to about 17 mmHg, about 14 mmHg to about 18 mmHg, about 14 mmHg to about 19 mmHg, about 14 mmHg to about 20 mmHg, about 14 mmHg to about 21 mmHg, about 15 mmHg to about 16 mmHg, about 15 mmHg to about 17 mmHg, about 15 mmHg to about 18 mmHg, about 15 mmHg to about 19 mmHg, about 15 mmHg to about 20 mmHg, about 15 mmHg to about 21 mmHg, about 16 mmHg to about 17 mmHg, about 16 mmHg to about 18 mmHg, about 16 mmHg to about 19 mmHg, about 16 mmHg to about 20 mmHg, about 16 mmHg to about 21 mmHg, about 17 mmHg to about 18 mmHg, about 17 mmHg to about 19 mmHg, about 17 mmHg to about 20 mmHg, about 17 mmHg to about 21 mmHg, about 18 mmHg to about 19 mmHg, about 18 mmHg to about 20 mmHg, about 18 mmHg to about 21 mmHg, about 19 mmHg to about 20 mmHg, about 19 mmHg to about 21 mmHg, or about 20 mmHg to about 21 mmHg. In some embodiments, the IOP may be about 11 mmHg, about 12 mmHg, about 13 mmHg, about 14 mmHg, about 15 mmHg, about 16 mmHg, about 17 mmHg, about 18 mmHg, about 19 mmHg, about 20 mmHg, or about 21 mmHg. In some embodiments, the IOP may be at least about 11 mmHg, at least about 12 mmHg, at least about 13 mmHg, at least about 14 mmHg, at least about 15 mmHg, at least about 16 mmHg, at least about 17 mmHg, at least about 18 mmHg, at least about 19 mmHg, at least about 20 mmHg, or at least about 21 mmHg. In some embodiments, the IOP may be at most about 11 mmHg, at most about 12 mmHg, at most about 13 mmHg, at most about 14 mmHg, at most about 15 mmHg, at most about 16 mmHg, at most about 17 mmHg, at most about 18 mmHg, at most about 19 mmHg, at most about 20 mmHg, or at most about 21 mmHg.

Histopathology may be an anatomic assessment of the condition of the eye after the study has been terminated. Histopathology results may be interpreted within the full context of a study (e.g., including all of the interventions and exposures experienced by the subjects and the clinical examination findings recorded during the study). The absence of inflammatory cells or fibrotic in the immediate vicinity of the ophthalmic article can supports biocompatibility and safety when implanted in the eye. Furthermore, the absence of inflammation, fibrosis, hypertrophy, atrophy and/or other pathologic findings throughout the eye tissues further supports a safety of the of the ophthalmic article for intraocular use.

In some embodiments, a posterior capsular opacification (PCO) score of an eye of a subject implanted with the ophthalmic article may be approximately 1 unit lower than an untreated control (e.g., with ocular device, such as IOL, alone) or subject treated with a topical eye drop. In some embodiments, a posterior capsular opacification (PCO) score of an eye of a subject implanted with the ophthalmic article may be approximately at least 1 unit lower than an ophthalmic article without active agent and/or diagnostic agent control-treated subject, 60 days following the surgery. PCO is scored on 4-point scale (0=none visible, 1=mild/focal, 2=moderate/focal, 3=moderate/diffuse, 4=severe/diffuse). PCO may be a natural complication of cataract surgery whereby residual lens epithelial cells inside the lens capsule migrate and proliferate along the posterior lens capsule forming an opaque membrane that decreases visual acuity. An ophthalmic article that prevents or at least substantially slows this process can benefit the subject by maintaining their vision.

In some embodiments, the PCO score of the eye of the subject implanted with the ophthalmic article may be lower than a control subject (e.g., an untreated control, the subject treated with the optical eye drop, the subject treated with the ophthalmic article without active agent and/or diagnostic agent, etc.) by about 0.5 units to about 3.5 units. In some embodiments, the PCO score of the eye of the subject implanted with the ophthalmic article may be lower than the control subject by about 0.5 units to about 1 unit, about 0.5 units to about 1.5 units, about 0.5 units to about 2 units, about 0.5 units to about 2.5 units, about 0.5 units to about 3 units, about 0.5 units to about 3.5 units, about 1 unit to about 1.5 units, about 1 unit to about 2 units, about 1 unit to about 2.5 units, about 1 unit to about 3 units, about 1 unit to about 3.5 units, about 1.5 units to about 2 units, about 1.5 units to about 2.5 units, about 1.5 units to about 3 units, about 1.5 units to about 3.5 units, about 2 units to about 2.5 units, about 2 units to about 3 units, about 2 units to about 3.5 units, about 2.5 units to about 3 units, about 2.5 units to about 3.5 units, or about 3 units to about 3.5 units. In some embodiments, the PCO score of the eye of the subject implanted with the ophthalmic article may be lower than the control subject by about 0.5 units, about 1 unit, about 1.5 units, about 2 units, about 2.5 units, about 3 units, or about 3.5 units. In some embodiments, the PCO score of the eye of the subject implanted with the ophthalmic article may be lower than the control subject by at least about 0.5 units, at least about 1 unit, at least about 1.5 units, at least about 2 units, at least about 2.5 units, at least about 3 units, or at least about 3.5 units. In some embodiments, the PCO score of the eye of the subject implanted with the ophthalmic article may be lower than the control subject by at most about 0.5 units, at most about 1 unit, at most about 1.5 units, at most about 2 units, at most about 2.5 units, at most about 3 units, or at most about 3.5 units.

In some embodiments, an inflammation score comprising the iris and anterior chamber (AC) subscores on a standardized grading scale (e.g. the modified Hackett and McDonald ocular grading system) in a subject implanted with the ophthalmic article may be at least 1 unit lower than the inflammation score of an untreated subject and 2 units lower than the inflammation score of a subject treated with topical anti-inflammatory eye drops or subject with the ophthalmic article without the active agent and/or diagnostic agent, 90 days following the surgery.

In some embodiments, the inflammation score in the subject implanted with the ophthalmic article may be lower than the inflammation score of a control subject (e.g., the untreated subject, the subject treated with topical anti-inflammatory eye drops, the subject treated with the ophthalmic article without the active agent and/or diagnostic agent, etc.) by about 0.5 to about 12.5. In some embodiments, the inflammation score in the subject implanted with the ophthalmic article may be lower than the inflammation score of the control subject by about 0.5 to about 1, about 0.5 to about 1.5, about 0.5 to about 2, about 0.5 to about 2.5, about 0.5 to about 3, about 0.5 to about 4, about 0.5 to about 6, about 0.5 to about 8, about 0.5 to about 10, about 0.5 to about 12, about 0.5 to about 12.5, about 1 to about 1.5, about 1 to about 2, about 1 to about 2.5, about 1 to about 3, about 1 to about 4, about 1 to about 6, about 1 to about 8, about 1 to about 10, about 1 to about 12, about 1 to about 12.5, about 1.5 to about 2, about 1.5 to about 2.5, about 1.5 to about 3, about 1.5 to about 4, about 1.5 to about 6, about 1.5 to about 8, about 1.5 to about 10, about 1.5 to about 12, about 1.5 to about 12.5, about 2 to about 2.5, about 2 to about 3, about 2 to about 4, about 2 to about 6, about 2 to about 8, about 2 to about 10, about 2 to about 12, about 2 to about 12.5, about 2.5 to about 3, about 2.5 to about 4, about 2.5 to about 6, about 2.5 to about 8, about 2.5 to about 10, about 2.5 to about 12, about 2.5 to about 12.5, about 3 to about 4, about 3 to about 6, about 3 to about 8, about 3 to about 10, about 3 to about 12, about 3 to about 12.5, about 4 to about 6, about 4 to about 8, about 4 to about 10, about 4 to about 12, about 4 to about 12.5, about 6 to about 8, about 6 to about 10, about 6 to about 12, about 6 to about 12.5, about 8 to about 10, about 8 to about 12, about 8 to about 12.5, about 10 to about 12, about 10 to about 12.5, or about 12 to about 12.5. In some embodiments, the inflammation score in the subject implanted with the ophthalmic article may be lower than the inflammation score of the control subject by about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, or about 12.5. In some embodiments, the inflammation score in the subject implanted with the ophthalmic article may be lower than the inflammation score of the control subject by at least about 0.5, at least about 1, at least about 1.5, at least about 2, at least about 2.5, at least about 3, at least about 3.5, at least about 4, at least about 4.5, at least about 5, at least about 5.5, at least about 6, at least about 6.5, at least about 7, at least about 7.5, at least about 8, at least about 8.5, at least about 9, at least about 9.5, at least about 10, at least about 10.5, at least about 11, at least about 11.5, at least about 12, or at least about 12.5. In some embodiments, the inflammation score in the subject implanted with the ophthalmic article may be lower than the inflammation score of the control subject by at most about 0.5, at most about 1, at most about 1.5, at most about 2, at most about 2.5, at most about 3, at most about 3.5, at most about 4, at most about 4.5, at most about 5, at most about 5.5, at most about 6, at most about 6.5, at most about 7, at most about 7.5, at most about 8, at most about 8.5, at most about 9, at most about 9.5, at most about 10, at most about 10.5, at most about 11, at most about 11.5, at most about 12, or at most about 12.5.

In some cases, the inflammation sub-scores of the untreated subject and the subject treated with topical anti-inflammatory eye drops are 4-fold (e.g., 4.5-fold) and 7-fold higher than the subject treated with the ophthalmic article, 90 days following surgery. These absolute and/or relative reductions in inflammation scores can support the therapeutic potential of the ophthalmic article to reduce the iris-anterior chamber sub-score relative to topical eye drops, untreated controls, and/or topical anti-inflammatory eye drops. This therapeutic benefit of the ophthalmic article for reduction of inflammation can also indicate a greater capacity of the ophthalmic article to treat inflammation after cataract surgery.

In some examples, the inflammation sub-scores of a control subject (e.g., the untreated subject, the subject treated with the topical anti-inflammatory eye drops, etc.) may be higher than that of the subject treated with the ophthalmic article (e.g., 90 days following such surgery) by about 1-fold to about 20-fold. In some examples, the inflammation sub-score of the control subject may be higher than that of the subject treated with the ophthalmic article by about 1-fold to about 2-fold, about 1-fold to about 3-fold, about 1-fold to about 4-fold, about 1-fold to about 5-fold, about 1-fold to about 6-fold, about 1-fold to about 7-fold, about 1-fold to about 8-fold, about 1-fold to about 9-fold, about 1-fold to about 10-fold, about 1-fold to about 15-fold, about 1-fold to about 20-fold, about 2-fold to about 3-fold, about 2-fold to about 4-fold, about 2-fold to about 5-fold, about 2-fold to about 6-fold, about 2-fold to about 7-fold, about 2-fold to about 8-fold, about 2-fold to about 9-fold, about 2-fold to about 10-fold, about 2-fold to about 15-fold, about 2-fold to about 20-fold, about 3-fold to about 4-fold, about 3-fold to about 5-fold, about 3-fold to about 6-fold, about 3-fold to about 7-fold, about 3-fold to about 8-fold, about 3-fold to about 9-fold, about 3-fold to about 10-fold, about 3-fold to about 15-fold, about 3-fold to about 20-fold, about 4-fold to about 5-fold, about 4-fold to about 6-fold, about 4-fold to about 7-fold, about 4-fold to about 8-fold, about 4-fold to about 9-fold, about 4-fold to about 10-fold, about 4-fold to about 15-fold, about 4-fold to about 20-fold, about 5-fold to about 6-fold, about 5-fold to about 7-fold, about 5-fold to about 8-fold, about 5-fold to about 9-fold, about 5-fold to about 10-fold, about 5-fold to about 15-fold, about 5-fold to about 20-fold, about 6-fold to about 7-fold, about 6-fold to about 8-fold, about 6-fold to about 9-fold, about 6-fold to about 10-fold, about 6-fold to about 15-fold, about 6-fold to about 20-fold, about 7-fold to about 8-fold, about 7-fold to about 9-fold, about 7-fold to about 10-fold, about 7-fold to about 15-fold, about 7-fold to about 20-fold, about 8-fold to about 9-fold, about 8-fold to about 10-fold, about 8-fold to about 15-fold, about 8-fold to about 20-fold, about 9-fold to about 10-fold, about 9-fold to about 15-fold, about 9-fold to about 20-fold, about 10-fold to about 15-fold, about 10-fold to about 20-fold, or about 15-fold to about 20-fold. In some examples, the inflammation sub-score of the control subject may be higher than that of the subject treated with the ophthalmic article by about 1-fold, about 2-fold, about 3-fold, about 4-fold, about 5-fold, about 6-fold, about 7-fold, about 8-fold, about 9-fold, about 10-fold, about 15-fold, or about 20-fold. In some examples, the inflammation sub-score of the control subject may be higher than that of the subject treated with the ophthalmic article by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, or at least about 20-fold. In some examples, the inflammation sub-score of the control subject may be higher than that of the subject treated with the ophthalmic article by at most about 1-fold, at most about 2-fold, at most about 3-fold, at most about 4-fold, at most about 5-fold, at most about 6-fold, at most about 7-fold, at most about 8-fold, at most about 9-fold, at most about 10-fold, at most about 15-fold, or at most about 20-fold.

In some embodiments, within 7 days after implantation, the one or more ophthalmic articles releases the one or more active agents and results in an inflammation score of at most 1 (e.g., as measured by an anterior chamber cell score using slit lamp biomicroscopy) and/or absence of eye pain (e.g., as measure by a 10-point visual analog scale). In some embodiments, the anterior chamber cell score may be a mean anterior chamber cell score.

In some embodiments, within 7 days after implantation, the one or more ophthalmic articles releases the one or more active agents and results in an inflammation score from 0 to 1. The inflammation score may be from about 0 to about 0.1, about 0 to about 0.2, about 0 to about 0.3, about 0 to about 0.4, about 0 to about 0.5, about 0 to about 0.6, about 0 to about 0.7, about 0 to about 0.8, about 0 to about 0.9, about 0 to about 1, about 0.1 to about 0.2, about 0.1 to about 0.3, about 0.1 to about 0.4, about 0.1 to about 0.5, about 0.1 to about 0.6, about 0.1 to about 0.7, about 0.1 to about 0.8, about 0.1 to about 0.9, about 0.1 to about 1, about 0.2 to about 0.3, about 0.2 to about 0.4, about 0.2 to about 0.5, about 0.2 to about 0.6, about 0.2 to about 0.7, about 0.2 to about 0.8, about 0.2 to about 0.9, about 0.2 to about 1, about 0.3 to about 0.4, about 0.3 to about 0.5, about 0.3 to about 0.6, about 0.3 to about 0.7, about 0.3 to about 0.8, about 0.3 to about 0.9, about 0.3 to about 1, about 0.4 to about 0.5, about 0.4 to about 0.6, about 0.4 to about 0.7, about 0.4 to about 0.8, about 0.4 to about 0.9, about 0.4 to about 1, about 0.5 to about 0.6, about 0.5 to about 0.7, about 0.5 to about 0.8, about 0.5 to about 0.9, about 0.5 to about 1, about 0.6 to about 0.7, about 0.6 to about 0.8, about 0.6 to about 0.9, about 0.6 to about 1, about 0.7 to about 0.8, about 0.7 to about 0.9, about 0.7 to about 1, about 0.8 to about 0.9, about 0.8 to about 1, or about 0.9 to about 1.

In some embodiments, within 7 days after implantation, the one or more ophthalmic articles releases the one or more active agents and results in an inflammation score of at least about 0, at least about 0.1, at least about 0.2, at least about 0.3, at least about 0.4, at least about 0.5, at least about 0.6, at least about 0.7, at least about 0.8, at least about 0.9, or at least about 1. In some embodiments, within 7 days after implantation, the one or more ophthalmic articles releases the one or more active agents and results in an inflammation score of at most about 0, at most about 0.1, at most about 0.2, at most about 0.3, at most about 0.4, at most about 0.5, at most about 0.6, at most about 0.7, at most about 0.8, at most about 0.9, or at most about 1.

In some embodiments, within 7 days after implantation, the one or more ophthalmic articles releases the one or more active agents and results in an inflammation score of about 0, about 0.1, about 0.2, about 0.3, about 0.4, about 0.5, about 0.6, about 0.7, about 0.8, about 0.9, or about 1.

In some embodiments, the one or more ophthalmic articles releases the one or more active agents and results in a low inflammation score (e.g., from about 0.4 to about 0.6) within about 1 day to about 28 days. In some embodiments, the one or more ophthalmic articles releases the one or more active agents and results in a low inflammation score within about 1 day to about 2 days, about 1 day to about 3 days, about 1 day to about 4 days, about 1 day to about 5 days, about 1 day to about 6 days, about 1 day to about 7 days, about 1 day to about 14 days, about 1 day to about 21 days, about 1 day to about 28 days, about 2 days to about 3 days, about 2 days to about 4 days, about 2 days to about 5 days, about 2 days to about 6 days, about 2 days to about 7 days, about 2 days to about 14 days, about 2 days to about 21 days, about 2 days to about 28 days, about 3 days to about 4 days, about 3 days to about 5 days, about 3 days to about 6 days, about 3 days to about 7 days, about 3 days to about 14 days, about 3 days to about 21 days, about 3 days to about 28 days, about 4 days to about 5 days, about 4 days to about 6 days, about 4 days to about 7 days, about 4 days to about 14 days, about 4 days to about 21 days, about 4 days to about 28 days, about 5 days to about 6 days, about 5 days to about 7 days, about 5 days to about 14 days, about 5 days to about 21 days, about 5 days to about 28 days, about 6 days to about 7 days, about 6 days to about 14 days, about 6 days to about 21 days, about 6 days to about 28 days, about 7 days to about 14 days, about 7 days to about 21 days, about 7 days to about 28 days, about 14 days to about 21 days, about 14 days to about 28 days, or about 21 days to about 28 days. In some embodiments, the one or more ophthalmic articles releases the one or more active agents and results in a low inflammation score (e.g., from about 0.4 to about 0.6) within about 1 day, about 2 days, about 3 days, about 4 days, about 5 days, about 6 days, about 7 days, about 14 days, about 21 days, or about 28 days. In some embodiments, the one or more ophthalmic articles releases the one or more active agents and results in a low inflammation score within at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days. In some embodiments, the one or more ophthalmic articles releases the one or more active agents and results in a low inflammation score within at most about 1 day, at most about 2 days, at most about 3 days, at most about 4 days, at most about 5 days, at most about 6 days, at most about 7 days, at most about 8 days, at most about 9 days, at most about 10 days, at most about 11 days, at most about 12 days, at most about 13 days, at most about 14 days, at most about 15 days, at most about 16 days, at most about 17 days, at most about 18 days, at most about 19 days, at most about 20 days, at most about 21 days, at most about 22 days, at most about 23 days, at most about 24 days, at most about 25 days, at most about 26 days, at most about 27 days, at most about 28 days, at most about 29 days, or at most about 30 days.

Various methods may be used to produce the ophthalmic articles. Methods may comprise solvent casting, phase separation, interfacial methods, molding, compression molding, injection molding, extrusion, co-extrusion, heat extrusion, die cutting, heat compression, and combinations thereof. In another aspect, the present disclosure provides a method for preparing at least one ophthalmic article. One or more active agents and/or diagnostic agents in a solvent may be combined with a biocompatible material (e.g., biocompatible polymeric matrix in the solvent), thereby generating a combined mixture in the solvent. The solvent may be removed from the combined mixture to generate an evaporated mixture comprising the one or more active agents and/or diagnostic agents. Next, a weighted tool may be used to compress the evaporated mixture to generate a compressed mixture. A shaping tool and/or an orifice tool may be used to extract the at least one ophthalmic article from the compressed mixture.

In some embodiments, a polymeric material (e.g., biocompatible copolymer matrix) may be dispersed or dissolved in a solvent to form a dispersion, suspension or solution, heated and shaken to form a polymer mixture. The solvent may be selected for its compatibility with the polymeric material. The temperature and rate of shaking may be selected to achieve homogeneous mixing in timely manner. For example, a polymer material comprising a biodegradable, biocompatible copolymer of caprolactone, as disclosed herein, may be dissolved in dichloromethane and shaken in an orbital shaker at a speed of 300 RPM at a temperature between about 50° C. and 70° C. for about 1 hour to 4 hours.

One or more active agents and/or diagnostic agents may dissolve in the solvent to form a solution. If one or more agents are included in the ophthalmic article, the material may be homogenous or non-homogenous (i.e., heterogenous). In some examples, the ophthalmic article can include a plurality of agents and can be homogenous. In some examples, the ophthalmic article can include a plurality of agents and can be non-homogenous. For example, one agent can be coated on the surface of the ophthalmic article. In yet other examples, the ophthalmic article can be formulated to have pre-designated regions or layers including different agents. In yet other examples, the ophthalmic article can be formulated to have pre-designated regions or layers having the same agent, but at different concentrations. For example, in some cases, an outer region or layer of the ophthalmic article can have a higher concentration of the agent to deliver a higher initial dose or burst of the agent followed by a prolonged lower dose over a period of days or weeks. Further, in some examples, different regions of the ophthalmic article can be adapted to biodegrade at different rates.

Next, the polymer mixture may be combined with the mixture of the active agent and/or diagnostic agent to form a mixture of the polymeric material and the active agent and/or diagnostic agent. Then, the mixture of the polymeric material and the active agent and/or diagnostic agent can be heated to remove the solvent to form an evaporated mixture. In a non-limiting example, the mixture may be heated to about 50° C. or about 70° C. and shaken at a speed of about 300 RPM to complete evaporation in about 16 hours. Once the solvent has mostly or completely evaporated, a weighted tool may be used to compress the evaporated mixture into a sheet. In some embodiments, the weighted tool may comprise a steel plate. In some embodiments, the weighted tool may be a heated steel plate. In some embodiments, the weighted tool may a heated steel plate with Teflon. Next, a shaping tool and an orifice tool may be used to extract the at least one ophthalmic article from the compressed sheet. In some embodiments, the shaping tool may comprise a shaping portion with a shape and size suitable for generating an ophthalmic article of any of the geometries, sizes, and designs described herein. The orifice tool may comprise a portion for creating any of the internal structures (e.g., hole), described herein, for the ophthalmic article. For example, the shaping tool (e.g., a stainless steel tube or follicular unit extraction punch) may be used to mold the ophthalmic article. And, the orifice tool (e.g., a stainless steel tube or follicular unit extraction punch) may be used under a microscope to create a hole in the center of the ophthalmic article. In some embodiments, the shaping tool and orifice tool may be opposite sides of the same tool. In some embodiments, the shaping tool and orifice tool may be different tools.

EXAMPLES

The examples below are illustrative and non-limiting.

Example 1: An Ophthalmic Article Placed on an Intraocular Lens

FIG. 7A illustrates an example of an ophthalmic article. The ophthalmic article 100 was shaped like an extruded annulus with an inner structure (e.g., hole) 110.

FIG. 7B illustrates an example of an ophthalmic article placed on an ocular device. The ophthalmic article 100 was place was stretched to a stretched state and placed on the haptic 302 of an intraocular lens (IOL) 300 (e.g., Tecnis 1-piece by Johnson & Johnson Surgical Vision).

Figure 7D:
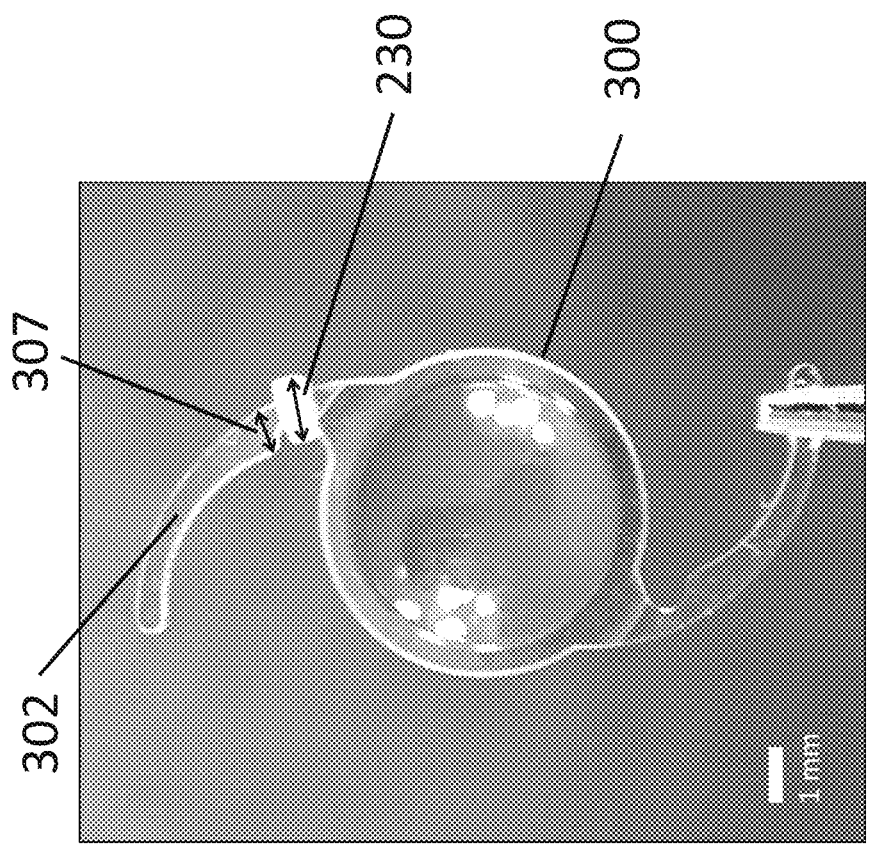
FIG. 7D illustrates plan view of an exemplary ophthalmic article.
Figure 7C:
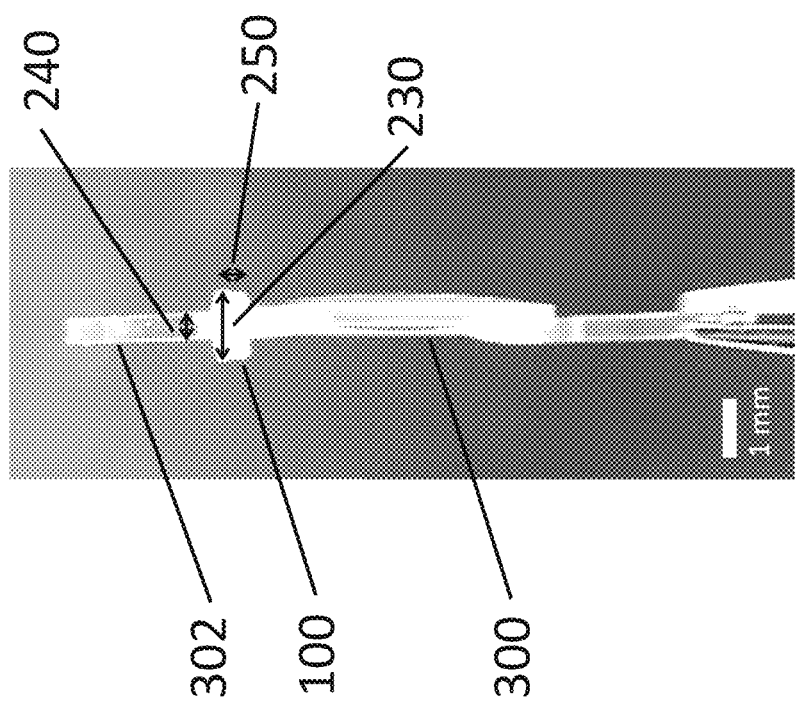
FIG. 7C illustrates a side view of an exemplary ophthalmic article.

FIG. 7C illustrates a side view of an exemplary ophthalmic article. The exemplary ophthalmic article 100 was comprised of about 12% percentage weight (wt %) ketorolac tromethamine and about 88% (wt %) of poly(L-lactide-co-caprolactone) at about 60:40 ratio (e.g., molar ratio) of L-lactide to caprolactone. The ophthalmic article was placed on a haptic 302 of an intraocular lens (IOL) 300 (e.g., Tecnis 1-piece by Johnson & Johnson Surgical Vision). The ophthalmic article 100 was shaped like an extruded annulus. An outer diameter 230 of the ophthalmic article 100 may be approximately 1 mm and in this illustrative embodiment, the outer diameter 230 was about 1.1 millimeter (mm) wide. An internal structure (e.g., a hole in the center) 110 of the ophthalmic article 100 may have an inner diameter 240 of approximately 0.6 mm and in this illustrative embodiment, the inner diameter 240 was about 0.65. The illustrative ophthalmic article 110 can have a cross sectional thickness 250 of about 0.5 The ophthalmic article 100 was stretched to a stretched state and placed on the haptic 302 of the IOL 300. The ophthalmic article 100, in shape of an extruded annulus, can be stretched by a handpiece (e.g., forceps) and placed over and around the haptic 302 of an IOL 300. The inner diameter 240 of the ophthalmic article 100 was at least about the same as the cross-sectional length 307 of the haptic 302. The cross-sectional length 307 of the haptic 302 can be about 0.7 millimeters (mm) wide and in this exemplary embodiment the cross sectional length 307 was about 0.73.

FIG. 7D illustrates plan view of an exemplary ophthalmic article. The ophthalmic article 100 was comprised of 12% (wt %) ketorolac tromethamine and 88% (wt %) poly(L-lactide-co-caprolactone) at 70:30 ratio (e.g., molar ratio) of L-lactide to caprolactone. The ophthalmic article 100 was placed on a haptic 302 of an intraocular lens (IOL) 300 (e.g., Tecnis 1-piece by Johnson & Johnson Surgical Vision). An outer diameter 230 of the ophthalmic article 100 may be approximately 1 mm and in this illustrative embodiment, the outer diameter 230 was about 1.1 millimeter (mm) wide. The ophthalmic article 100 was stretched to a stretched state and placed on the haptic 302 of the IOL 300. The inner diameter 240 of the ophthalmic article 100 was at least about the same as the cross-sectional length 307 of the haptic 302.

Example 2: An Ophthalmic Article Stretch Test

FIG. 8A illustrates an example of an ophthalmic article 100 placed on a haptic 302 of an IOL (e.g., Aurovue IOL) 300. In this illustrative embodiment, the ophthalmic article 100 was comprised of about 12% (wt %) ketorolac tromethamine and about 88% (wt %) poly(L-lactide-co-caprolactone) at 60:40 ratio of L-lactide to caprolactone. The illustrative ophthalmic article 100 was shaped like an extruded annulus. The ophthalmic article can have an outer diameter of about 1.2 mm and an inner structure (e.g., a hole) with an inner diameter of about 0.6 mm; in this illustrative embodiment, the ophthalmic article 100 has an outer diameter 230 of about 1.25 mm, an inner diameter of about 0.65 mm and a cross sectional thickness 250 of 0.5 mm. The illustrative ophthalmic article 100 was tested for an elongation required to place the illustrative ophthalmic article 100 on a haptic 302 of an IOL 300. Cross sectional dimensions of the haptic 302 at a widest part 307 can be approximately 1.00 mm×0.3 mm, and in this illustrative example the cross-sectional dimensions of the haptic 302 at a widest part 307 were about 1.00 mm×0.32 mm.

FIG. 8B schematically illustrates an ophthalmic article. The ophthalmic article can have a circumference or perimeter of about 1.5 and can be stretched to at least about 2.7; and in this illustrative embodiment, for the ophthalmic article 100 ophthalmic article to fit onto the widest part 307 of the haptic 302 (FIG. 8A), the ophthalmic article 100 must stretch from an annulus of about 1.57 mm circumference to form a rectangle having a perimeter of about 2.64 mm.

Therefore, in this illustrative embodiment, the ophthalmic article 100 was required to stretch or elongate at least about 168% in order to be placed on the haptic 302 of the IOL 300 (e.g., Aurovue IOL) shown in FIG. 8A. An equivalent calculation for a foldable acrylic IOL (e.g., Tecnis 1-piece by Johnson & Johnson Surgical Vision) was performed. In an illustrative example, an ophthalmic article 100 may be required to stretch or elongate at least about 150% to accommodate an approximately 0.7×0.5 mm rectangle, which can be a widest part of the foldable acrylic IOL (e.g., Tecnis 1-piece by Johnson & Johnson Surgical Vision).

Example 3: An Ophthalmic Article Elongation Test

FIG. 9A, FIG. 9B, and FIG. 9C schematically illustrate results of an elongation at break test of an ophthalmic article 100, disclosed herein, using forceps 905. In this illustrative embodiment, the ophthalmic article 100 was comprised of about 12% (wt %) ketorolac tromethamine and about 88% (wt %) poly(L-lactide-co-caprolactone) at 60:40 ratio of L-lactide to caprolactone. FIG. 9A illustrates a pre-stretched state of the ophthalmic article 100. FIG. 9B illustrates an elongated state of the ophthalmic article 100 stretched to about 1.8 times the pre-stretched state of the ophthalmic article 100 using the forceps 905. FIG. 9C illustrates a recovered state of the ophthalmic article 100 in about four seconds after a pressure from the forceps 905 was released.

Example 4: Elongation at Break Test

Figure 10:
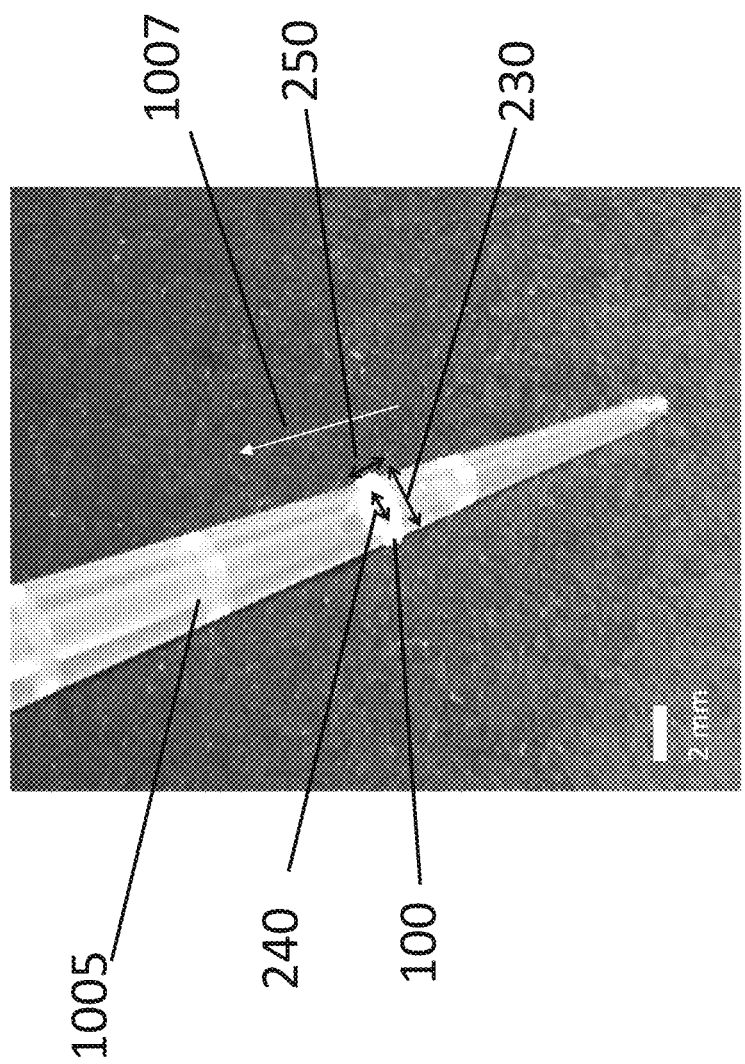
FIG. 10 illustrates elongation at break test performed on an ophthalmic article.

An elongation at break test was performed on an ophthalmic article as shown in FIG. 10. In this illustrative embodiment, the article was comprised of about 12% (wt %) ketorolac tromethamine and about 88% (wt %) poly(L-lactide-co-caprolactone) at 60:40 molar ratio of L-lactide to caprolactone. The ophthalmic article can have an outer diameter of about 1.2 mm and an inner structure (e.g., a hole) with an inner diameter of about 0.6 mm; in this illustrative embodiment, the ophthalmic article 100 has an outer diameter 230 of about 1.25 mm, an inner diameter 240 of about 0.65 mm and a cross sectional thickness 250 of 0.5 mm. The exemplary ophthalmic article 100 in this illustrative embodiment was applied to the tip of a standard 200 microliter (μl) micropipette 1005 and slowly advanced upward 1007 with forceps until break occurred. The elongation at break test was performed in a triplicate. The ophthalmic article's diameter at break (break diameter) was recorded for each test using a micro-caliper. The break diameter can be about 3 mm to about 5 mm; in this illustrative embodiment, the break diameters for the triplicate were about 3.37 mm, 3.25 mm, and 4.30 mm. The break diameters were 674%, 650%, and 860% wider compared to the ophthalmic article's diameter before the test indicating a wide range of elongation for the ophthalmic article. An elongation capacity of the ophthalmic article 100 as described herein ensures that the ophthalmic article 100 can be stretched to be applied to an ocular device (e.g., a haptic of an IOL) without breakage.

An ophthalmic device and/or ocular devices such as intraocular lenses may exhibit sufficient strength to allow them to be folded without fracturing. Devices made from polymers which may break at less than 150% elongation may not endure the distortion which necessarily occurs when they are rolled or folded to a dimension small enough to pass through a small incision.

Therefore, the elongation capacity of the ophthalmic article may not only enable it to be stretched for application to an ocular device (e.g., an IOL), it may also ensure that the ophthalmic article attached to an ocular device (e.g., IOL), can be folded, rolled or otherwise deformed into a low profile condition for insertion into the eye using standard surgical technique.

Example 5: Linear Stretch of an Ophthalmic Article

Figure 11:
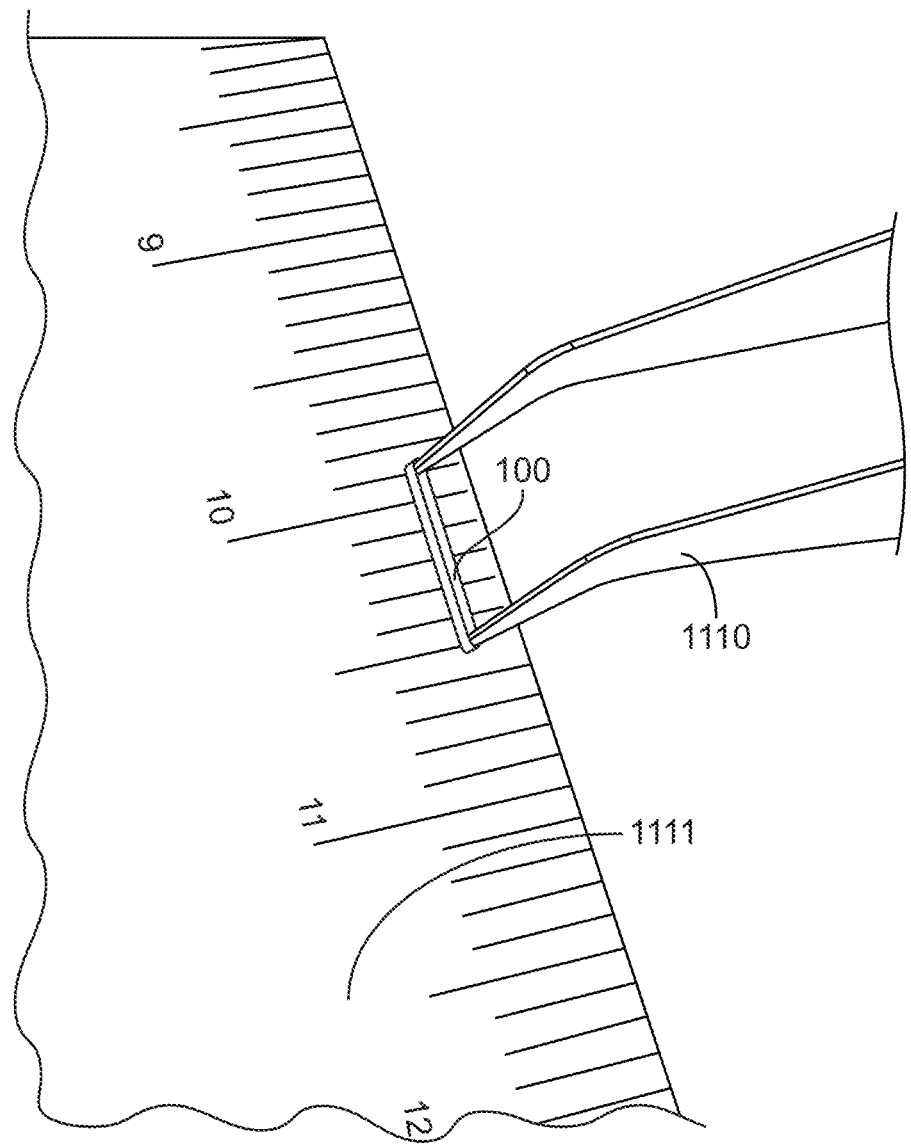
FIG. 11 illustrates a stretched state of the ophthalmic article.

A linear stretch test was performed on an ophthalmic article 100. In this illustrative embodiment, the ophthalmic article 100 comprised of 12% (wt %) tromethamine and 88% (wt %) poly(L-lactide-co-caprolactone) at 60:40 ratio of L-lactide to caprolactone. The dimensions of the ophthalmic article 100 was the same as in the illustrative Example 4. The ophthalmic article was stretched linearly using a dilation forceps 1110 (e.g., a 5⅓", angled 45°, 0.3 mm diameter tips, and 9.0 mm wide flat handle Ambler Surgical Dilator forceps). The amount of stretch was measured using a ruler 1111 as shown in FIG. 11. The experiment was performed in a triplicate. In this illustrative example, all three samples were stretched to 6 mm without breaking, which was about 1200% elongation compared to the ophthalmic article's diameter before the test. An elongation capacity of the ophthalmic article 100 ensures that the ophthalmic article can be stretched to be placed onto an ocular device (e.g., a haptic of an IOL) without breakage. As described in this illustrative example, the capacity of the ophthalmic article to stretch, flex and deform can be consistent with the properties of the IOL to which it was placed upon, and such properties may enable an ocular device and the ophthalmic article attached to it to be inserted into the eye through a small incision in accordance with some standard surgical technique.

Example 6: An Example of an Ophthalmic Article Loaded with a Drug

Figure 12:
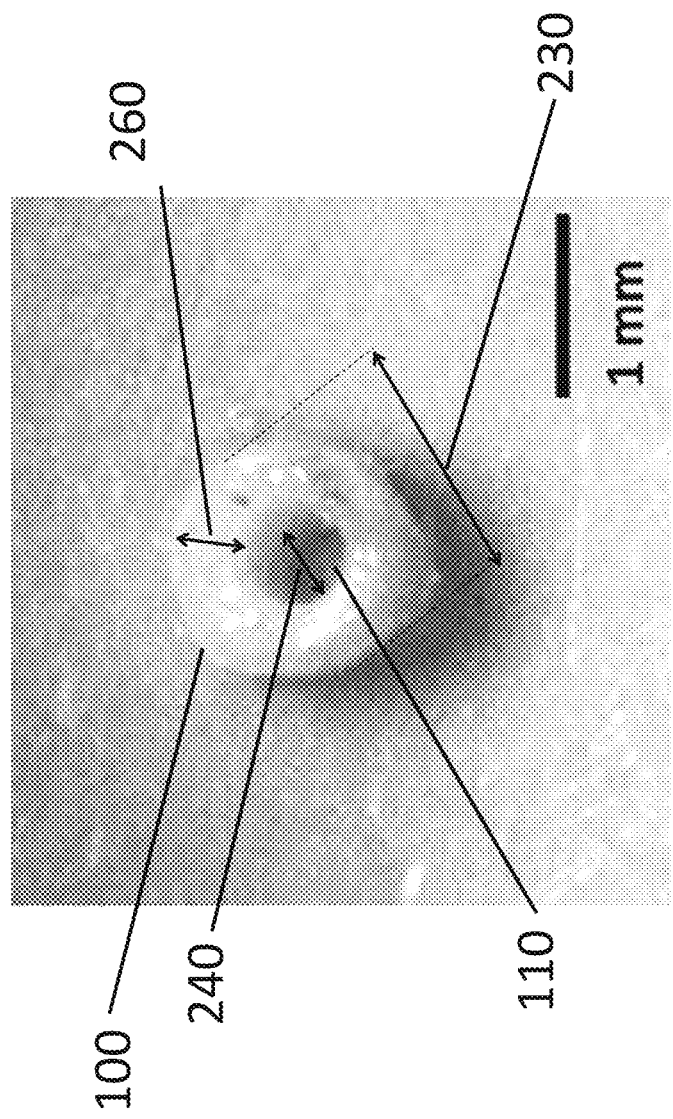
FIG. 12 shows an illustrative embodiment of an ophthalmic article.

FIG. 12 shows an illustrative embodiment of an ophthalmic article 100 for delivery of a drug (e.g., an antibiotic substance) into the eye. In this illustrative embodiment, the ophthalmic article 100 was shaped like an extruded annulus with an outer diameter 230 of about 1.3 mm, an inner structure diameter 240 of about 0.5 mm and a wall thickness of about 0.7 mm. The ophthalmic article 100 can comprise approximately 22% (wt %) of a drug (e.g., moxifloxacin antibiotic drug) and 78% (wt %) of a copolymer. In this illustrative embodiment, the copolymer comprises poly(L-lactide-co-caprolactone) at 50:50 molar ratio of L-lactide to caprolactone with a molecular mass ($M_n$) of about 75 to 85 kDa.

Example 7: Another Example of an Ophthalmic Article Loaded with a Drug

Figure 13:
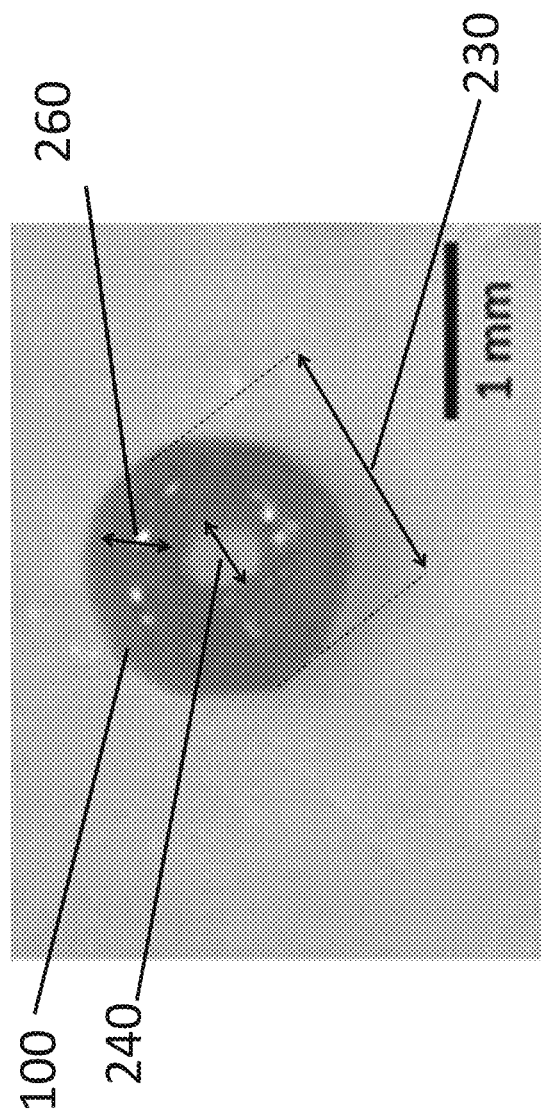
FIG. 13 shows another illustrative embodiment of an ophthalmic article.

FIG. 13 shows another illustrative embodiment of an ophthalmic article 100. In this illustrative embodiment, the ophthalmic article 100 was shaped like an extruded annulus with an outer diameter 230 of about 1.3 mm, an inner structure diameter 240 of about 0.5 mm and a wall thickness of about inner 0.7 mm. The ophthalmic article may comprise about 17% (wt %) of a drug and about 83% (wt %) of a copolymer. In this illustrative embodiment the ophthalmic article comprised approximately 16.7% (wt %) of a corticosteroid (e.g., dexamethasone) and about 83.3% (wt %) of a copolymer. In this illustrative embodiment, the copolymer comprised poly(L-lactide-co-caprolactone) at 50:50 molar ratio of L-lactide to caprolactone with a molecular mass ($M_n$) of about 75 to 85 kDa.

Example 8: An Example of an Ophthalmic Article Placed on an Ocular Device

Figure 14A:
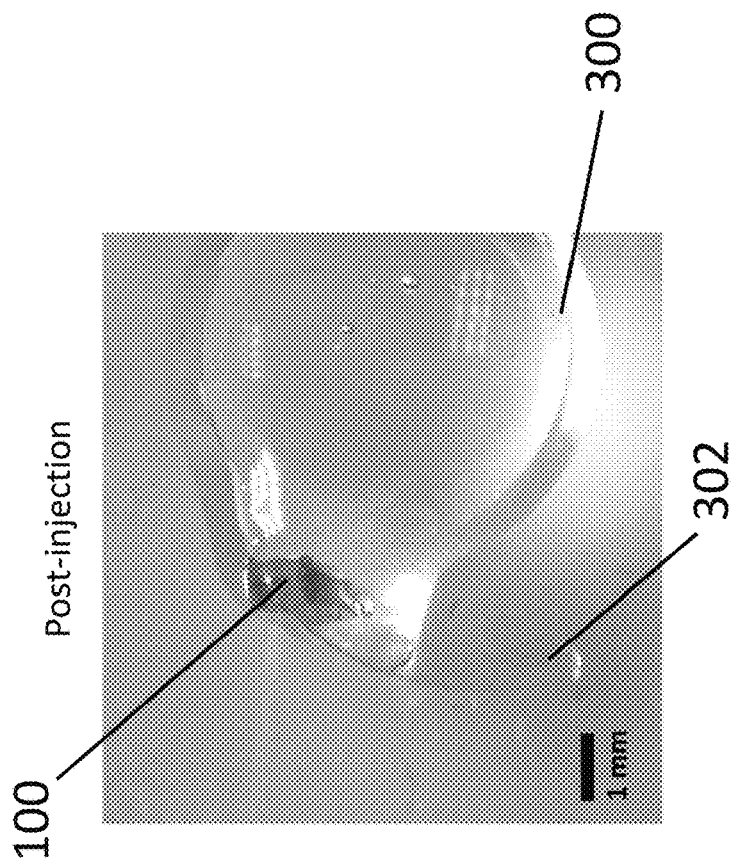
FIG. 14A shows an exemplary appearance of the ophthalmic article and IOL before an in vitro IOL injection.
Figure 14B:
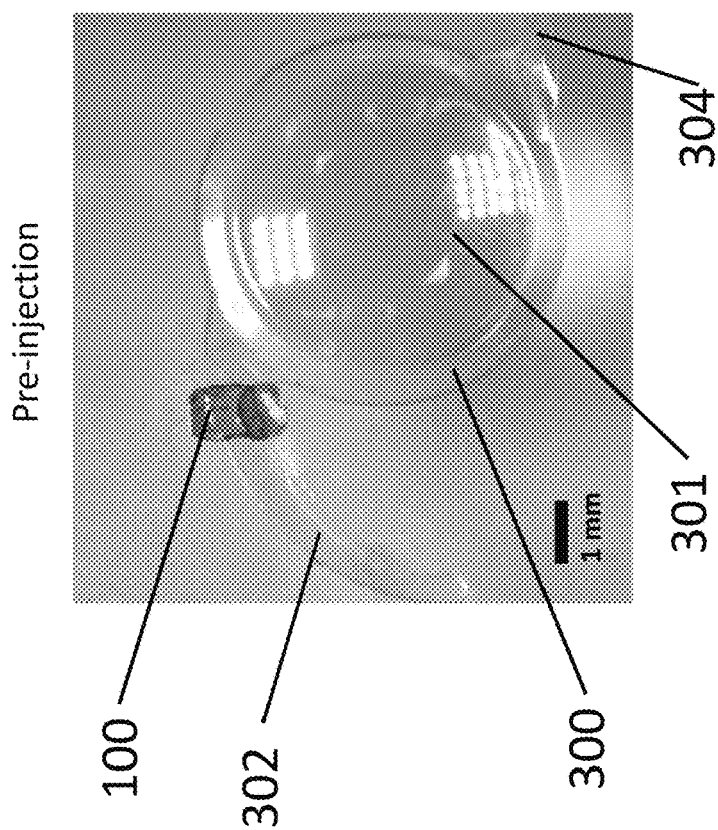
FIG. 14B shows the exemplary appearance of the ophthalmic article and the IOL after the in vitro IOL injection was performed.

FIG. 14A and FIG. 14B illustrate an example of an ophthalmic article 100 made from a copolymer. The ophthalmic article 100 was shaped like an extruded annulus with an outer diameter 230 of about 1.3 mm, an inner structure diameter 240 of about 0.5 mm and a wall thickness of about 0.7 mm. In this illustrative embodiment, the copolymer comprised poly(L-lactide-co-caprolactone) at 50:50 molar ratio of L-lactide to caprolactone with a molecular mass ($M_n$) of about 75 to 85 kDa. An in vitro injection was performed to qualitatively test the ophthalmic article placed on an IOL before and after an IOL injection. The in vitro IOL injection was similar to an IOLs injection process in a cataract surgery other than that the IOL and ophthalmic device were ejected into a phosphate-buffered saline (PBS) rather in a subject's eye. FIG. 14A shows an exemplary appearance of the ophthalmic article 100 and IOL 300 before an in vitro IOL injection was performed. FIG. 14B shows the exemplary appearance of the ophthalmic article 100 and the IOL 300 after the in vitro IOL injection was performed. During the in vitro IOL injection, the ophthalmic article 100 and IOL 300 were loaded into an injector cartridge (e.g., an injector cartridge with a 1.2 mm diameter tip) designed for use with the IOL (e.g., Tecnis, Johnson & Johnson Surgical Vision) along with a small amount of viscoelastic substance as customary with IOL injection procedures. The filled cartridge was then loaded into the accompanying injector device. The ophthalmic article 100 and the IOL 300 were then manually ejected from the injector into a small volume of PBS and allowed to unfold at room temperature for approximately 3 minutes. Following the injection, the IOL 300 returned to its original size and shape, but the ophthalmic article 100 was misshapen (FIG. 14B). The ophthalmic article 100 was located in the original position on the haptic, but some aspects of the ophthalmic article 100 appeared to be elongated and narrowed in the region closest to the body of the IOL 300.

Without wishing to be bound by theory, a partially distorted appearance of the ophthalmic article 100 after the in vitro injection may be explained, by the mechanical stress imposed on the ophthalmic article 100 during the in vitro injection process and the intrinsic material properties of the ophthalmic article. As part of the in vitro injection process, the haptics 302 and 304 of the IOL 300 were folded over the optic portion 301 of the IOL 300 as it was rolled into a narrower profile to facilitate passage through a narrow aperture of the injector tip. Without wishing to be bound by theory, this likely imposed pressure on the ophthalmic article 100 at the location where it appeared to be elongated and narrowed. An ophthalmic article that, when injected with an IOL for cataract surgery retains its position on the IOL to which it was attached but does not fully recover its original shape after injection may be suitable but may not optimal for use in cataract surgery.

Example 9: Another Example of an Ophthalmic Article Placed on an Ocular Device

FIG. 15A and FIG. 15B illustrate examples of an ophthalmic article 100 placed on a haptic 302 of an IOL 300. In this illustrative embodiment, the ophthalmic article was shaped like an extruded annulus of approximately 1.3 mm outer diameter, 0.5 mm hole or inner diameter and 0.7 mm thickness. The ophthalmic article comprised approximately 22% (wt %) moxifloxacin antibiotic drug and 78% (wt %) poly(L-lactide-co-caprolactone) at 50:50 ratio with a molecular mass ($M_n$) of about 75 to 85 kDa. The ophthalmic article 100 was positioned on the haptic 302 of a foldable acrylic IOL 300 (e.g., Aurovue by Aurolab). FIG. 15A shows an exemplary appearance of the ophthalmic article 100 and IOL 300 before an in vitro IOL injection was performed. FIG. 15B shows the exemplary appearance of the ophthalmic article 100 and IOL 300 after the in vitro IOL injection was performed. During the in vitro IOL injection, the ophthalmic article 100 and IOL 300 loaded into an injector cartridge (e.g., a cartridge with a tip inner diameter of 1.7 mm) designed for use with the IOL 300 (e.g., Aurovue IOL) along with a small amount of viscoelastic substance as customary with an IOL injection procedures. The filled cartridge was then loaded into the accompanying injector device. The ophthalmic article 100 and IOL 300 were then manually ejected from the injector into a small volume of phosphate-buffered saline (PBS) and were allowed to unfold at room temperature for approximately 3 minutes. Following the injection, the ophthalmic article 100 and IOL 300 returned to original size and shape (FIG. 15B), and the ophthalmic article 100 was located in the same position on the haptic without significant distortion or disruption of its original physical appearance shown in FIG. 15A.

Example 10: An Example of an Ophthalmic Article after an In Vitro Injection

FIG. 16A and FIG. 16B illustrate examples of an ophthalmic article 100 placed on a haptic 302 of an IOL 300. In this illustrative embodiment, the ophthalmic article 100 was shaped like an extruded annulus of approximately 1.3 mm outer diameter 230, about 0.5 mm inner diameter 240 and about 0.7 mm cross sectional thickness 250. The ophthalmic article 100 comprised approximately 20% (wt %) dexamethasone antibiotic drug and about 80% (wt %) poly(L-lactide-co-caprolactone) at about 50:50 molar ratio with a molecular mass ($M_n$) of about 75 to 85 kDa. The ophthalmic article 100 was positioned on a haptic 302 of a foldable acrylic IOL 300 (e.g., Tecnis 1-piece by Johnson & Johnson Surgical Vision). FIG. 16A shows an exemplary appearance of the ophthalmic article 100 and IOL 300 before an in vitro IOL injection was performed. FIG. 16B shows the exemplary appearance of the ophthalmic article 100 and IOL 300 after the in vitro IOL injection was performed. During the in vitro IOL injection, the ophthalmic article 100 and IOL 300 were loaded into an injector cartridge (e.g., UNFOLDER Platinum 1 Series by Johnson & Johnson Surgical Vision with a tip inner diameter of about 1.2 mm) designed for use with the IOL 300 (e.g., Tecnis 1-piece by Johnson & Johnson Surgical Vision) along with a small amount of viscoelastic substance as customary with IOL injection procedures. The filled cartridge was then loaded into the accompanying injector device. The ophthalmic article 100 and IOL 300 were then manually ejected from the injector into a small volume of phosphate-buffered saline (PBS) and were allowed to unfold at room temperature for approximately 3 minutes. Following the injection, the ophthalmic article 100 IOL 300 returned to original size and shape (FIG. 16A), and the ophthalmic article 100 was located in the same position on the haptic. However, the injection process resulted in partial distortion of the ophthalmic article 100 as evidenced by narrowing and elongation in the region 1610 of the device adjacent to the body of the IOL 300.

Example 11: An Ophthalmic Article Comprising a Copolymer

FIG. 17A and FIG. 17B illustrate examples of an ophthalmic article 100 placed on a haptic 302 of an IOL 300. In this illustrative embodiment, the ophthalmic article 100 comprised approximately 9% (wt %) dexamethasone and 91% (wt %) poly(L-lactide-co-caprolactone) at 60:40 molar ratio of L-lactide to caprolactone with a molecular mass ($M_n$) of about 75 to 85 kDa. In this illustrative embodiment, the ophthalmic article 100 was shaped like an extruded annulus of approximately 1.3 mm outer diameter 230, about 0.5 mm inner diameter 240 and about 0.7 mm cross sectional thickness 250. FIG. 17A shows an exemplary appearance of the ophthalmic article 100 and IOL 300 before an in vitro IOL injection was performed. FIG. 17B shows the appearance of ophthalmic article 100 and IOL 300 after the in vitro IOL injection is performed. During the in vitro IOL injection, the ophthalmic article 100 attached to the IOL 300 were loaded into an injector cartridge) (e.g., UNFOLDER Platinum 1 Series by Johnson & Johnson Surgical Vision with a tip inner diameter 1.2 mm) designed for use with the IOL 300 (e.g., Tecnis 1-piece by Johnson & Johnson Surgical Vision along with a small amount of viscoelastic substance as customary with IOL 300 injection procedures. The filled cartridge was then loaded into the accompanying injector device. The ophthalmic article 100 and IOL 300 were then manually ejected from the injector into a small volume of phosphate-buffered saline (PBS) and allowed to unfold at room temperature for approximately 3 minutes. Following the injection, the ophthalmic article 100 and IOL 300 returned to original size and shape before the injection (FIG. 17A), and the ophthalmic article 100 was located in the same position on the haptic without significant distortion or disruption of its original physical appearance as shown in FIG. 17A.

Example 12: Durability of Surface Coatings for Drug Delivery on IOLs

Experiments were performed to assess the durability of surface coatings on IOLs as potential vehicles for drug delivery. Surfaces coatings were applied to foldable acrylic IOLs 300 (e.g., Tecnis 1-piece by Johnson & Johnson Surgical Vision) on the periphery of the optic and entirety of the haptics using layer-by-layer coating methods. The coatings were comprised of either 30 bilayers of chitosan and polyglutamic acid (FIGS. 18A-18B), 30 bilayers of poly(L-lysine) and polyglutamic acid (FIGS. 18C-18D) or 30 bilayers of poly(L-lysine) and polyacrylic acid glutamic (FIGS. 18E-18F). All of the layered coating were impregnated with Trypan blue dye as a model drug that is easily visualized. FIGS. 18A, 18C and 18E show the appearances of coated IOLs before in vitro IOL injections are performed. FIGS. 18B, 18D and 18F show the appearances of the coated IOL after in vitro IOL injections are performed. During the in vitro IOL injection, the coated IOL 300 was loaded into an injector cartridge (e.g., UNFOLDER Platinum 1 Series by Johnson & Johnson Surgical Vision with a tip inner diameter 1.2 mm) designed for use with the IOL (e.g., Tecnis 1-piece by Johnson & Johnson Surgical Vision) along with a small amount of viscoelastic substance as customary with IOL injection procedures. The filled cartridge was then loaded into the accompanying injector device. The coated IOL 300 was then manually ejected from the injector into a small volume of phosphate-buffered saline (PBS) and allowed to unfold at room temperature for approximately 3 minutes. After injection the coatings on the IOLs 300 were not intact. Large portions of the coating appeared to have peeled off 1805 as a result of the injection process FIGS. 18B, 18D and 18F. These results demonstrate the lack of durability of IOL surface coatings as potential vehicles for drug delivery.

Additional experiments were performed to further assess the durability of surface coatings with a different model IOL 300 (e.g. Micromed Intl. 1-piece foldable acrylic). Surface coatings were applied to foldable acrylic IOLs 300 on the periphery of the optic 301 and entirety of the haptics 302 using layer-by-layer coating methods. The coatings were comprised of either 30 bilayers of FITC-chitosan and dextran sulfate (FIGS. 19A-19B), 30 bilayers of FITC-chitosan and hyaluronic acid (FIGS. 19C-19D) or 30 bilayers of FITC-chitosan and polyglutamic acid glutamic (FIGS. 19E-19F). FIGS. 19A, 19C and 19E show the appearances of coated IOLs before in vitro IOL injections are performed. FIGS. 19B, 19D and 19F show the appearances of the coated IOL 300 after in vitro IOL injections are performed. During the in vitro IOL injection, the coated IOL was loaded into an injector cartridge (tip inner diameter 1.2 mm) (e.g., UNFOLDER Platinum 1 Series by Johnson & Johnson Surgical Vision) designed for use with the IOL (e.g., Tecnis 1-piece by Johnson & Johnson Surgical Vision) along with a small amount of viscoelastic substance as customary with IOL injection procedures. The filled cartridge was then loaded into the accompanying injector device. The coated IOL 300 was then manually ejected from the injector into a small volume of phosphate-buffered saline (PBS) and allowed to unfold at room temperature for approximately 3 minutes. After injection the coatings on the IOLs 300 were not intact. Large portions of the coating appeared to have peeled off as a result of the injection process FIGS. 19B, 19D and 19F. These results further demonstrated the lack of durability of IOL surface coatings as potential vehicles for drug delivery.

Example 13: Qualitative Testing of a Copolymer

Figure 20C:
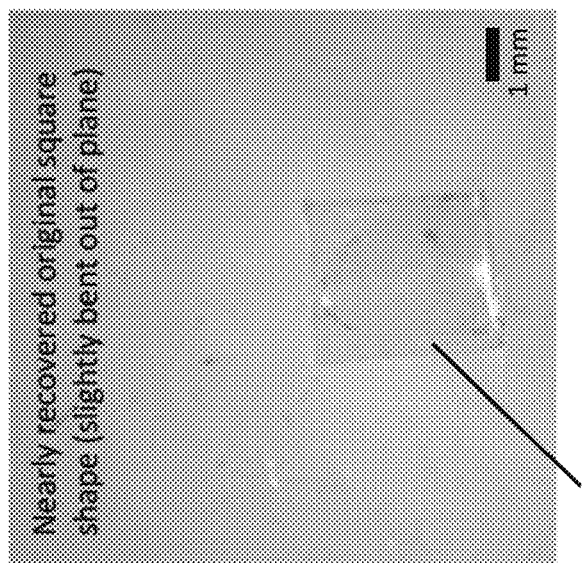
Figure 20B:
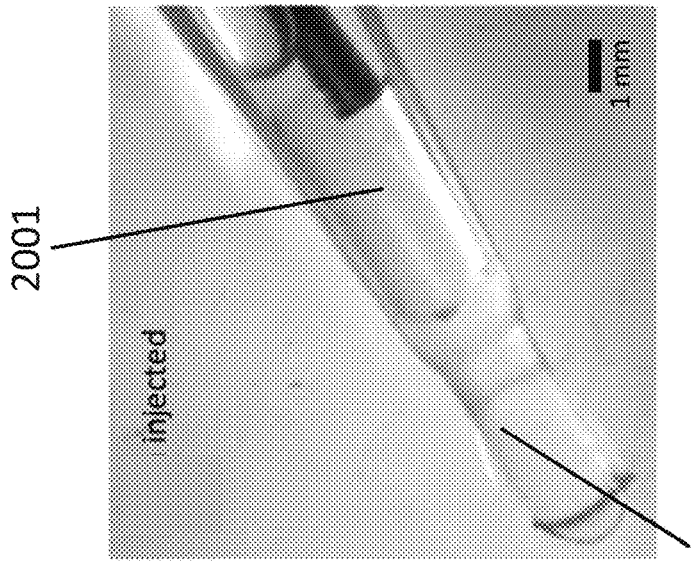
Figure 20A:
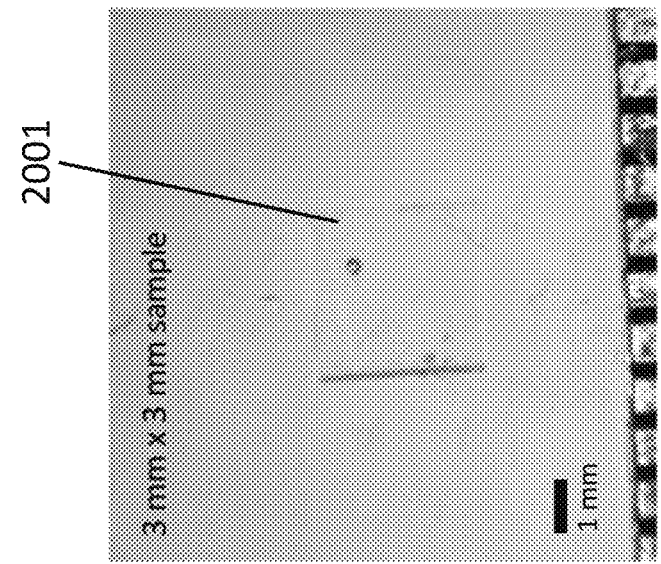
Figure 20D:
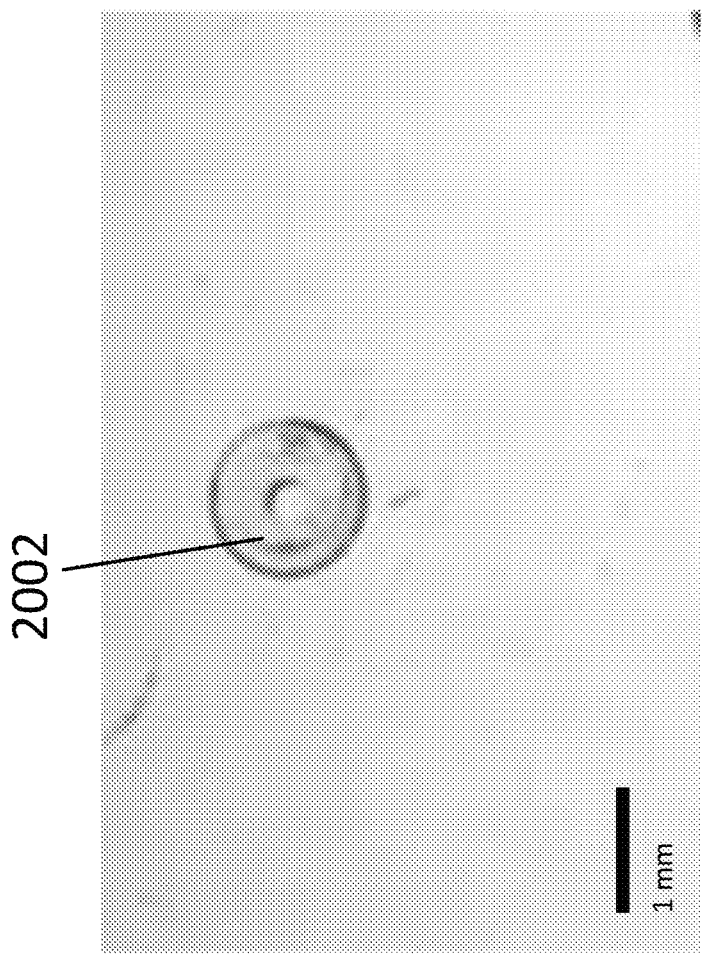

Different compositions of copolymers were tested. FIGS. 20A-20F show an example of a qualitative testing of a copolymer (e.g., Bezwada CARBOMAXX TL640). The copolymer comprised trimethylene carbonate (TMC) and L-Lactide at 60 to 40 molar ratio, respectively. A 3 mm×3 mm rectangular piece 2001 with 0.5 mm thickness of the copolymer was formed for the qualitative testing (FIG. 20A). The rectangular piece of the copolymer 2001 was then place inside an injection device 2010 (e.g., UNFOLDER Platinum 1 Series by Johnson & Johnson Surgical Vision) (FIG. 20B). The rectangular piece of the copolymer 2001 was injected out of the injection device (FIG. 20C). The rectangular piece of the copolymer 2001 recovered almost fully back to original shape shown in FIG. 20A within 30 seconds after the injection. An annulus shape ring 2002 was punched from a 0.5 mm thick sheet of the copolymer using a 16G and a 22G needle (FIG. 20D). The ring-shaped copolymer 2002 was then placed on a haptic 302 of an IOL 300 (e.g., Tecnis 1-piece by Johnson & Johnson Surgical Vision) (FIG. 20E). The copolymer ring 2002 was not easy to stretch and was difficult to place on the haptic 302 of the IOL 300. The copolymer ring and IOL were tested through an in vitro injection. FIG. 20E shows the appearance of the copolymer ring 2002 and IOL before the in vitro IOL 300 injection was performed. FIG. 20F shows the appearance of copolymer ring 2002 and IOL 300 after the in vitro IOL injection was performed. During the in vitro IOL injection, the ring 2002 and IOL 300 were loaded into an injector cartridge (e.g., UNFOLDER Platinum 1 Series by Johnson & Johnson Surgical Vision with a tip inner diameter 1.2 mm) designed for use with the IOL 300 (e.g., Tecnis 1-piece by Johnson & Johnson Surgical Vision) along with a small amount of viscoelastic substance as customary with IOL injection procedures. The filled cartridge was then loaded into the accompanying injector device 2010. The copolymer ring and IOL were then manually ejected from the injector 2010 into a small volume of phosphate-buffered saline (PBS) and allowed to unfold at room temperature for approximately 3 minutes. Following the injection, the copolymer ring 2002 shown in FIG. 20F retained its original shape prior to the in vitro injection 2020 shown in FIG. 20E.

Example 14: Qualitative Testing of Another Copolymer

Figures 21A, 21B:
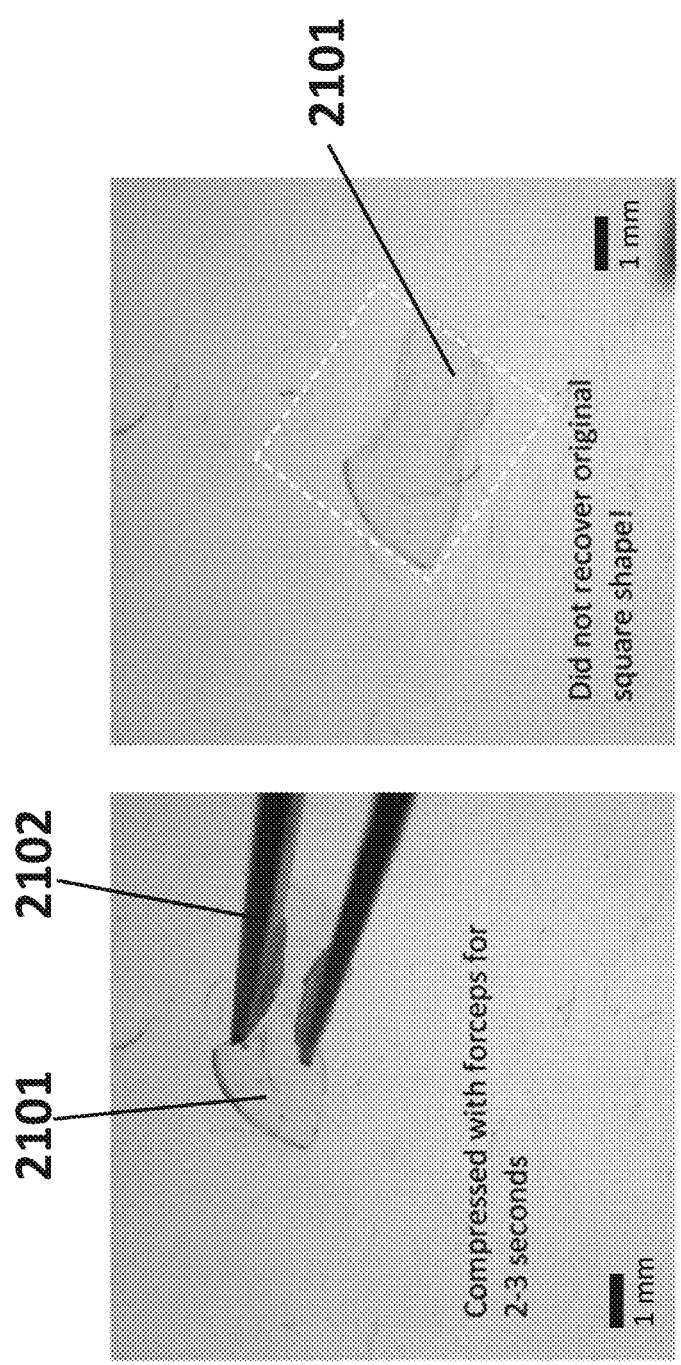
FIGS. 21A-21E show an example of a qualitative testing of another copolymer.
Figure 21D:
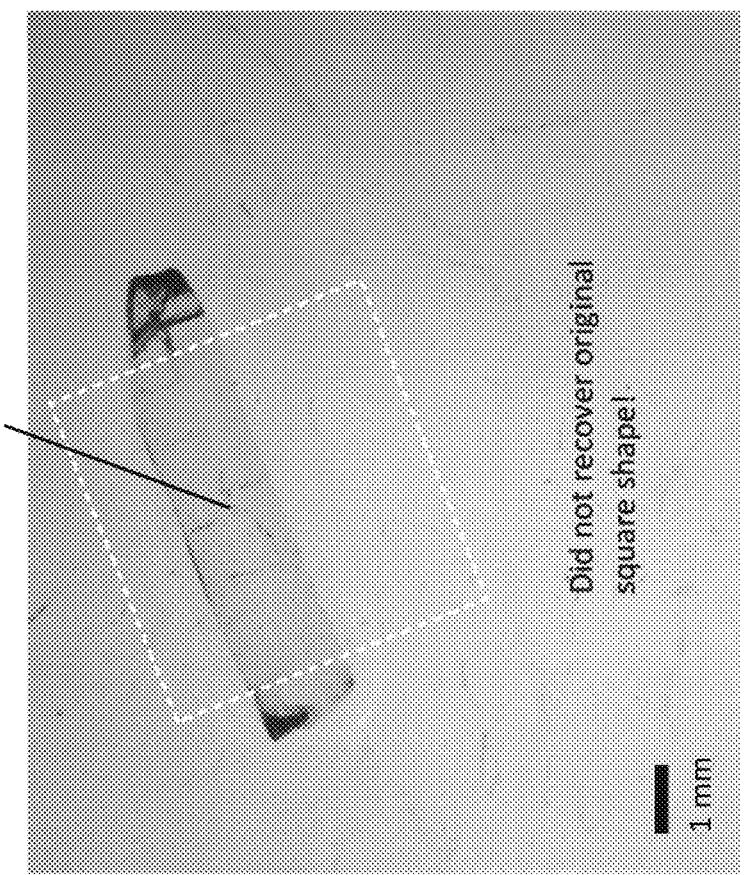
Figure 21C:
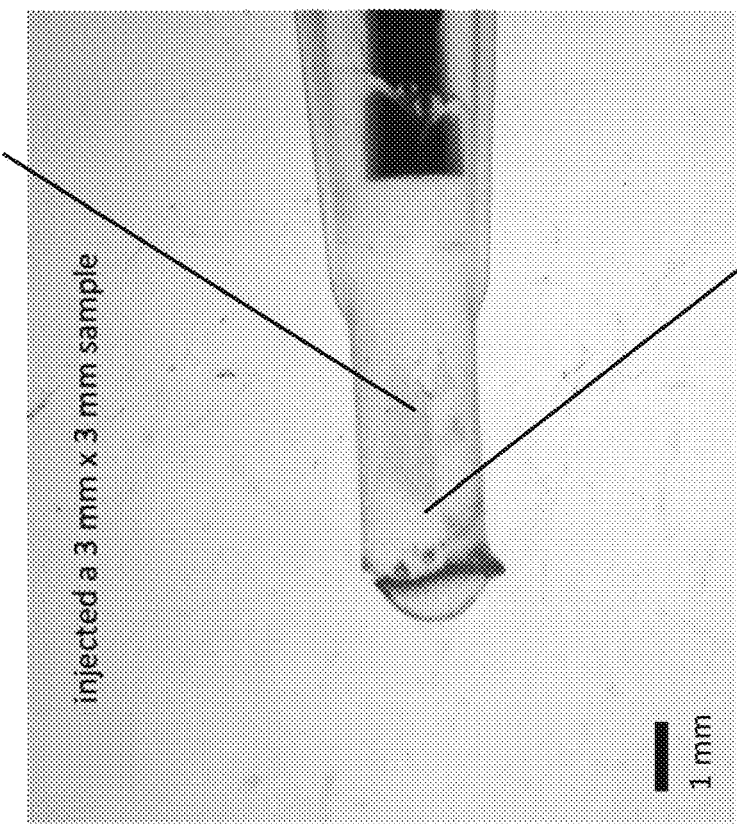
Figure 21E:
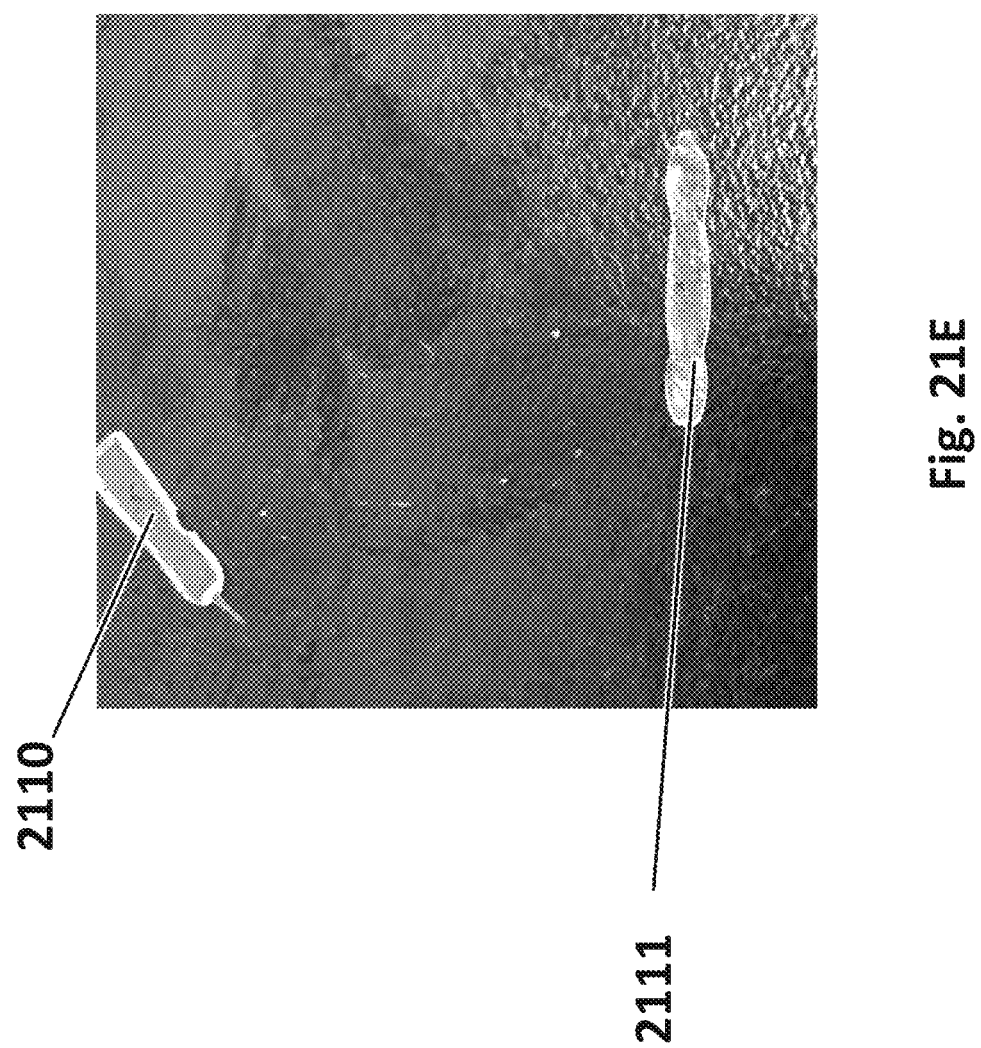

FIGS. 21A-21F show an example of a qualitative testing of another copolymer (e.g., Bezwada CARBOMAXX TL910). The copolymer comprised trimethylene carbonate (TMC) and L-Lactide at 90 to 10 molar ratio, respectively. A 3 mm×3 mm rectangular piece 2101 with 0.5 mm thickness of the copolymer was compressed using forceps 2102 (FIG. 21A). Compression was removed from the rectangular piece 2101 allowing it to recover its original shape; the rectangular piece of copolymer 2101 did not recover its original shape after approximately 75 seconds (FIG. 21B). The rectangular piece of the copolymer 2101 was then place inside an injection device 2010 (e.g., UNFOLDER Platinum 1 Series by Johnson & Johnson Surgical Vision) (FIG. 21C) The rectangular piece of the copolymer 2101 was injected out of the injection device 2010 (FIG. 21D). The rectangular piece of the copolymer 2101 did not recover its original shape after the injection 2102. The injected piece 2102 appeared narrow and elongated in approximately the same shape and proportions as the tip of the injector 2010 from which it was ejected. Additional pieces of the same copolymer were cut into strips approximately 3 mm×12 mm by 0.5 mm, and a strip was stretched lengthwise and observed for recovery of its shape. FIG. 21E shows an intact unstretched strip 2110 and a stretched strip 2011 which remained elongated and never recovered its original shape.

Example 15: Qualitative Testing of Another Copolymer

Figure 22B:
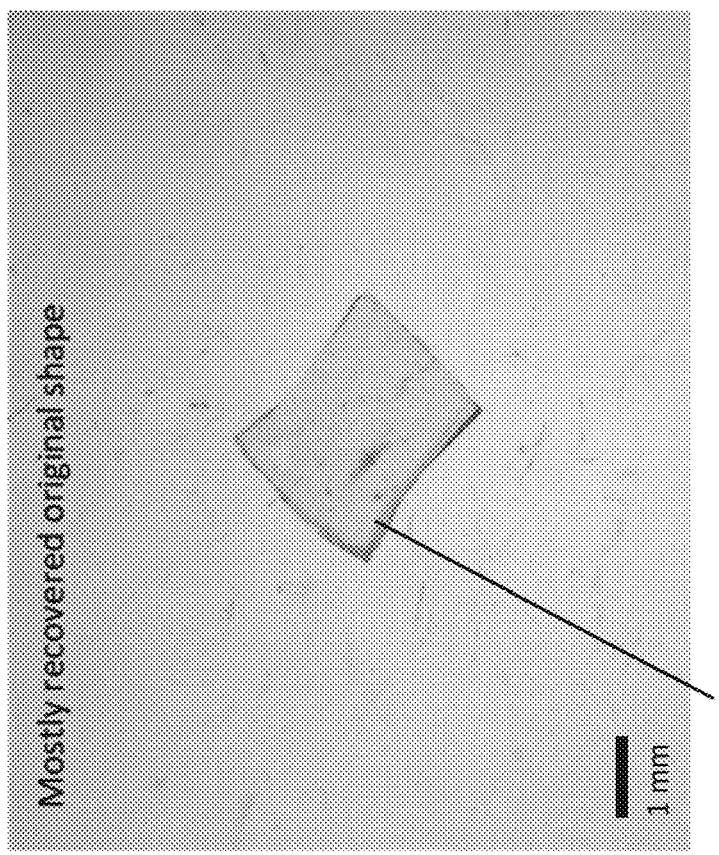
FIGS. 22A-22F show an example of a qualitative testing of another copolymer.
Figure 22A:
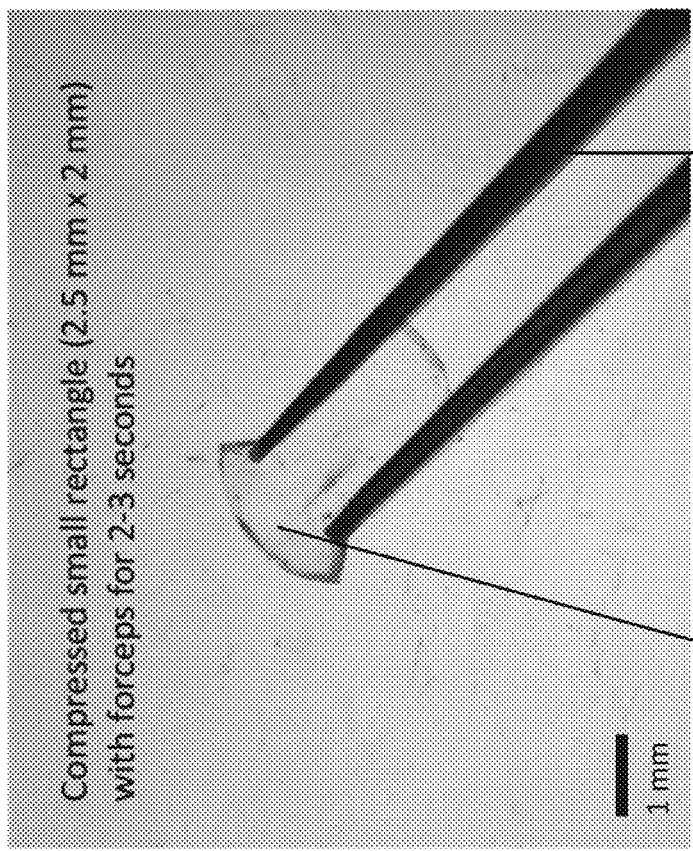
Figure 22D:
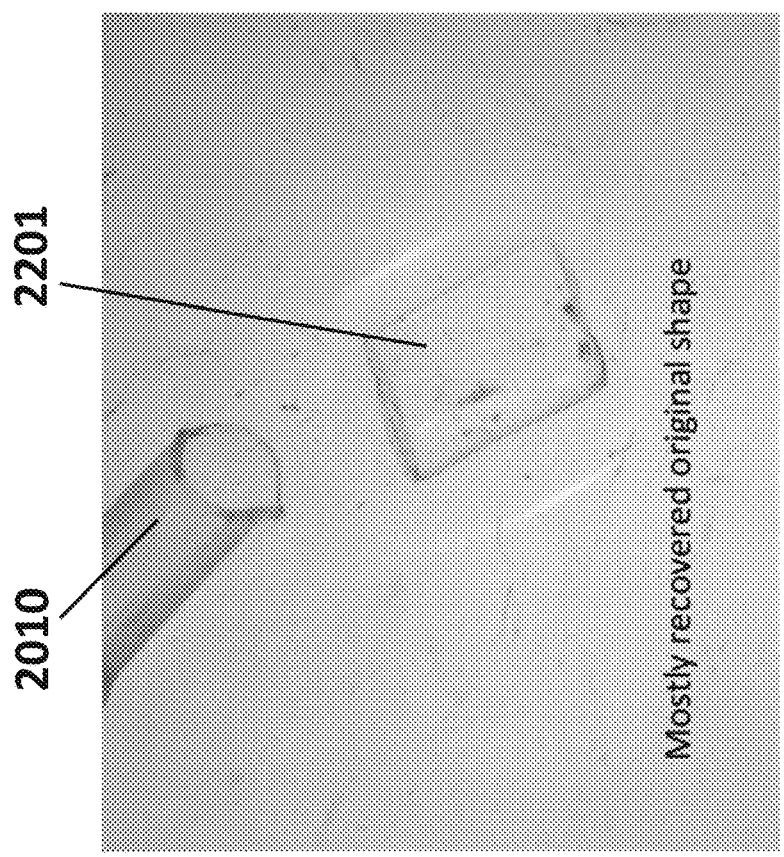
Figure 22C:
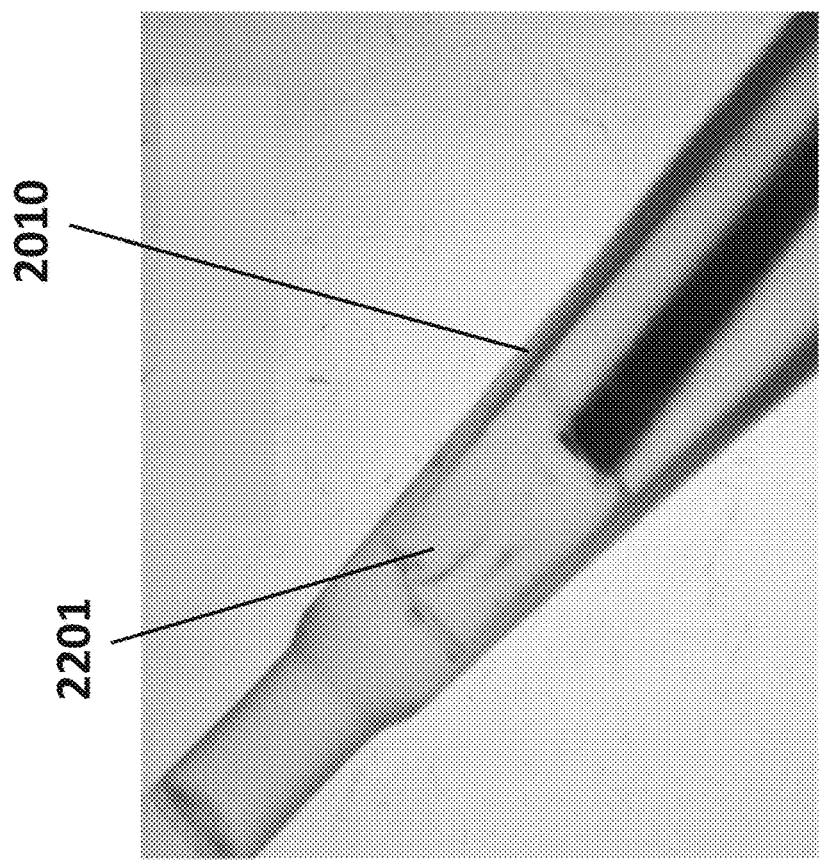
Figure 22E:
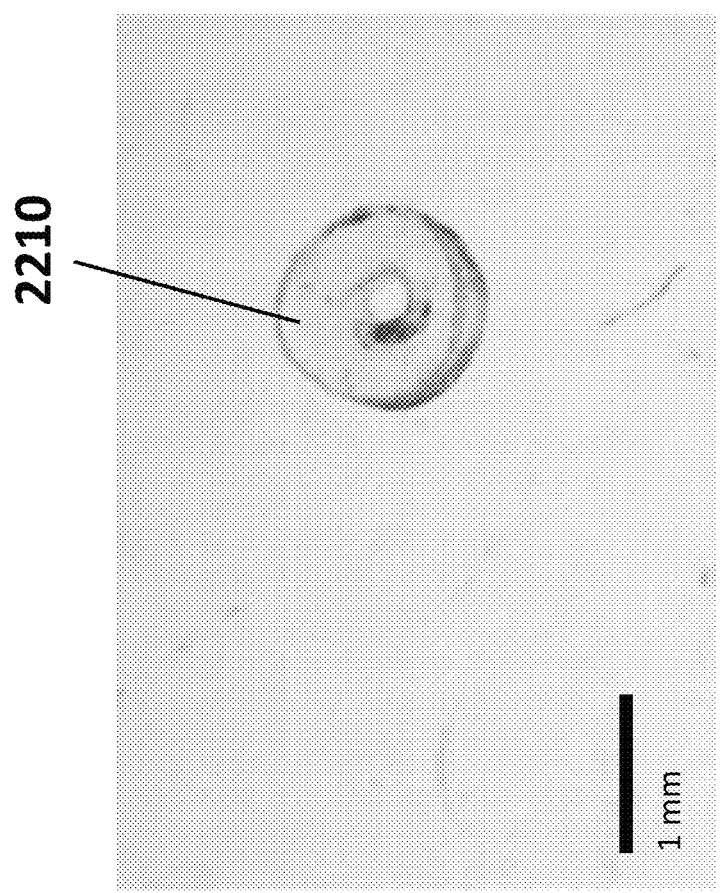
Figure 22F:
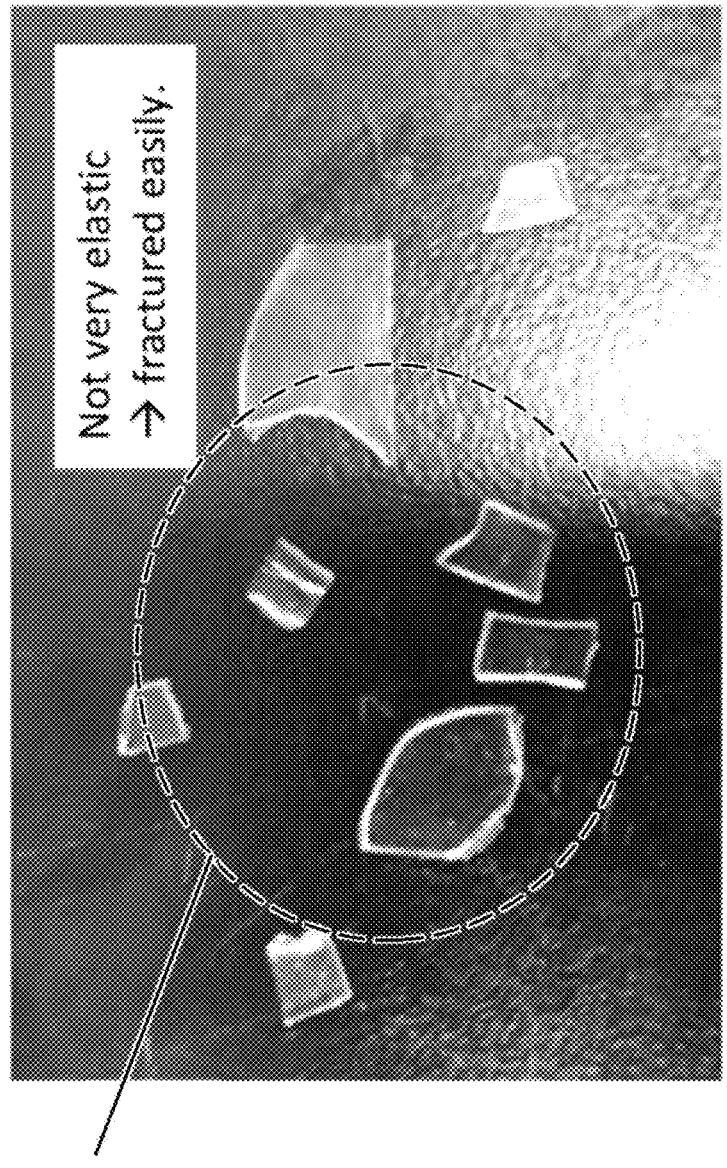

FIGS. 22A-22F show an example of a qualitative testing of another copolymer (e.g., Bezwada CARBOMAXX TC910). The copolymer comprised trimethylene carbonate (TMC) and Caprolactone at 90 to 10 molar ratio, respectively. A 2.5 mm×2 mm×0.5 mm thick rectangular piece 2202 of the copolymer was compressed using a pair of forceps 2203 (FIG. 22A). Compression was removed from the rectangular piece 2202 allowing it to recover its original shape shown in FIG. 22A after about 15 seconds. A rectangular piece of the copolymer 2201 was then place inside an injection device 2010 (FIG. 22C) (e.g., UINIFOLDER® Platinum 1 Series by Johnson & Johnson Surgical Vision). The rectangular piece of the copolymer 2201 was injected out of the injection device 2010 (FIG. 22D). FIG. 22D shows the rectangular piece of the copolymer 2201, which recovered its original shape (e.g., almost back to original shape). An annulus shape ring 2210 was punched from a 0.5 mm thick sheet of the copolymer using a 16G and a 22G needle (FIG. 22E). A rectangular piece of the copolymer approximately 1 cm×1 cm by 0.5 mm tick was stretch manually. The copolymer rectangle was brittle and fractured easily 2211 (FIG. 22F). It is notable that this polymer exhibited elasticity and recovery of shape when compressed with forceps 2203 and injected thought an IOL injector system 2010. However, it exhibited little to no elasticity under stretch shown in FIG. 22F.

Example 16: Qualitative Testing of a Polymer to Make an Ophthalmic Article

Figures 23A, 23B, 23C, 23D:
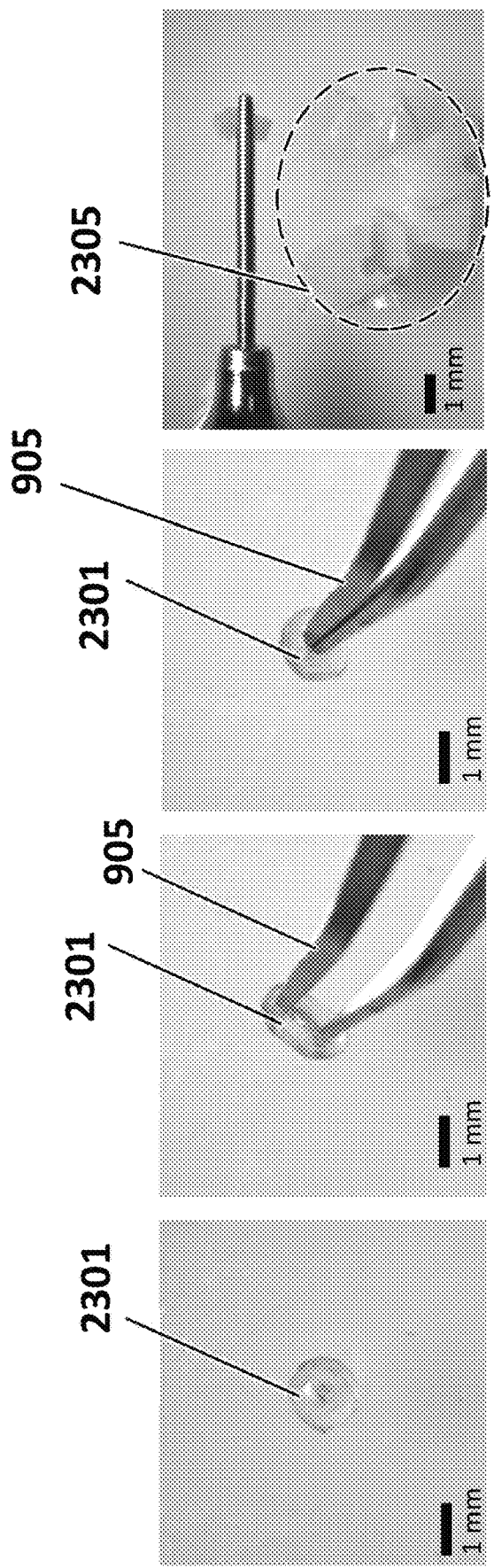
FIGS. 23A-D show an annulus-shaped ring made from a copolymer.

FIG. 23A, FIG. 23B, and FIG. 23C show an annulus-shaped ring 2301 made from a copolymer (e.g., Bezwada GLYCOMAXX GC5545). The copolymer comprised glycolic acid and caprolactone at 55 to 45 molar ratio, respectively. The polymer ring 2301 showed flexibility to be stretched easily when outward forced was applied to it using forceps 905 as shown in FIG. 23B. The polymer ring 2301 also showed shape recovery (e.g., shape memory properties) after releasing the force from the forceps 905 (FIG. 23C). The polymer was mixed with Ketoroloac, which changed the mechanical properties of the polymer drastically to be brittle and wax-like 2305 (FIG. 23D) rendering it incompatible with the stretching required to attach it to an ocular device (e.g., haptic of an IOL) and lacking the deformable-elastic properties desired for injection, for example, with IOL through a small incision using a standard IOL injection technique.

Figure 24D:
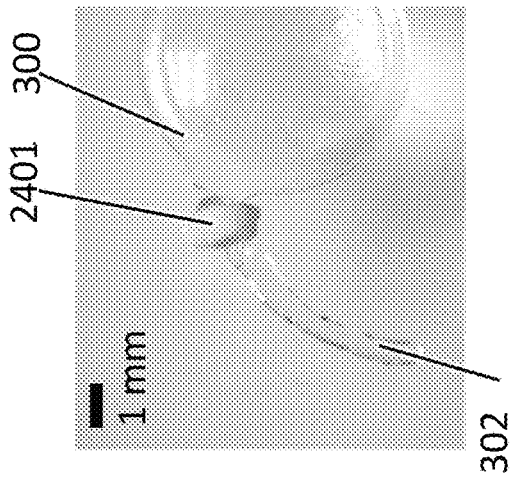
FIG. 24D shows an ophthalmic article's state post injection.
Figure 24C:
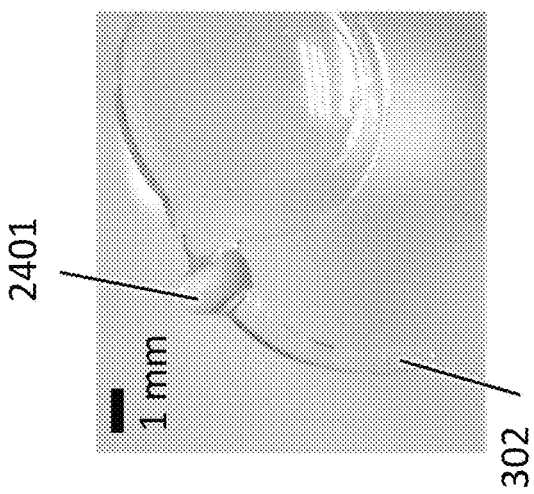
FIG. 24C shows the appearance of the polymer ring and IOL before the in vitro IOL injection was performed.
Figure 24A:
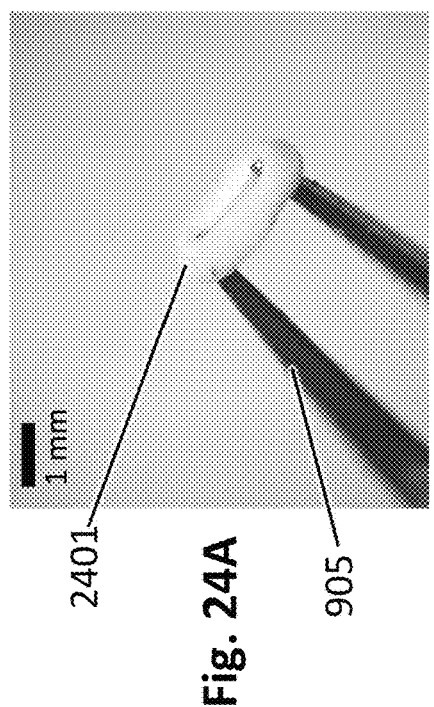
FIG. 24A shows an annulus shaped ring comprised of copolymer.
Figure 24B:
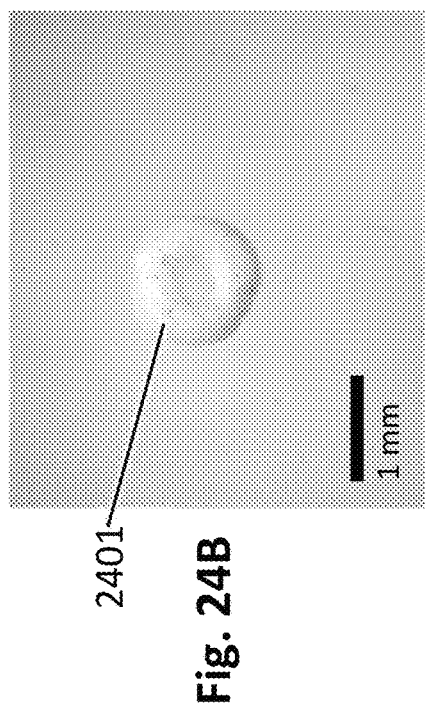
FIG. 24B shows an ophthalmic article in a post stretched state.

Example 17: Qualitative Testing of Another Polymer to Make an Ophthalmic Article FIG. 24A shows an annulus shaped ring 2401 comprised of copolymer (L-lactide and caprolactone at a molar ratio of 70 to 30) 90% (wt %) and ketorolac tromethamine 10% (wt %). The annulus shape ring 2401 was punched from a 0.5 mm thick sheet of the copolymer and ketorolac 90:10 mixture incubated at 70° C. using a 16G and a 22G needle. Attempts were made to punch the ring at room temperature, but the copolymer-ketorolac sheet was too hard rendering the material difficult to punch the ring out of. The polymer ring 2401 was elastic to a low degree and could be forced stretched using forceps 905 (FIG. 24A). The polymer ring 2401 recovered its original shaped when the stretching force from the forceps 905 was removed (FIG. 24B). The polymer ring 2401 was then placed on a haptic 302 of an IOL 300 (e.g., Tecnis 1-piece by Johnson & Johnson Surgical Vision) with difficulty as the material was not very elastic and easy to stretch. An in vitro injection procedure was performed with the polymer ring 2401 attached to the IOL 300. FIG. 24C shows the appearance of the polymer ring 2401 and IOL 300 before the in vitro IOL injection was performed. During the in vitro IOL injection, the polymer ring 2401 and IOL 300 were loaded into an injector cartridge (e.g., UNFOLDER Platinum 1 Series by Johnson & Johnson Surgical Vision with a tip inner diameter 1.2 mm) designed for use with the IOL 300 (e.g., Tecnis 1-piece by Johnson & Johnson Surgical Vision) along with a small amount of viscoelastic substance as customary with IOL injection procedures. The filled cartridge was then loaded into the accompanying injector device. The polymer ring 2401 and IOL 300 were then manually ejected from the injector into a small volume of phosphate-buffered saline (PBS) and allowed to unfold at room temperature for approximately 3 minutes. Following the injection, the IOL 300 returned to its original size and shape (FIG. 24D), and the polymer ring 2401 retained its position on the haptic 302, size and shape (FIG. 24D).

Example 18: Methods for Pharmacokinetic Studies

Methods described herein were used to perform in vitro drug release experiments as well as in vivo pharmacokinetic experiments.

Methods of Drug Quantification

Drug quantification methods described herein were used for detection of dexamethasone, ketorolac and/or moxifloxacin in stability samples, rabbit plasma, rabbit aqueous humor, and/or in PBS. Chromatographic separation was performed at 25° C. using a two-solvent linear gradient by reversed-phase high performance liquid chromatography (RP-HPLC) with an HPLC column (e.g., Phenominex-C18 Luna 50×2 mm 5 μm column for ketorolac and/or dexamethasone or a Phenomenex-C8 Luna 50×2 mm 5 μm column for moxifloxacin). A first mobile Phase (A) comprised 5 mM ammonium acetate with 0.1% Formic acid, pH 2.5. A second mobile phase (B) comprised acetonitrile. A liquid chromatography (LC) time program was adjusted as follows: about 20% B until about 0.3 minutes (min), linear increase from about 20% B to about 90% B from about 0.3 min to about 3 min, return to about 20% B at about 3.1 min and re-equilibration until about 5.5 min. The flow rate was set to about 350 μl/min. Ketorolac and Dexamethasone samples were analyzed in positive ion electrospray ionization mode on a mass spectrometry system (e.g., an API 4000 LC/MS/MS system) coupled with a LC system (e.g., an Agilent 1100 series liquid chromatograph); ketorolac and/or dexamethasone were used as internal standards (e.g., the opposite analyte). A similar mass spectrometry method was used for analyzing both ketorolac or dexamethasone. Detection of ions was performed by monitoring the transitions of mass to charge ratio (m/z) from 256.3 m/z to 105.1 m/z for ketorolac and m/z transition from 393.156 m/z to 373.1 m/z or from 393.156 m/z to 355.1 m/z for dexamethasone. Analytes were quantified based on an area-under-the-peak ratios of analyte and an internal standard. Positive electrospray ionization (ESI) was performed by applying the following settings: Declustering potential (DP), Entrance potential (EP), Collision Energy (CE), and Collision Cell Exit Potential (CXP) were set to 66, 15, 25, and 8 for ketorolac and 86, 10, 11, and 16 for dexamethasone; ion spray voltage was set to 5,500 V, at 300° C. ion source heater temperature, source gas 1 at 20 psi, source gas 2 at 20 psi, and curtain gas was set at 10 psi.

Moxifloxacin precursor ions detection was performed on a mass spectrometry system (e.g., an API 4000 LC/MS/MS system) coupled with a chromatograph (e.g., an Agilent 1100 series liquid chromatograph) in Q1 (MS) mode. Positive ESI was performed applying the following settings: Declustering potential (DP) was set to 31, Entrance potential (EP) was set to 10V, 5,000 V ion spray voltage, 350° C. ion source heater temperature, 20 psi source gas 1, 20 psi source gas 2, and 10 psi curtain gas. A plasma Ketorolac standard curve (1-1000 ng/mL) was generated using peak area ratio and a quadratic fitting. An area under a peak or peak area count in chromatography can show a measure of the concentration of the compound it represents. The peak area can be calculated by measuring the area under a peak in a chromatography output diagram. The peak area ratio can be used to compare the concentration of two or more compounds (e.g., analytes) in a chromatography sample. The correlation coefficient of the calibration curves was $r^2$=0.99. A lower limit of quantification (LLOQ) for ketorolac in rabbit plasma was determined as 1 ng/mL. The plasma Dexamethasone standard curve (1-4000 ng/mL) was generated using peak area ratio and a quadratic fitting. The correlation coefficient of the calibration curves was r2≥0.99. LLOQ for ketorolac in rabbit plasma was determined as 1 ng/mL. The aqueous humor Ketorolac standard curve (1-4000 ng/mL) was prepared on rabbit aqueous humor (e.g., Pel-Freeze rabbit aqueous humor) diluted 5 times with PBS. Standard curve was generated using peak area ratio and a quadratic fitting. The correlation coefficient of the calibration curves was r2≥0.99. LLOQ for ketorolac in rabbit plasma was determined as 1 ng/mL.

The aqueous humor (AH) Dexamethasone standard curve (1-2000 ng/mL) was prepared on rabbit aqueous humor (e.g., Pel-Freeze rabbit aqueous humor) diluted 5 times with PBS. Standard curve was generated using peak area ratio and a quadratic fitting. The correlation coefficient of the calibration curves was r2>0.99. LLOQ for ketorolac in rabbit plasma was determined as 1 ng/mL. Moxifloxacin standards curve (100-10000 ng/mL) was prepared on PBS. LLOQ for was determined as 100 ng/mL.

Preparation of Plasma Samples

Plasma standard curve and quality controls (QC) were performed. The concentrations of the standards ranged from 1.00-4000 ng/mL of plasma in 50 μL aliquots transferred into deep 96 well plate for extraction. QC concentration at low, middle and high levels were prepared at concentrations of 40 ng/mL; 200 ng/mL and 1000 ng/mL in 50 μL aliquots transferred into a deep well 96 well plate.

Study samples were prepared by thawing plasma unassisted at room temperature and transferring 50.0 μL aliquots to a deep well 96 well plate for analysis. The unused samples were returned to storage at −20° C. Ketorolac standards, QCs and study samples received 250 μL of 0.25 ng/mL dexamethasone in acetonitrile (Internal Standard, IS).

Dexamethasone standards, QCs and study samples received 250 μL of 0.25 ng/mL ketorolac in acetonitrile (Internal Standard, IS). The samples were vortex mixed and centrifuged for 10 min at ca. 3400×g. The supernatant was transferred to a new 96 deep well plate and dried using an evaporation system (e.g., Zymark TurboVap 96 N2 evaporation system). Samples were reconstituted with 100 μL of 95% 5 mM Ammonium acetate and 0.1% formic acid, and 5% Acetonitrile, vortexed to solubilize and placed in the autosampler.

Preparation of Aqueous Humor Samples

Rabbit aqueous humor (e.g., Pel-Freeze rabbit aqueous humor) was diluted 5 times with PBS. The concentrations of the standards ranged from 1.00-4000 ng/mL of plasma in 50 aliquots transferred into a deep well 96 well plate for extraction. QC concentrations at low, middle and high levels were prepared at concentrations of 40 μg/ml; 200 μg/ml and 1000 μg/ml in 50 aliquots transferred into deep well 96 well.

Study samples were prepared by thawing aqueous humor samples unassisted at room temperature and transferring 50.0 μL aliquots to deep well 96 well plate for analysis. The unused samples were returned to storage at −20° C. Ketorolac standards, QCs and study samples received 250 μL of 0.25 ng/mL dexamethasone in acetonitrile (Internal Standard, IS). Dexamethasone standards, QCs and study samples received 250 μL of 0.25 ng/mL ketorolac in acetonitrile (Internal Standard, IS).

The samples were vortex mixed and centrifuged for 10 min at ca. 3400×g. The supernatant was transferred to a new 96 deep well plate and dried using an evaporation system (e.g., Zymark TurboVap 96 N2 evaporation system). Samples were reconstituted with 100 μL of 95% 5 mM Ammonium acetate with 0.1% formic acid, and 5% Acetonitrile, vortexed to solubilize and placed in the autosampler.

Example 19: An In Vitro Drug Release Profile for an Ophthalmic Article

Annulus-shaped ophthalmic articles were prepared comprising 9% (wt %) of a drug (e.g., dexamethasone or ketorolac) and 91% (wt %) of a copolymer. The copolymer comprised poly(L-lactide-co-caprolactone) at about 60:40 molar ratio f L-lactide to caprolactone with a molecular mass ($M_n$) of about 75 to 85 kDa. The ophthalmic article can have an outer diameter of about 1.2 mm, an inner structure (e.g., a hole) with an inner diameter of about 0.6 mm, and a cross sectional thickness of about 0.5 mm; and in this illustrative embodiment, the ophthalmic article had approximate dimensions of rings were about 1.25 mm outer diameter, about 0.5 mm inner diameter and about 0.5 mm cross sectional thickness.

Figure 25A:
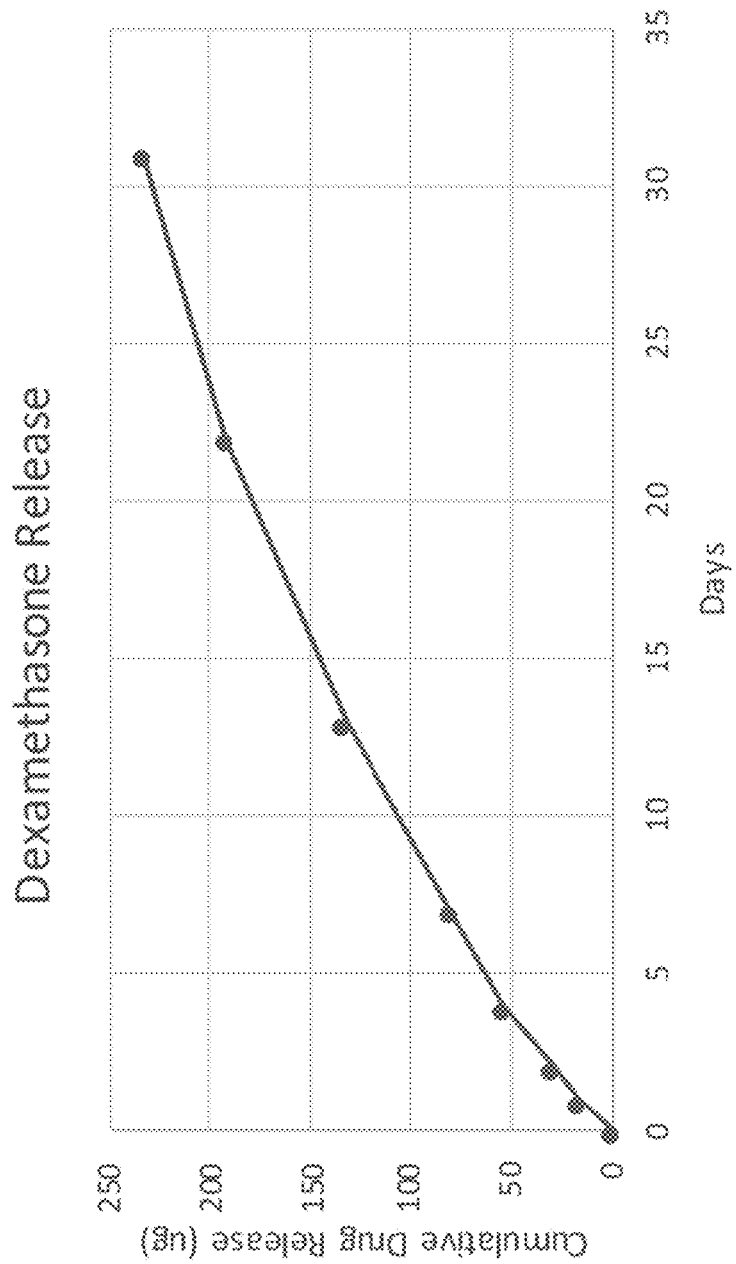
FIG. 25A shows cumulative amounts of dexamethasone released from the ophthalmic articles.

In order to perform an invitro drug release study for dexamethasone-loaded ophthalmic article, eight ophthalmic articles with a combined mass of 4 mg were inserted into a microcentrifuge tube for drug release testing. A drug release study was performed using the ophthalmic articles mentioned herein over a 32 day period. The ophthalmic articles were placed in a phosphate-buffered saline (PBS) solution at 37° C. An amount of dexamethasone present in the solution was measured at predefined timepoints throughout the study according to methods described hereinbefore. Cumulative amounts of dexamethasone released from the ophthalmic articles are shown in FIG. 25A. Dexamethasone concentrations were still detectable at day 32 of the study.

Figure 25B:
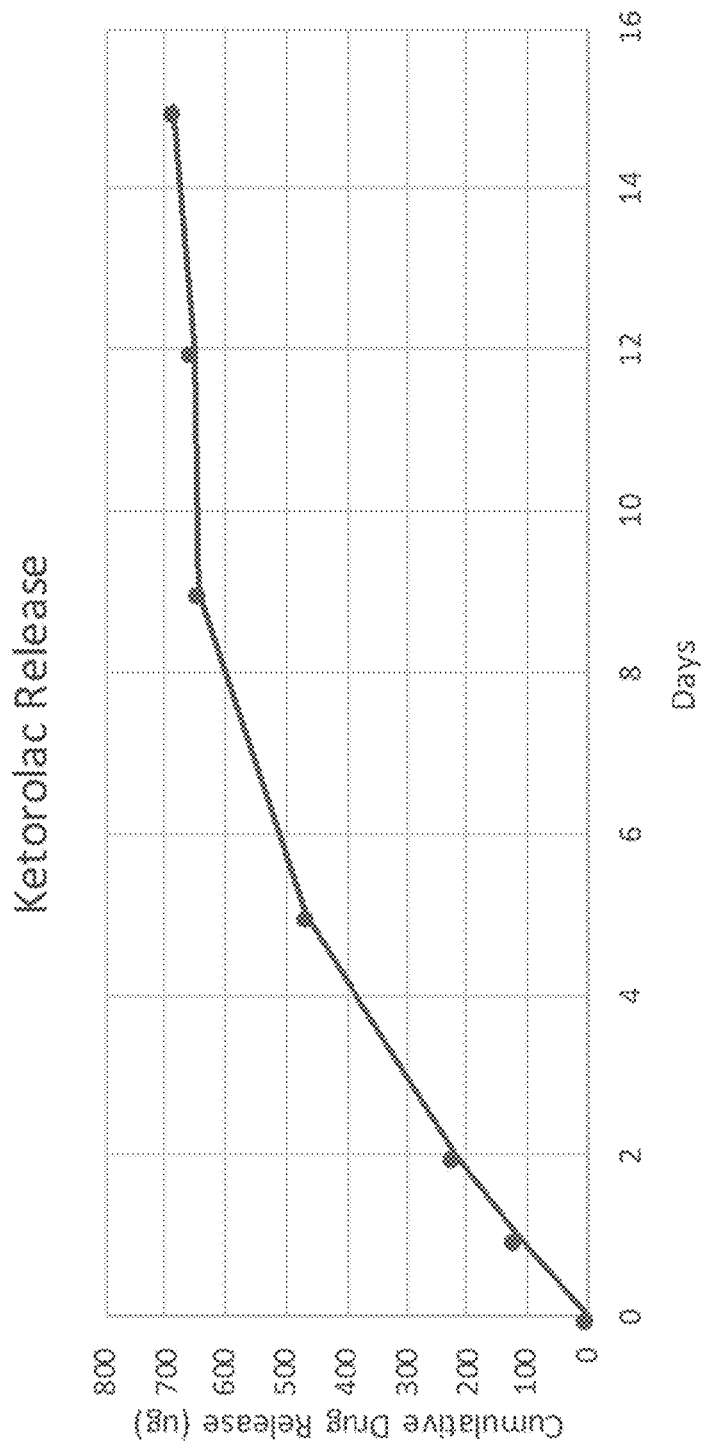
FIG. 25B shows cumulative amounts of ketorolac released from the ophthalmic articles.

In order to perform an invitro drug release study for ketorolac-loaded ophthalmic article, nine ophthalmic articles with a combined mass of 7.5 mg were inserted into a microcentrifuge tube for drug release testing. A drug release study was performed using the ophthalmic articles mentioned herein over a 32 day period. The ophthalmic articles were placed in a phosphate-buffered saline (PBS) solution at 37° C. An amount of ketorolac present in the solution was measured at predefined timepoints throughout the study according to methods described above. Cumulative amounts of ketorolac released from the ophthalmic articles are shown in FIG. 25B. Presence of ketorolac was not detectable after day 15.

Figure 26:
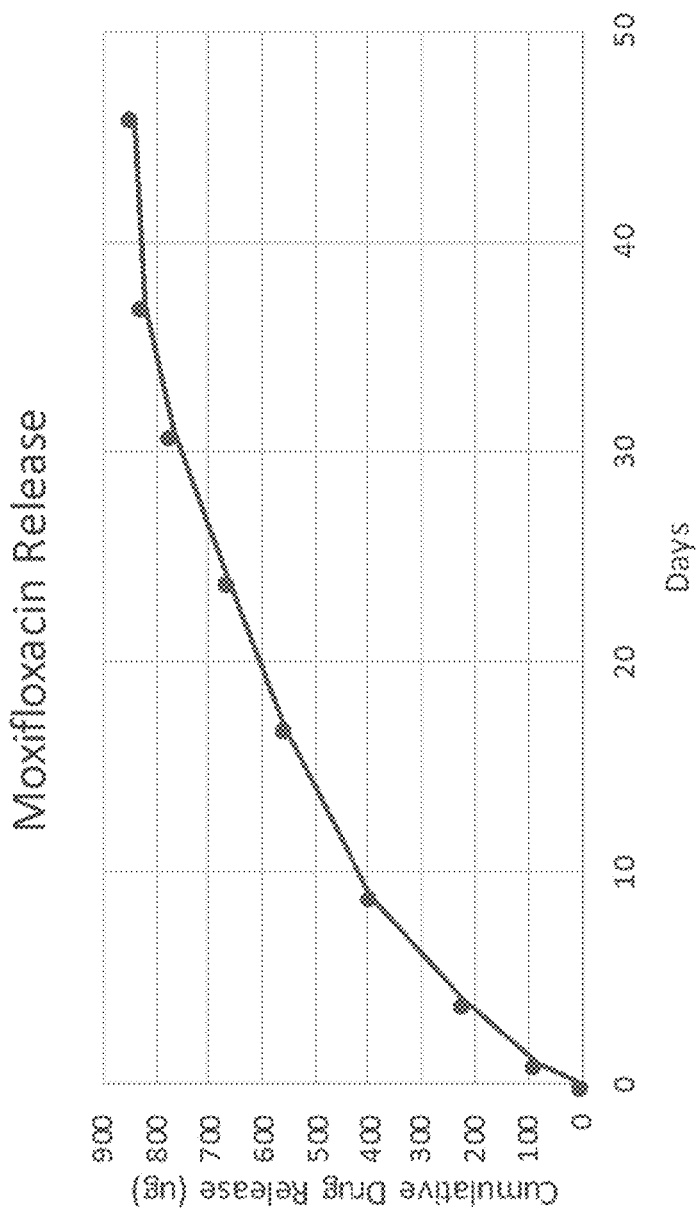
FIG. 26 shows cumulative amounts of moxifloxacin released from the ophthalmic articles.

Example 20: In Vitro Drug Release Profile for Moxifloxacin-Loaded Ophthalmic Article Annulus-shaped ophthalmic articles were prepared comprising 9% (wt %) of moxifloxacin and 91% (wt %) of a copolymer. The copolymer comprised poly(L-lactide-co-caprolactone) at about 50:50 molar ratio of L-lactide to caprolactone with a molecular mass ($M_n$) of about 75 to 85 kDa. The approximate dimensions of the ophthalmic article in this illustrative embodiment were 1.3 mm outer diameter, 0.5 mm inner diameter and 0.7 mm cross sectional thickness. Nine ophthalmic articles with a combined mass of 7.5 mg were inserted into a microcentrifuge tube for drug release testing. A drug release study was performed using the ophthalmic articles mentioned herein over a 45-day period. The ophthalmic articles were placed in a phosphate-buffered saline (PBS) solution at 37° C. An amount of moxifloxacin present in the solution was measured at predefined timepoints throughout the study according to methods described hereinbefore. Cumulative amounts of moxifloxacin released from the ophthalmic articles are shown in FIG. 26.

Example 21: A Moxifloxacin-Loaded Ophthalmic Article Antibiotic Activity

Figure 27:
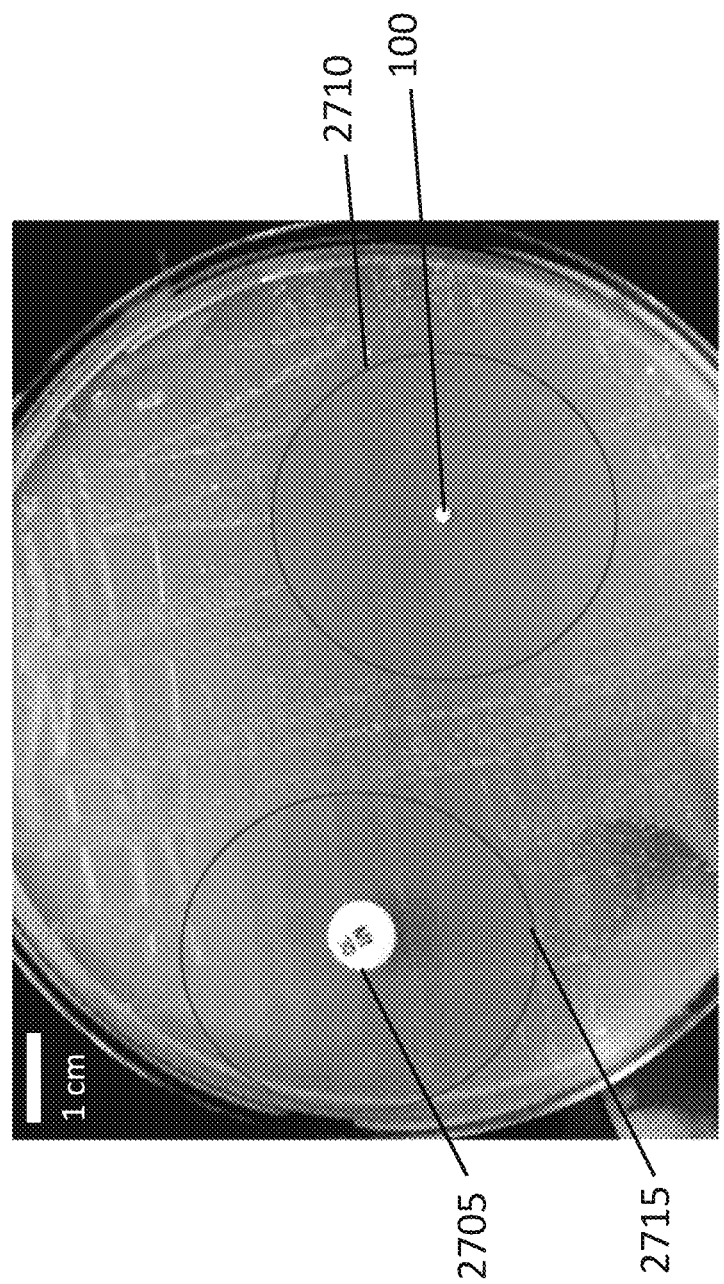
FIG. 27 illustrates an example of antibiotic activity of a drug (e.g., moxifloxacin) released from the ophthalmic article.

Annulus-shaped ophthalmic article 100 were prepared comprising 9% (wt %) moxifloxacin and 91% (wt %) poly(L-lactide-co-caprolactone) at 60:40 molar ratio of L-lactide to caprolactone with a molecular mass ($M_n$) of about 75 to 85 kDa. The approximate dimensions of the ophthalmic article 100 were 1.3 mm outer diameter, 0.5 mm inner diameter and 0.5 mm cross sectional thickness. FIG. 27 illustrates an example of antibiotic activity of a drug (e.g., moxifloxacin) released from the ophthalmic article 100. An extent of a zone of inhibition marked by a circle 2710 for the ophthalmic article 100 can be comparable in dimension to an extent of a zone of inhibition 2715 for a positive control antibiotic disc 2705.

Figures 28A, 28B:
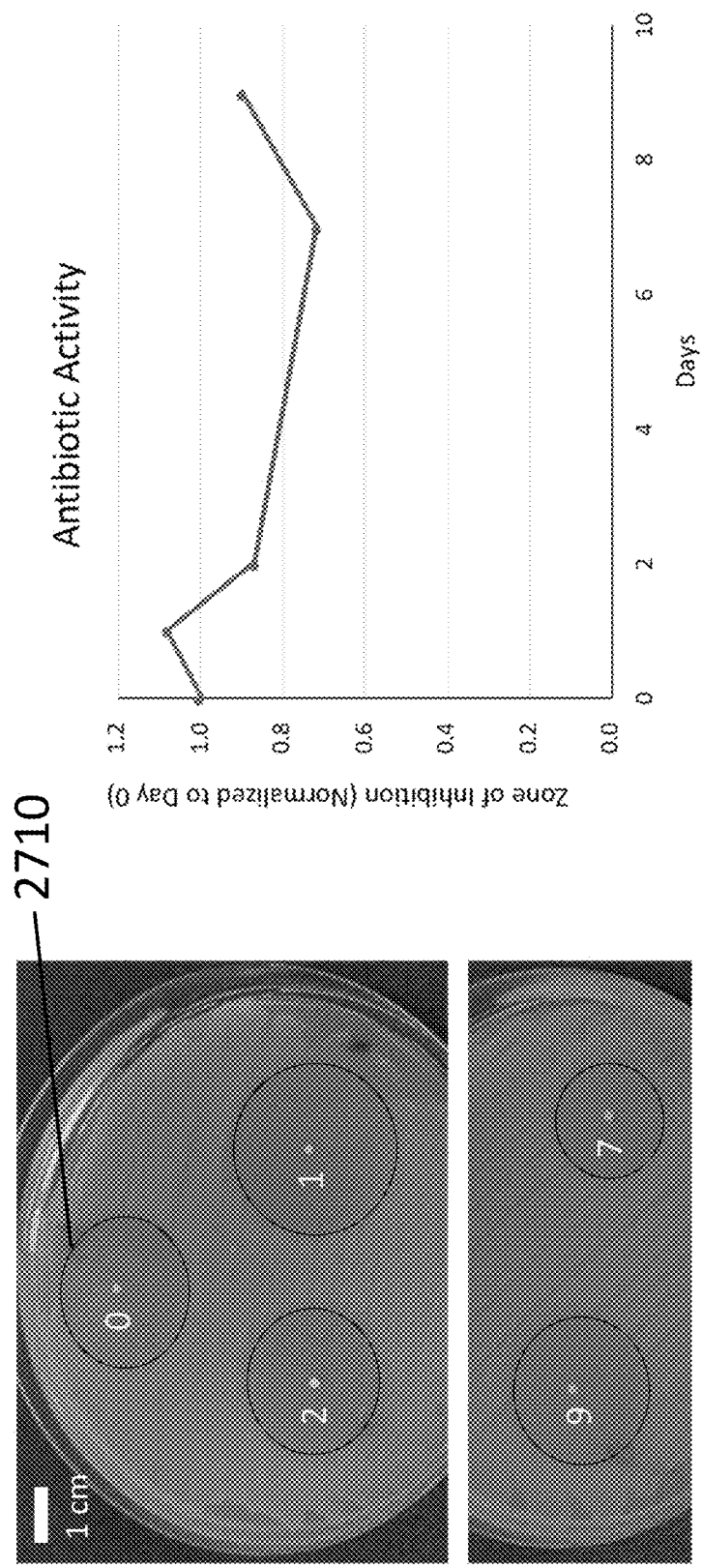
FIG. 28A illustrates the diameter of the zone of inhibition at day 0, 1, 2, 7, and 9.
FIG. 28B illustrates the diameter of the zone of inhibition at day 0, 1, 2, 7, and 9.

In order to study the antibiotic activity of a drug (e.g., moxifloxacin) released from the ophthalmic article 100 over time, a first ophthalmic article 100 was frozen at day 0. A second, a third, and a fourth ophthalmic articles were incubated in separate tubes containing phosphate-buffered saline (PBS) solution at 37° C. for up to nine days. Individual ophthalmic articles were removed from the incubation medium and were frozen on day 1, 2, 7 and 9. After 9 days, the frozen samples were thawed and tested for antibiotic activity using the agar diffusion method (FIG. 28A). FIG. 28A illustrates the diameter of the zone of inhibition 2710 at day 0, 1, 2, 7, and 9. The graph representing the diameter of the zone of inhibition at day 0, 1, 2, 7 and 9 is shown in FIG. 28B. These results demonstrate sustained antibiotic activity of a moxifloxacin-loaded ophthalmic article 100 for at least nine days.

Example 22: IOL Position in an Eye

Figure 29:
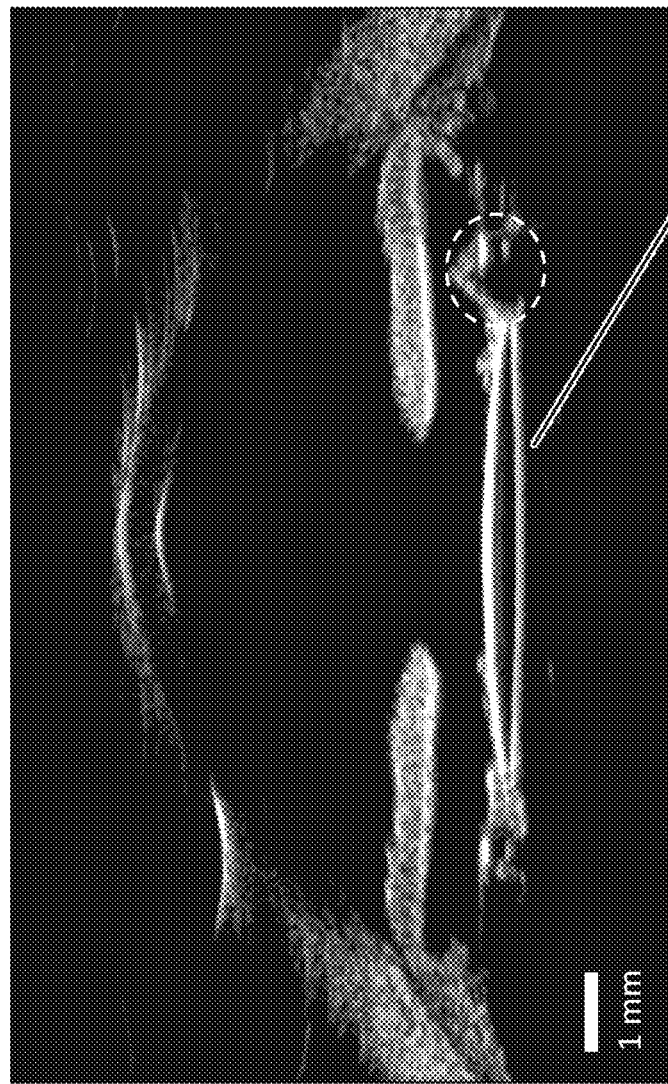
FIG. 29 shows an example of a position of an IOL in a subject's eye that received cataract surgery.

FIG. 29 shows an example of a position of an IOL 300 in a subject's eye that received cataract surgery. Eye anatomy may vary between subjects and/or may be altered as a result of the cataract surgery. For example, the angle of an iris can shift after a native lens of an eye of the subject is removed in the cataract surgery. The position of the IOL may shift as a lens capsule contracts around the IOL. FIG. 29 shows that IOL 300 is placed in the subject's eye without any noticeable shift.

Example 23: Materials and Methods Used in Preclinical Studies

Test Materials

Preclinical studies were performed on a rabbit model of cataract surgery. The results of these studies are discussed herein in Example 24, Example 25, Example 26, and Example 27. Materials and methods used in these studies are disclosed herein in Example 23. Intraocular lens implant (IOLs) were obtained from an intraocular lens manufacturer (e.g, Tecnis 1-piece monofocal hydrophobic acrylic IOLs by Johnson & Johnson Vision). IOLs were pre-coupled to the ophthalmic article 100s or the vehicle implants (e.g., OcuRing polymer only) prior to their use in the cataract surgery model. All of the ophthalmic articles and vehicles used in the animal models of cataract surgery were approximately 1.3 mm outer diameter, 0.5 mm inner diameter and 0.7 mm thick. The composition of each ophthalmic article and vehicle tested in the Examples 24-27 is summarized in Table 1.

TABLE 1

Exemplary Ophthalmic article compositions used in animal studies

| Example | Test article | Drug | Drug % (wt %) | Drug Dose (ug) | Polymer | Polymer % (w %) |
|---|---|---|---|---|---|---|
| 24 | OcuRing-D | dexamethasone | 20 | 300 | PLCL 50:50[1] | 80% |
| 24 | Vehicle | — | — | — | PLCL 50:50[1] | 100% |
| 25 | OcuRing-D | dexamethasone | 10 | 150 | PLCL 60:40[2] | 90% |
| 25 | OcuRing-K | ketorolac | 10 | 150 | PLCL 60:40[2] | 90% |
| 25 | Vehicle | — | — | — | PLCL 60:40[2] | 100% |
| 26 | OcuRing-D | dexamethasone | 10 | 150 | PLCL 60:40[2] | 90% |
| 26 | OcuRing-K | ketorolac | 10 | 150 | PLCL 60:40[2] | 90% |
| 27 | OcuRing-D | dexamethasone | 10 | 150 | PLCL 60:40[2] | 90% |
| 27 | Vehicle | — | — | — | PLCL 60:40[2] | 100% |

[1]PLCL 6040 = A copolymer comprised poly(L-lactide-co-caprolactone) at 60:40 molar ratio of L-lactide to caprolactone with a molecular mass ($M_n$) of about 75 to 85 kDa
[2]PLCL 6040 = A copolymer comprised poly(L-lactide-co-caprolactone) at 60:40 molar ratio of L-lactide to caprolactone with a molecular mass ($M_n$) of about 75 to 85 kDa.

Generally, for all the results obtained from the examples, it is important to tie the results back to what (e.g., polymer composition, active agent amount, IOL contribution) contributed to a particular result.

On the day of implantation, all animals underwent bilateral phacoemulsification procedures.

Test System: Animals Housing, and Environmental Conditions

Ear tagging and cage cards were used to identify the animals. Caging comprised stainless steel cages (e.g., 17 inches wide×27 inches deep×15 inches tall or larger) with slatted bottoms without additional bedding. One rabbit was kept in each cage. Environmental conditions comprised 12 hours of light and 12 hours of darkness while the temperature was maintained at 68±2° F. All animals were fed Purina Hi Fiber Lab Rabbit Diet. Water (e.g., Durham city water) was given to the animals using bottles with sipper tubes. Water has been tested for contamination in at least every 6 months.

Animal Health, Acclimation, and Pain Control

Animals were acclimated to the study environment (e.g., for 1-2.5 weeks) prior to a procedure (e.g., dosing procedure). At the completion of the acclimation period, each animal was physically examined by a laboratory animal technician for determination of suitability for study participation. Animals determined to be in good health were released to the study. Institutional Animal Care and Use Committee (IACUC) approved the protocols mentioned herein. According to the IACUC and research facility procedures, cage-side examinations were completed at least twice daily (no less than 6 hours apart) for signs of overt discomfort, such as severe blepharospasm, severe conjunctival hyperemia, epiphora, excessive rubbing at the eye, and not eating. Per the protocol, if these conditions were observed and persisted for 12 hours, the animals were to be humanely euthanized. None of these conditions were observed in any of the studies.

Animals were assigned to each study by animal number and were uniquely identified by corresponding cage card number and matching ear tag number.

Implantation Procedures (Day 0)

On day 0, the rabbits' pupils were dilated using 1.0% tropicamide hydrochloride. The animals then received a subcutaneous (SC) injection of buprenorphine (e.g., 0.01-0.05 mg/kg SC), and were anesthetized with an intramuscular (IM) injection of ketamine hydrochloride (e.g., 50-80 mg/kg) and xylazine hydrochloride (5-10 mg/kg). Aseptic precautions were taken for the surgical procedure. All animals received a single intravenous (IV) dose of enrofloxacin (e.g., Baytril, 5 mg/kg) once on the day of surgery as an antibiotic prophylactic.

A clear corneal incision (e.g., 2.5 millimeters (mm) or 2.8 mm long) was made at the superior limbus, a fornix-based conjunctival flap was fashioned, and homeostasis was obtained at the limbus with light cautery, when necessary. A corneal-scleral incision was then made using a crescent blade, or the generic equivalent, and the anterior chamber was entered (e.g., with a 2.8 mm keratome). Following instillation of epinephrine in balanced salt solution (BSS) (e.g., 1:10,000), the anterior chamber was then inflated (e.g., with 1.8% hyaluronic acid viscoelastic).

Capsulorhexis forceps were used to create a well-centered continuous curvilinear capsulotomy (CCC), with a diameter of approximately 5.5 mm. After BSS hydro dissection, a phacoemulsification handpiece (e.g., Alcon Constellation system) was inserted into the posterior chamber for removal of lens nucleus and cortical material. One milliliter (mL) of epinephrine 1:1,000 (1 mg/mL) and 0.5 mL of heparin (10,000 USP units/mL) were added to each 500 mL of irrigation solution to facilitate pupil dilation and control inflammation. The endocapsular technique was used with the phacoemulsification to take place (e.g., entirely) within the capsular bag. The residual cortex was then removed with a handpiece (e.g., with the irrigation/aspiration (FA) handpiece). Viscoelastic was used to expand the capsular bag (e.g., to at most about 2.7 or at most about 2.8 mm).

Pre- and post-operative pain medication were dictated following approval of a veterinarian. Post-surgery, animals received a single drop of neopolygram in each eye and a second dose of buprenorphine (e.g., 0.01-0.05 mg/kg SC) in the afternoon following surgery. The rabbits' body weights were collected prior to surgery following the end of acclimation and prior to necropsy. During acclimation and during the studies as described in examples 2, 3 and 4, animals were evaluated for mortality and morbidity as well as general health, with particular attention paid to the eyes.

Ocular Examination and Irritation Scores

Ocular examinations (OEs) were performed using a slit lamp biomicroscope and indirect ophthalmoscope to evaluate ocular surface morphology and anterior and posterior segment inflammation on all animals prior to implantation procedures to serve as a baseline and at predefined timepoints in each study as mentioned elsewhere herein. A modified Hackett and McDonald ocular grading system with additional scoring parameters for the ocular posterior segment was used to grade inflammation. The extent of capsular fibrosis was also evaluated, at predefined timepoints in each study as mentioned elsewhere herein, by slit lamp retro illumination photography. Posterior capsular opacification (PCO) scores were evaluated for each animal utilizing a scoring system (e.g., a 0-4 PCO Scoring System including: none visible or 0, mild/focal or 1, moderate/focal or 2, moderate/diffuse or 3, Severe/diffuse or 4). A topical mydriatic was given following the anterior segment examination to facilitate examination of the ocular fundus. Animals were not tranquilized for the examinations.

Tonometry

Intraocular pressure (IOP) was measured in both eyes of all animals after OEs with a probe (e.g., with a Tonovet probe) at predefined timepoints in each study as mentioned elsewhere herein. The IOP measurements were performed with the animal maintained in an upright position. With the Tonovet probe, the tip of the probe was directed to gently contact the central cornea. A plurality of consecutive measurements (e.g., six consecutive measurements) were obtained and the average IOP shown on the display was recorded. A plurality of independent measurements (e.g., three) were obtained and recorded for each eye, at predefined timepoints in each study as mentioned elsewhere herein.

Aqueous Humor Collections

At predefined timepoints in each study as mentioned elsewhere herein, animals were given buprenorphine (e.g., 0.01-0.05 mg/kg SC once daily). Prior to aqueous humor (AH) collections, animals were tranquilized (e.g., with 50 mg/kg ketamine and 10 mg/kg xylazine intramuscular (IM) and the eyes were aseptically prepared (e.g., using topical 5% betadine solution, followed by rinsing with sterile eye wash, and application of one drop of 0.5% proparacaine HCL). Approximately 100 microliter (µL) of AH were collected from both eyes (e.g., at approximately the 12 o'clock position using a 30-gauge needle). After AH collection, samples were weighed, flash frozen, and stored at −80° C. and animals were allowed to recover normally from anesthesia.

Blood Collections

Following AH collections, plasma was collected (e.g., at least 0.5 mL of whole blood was drawn from the marginal ear vein into K2EDTA tubes) at predefined timepoints in each study as mentioned elsewhere herein. After collection, the collected blood was gently mixed (e.g., by inverting the tubes 5-8 times). Blood samples were stored on wet ice prior to plasma processing. The samples were centrifuged (e.g., at 4° C. for 10 minutes at 2000 g) in a swinging bucket refrigerated centrifuge. Following blood collection (e.g., within 20 minutes), the clear plasma was stored (e.g., clear plasma was transferred to a prelabelled polypropylene tube, snap frozen and stored frozen at −80° C.).

Ocular Histopathology

In some cases, following surgical procedures (e.g., within at least about 28 days), animals were euthanized, for example, with an overdose of sodium pentobarbital followed by auscultation to ensure death. Both eyes were immediately enucleated and fixed (e.g., in Davidson's solution for 24 hours, followed by alcohol). Tissue specimens were stored (e.g., at −80° C.) for ocular histopathology. In other cases, following surgical procedures (e.g., within at least about 30 days), animals were tranquilized with one or more drugs (e.g., 50/10 mg/kg IM of ketamine/xylazine) and were euthanized, for example, with an overdose of sodium pentobarbital followed by auscultation to ensure death. Immediately after euthanasia, all eyes were enucleated and fixed (e.g., in Davidson's solution overnight at room temperature). The following day, eyes were washed (e.g., in 70% ethanol) and stored (e.g., in 70% ethanol) until paraffin embedding. Central sections of selected eyes, including the optic nerve, were stained (e.g., with hematoxylin and eosin) and examined using light microscopy.

Example 24. Efficacy and Tolerability One-Week

Efficacy and tolerability of the ophthalmic article (e.g., OcuRing-D dexamethasone) implants following phacoemulsification with intraocular lens (IOL) implantation were evaluated in a rabbit model of cataract surgery over 7 days following the surgery. The ophthalmic article (e.g., OcuRing) can be a substantially small bioerodible ring that can attach to an IOL (e.g., to the haptic of the IOL) and provide sustained-release of a drug at a predefined dosage (e.g., 300 µg or 600 µg of dexamethasone), for example, during the postoperative period. Phacoemulsification is a modern cataract surgery method in which the eye's internal lens is emulsified with an ultrasonic handpiece and aspirated from the eye. Aspirated fluids are replaced with irrigation of balanced salt solution to maintain the anterior chamber.

Rabbit is the preferred species for assessing safety of intraocular devices, and United States Food and Drug Administration (US FDA), the American National Standards Institute (ANSI), and International Standards Organization/Committee European Normalization (ISO/CEN) have all implemented guidelines for the conduction of studies utilizing the rabbit model.

Figure 30:
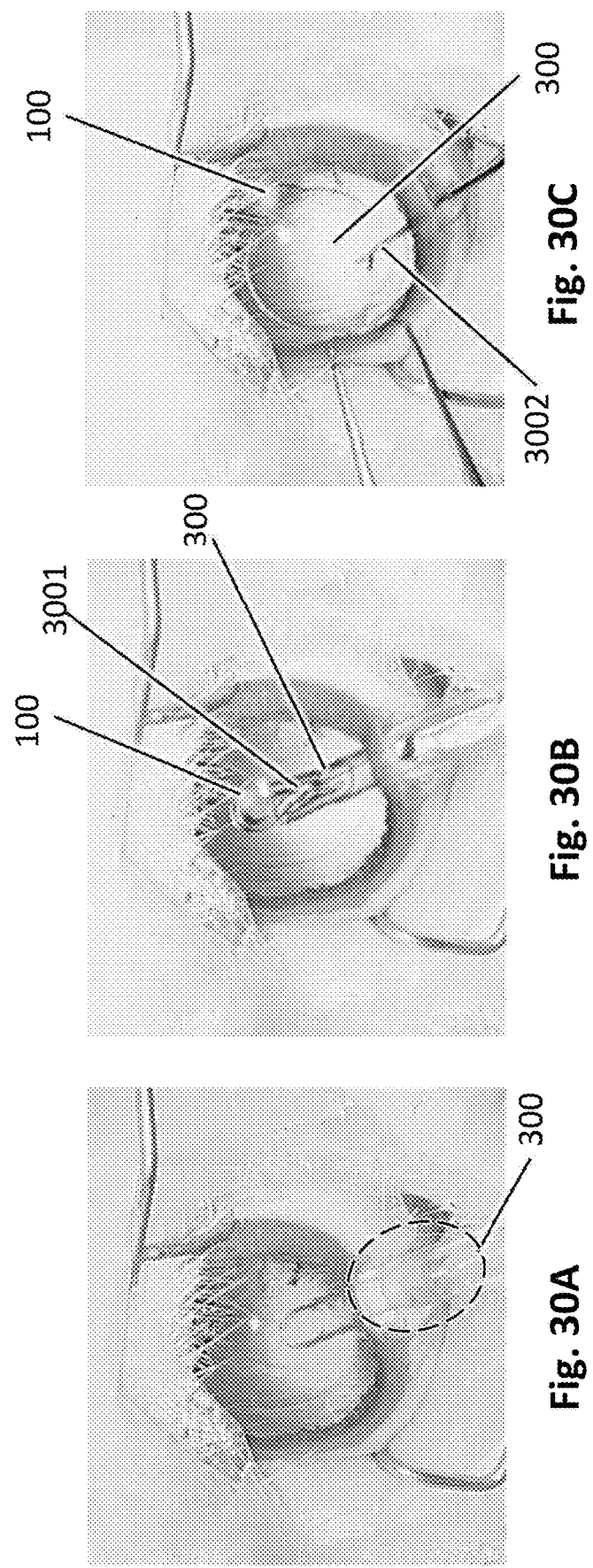
FIGS. 30A-30C schematically illustrates a representative surgical implantation.

Phacoemulsification was performed bilaterally. Corneal incisions of animals that underwent surgery were closed with continuous suture pattern of 9-0 Nylon. Surgery was followed by implantation of either a control IOL or IOL carrying the ophthalmic article (e.g., OcuRing-D). The control IOL was either an IOL without an attached ophthalmic article or a vehicle implant. A vehicle implant comprised an IOL with the ophthalmic article attached (e.g., only a polymer ring) carrying no drug. Videos were recorded through the surgical microscope for each implantation procedure. Still photos from a representative surgical video are shown in FIGS. 30A-30C. In FIG. 30A, the injector cartridge tip 3001 is shown extending through the corneal incision into the anterior chamber with the ophthalmic article attached to leading haptic of the IOL 300, together rolled and compressed inside the tip of the injector cartridge 3001. In FIG. 30B, the ophthalmic article 100 and IOL 300 are shown protruding from the injector tip 3001 into the anterior chamber. Note that the exposed portion of the IOL 300 has begun to unroll, but the portion of the IOL remaining inside the injector tip remained rolled. In FIG. 30B, the ophthalmic article 100 and IOL 300 are shown fully unrolled inside the capsular bag of the eye. The tip of an instrument 3002 is visible, which the surgeon uses to rotate and center the IOL 300 in its proper position.

Experimental Design

A total of eight male New Zealand white adult rabbits, 6.5 months old, were randomly divided into two groups. Four rabbits were assigned to each group. A first group received vehicle implant and IOL in their left eyes (OS), and the ophthalmic article (e.g., OcuRing-D) loaded with dexamethasone (300 µg) and IOL in their right eyes (OD). A second group received IOL without the ophthalmic article in their left eyes (OS) and received the ophthalmic article (e.g., OcuRing-D) loaded with 600 µg of dexamethasone and IOL in their right eyes (OD). Two rabbits were kept as spares. Animals were acclimated to the environment of the study for a minimum of 2 weeks prior to dosing or prior to implantation and were evaluated over a one-week period following the dosing or implantation.

Mortality and morbidity were observed twice daily along with cage-side observations with particular attention paid to both eyes. Intraocular pressure (IOP) as well as complete ocular examinations (OEs) comprising ocular surface morphology and ocular inflammation at predefined timepoints. The predefined timepoints included day 0 (baseline), day 1, 2, 4, and 7. Animals were euthanized on day 7 following surgical procedure. Animals' body weights were collected prior to surgery on day 0 and prior to necropsy. An illustrative study design is summarized in Table 2. Details on animals, housing, and environmental conditions as well as animals' diet and water are shown in Table 3.

TABLE 2

Illustrative Study Design Summary

| Group # | # of Animals | Treatment | End Points | Euthanasia |
|---|---|---|---|---|
| 1 | 4 | OS: 1 Vehicle implant (OcuRing without drug) OD: OcuRing-D™ dexamethasone implant (300 µg) | IOL insertion- All animals Ocular examinations/Photography- Baseline, Days 1, 2, 4, and 7 following surgery Tonometry - Baseline, Days 1, 2, 4, and 7 following surgery. | Day 7 |
| 2 | 4 | OS: No OcuRing OD: 2 OcuRing-D dexamethasone implants (600 µg) | | |

TABLE 3

Animals, Housing, Food, Water, and Environmental Conditions

| | | |
|---|---|---|
| Species/Strain | | Rabbit (*Oryctolagus cuniculus*)/New Zealand White |
| Source | | Covance, Denver, PA |
| Age Range at First Dosing | | 6.5 months |
| Weight Range at First Dosing | | 3.0 ± 0.23 kg |
| Identification | | Cage card |
| Physical Examination Time | | During acclimation |
| Caging | | Stainless steel; 17 inches wide × 27 inches deep × 15 inches tall or larger, slatted bottoms. No additional bedding. |
| Number per cage | | 1 |
| Environmental Conditions | | Photoperiod: 12 hrs. light/12 hrs. darkness Temperature: 68 ± 2° F. |
| Feed | Type | Hi Fiber Rabbit Diet |
| | Name | Hi Fiber Lab Rabbit Diet #5P25, Purina, St. Louis, MO |
| | Availability | ad libitum |
| | Analysis for Contaminants | Not routinely performed, No contaminants expected |

TABLE 3-continued

Animals, Housing, Food, Water, and Environmental Conditions

| Water | Source | Durham City Water |
|---|---|---|
| | Availability | ad libitum via water bottles with sipper tubes. |
| | Analysis for Contaminants | Every 6 months, No contaminants found |

Results

Surgical implantation of IOLs with and without the ophthalmic article implants (e.g., OcuRing) were performed without complication. The ease of injector loading, insertion into the eye, unfolding and positioning within the lens capsule was comparable between IOLs with attached ophthalmic article implants (e.g., OcuRing) and IOLs without the ophthalmic article. Once implanted within the eye, there was no observations of tilt or decentration for IOLs with attached ophthalmic article implants (e.g., OcuRing). All surviving animals remained healthy while on study, including normal activity, eating, urinations, and defecations. The animals weighed 3.0±0.23 kg prior to surgery and 3.0±0.23 kg upon necropsy. Individual animals maintained their weight or gained a small amount over the course of this study.

Posterior capsular opacification scoring showed a higher score in the eyes receiving the high dosage of dexamethasone (the second group OD: 600 µg Dexamethasone) IOLs. Lens opacification was not observed, indicating lack of calcification for the duration of the study. Overall the ophthalmic article loaded with dexamethasone and IOL implants were well tolerated in the rabbits.

Figure 31:
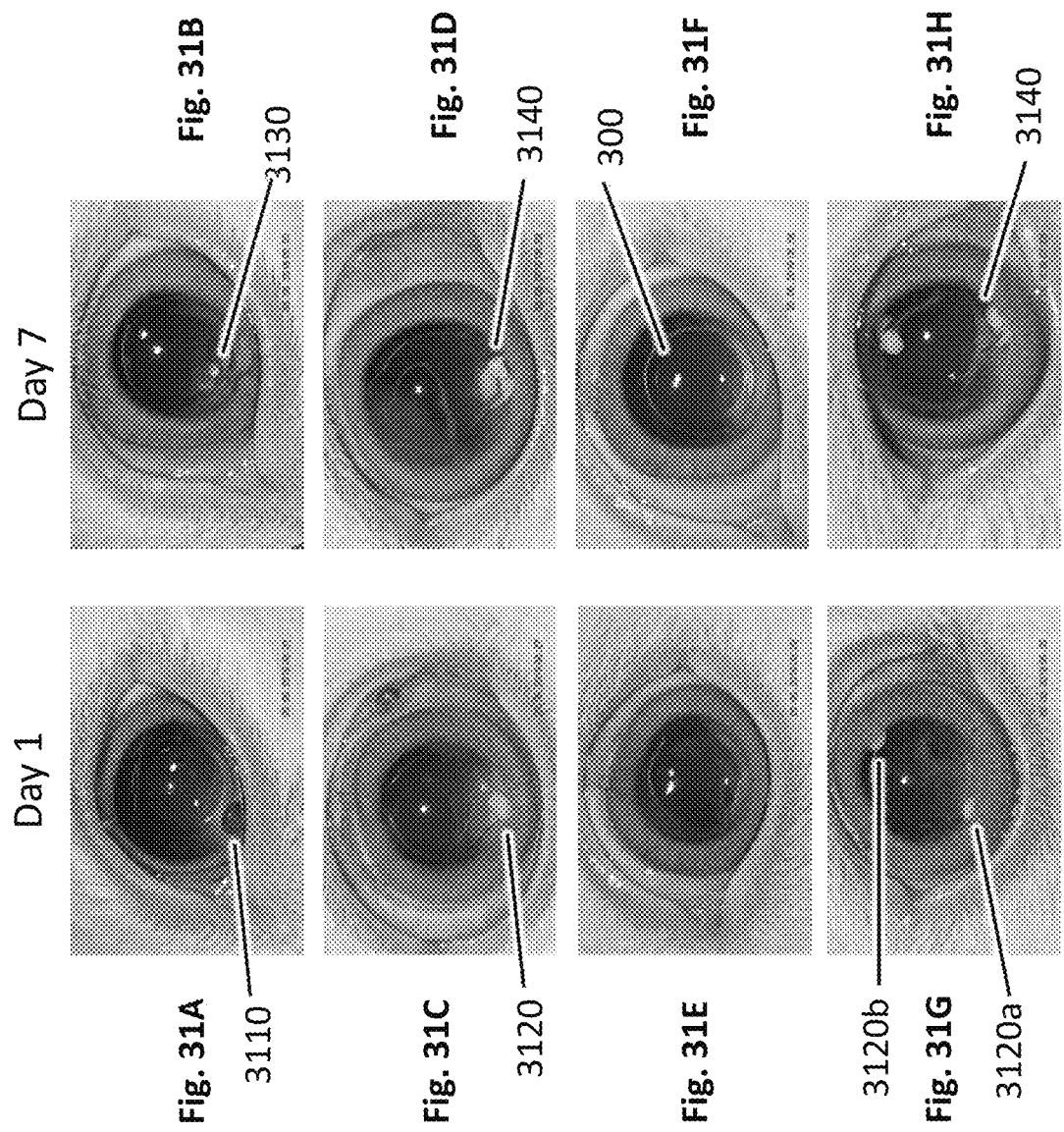
FIGS. 31A-31H illustrate examples of digital planar photographs of rabbit eyes at day 1 and 7.

At predefined timepoints as mentioned herein, OE was performed on all animals and irritation scores were collected. FIGS. 31A-31H illustrate examples of digital planar photographs of rabbit eyes at day 1 and 7. FIGS. 31A, 31C, 31E, 31G are representative photographs from Day 1, and FIGS. 31B, 31D, 31F, 31H are representative photographs from day 7. A representative image of the IOL 300 is shown in FIG. 31F; as mentioned hereinbefore IOL 300 was implanted in all the animals. Vehicle implants 3110 and dexamethasone implants 3120 all appeared to be intact and properly positioned on Day 1. By Day 7, the shape of some of the vehicle implants 3130 and dexamethasone implants 3140 had changed, though they remained in the proper position on the IOLs. Without wishing to be bound by theory, implanted devices can change shape under physiologic conditions, and the degree to which this occurs with a given formulation may not predictable. In this example, without wishing to be bound by theory, one might conclude that the drug and/or polymer composition of the devices presented in this example may exhibit less in vivo shape retention than some of the other device compositions presented in the subsequent examples. FIG. 31G illustrate two ophthalmic devices 3120a and 3120b loaded with a drug (e.g., dexamethasone).

Figure 32:
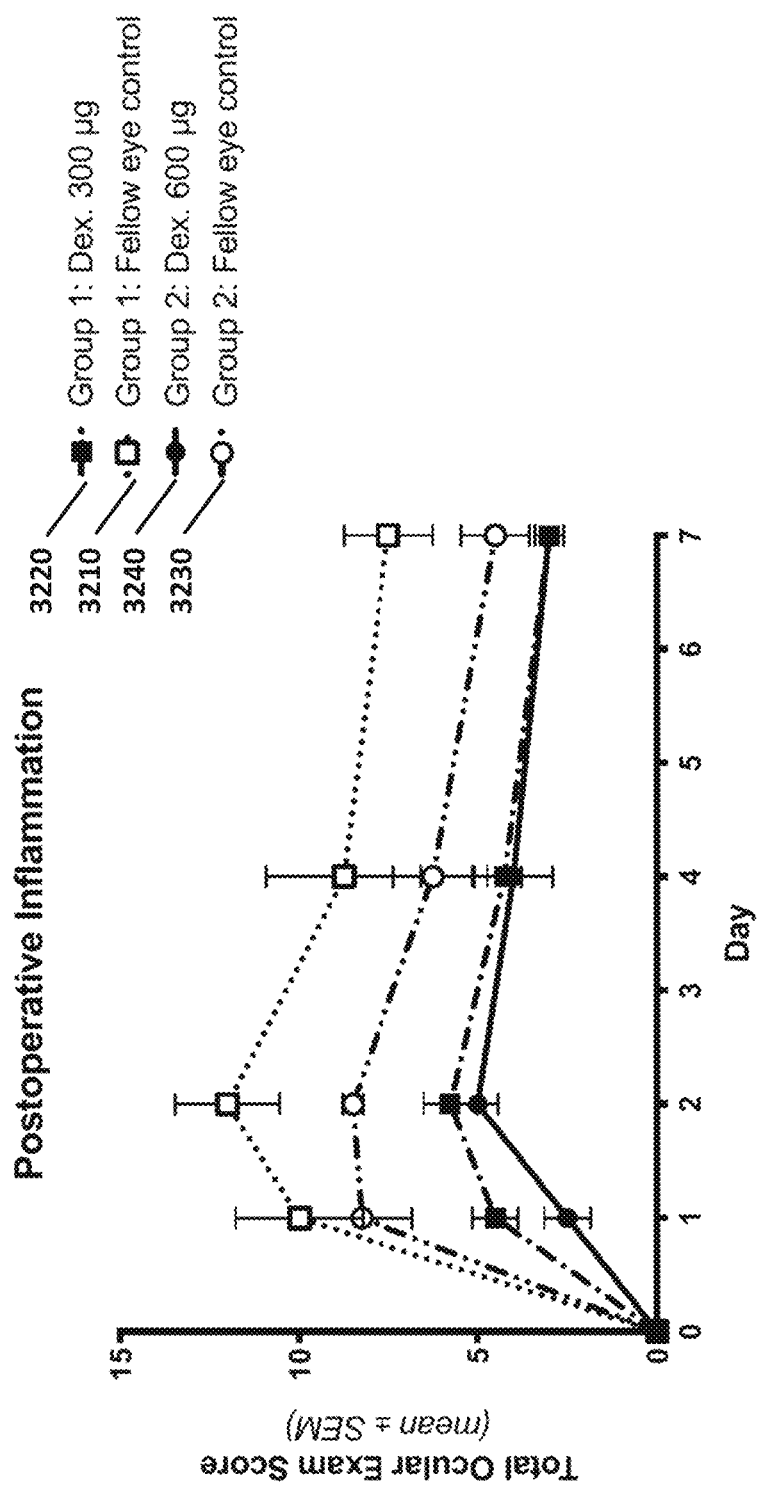
FIG. 32 shows average ocular examination scores at day 0 (baseline), day 1, day 2, day 4, and day 7.

FIG. 32 shows average total OE scores at day 0 (baseline), day 1, day 2, day 4, and day 7. Error bars represent standard error of the mean. The unfilled squares connected with a dotted line curve 3210 represent the OE scores of the left eyes carrying the vehicle control in the animals in the first group. The solid filled dark squares connected with a dashed dotted line 3220 represent the OE scores of the right eyes of the animals in the first group carrying the ophthalmic article loaded with 300 µg of dexamethasone. OE scores of the left eyes of the animals in the second group carrying only the IOL are represented with unfilled circle connected with a dashed double-dotted line 3230. The solid filled dark circles connected with a solid dark line 3240 represent the OE scores of the right eyes of the animals in the second group carrying the ophthalmic article loaded with 600 µg of dexamethasone. OE scores showed modest inflammation across all groups for the first two days post-implantation, and OE scores for both the 300 µg dexamethasone-loaded IOLs 3220 and 600 µg dexamethasone-loaded IOLs 3240 were notably lower at all timepoints examined relative to fellow eye control 3210 and 3230. The fellow eye control 3210 received the vehicle implant (e.g., the ophthalmic article and IOL without a drug). The fellow eye control 3230 received only the IOL. The OS (fellow eye control) of the animals treated with 600 µg dexamethasone implants 3240 had lower inflammation scores than the fellow eyes of the animals treated with 300 µg dexamethasone 3220 at all timepoints after cataract surgery. Total OE scores for dexamethasone-loaded implants were, on average, lower than control IOLs throughout the duration of this study, with peak inflammatory response on day 2 following implantation. Overall, IOLs were well tolerated, with moderate inflammation post-implantation that began to resolve 2 days after surgery.

Figure 33:
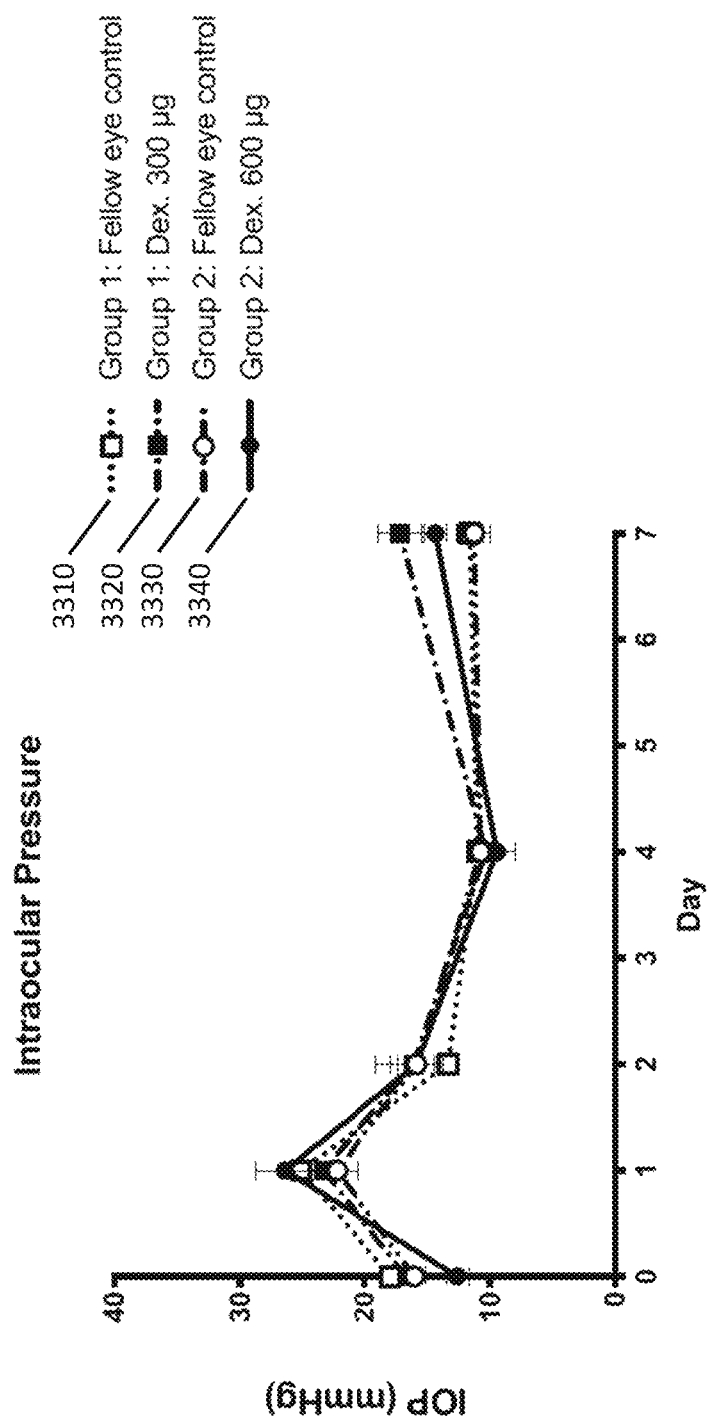
FIG. 33 shows the average intraocular pressure measured at day 0 (baseline), 1, 2, 4 and 7.

Intraocular pressure (IOP) was measured in all the animals at predetermined timepoints. FIG. 33 shows the average IOP measured at day 0 (baseline), 1, 2, 4 and 7. Error bars represent standard error of the mean. IOPs for the animals in the first group are shown using unfilled squares with dotted line 3310 for the OS (fellow eye control) that received a vehicle implant, and solid filled squares with dashed dotted line 3320 for the OD (300 µg dexamethasone) eye that received the ophthalmic article loaded with 300 µg of dexamethasone and IOL. IOP for the animals in the second group are represented with unfilled circles and dashed dotted line 3330 in their left eyes (OS) that received IOL only (fellow eye control), and solid filled circles and solid line 3340 in their right eyes (OD) that received the IOL with the ophthalmic article loaded with 600 µg of dexamethasone. In general, IOPs followed a pattern similar to changes in the OE scores, increasing on the first day post-implantation, then decreasing by day 2. All of the eyes were within a normal IOP range by end of study. These findings provide preliminary support for the safety of dexamethasone-loaded and vehicle devices for use in cataract surgery.

Example 25. Efficacy and Tolerability Four-Week

Efficacy and tolerability of the ophthalmic article (e.g., OcuRing-D dexamethasone or OcuRing-K ketorolac) implants following phacoemulsification with intraocular lens (IOL) implantation were evaluated in a rabbit model of cataract surgery over 30 days following the surgery. The ophthalmic article (e.g., OcuRing) can be a substantially small bioerodible ring that can attach to an IOL (e.g., to the haptic of the IOL) and provide sustained-release of a drug at a predefined dosage (e.g., 300 µg or 600 µg of dexamethasone or 150 µg or 300 µg of ketorolac), for example, during the postoperative period. Phacoemulsification is a modern cataract surgery method in which the eye's internal lens is emulsified with an ultrasonic handpiece and aspirated from the eye. Aspirated fluids are replaced with irrigation of balanced salt solution to maintain the anterior chamber.

Phacoemulsification was performed bilaterally. Corneal incisions of the animals that underwent surgery were closed with continuous suture pattern of 9-0 Vicryl. Surgery was followed by implantation of either a control IOL or IOL carrying the ophthalmic article (e.g., OcuRing-D or OcuRing-K). The control IOL was either an IOL without an ophthalmic article attached or a vehicle implant. A vehicle implant comprised an IOL with the ophthalmic article attached carrying no drug (e.g., polymer only).

Experimental Design

A total of eight male New Zealand white adult rabbits, 6.0 months old, were randomly divided into two groups. Four rabbits were assigned to each group. A first group received a vehicle implant and IOL (e.g., IOL with OcuRing polymer only) in their left eyes and the ophthalmic article loaded with 150 μg of ketorolac and IOL implant (e.g., IOL with OcuRing-K) in their right eyes (OD). A second group received a vehicle implant and IOL (e.g., IOL with OcuRing polymer only) in their left eyes and the ophthalmic article loaded with 150 μg of Dexamethasone and IOL implant (e.g., IOL with OcuRing-D) in their right eyes (OD). Two rabbits were kept as spares. Animals were acclimated to the environment of the study for a minimum of 1 week prior to dosing or implantation and were evaluated over a four-week period following the surgery.

Complete OE and photography as well as tonometry were done for all animals at day 0 (baseline), 1, 3, 7, 14, 21 and 30 following surgery. All animals were euthanized at day 30 following surgery and both eyes were enucleated for ocular histology as described herein. Study design is summarized in Table 4. Details on animals, housing, and environmental conditions as well as animals' diet and water are shown in Table 5 and Table 6, respectively.

TABLE 4

Illustrative Study Design Summary

| Group # | # of Animals | Treatment | End Points | Euthanasia |
|---|---|---|---|---|
| 1 | 4 | OS: OcuRing Vehicle Implant (polymer only) OD: OcuRing-K ketorolac implant (150 μg) | IOL insertion- All animals Ocular examinations/Photography (w/PCO scoring)- Baseline, | Day 30 |
| 2 | 4 | OS: OcuRing Vehicle Implant (polymer only) OD: OcuRing-D dexamethasone implants (150 μg) | Day 1, 3, 7, 14, 21 and 30 following surgery, Tonometry - Baseline, Day 1, 3, 7, 14, 21 and 30 following surgery. Histology (both eyes) | |

TABLE 5

Animals, Housing, and Environmental Conditions

| | |
|---|---|
| Species/Strain | Rabbit (*Oryctolagus cuniculus*) New Zealand White |
| Source | Covance, Denver, PA |
| Age Range at First Dosing | 6.0 months |
| Weight Range at First Dosing | 2.9 ± 0.14 kg |
| Identification | Cage Card |
| Physical Examination Time | During Acclimation |
| Caging | Stainless steel; 17 inches wide × 27 inches deep × 15 inches tall or larger, slatted bottoms, No additional bedding. |
| Number per cage | 1 |
| Environmental Conditions | Photoperiod: 12 hrs. light/12 hrs. darkness Temperature: 68 ± 2° F. |

TABLE 6

Food and Water Provided To Rabbits

| | | |
|---|---|---|
| Feed | Type | Hi Fiber Rabbit Diet |
| | Name | Hi Fiber Lab Rabbit Diet #5P25, Purina, St. Louis, Mo |
| | Availability | ad libitum |
| | Analysis for Contaminants | Not routinely performed, No contaminants expected |
| Water | Source | Durham City Water |
| | Availability | ad libitum via water bottles with sipper tubes. |
| | Analysis for Contaminants | Every 6 months, No contaminants found |

Results

Surgical implantation of IOLs with and without the ophthalmic article implants (e.g., OcuRing) were performed without complication. Once implanted within the eye, there was no evidence of tilt or decentration for IOLs with attached ophthalmic article implants (e.g., OcuRing). All surviving animals remained healthy while on study, including normal activity, eating, urinations, and defecations. The animals weighed 2.9±0.14 kg prior to surgery and 3.3±0.29 kg upon necropsy. Individual animals maintained their weight or gained a small amount over the 4 week course of this study.

Figure 34:
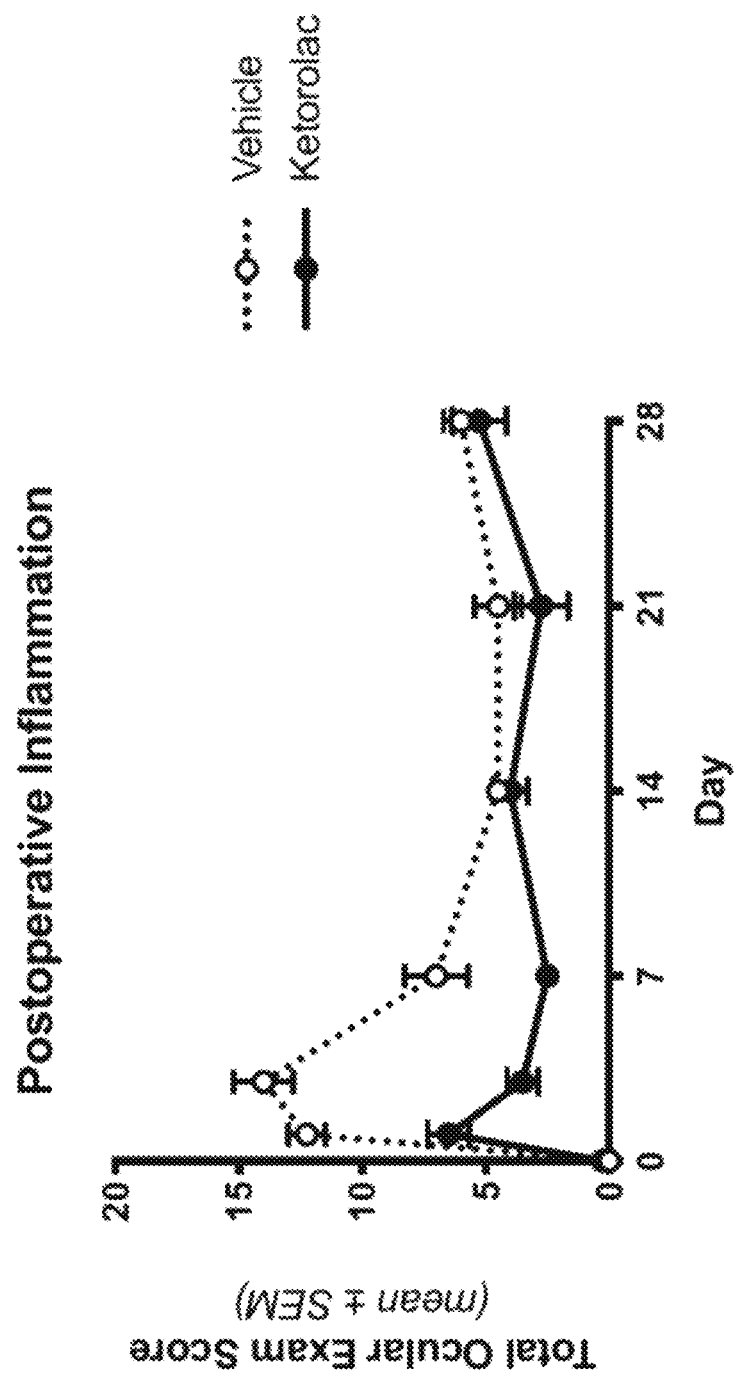
FIG. 34 shows ocular examination scores for a group that received implants comprising vehicle or ketorolac.
Figure 35:
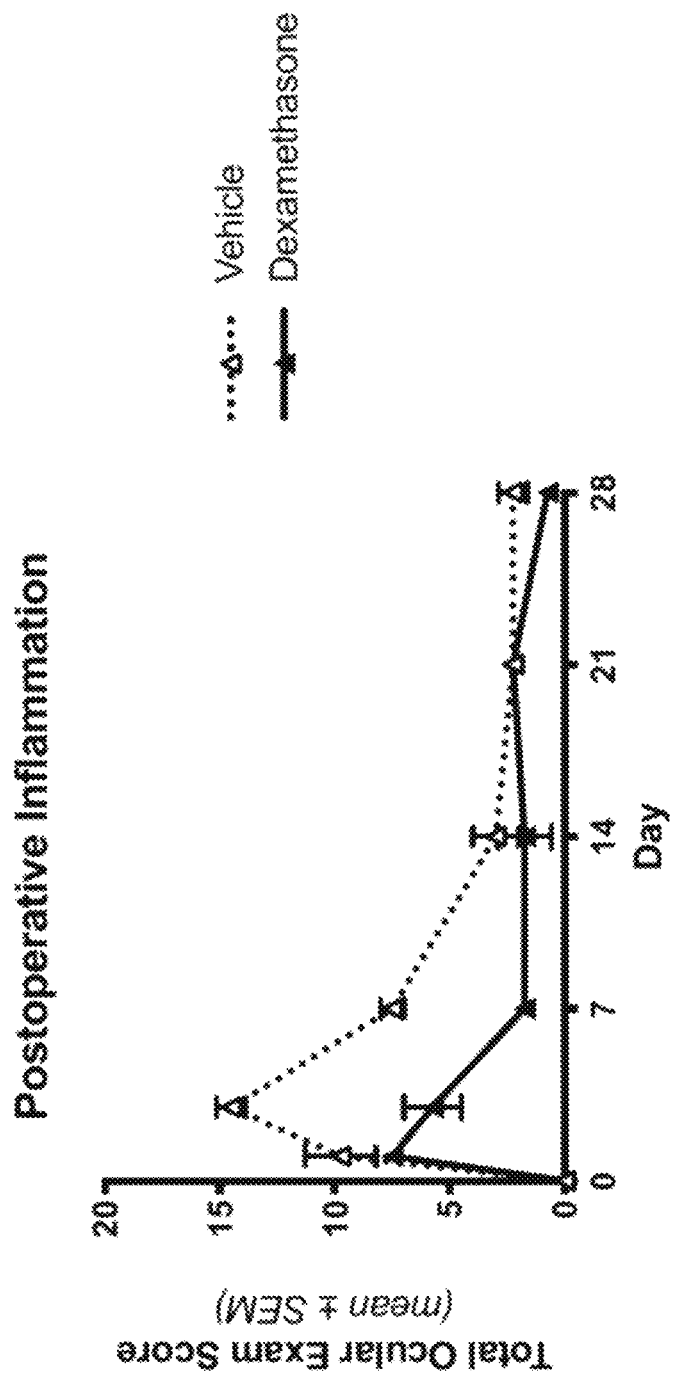
FIG. 35 shows ocular examination scores for a group that received implants comprising vehicle or dexamethasone.

In order to evaluate postoperative inflammation, OE was performed on all the animals at day 0 (baseline), 1, 3, 7, 14, 21, and 29. Average total OE scores with corresponding standard error of the mean (error bars) for the first group that received implants comprising vehicle or ketorolac is shown in FIG. 34 and for the second group that received implants comprising vehicle or dexamethasone is shown in FIG. 35. Total ocular examination scores for the eyes that received the ophthalmic article with the dexamethasone or ketorolac were, on average, lower than eyes that received vehicle implants until day 14, when inflammation scores in the control IOL groups decreased to the levels observed in the eyes that received the ophthalmic articles with ketorolac or dexamethasone. A peak inflammatory response was observed for vehicle controls on day 3 following surgery, while peak inflammation for the eyes that received the ophthalmic articles with ketorolac or dexamethasone was observed on day 1.

Illustrative examples of digital planar photographs associated with the OE of rabbit's eyes in group 1 (FIG. 36) and group 2 (FIG. 37) are shown for day 3, day 14 and day 29 following surgery. Each row shows three digital planar photographs of the same eye in a rabbit. Representative images of the left eye of a rabbit in the first group that received the vehicle implant and IOL are shown for day 3 (FIG. 36A), day 14 (FIG. 36B) and day 29 (FIG. 36C). Representative images of the right eye of a rabbit in the first group that received ophthalmic article loaded with 150 µg of ketorolac (e.g., OcuRing-K) and IOL are shown at day 3 (FIG. 36D), day 14 (FIG. 36E) and day 29 (FIG. 36F). Representative images of the left eye of a rabbit in the second group with the vehicle implant and IOL are shown at day 3 (FIG. 36G), day 14 (FIG. 36H) and day 29 (FIG. 36I). Representative images of the right eye of a rabbit in the second group that received ophthalmic article loaded with 150 µg of dexamethasone (e.g., OcuRing-D) and IOL are shown at day 3 (FIG. 36J), day 14 (FIG. 36K) and day 29 (FIG. 36L). Photographs from the vehicle-treated eyes in the first group and the second group on day 3 appears to show more inflammation than the ketorolac- or dexamethasone-treated eyes. By Day 14 the eyes of all animals appear to have less inflammation present, and this observation continues through Day 29. These findings are consistent with the trends observed with the OE scores (FIG. 34 and FIG. 35). The absence of significant inflammation by Day 29 observed for eyes implanted with either vehicle or drug-loaded implants supports the potential safety and biocompatibility of the device materials for use in human cataract surgery.

Figure 37A:
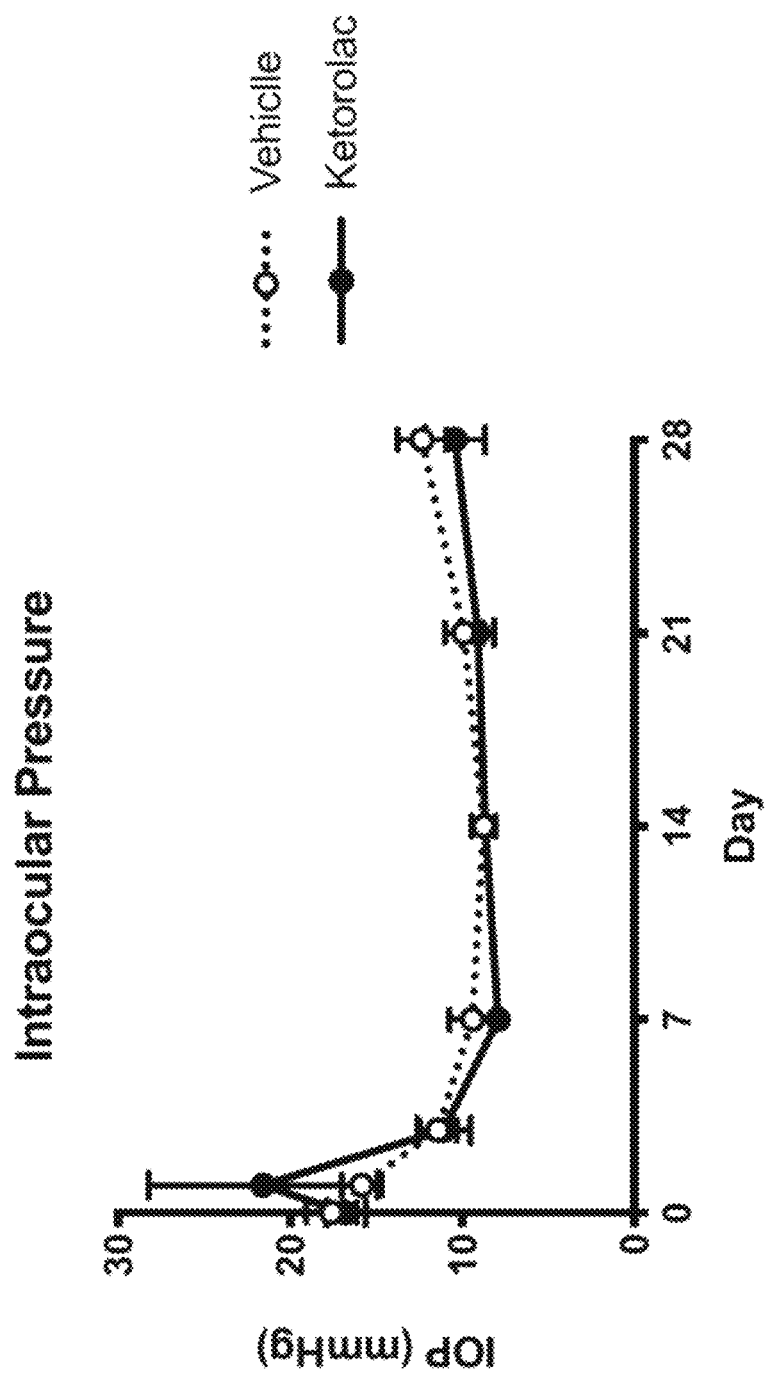
FIG. 37A shows average intraocular pressure measured at day 0, 1, 3, 7, 14, 21, and 29 for a group.
Figure 37B:
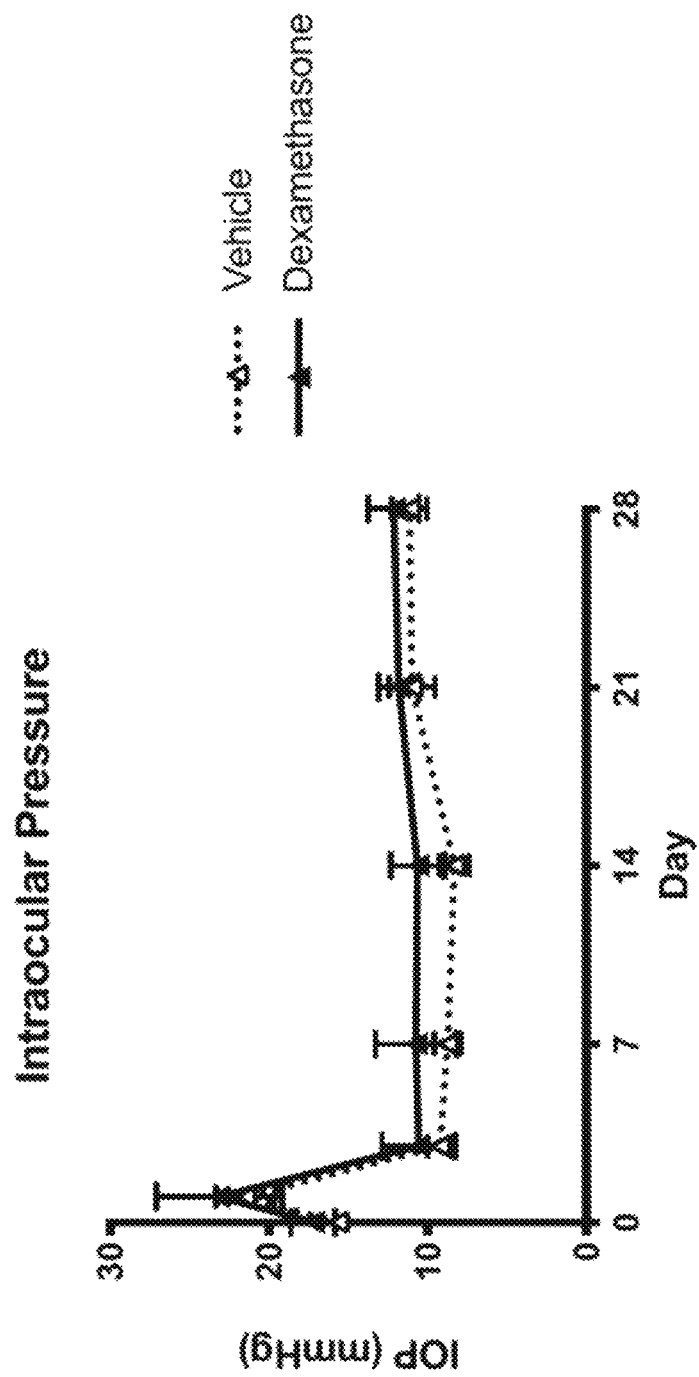
FIG. 37B shows average intraocular pressure measured at day 0, 1, 3, 7, 14, 21, and 29 for another group.

Intraocular pressure (IOP) was measured in all the animals at predetermined timepoints. Average IOP measured at day 0 (baseline), 1, 3, 7, 14, 21, and 29 are shown in FIG. 37A for the first group that received implants comprising vehicle or ketorolac and in FIG. 37B for the second group that received implants comprising vehicle or dexamethasone. Error bars represent standard error of the mean. IOPs of the left eyes of the animals in the first group carrying the vehicle implants are represented using unfilled circles and the second group carrying the vehicle implants are represented using triangles with dashed lines. IOPs of the right eyes of the animals in the first and the second groups carrying the ophthalmic article implants are shown using filled circles and triangles with solid lines, respectively. IOP scores increased on the first day following surgery, then decreasing by day 3 for both eyes of the animals in both groups. From Day 3 to 29, the IOP measurements for all groups remained in a normal range. These findings provide preliminary support for the safety of dexamethasone-loaded and vehicle devices for use in cataract surgery.

Figure 38B:
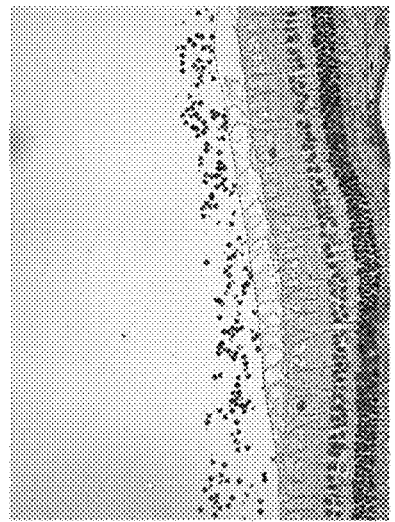
FIGS. 38A-38D shows representative images of histopathology sections of the eyes of the animals in a group.
Figure 38D:
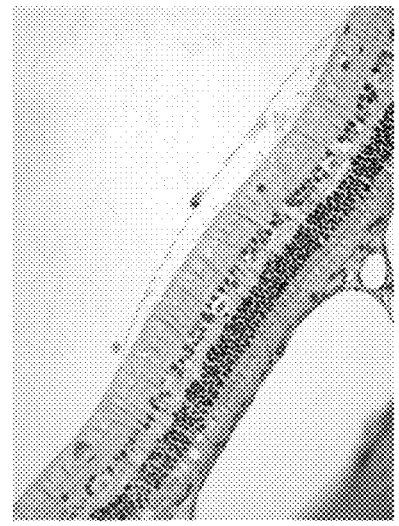
Figure 38A:
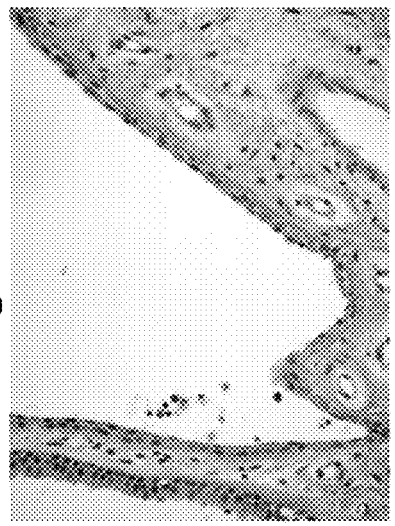
Figure 38C:
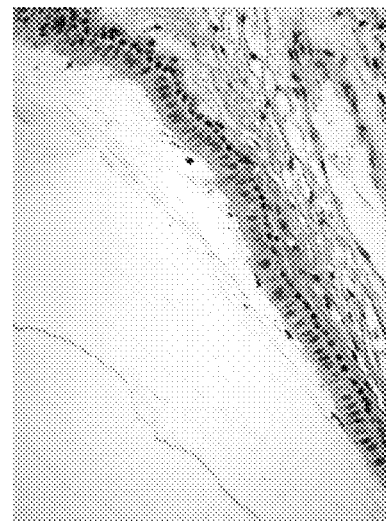
Figure 39A:
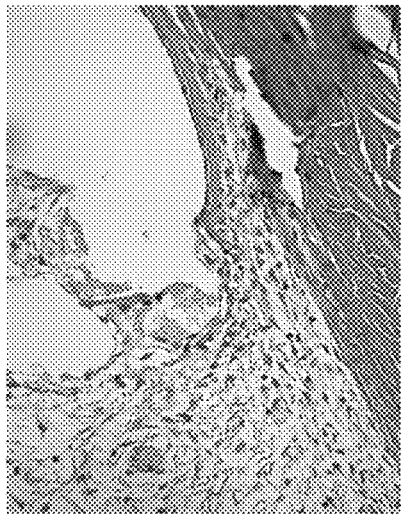
Figure 39B:
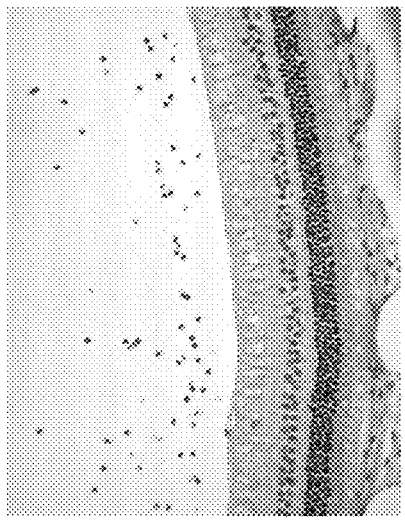
Figure 39C:
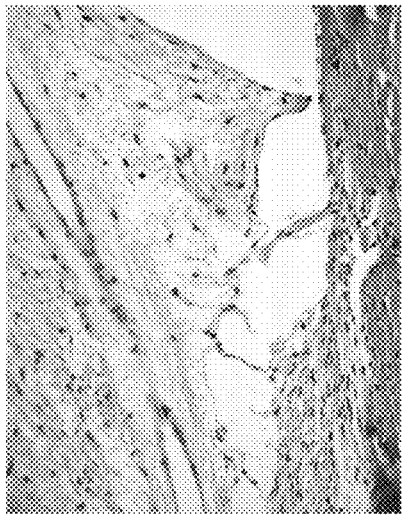
Figure 39D:
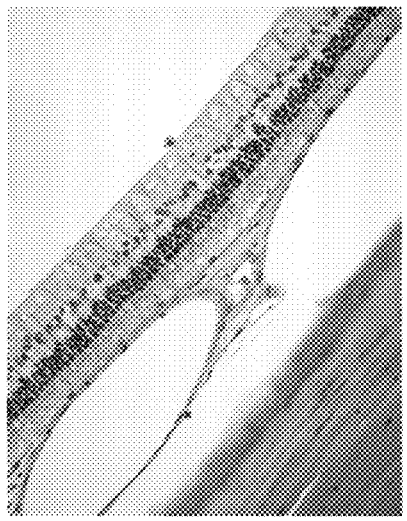

Euthanasia and tissue collections were successfully conducted as described hereinbefore. Representative images of histopathology sections of the eyes of the animals in the first group (FIGS. 38A-38D) and the second group (FIGS. 39A-39D). Representative histopathology sections from the left eyes (OS) of the animals receiving the vehicle control (fellow eye controls) are shown for the iris and ciliary body (FIGS. 38A and 39A) and for vitreous and retina (FIGS. 38B and 39B). representative histopathology sections from the right eyes (OD) of the animals receiving the ophthalmic article implant are shown for the iris and ciliary body (FIGS. 38C and 39C) and for vitreous and retina (FIG. 38D and FIG. 39D). From the slides examined, fellow eye controls in the first group that received the vehicle implants had consistently moderate cellular infiltrate that was predominantly mononuclear in nature in the iris and ciliary body (FIG. 38A) and mild-to-moderate cells in the vitreous body (FIG. 38B). The eyes in the first group that received the ophthalmic article (e.g., OcuRing-K) loaded with 150 µg of ketorolac implant had substantially less anterior and posterior segment inflammation, most with absent or mild inflammation in both segments (FIGS. 38C and 38D). The left eyes in the animals in the second group that received vehicle control had mild to moderate cellular infiltrate (FIGS. 39A and 39B). The right eyes of the animals in the second group that received the ophthalmic article loaded with 150 ug dexamethasone (e.g., OcuRing-D) had absent or very mild inflammation (FIGS. 39C and 39D), the lowest inflammation observed among the four groups in this study.

Conclusions

The study was conducted to evaluate the potential efficacy and tolerability of the ophthalmic article loaded with a drug either ketorolac (e.g., OcuRing-K) or dexamethasone (e.g., or OcuRing-D) in comparison to the ophthalmic article without a drug (e.g., OcuRing), mentioned as vehicle implants herein, attached to IOLs inserted into the eyes of a rabbit model of cataract surgery. IOL and ophthalmic article implants (e.g., OcuRing/IOL) were successful in all the animals. Ocular examinations showed modest inflammation that peaked on day 1 for the groups that received the ophthalmic article loaded with either ketorolac (e.g., OcuRing-K) or dexamethasone (e.g., or OcuRing-D) while inflammation was higher and peaked later (e.g., at day 3) for the eyes with the vehicle control. OE scores for eyes carrying the ophthalmic articles loaded with either ketorolac or dexamethasone were notably lower at all timepoints relative to the eyes carrying the vehicle controls through day 7, after which the OE scores for the vehicle-treated eyes decreased to levels in range with the eyes that received the ophthalmic articles loaded with either ketorolac (e.g., OcuRing-K) or dexamethasone (e.g., or OcuRing-D). Additionally, histopathology revealed significantly lower or even absent inflammation and edema in the eyes that received the ophthalmic articles loaded with either ketorolac (e.g., OcuRing-K) or dexamethasone (e.g., or OcuRing-D).

Example 26. Pharmacokinetics

Pharmacokinetics (PK) of one or more drugs (e.g., dexamethasone, or ketorolac) delivered using the ophthalmic article (e.g., OcuRing) attached to an intraocular lens (IOL) implanted following phacoemulsification and aspiration of the lens in a rabbit model of cataract surgery was evaluated over 28 days following the surgery. The ophthalmic article (e.g., OcuRing) can be a substantially small bioerodible ring that can attach to an IOL (e.g., to the haptic of the IOL) and provide sustained-release of a drug at a predefined dosage (e.g., 300 μg or 600 μg of dexamethasone or 150 μg or 300 μg of ketorolac), for example, during the postoperative period. Phacoemulsification is a modern cataract surgery method in which the eye's internal lens is emulsified with an ultrasonic handpiece and aspirated from the eye. Aspirated fluids are replaced with irrigation of balanced salt solution to maintain the anterior chamber.

Phacoemulsification was performed bilaterally in all the animals. Corneal incisions of the animals underwent surgery were closed with continuous suture pattern of 9-0 Vicryl. Surgery was followed by implantation of either an IOL carrying the ophthalmic article loaded with dexamethasone (e.g., OcuRing-D dexamethasone) or an IOL carrying the ophthalmic article loaded with ketorolac (e.g., OcuRing-K ketorolac). A total of eight male New Zealand white adult rabbits, 6.5 months old, were randomly divided into two groups. Four rabbits were assigned to each group. A first group received the ophthalmic article loaded with 150 μg of ketorolac and IOL implant in both eyes (OU). A second group received the ophthalmic article loaded with 150 μg of dexamethasone and IOL implant in both eyes (OU). Two rabbits were kept as spares. Animals were acclimated to the environment of the study for a minimum of 1 week prior to surgery and were evaluated over a four-week period following the surgery.

Complete OE and photography as well as AH collections were performed for all animals at day 0 (baseline), 1, 3, 7, 14, 21 and 28 following surgery. IOLs were explanted on day 28 for PK analysis. All animals were euthanized at day 28 following surgery and final AH collection. Right eyes of the animals were enucleated, snapped frozen in liquid nitrogen and stored at −80 C for PK tissue analysis. Study design is summarized in Table 7. Details on animals, housing, and environmental conditions as well as the animals' diet and water are shown in Table 8.

TABLE 7

Illustrative Study Design Summary

| Group # | # of Animals | Treatment | End Points | Euthanasia |
|---|---|---|---|---|
| 1 | 3 | OU: 1 OcuRing-K ketorolac implant (150 μg) | IOL insertion- All animals | Day 28 |
| 2 | 3 | OU: 2 OcuRing-D™ dexamethasone implants (150 μg) | Aqueous humor collections - Baseline, Day 3, 7, 14, 21 and 28 IOL explant (Day 28) for PK analysis | |

TABLE 8

Animals, Housing, Environmental, Food, and Water Conditions

| | | |
|---|---|---|
| Species/Strain | | Rabbit (*Oryctolagus cuniculus*)/New Zealand White |
| Source | | Covance, Denver, PA |
| Age Range at First Dosing | | 6.5 months |
| Weight Range at First Dosing | | 2.8 ± 0.12 kg |
| Identification | | Cage card |
| Physical Examination Time | | During acclimation |
| Caging | | Stainless steel; 17 inches wide × 27 inches deep × 15 inches tall or larger, slatted bottoms. No additional bedding. |
| Number per cage | | 1 |
| Environmental Conditions | | Photoperiod: 12 hrs. light/12 hrs. darkness Temperature: 68 ± 2° F. |
| Feed | Type | Hi Fiber Rabbit Diet |
| | Name | Hi Fiber Lab Rabbit Diet #5P25, Purina, St. Louis, MO |
| | Availability | ad libitum |
| | Analysis for Contaminants | Not routinely performed, No contaminants expected |
| Water | Source | Durham City Water |
| | Availability | ad libitum via water bottles with sipper tubes. |
| | Analysis for Contaminants | Every 6 months, No contaminants found |

Results

Surgical implantation of IOLs with the ophthalmic article implants (e.g., OcuRingK or OcuRingD) were performed without complication. Once implanted within the eye, there was no evidence of tilt or decentration for IOLs with attached ophthalmic article implants (e.g., OcuRing). All surviving animals remained healthy while on study, including normal activity, eating, urinations, and defecations. The animals weighed 2.8±0.12 kg prior to surgery and 3.1±0.14 kg upon necropsy. Individual animals maintained their weight or gained a small amount over the 4-week course of this study.

Pharmacokinetic Analysis

Figure 40:
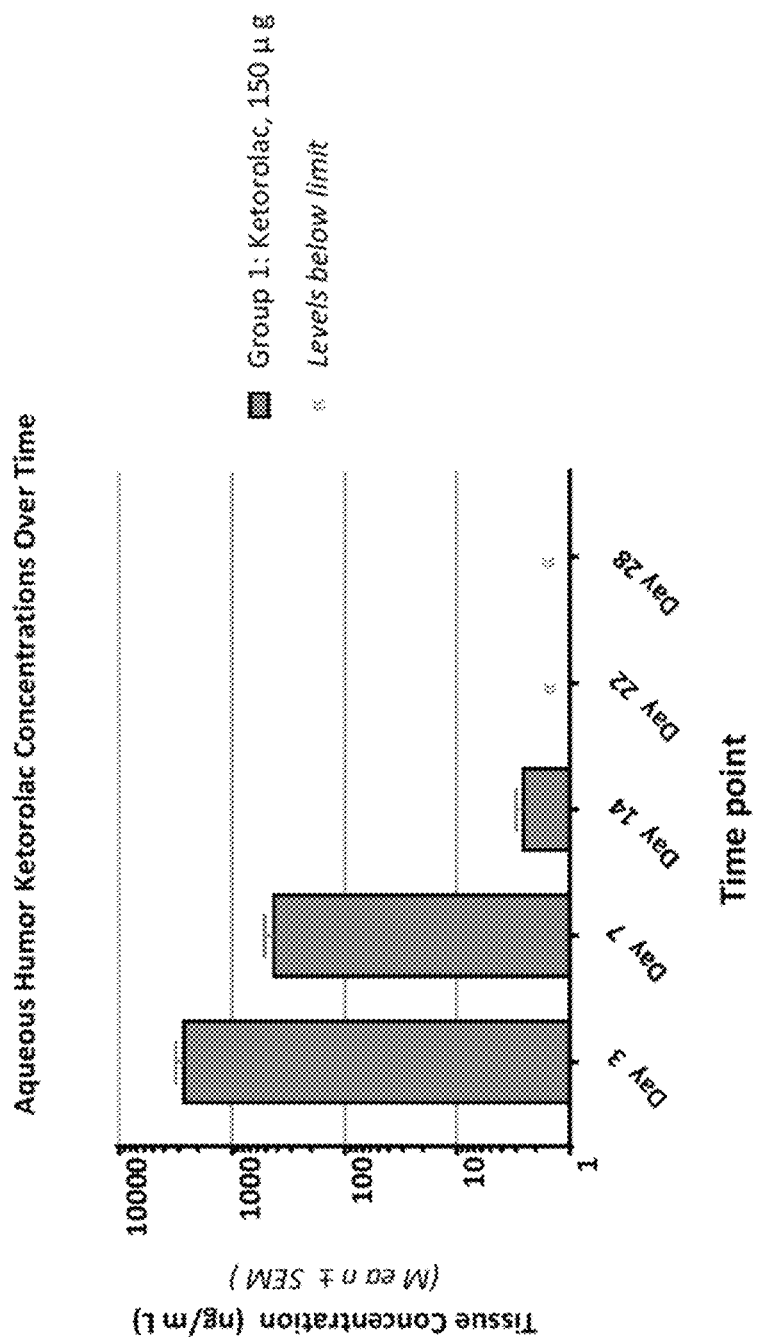
FIG. 40 illustrates tissue concentrations of ketorolac in aqueous humor.
Figure 41:
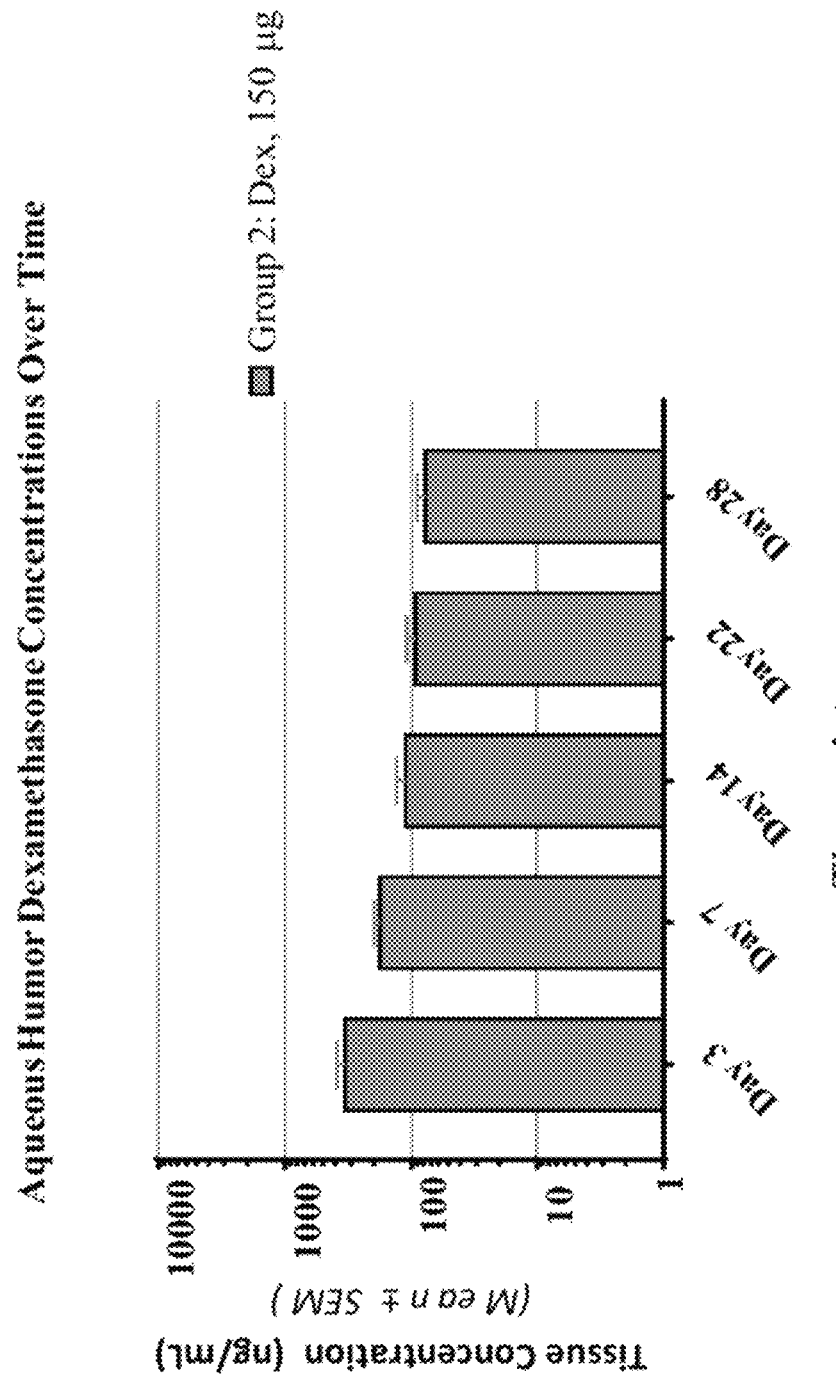
FIG. 41 illustrates tissue concentrations of dexamethasone in aqueous humor.

Aqueous humor and plasma were collected at predefined timepoints specified hereinbefore. The concentration of ketorolac and dexamethasone in plasma and aqueous humors were measured according to the above methods. With the exception of one animal in the first group (#5315, plasma levels of the drug on day 3 post-implantation: 1.71 ng/mL), all plasma test levels in all of the study rabbits were below the limit of quantification (BLQ); Plasma Ketorolac was below the lower limit of quantification (LLOQ)<1 ng/mL; Plasma Dexamethasone was below LLOQ<1 ng/mL). Average tissue concentrations of drugs in aqueous humor are shown in FIG. 40 for ketorolac and in FIG. 41 for dexamethasone. Error bars represent standard error of the mean (SEM). In the first group ketorolac test article levels ranged from 2,500 ng/mL on day 3 to 2.5 ng/mL on day 14 and was detectable in all samples from day 3 to 14. At days 22 and 28, all samples were below the limit of quantification (LLOQ<1 ng/mL). In the second group, dexamethasone levels were detectable at all timepoints following surgery and ranged from 350 ng/mL on day 3 to 80 ng/mL on day 28, with the exception of one aqueous humor sample on day 22 for the left eye of the rabbit #5317, which was below the limit of quantitation (LLOQ<1 ng/mL).

Figure 42:
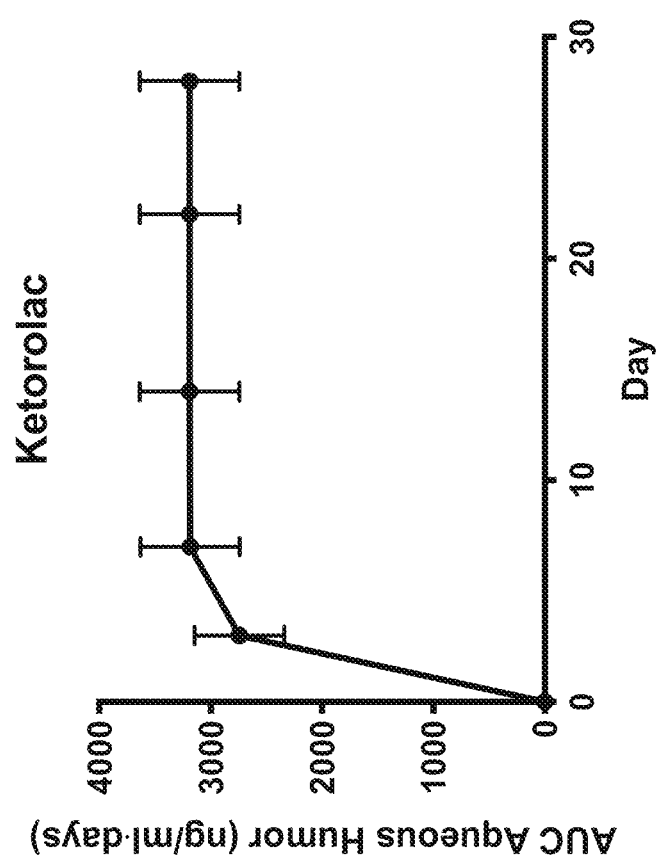
FIG. 42 illustrates an area under the curve analyses for ketorolac concentrations in aqueous humor.
Figure 43:
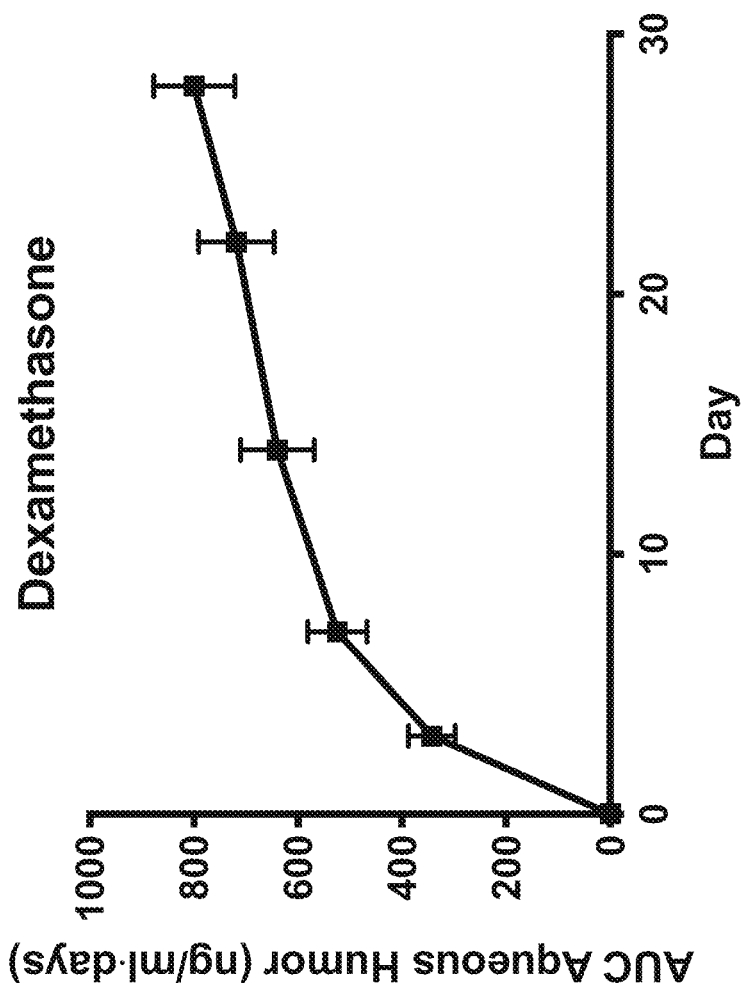
FIG. 43 illustrates an area under the curve analyses for dexamethasone concentrations in aqueous humor.

Area under the curve (AUC) analyses are shown for ketorolac (FIG. 42) and dexamethasone (FIG. 43) concentrations in aqueous humor (AH). The AUC curves provide an estimate of the cumulative release of drug inside the eye over time. It is notable that these in vivo release profiles for ketorolac and/or dexamethasone resemble the general trends observed in vitro described hereinbefore in durations of release of about 2 weeks for ketorolac and at least 4 weeks for dexamethasone. Furthermore, measurement of ketorolac and/or dexamethasone inside the eye for at least 2 weeks is consistent with the observed duration of reduction in inflammation relative to vehicle shown in FIGS. 34 and 35.

Conclusion

Pharmacokinetics of the ophthalmic article loaded with 150 μg of ketorolac (e.g., OcuRing-K) or 150 μg of dexamethasone (e.g., OcuRing-D) attached to an IOL implanted following a cataract surgery in a rabbit model was evaluated. Phacoemulsification was performed bilaterally in two groups of animals. The first group received ophthalmic articles loaded with ketorolac μg attached to IOLs and the second group received ophthalmic articles loaded with 150 μg of dexamethasone attached to IOLs.

Quantification of ketorolac and dexamethasone in aqueous humor and plasma samples taken throughout the study revealed that ketorolac in the aqueous humor was detectable through day 14 while dexamethasone in the aqueous humor was detectable at all timepoints examined through day 28. Plasma levels of either test articles were below the limit of quantification at all timepoints examined. Ocular examinations showed modest inflammation that peaked on day 22 in the first group with ketorolac treatment and day 14 in the second group with dexamethasone treatment. OE scores in the second group carrying the ophthalmic article with dexamethasone (e.g., OcuRing-D) were consistently lower on average than the first group carrying the ophthalmic article with ketarolac (e.g., OcuRing-K) at all timepoints examined. Posterior capsular opacification scoring showed little to no difference between the first group and the second group during the study described herein. Lens opacification was not observed, indicating lack of calcification for the duration of the study described herein. Drug levels released from the ophthalmic article (e.g., OcuRing-D or OcuRing-K) implants persisted for at least two weeks in the aqueous humor and were well tolerated in the rabbits in both groups.

Example 27: Ophthalmic Article Comparison with Topical Drugs 90-Day Study

Following a cataract surgery, a common treatment may comprise use of topical anti-inflammatory drugs such as 0.1% dexamethasone eye drop. As mentioned hereinbefore nonadherence is a common shortcoming of such treatments (e.g. eyedrops). An ophthalmic article with time release capability that can be implanted with the intraocular lens (IOL) at the time of the cataract surgery can eliminate the nonadherence concerns. In a 90-day long study efficacy of the ophthalmic article, disclosed herein, was compared to a common topical drug (e.g., 0.1 dexamethasone eye drop) in a rabbit model of cataract surgery. Four treatment groups were included in this study. Rabbits were randomly assigned to a treatment group. All rabbits received a cataract surgery and an IOL implantation. A first treatment group received an ophthalmic article (e.g., OcuRing) placed on an IOL but no drug; the first group represented a vehicle control group. A second treatment group received an ophthalmic article loaded with dexamethasone 150 μg. (e.g., OcuRing) placed on the IOL. A third treatment group received only an IOL; the third group represents an IOL only control group. A fourth treatment group received of 0.1% dexamethasone eye drops tapered over a 4-week period. Study design is summarized in Table 9.

TABLE 9

Illustrative Study Design Summary

| | |
|---|---|
| Duration | 90 days |
| Species | New Zealand white rabbits |
| Interventions | IOL + OcuRing Vehicle |
| | IOL + OcuRing-D (dexamethasone) |
| | IOL only |
| | IOL + 0.1% dexamethasone eye drops (4-week taper) |
| Objectives | Compare efficacy of OcuRing-D to topical 0.1% dexamethasone drops |
| | Assess safety (IOP) |
| Endpoints | Clinical scoring (Modified Hackett-McDonald) |

Figure 44:
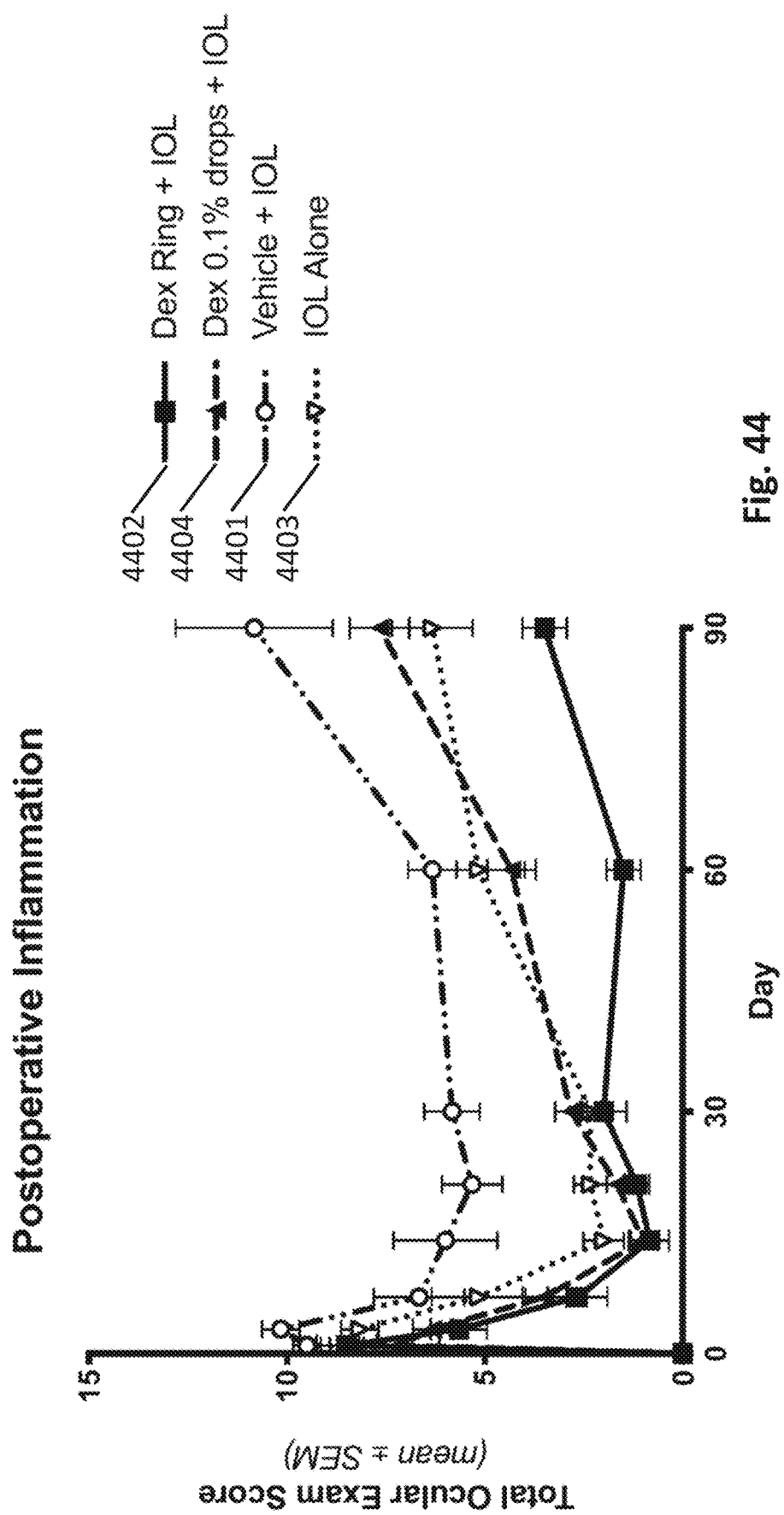
FIG. 44 illustrates average total ocular examination scores for treatment groups at days 0, 1, 3, 7, 14, 21, 30, 60 and 90.

At predefined timepoints as mentioned herein, ocular exam (OE) was performed on all rabbits. Average total OE scores for each treatment group are shown in FIG. 44 at days 0, 1, 3, 7, 14, 21, 30, 60 and 90. Error bars represent standard error of the mean. Empty circles connected with a dashed line 4401 represent the first treatment group or the vehicle control group. Solid dark filled squares connected with solid dark line 4402 represent the second treatment group that received a ophthalmic article loaded with dexamethasone and IOL. Empty downward triangles connected with a dotted line 4403 represent the third treatment group or the IOL only control group. Dark solid filled upward triangles connected with a dashed line 4404 represent the fourth treatment group that received 0.1% dexamethasone eye drops.

Figure 45:
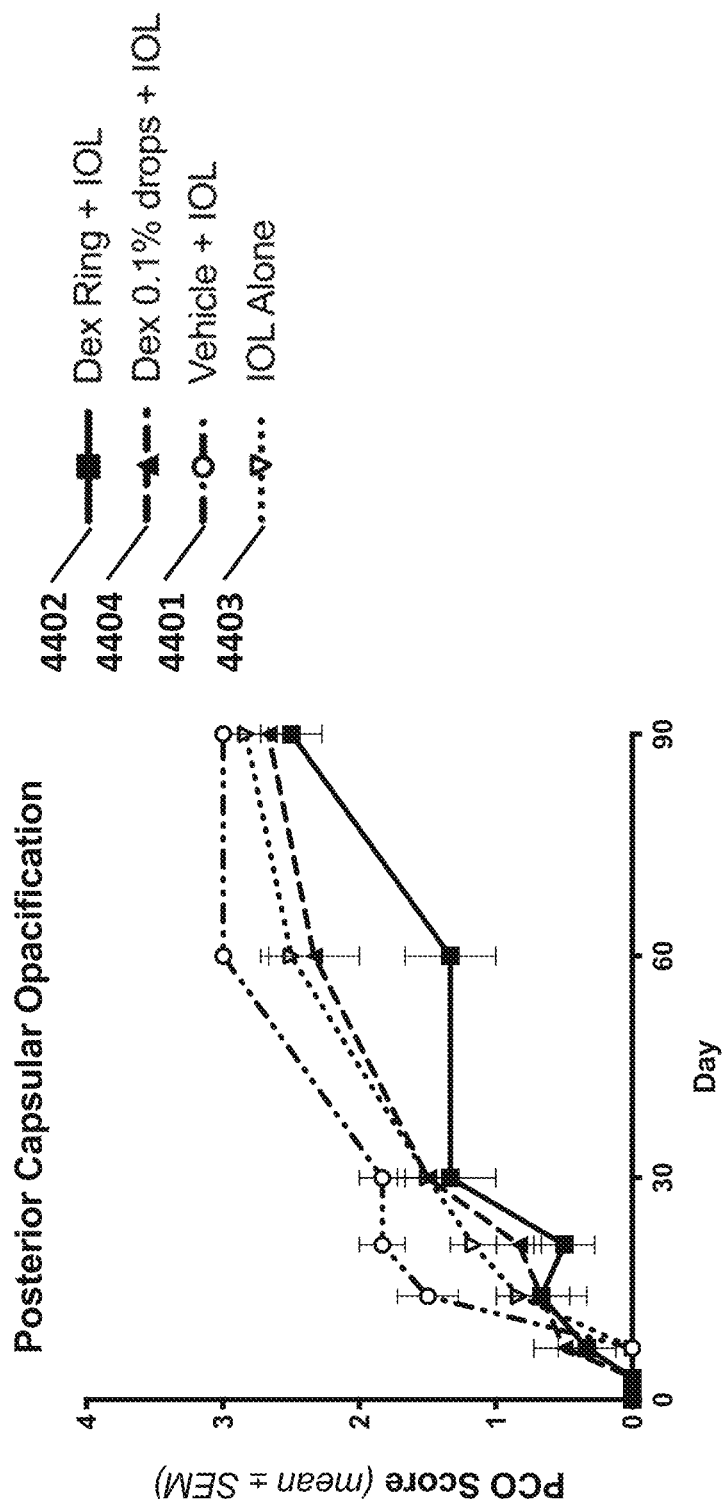
FIG. 45 shows PCO subscores on days 0, 1, 3, 7, 14, 21, 30, 60 and day 90 following the surgery.

Posterior capsular opacification (PCO) was quantified using a modified Hackett and McDonald ocular grading system reported as PCO subscores. FIG. 45 shows PCO subscores on days 0, 1, 3, 7, 14, 21, 30, 60 and day 90 following the surgery for the first group 4401, second treatment group 4402, the third group 4403, and the fourth treatment group 4404. The PCO scores for all groups increased over the 90-day period. The second group, which, received an ophthalmic article loaded with dexamethasone and IOL, showed significantly lower PCO subscore compared to the other groups. A Gompertz nonlinear regression was performed for all four groups. The analysis suggested that the PCO growth rate was lowest for the group 2, followed by group 4, group 3 and group 1, respectively. Results of the Gompertz analysis are summarized in table 10:

TABLE 10

Summary Of Gompertz Analysis Results

Summary of Gompertz Growth Analysis of PCO Results (Best-fit values)

| Parameter | Group 1 | Group 2 | Group 3 | Group 4 |
|---|---|---|---|---|
| YM | 2.903 | 2.855 | 2.762 | 2.678 |
| Y0 | 0.05111 | 0.1708 | 0.05063 | 0.09011 |
| K | 0.09661 | 0.02915 | 0.06806 | 0.05680 |
| 1/K | 10.35 | 34.30 | 14.69 | 17.61 |

Figure 46:
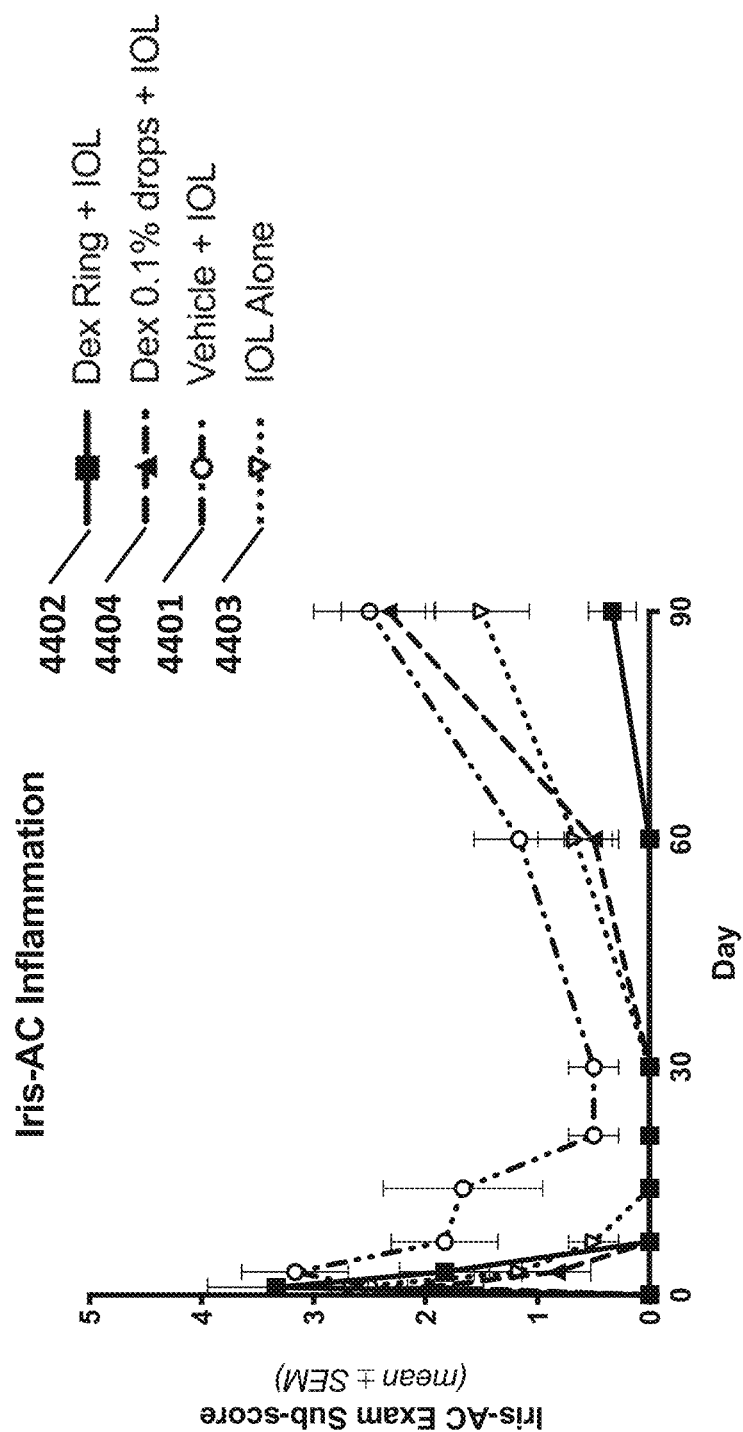
FIG. 46 illustrates total ocular examination scores assessed by the modified Hackett-MacDonald scale.

Y0: Starting population
YM: Maximum population
K: determines the lag time
1/K: X value of infection point The total OE scores assessed by the modified Hackett-MacDonald scale, as shown in FIG. 46, provided an aggregate indicator of ocular inflammation and other abnormalities across all ocular tissues. Without wishing to be bound by theory, when individual subscores, such as PCO, become very high compared to other tissue scores, it may pose difficulties to discern more subtle changes in these individual scores over time. In order to better assess the specific changes in inflammation inside the anterior segment of the eye over the course of the 90-day study, the iris and anterior chamber (AC) inflammation subscores were combined and analyzed. Average combined Iris-AC subscores through day 90 post surgery are shown for the first treatment group 4401, the second treatment group 4402, the third treatment group 4403, and the fourth treatment group 4404 in FIG. 46. Error bars represent standard error of the mean. The second group 4402 that received an ophthalmic article loaded with dexamethasone and IOL showed significantly lower combined iris/AC subscores compared to the fourth group 4404 that received 0.1% dexamethasone eye drops and the IOL control group 4403.

Figure 47:
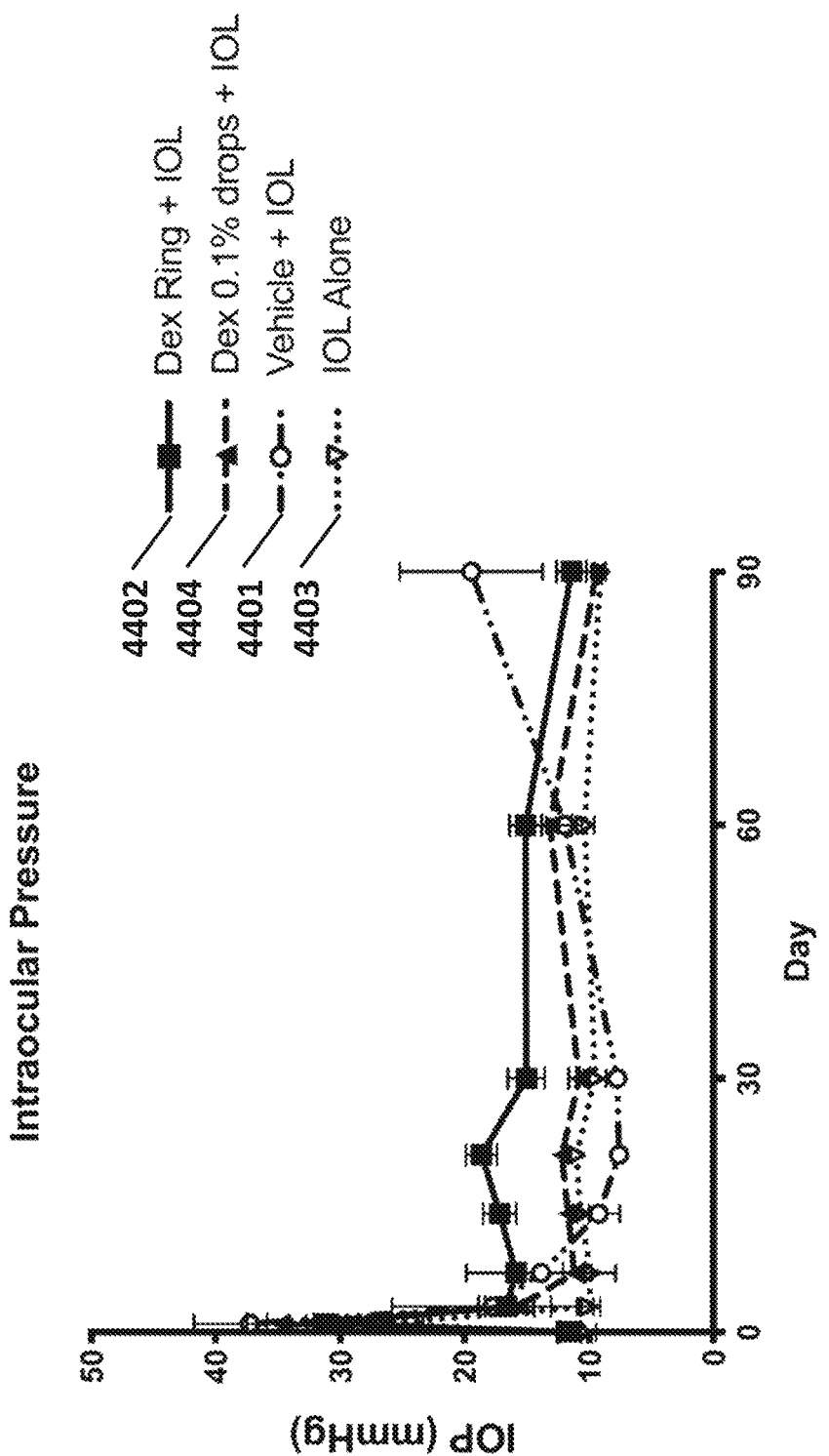
FIG. 47 illustrates intraocular pressure measurements at day 0, 30, 60, and 90 post surgery.

Intraocular pressure (IOP) was measured at day 0, 30, 60, and 90 post surgery in all rabbits (FIG. 47). Empty circles connected with a dashed line 4401 represent the first treatment group or the vehicle control group. Solid dark filled squares connected with solid dark line 4402 represent the second treatment group that received an ophthalmic article loaded with dexamethasone and IOL. Empty downward triangles connected with a dotted line 4403 represent the third treatment group or the IOL only control group. Dark solid filled upward triangles connected with a dashed line 4404 represent the fourth treatment group that received 0.1% dexamethasone eye drops. IOP levels were similar between all treatment groups.

Example 28: 28-Day Clinical Study

Efficacy and safety of an ophthalmic article (e.g., OcuRing) as described herein were evaluated in an open-label single-dose 4-week long clinical study. In this study, 5 subjects received the ophthalmic article attached to an intraocular lens (IOL) following cataract surgery. The ophthalmic article (e.g., OcuRingK ketorolac) used in this study was a substantially small bioerodible ring that was attach to an IOL (e.g., to the haptic of the IOL) and provided sustained-release of ketorolac for 14 days post-surgery. Efficacy evaluation of the ophthalmic article (e.g., OcuRing) included visual acuity, ophthalmic examinations, and patient-reported symptoms. Safety evaluation of the ophthalmic article (e.g., OcuRing) included measuring intraocular pressure, corneal thickness, and recording incidence of treatment emergent adverse events.

Cataract surgery is one of the most common outpatient surgical procedures worldwide. A cataract is a clouding of the lens that affects vision and is removed when the condition worsens to prevent daily activities. The most common cataract extraction is via phacoemulsification followed by intraocular lens (IOL) implantation. Phacoemulsification can consist of incising the side of the cornea and emitting ultrasound waves to break up the lens to allow removal by suction. The lens may then be replaced with an IOL. The most common side effect can be inflammation (pain, redness, and swelling), if left uncontrolled it can lead to pain, photophobia, impaired visual acuity, corneal edema, cystoid macular edema, posterior synechiae, uveitis and glaucoma. Pseudophakic cystoid macular edema (CME) is the most common cause of visual impairments following cataract surgery and is more common in subjects with increased postoperative inflammation. Other risks include retinal detachment, infection and bleeding.

Postoperative inflammation from cataract surgery is typically treated with topical corticosteroid, nonsteroidal anti-inflammatory drug (NDAID) eye drops, or a combination thereof. Corticosteroid eye drops are associated with an increased risk of intraocular pressure (IOP) as well as impaired corneal healing and increased risk of corneal infections. NSAID eye drops can cause pain on instillation resulting in poor drug tolerability. NSAIDs eye drops also impair corneal healing and have risks of corneal ulceration and perforation. Compliance with topical eye drops in general can be problematic, particularly for patients who undergo cataract surgery. This study was a first-in-human clinical trial designed to assess the safety, biocompatibility and preliminary efficacy of the ophthalmic article disclosed herein (e.g., OcuRing-K) implanted in patients that had cataract surgery.

The objectives of the study described herein include: (i) Assessing preliminary safety and efficacy of the ophthalmic article disclosed herein (e.g., OcuRing-K ketorolac) implanted in patients with cataract surgery, (ii) evaluating usability of the ophthalmic article disclosed herein (e.g., OcuRing-K ketorolac) in human cataract surgery and demonstrate that application of the ophthalmic article disclosed herein (e.g., OcuRing-K ketorolac) to an IOL may not require modification of a standard surgical technique, (iii) demonstrating that attaching the ophthalmic article disclosed herein (e.g., OcuRing-K ketorolac) to an IOL may not affect its centration or angulation within the lens capsule and (iv) demonstrating that the ophthalmic article disclosed herein (e.g., OcuRing-K ketorolac) may not produce untoward effects to the iris or lens capsule or migrate into the anterior chamber.

Clinical Study Design

The study disclosed herein was designed as single-arm open-label study assess preliminary safety and efficacy of the ophthalmic article (e.g., OcuRing-K) in human subjects undergoing cataract surgery.

Although it is common practice that patients undergoing cataract surgery receive both NSAID and steroid eye drops for management of postoperative inflammation, there were concerns that inclusion of topical steroid in addition to the drug (e.g., ketorolac) delivered to the subjects' eyes via the ophthalmic article (e.g., OcuRing-K) might affect the outcomes of the study or mask potential adverse events related to the device and its polymer ingredients. Therefore, all patients received the ophthalmic article (e.g., OcuRing-K) as a monotherapy, and the protocol permitted use of steroid eye drops as rescue therapy in the event of uncontrolled inflammation. A first eye of a subject that received the ophthalmic article and IOL is mentioned herein as a "study eye". A second eye of the subject that did not receive the ophthalmic article and IOL is mentioned herein as a "fellow eye".

Postoperative exams were scheduled at days 1, 7 and 28 following the surgery as is customary practice after a cataract surgery. Safety assessments were performed including visual acuity, intraocular pressure and treatment-emergent adverse events. Safety results were presented with descriptive statistics as mentioned herein.

Anterior chamber cell (ACC) and postoperative pain scores were used as measurements for efficacy for postoperative inflammation following the cataract surgery. The data was collected for all patients at baseline (day 0) and days 1, 7, and 28 post-surgery. Because this was a single-arm study, statistical comparisons between groups were not possible.

Slit lamp photos and refractive data were also collected to assess the position of the ophthalmic article (e.g., OcuRing-K) and the IOL within the eye to determine if the presence of the ophthalmic article (e.g., OcuRing-K) on the IOL in any way affected the position or tilt of the IOL or induced untoward effects on the iris and adjacent tissues.

Efficacy endpoints were selected based on the design of registration studies from existing products approved for treatment of postoperative inflammation after cataract surgery. Anterior chamber cell (ACC) scores were assessed using the Standardization of Uveitis Nomenclature (SUN) scale. Pain scores were assessed using a 10-point visual analog scale.

A summary of the study design is shown in Table 11.

TABLE 11

Illustrative Study Design Summary

| | |
|---|---|
| Study Phase | Phase 1 |
| Indication | Postoperative Inflammation. |
| Target Population | Patients Undergoing Cataract Surgery |
| Duration of Study | 28 Days |
| Enrollment | 5 subjects |
| Treament Arms | Ocuring-K (ketorolac) |
| Efficacy Endpoints | Anterior chamber cell (ACC) count, postoperative pain |
| Safety Endpoints | Visual acuity, intraocular pressure, frequency of adverse events |
| Study Timeline | Screening at seven days prior to surgery. Postoperative exams at 1 to 28 days after surgery. |

Subjects

Subjects were screened within one month prior to scheduling for the cataract surgery. Subject eligibility was assessed on the basis of medical and ophthalmic history including diagnostic testing as described herein. Eligible subjects were provided written informed consent to participate in the study.

Subjects, also mentioned herein as patients, were observed for 4 weeks following the cataract surgery and monitored for safety and efficacy at day 1, 7 and 28 post-surgery. Standard ophthalmic examination procedures were performed on the subjects to evaluate any response to treatment. The evaluation included grading and scoring according to established assessment scales as mentioned hereinafter. Rescue therapy consisting of corticosteroid eye drops were available to all patients.

A sample size could not be estimated as no prior human data for the ophthalmic article disclosed herein was available. The sample size of 5 participants was selected based on clinical and practical considerations. Descriptive statistics were used to tabulate and summarize study outcomes.

Criteria for Inclusion/Exclusion:

Inclusion Criteria

Criteria to accept subjects into the trial disclosed herein include: subjects to receive unilateral cataract extraction and implantation of a monofocal intraocular lens (IOL) implantation, male or female patients between 18 to 85 years of age, and subjects willing and able to comply with the protocol requirements. All subjects had gone through the consent process and had signed an approved informed consent form.

Exclusion Criteria

Subjects were excluded from the trial if they met any of the following criteria: severe/serious corneal pathology which may preclude study completion; any extraocular/intraocular inflammation in the study eye at screening visit (blepharitis allowed if mild only, and no concurrent conjunctivitis or lid erythema/edema) or ongoing, unresolved uveitis; ocular surgery of any kind in the study eye within 6 months prior to baseline visit; were scheduled for surgery in the fellow eye within the study period; any medical condition or clinical laboratory test which could make the subject unsuitable for the study; anterior chamber inflammation as measured by slit lamp examination at baseline; used any topical ocular medication in either eye, other than tear substitute for dry eye, at least 2 weeks prior to baseline visit; currently or within past 5 years, had a history of malignancy other than successfully treated squamous or basal cell carcinoma of the skin or successfully treated in situ cervical cancer; received oral corticosteroid within the past 14 days prior to the first visit or topical corticosteroid in less than 48 hours prior to the first visit; were prescribed nonsteroidal anti-inflammatory drugs (NSAIDs) or immunosuppressive agents, unless the dose was stable for six weeks and no change in dosing is anticipated for the duration of the study; received intravitreal or sub-Tenon corticosteroid treatment in the study eye within the past 6 months prior to the first visit; interocular pressure (IOP) of equal or greater than 25 mmHg at baseline, a history of glaucoma, or require ocular antihypertensive medications in the study eye; known steroid intraocular pressure responders in either eye; and/or participated in another investigational device or drug study within 3 months prior to this study.

Treatment Administered

The ophthalmic article (e.g., OcuRing-K) was attached to an IOL and was administered to the subject during the cataract surgery. All five subjects received a single-piece foldable hydrophobic acrylic IOL, commonly used in cataract surgeries, (e.g., Alcon AcrySof IQ Monofocal IOL). The ophthalmic article (e.g., OcuRing-K) was attached to the haptic of an intraocular lens (IOL) for implantation during cataract surgery. The ophthalmic article (e.g., OcuRing) delivered a therapeutic dose (e.g., 150 μg dose) of ketorolac inside the eye of the subject for approximately 14 days following the cataract surgery.

The ophthalmic article (e.g., OcuRing-K) described herein is made of a soft, flexible material that confirms to standard cataract surgical techniques and may not require specialized instruments for implantation into the eye. The ophthalmic article (e.g., OcuRing-K) can be made from biocompatible, biodegradable polymers that enable gradual release of ketorolac over at least a 14 to 21 day period. The ophthalmic article used in this clinical study (e.g., OcuRing-K) comprised 12% ketorolac tromethamine and 88% poly (L-lactide-co-caprolactone) at 60:40 ratio of L-lactide to caprolactone. The ophthalmic article can be shaped like an extruded annulus of approximately 1.2 mm outer diameter, 0.6 mm hole or inner structure diameter and 0.5 mm cross sectional thickness. In an illustrative embodiment, the ophthalmic article used in this study was shaped like an extruded annulus of approximately 1.25 mm outer diameter, 0.65 mm hole or inner diameter and 0.5 mm cross sectional thickness.

The ophthalmic articles (e.g., OcuRing-K) were supplied as a single-use sterile package labeled with the protocol number, name and address, manufacturer lot number and instructions for use and storage. Drug delivery devices (e.g., OcuRing-K) were refrigerated at about 2-8° C. On the day of surgery, the drug may be stored for up to 3 hours at room temperature (20-22° C.) ready to be used in the operating room.

Ketorolac is a non-steroidal anti-inflammatory (NSAID) medication with a longstanding history of use in cataract surgery. Ketorolac is the active ingredient in multiple marketed ophthalmic products (e.g., Acular eye drops by Allergan, Omidria ocular irrigation solution by Omeros Corporations). Additionally, existing evidence suggests that ketorolac has the potential to reduce pain and inflammation after cataract surgery as well as treat cystoid macular edema (CME) related to cataract surgery. The selected dose of 150 μg of ketorolac was based on prior nonclinical (e.g., preclinical) studies of formulations in animal models of cataract surgery (e.g., rabbit models of cataract surgery) disclosed herein.

The investigational ophthalmic article (e.g., OcuRing-K) was designed to be administered intraoperatively along with the IOL in the cataract surgery. In the study disclosed herein, the ophthalmic article (e.g., OcuRing-K) was attached to the IOL immediately prior to implantation, and they were implanted together inside the capsular bag of an eye of a subject. Prior and concomitant therapies were not allowed in the study disclosed herein. Due to the nature of the application of the ophthalmic article (e.g., an ocular implantation) as opposed to other methods such as eye drops, noncompliance by subjects of using the eyedrops was not a concern in the study.

All of the diagnostic tests and procedures associated with this study may be commonly used in clinical practice and do not commonly represent any risk above the standard of care for cataract surgery.

Benefits to Patients

The known safety and tolerability risks and compliance issues that may be associated with corticosteroid and NSAID eye drops are well known, as described herein. Eliminating administration of topical anti-inflammatory eye drops from the postoperative regimen can represent a clear efficacy and safety benefit to patients. Furthermore, the potential for intraocular ketorolac treatment to reduce the risks of pseudophakic CME can be an additional benefit, particularly in high-risk patients with a history of diabetes and other chronic ocular inflammatory conditions.

Demographic Information and Other Baseline Characteristics

Due to the relatively small sample size (n=5), the ages of the subjects did not follow a normal distribution. All of the subjects were of Hispanic ethnicity and the study was performed at a site in Mexico.

Out of the five subjects enrolled, three were females age 77, 85 and 87 with typical age-related cataracts. A first female subject had nonexudative age-related macular degeneration with geographic atrophy, a condition that may limit visual acuity after cataract surgery. A second female subject had previously been diagnosed as a glaucoma suspect with excavation of her optic nerve. This condition also has the potential to limit visual acuity after cataract surgery. The other two subjects, both males in their 40's, had early-onset cataracts. One of the male subjects had a history of diabetes mellitus, which is a known risk factor for early-onset cataracts. The other male subject had a history of smoking and alcoholism which also increases the risk of early-onset cataracts. A summary of the demographics of the subjects are provided in Table 12.

TABLE 12

Summary of The Demographics of the Subjects

| Demographic Parameter | OcuRing-K Treatment (n = 5) |
|---|---|
| Sex, n (%) | |
| Male | 2 (40) |
| Female | 3 (60) |
| Age | |
| Median | 77 |
| Range | 44, 87 |
| Ethnicity, n (%) | |
| Hispanic | 5 (100) |

A summary of all assessments and procedures performed at each study visits is provided in Table 13.

TABLE 13

Summary of All Assessments and Procedures

| Test/Procedure | Visit 1 Screening | Visit 2 Surgery | Visit 3 Day 1 | Visit 4 Day 7 (±1) | Visit 5 Day 28 (±2) |
|---|---|---|---|---|---|
| Informed Consent | ✓ | | | | |
| Demographics, Medical/Ocular History | ✓ | | | | |
| Inclusion/Exclusion Criteria | ✓ | | | | |
| Urine Pregnancy Test | ✓ | | | | |
| Complete Blood Count | ✓ | | | | |
| Blood Chemistry | ✓ | | | | |
| ECG | ✓ | | | | |
| Vital Signs | ✓ | | ✓ | ✓ | ✓ |
| Best Corrected Visual Acuity | ✓ | | ✓ | ✓ | ✓ |
| Intraocular Pressure | ✓ | | ✓ | ✓ | ✓ |
| Slit Lamp Exam | ✓ | | ✓ | ✓ | ✓ |
| Fundoscopic Exam | ✓ | | ✓ | ✓ | ✓ |
| Corneal Topography (Pentacam) | | | | | ✓ |
| Anterior Segment OCT | | | | | ✓ |
| Slit Lamp Photography | | | | | ✓ |
| Intraoperative Video | | ✓ | | | |
| Ocular Pain Assessment (Visual analog scale) | ✓ | | ✓ | ✓ | ✓ |
| IP Administration | | ✓ | | | |
| Adverse Events | | ✓ | ✓ | ✓ | ✓ |
| Concomitant Medications | ✓ | ✓ | ✓ | ✓ | ✓ |
| IOL Surgery procedure | | ✓ | | | |

A first visit included procedures that were performed within 30 days prior to the surgery. The procedures comprised of the following: obtain informed consent, collect demographic information, medical and ocular history, assess inclusion/exclusion criteria, perform urine pregnancy test, laboratory testing (e.g., complete blood count, blood chemistries), perform electrocardiogram (ECG) testing, measurement of vital signs, height, weight, best corrected visual acuity (BCVA), measurement of intraocular pressure, slit lamp examination, fundoscopic examination, and/or assessment of ocular pain using, for example, and/or visual analog scale.

The laboratory testing comprised: Hematology comprising white blood cell (WBC) count with differential (neutrophils, lymphocytes, eosinophils, monocytes, basophils), hemoglobin, hematocrit, platelet count, and/or red blood cell (RBC) count; serum chemistry profile comprising albumin, alkaline phosphatase (AP), alanine aminotransferase (ALT), aspartate aminotransferase (AST), blood urea nitrogen (BUN), calcium, chloride, bicarbonate, creatinine, glucose, potassium, sodium, total bilirubin and, total protein; and/or pregnancy test which was performed for women of reproductive potential including a urine pregnancy test. If positive, a serum βHCG was obtained to confirm the result. Any subject confirmed to be pregnant was excluded from the study.

A second visit was conducted on the day of the cataract surgery, the visit included: assessment of adverse events, review concomitant medications, measurement of vital signs cataract surgery, implantation of the ophthalmic article (e.g., Ocuring-K), and/or intraoperative surgical video.

A third visit and a fourth visit were performed on day 1 and day 7 (±1) following the cataract surgery, the visits included: assessment of adverse events, review concomitant medications, measurement of vital signs, best corrected visual acuity (BCVA), measurement of intraocular pressure, slit lamp examination, fundoscopic examination, assessment of ocular pain by, for example, a visual analog scale.

A fifth visit was conducted on day 28 (±2) following the cataract surgery, the visit included: assessment of adverse events, review concomitant medications, measurement of vital signs, best corrected visual acuity (BCVA), measurement of intraocular pressure, slit lamp examination, fundoscopic examination, assessment of ocular pain using, for example, a visual analog scale, corneal topography using an imaging device (e.g., a pentacam), anterior segment optical coherence tomography (oct), and/or slit lamp photography.

Vital signs were measured after at least 5 minutes rest, and included seated systolic blood pressure (SBP), diastolic blood pressure (DBP), heart rate (HR), respiratory rate (RR), and/or body temperature.

Adverse event (AE) may be any undesirable physical, psychological, or behavioral effect experienced by a subject during his/her participation in the study, in conjunction with the use of the drug, whether or not related to the implantation of the ophthalmic article and IOL. The occurrence of AEs was sought by non-directive questioning of the subject at each visit. AEs may be subjective or objective symptoms spontaneously offered by a subject and/or observed by an investigator or medical staff. AEs may also be changes in laboratory abnormalities that can be clinically relevant as assessed by an investigator or medical staff and for which a medical intervention was initiated. Disease signs, symptoms, and/or laboratory abnormalities existing prior to the use of the ophthalmic article may not be considered AEs after treatment unless they reoccur after the subject had recovered from the pre-existing condition or, in the opinion of an investigator; they can represent a clinically significant exacerbation in intensity or frequency. AEs were collected from the time a subject signed an informed consent form until the completion of the study (e.g., day 28 to day 30 following surgery). AEs reported prior to surgery/dosing were captured and considered non-treatment emergent AEs. This included any laboratory AE generated from laboratory tests which were performed during the first visit.

A severity of an AE was assessed based on the criteria such as awareness of sign or symptom, but easily tolerated categorized as mild, discomfort enough to cause interference with usual activity categorized as moderate, and/or incapacitating with inability to work or perform usual activity categorized as severe, and/or life threatening. Treatment emergent adverse events (TEAE) was defined as an AE that occurred during the study after the first dose of the ophthalmic article, IOL, and/or drug. Serious adverse event (SAE) was defined as any AE that resulted in any of the following outcomes: death including death that may be unrelated to the implantation of the ophthalmic article; life-threatening experience; required or prolonged inpatient hospitalization; Exceptions may comprise planned hospitalizations for include elective treatments unrelated to the study and treatment on an outpatient basis for an event not fulfilling any of the definitions of a SAE and not resulting in hospital admission; persistent or significant disability/incapacity; congenital anomaly; and/or important medical events that may not have resulted in death including immediately life threatening or one that required hospitalization was considered a SAE when, based upon medical judgment, it could jeopardize the patient and may have required intervention to prevent one of the outcomes mentioned hereinbefore.

Analysis of Efficacy

The mean anterior chamber cell (ACC) and pain scores for all study visits are summarized in Table 14.

TABLE 14

Mean Anterior Chamber Cell (ACC) and Pain Scores

| Efficacy Variable | Baseline (Day 0) | Day 1 | Day 7 | Day 28 |
|---|---|---|---|---|
| ACC Scores Mean (SEM) | 0 (0) | 0.6 (0.1) | 0.4 (0.1) | 0 (0) |
| Pain Score Mean (SEM) | 0 (0) | 0 (0) | 0 (0) | 0 (0) |

Figure 48:
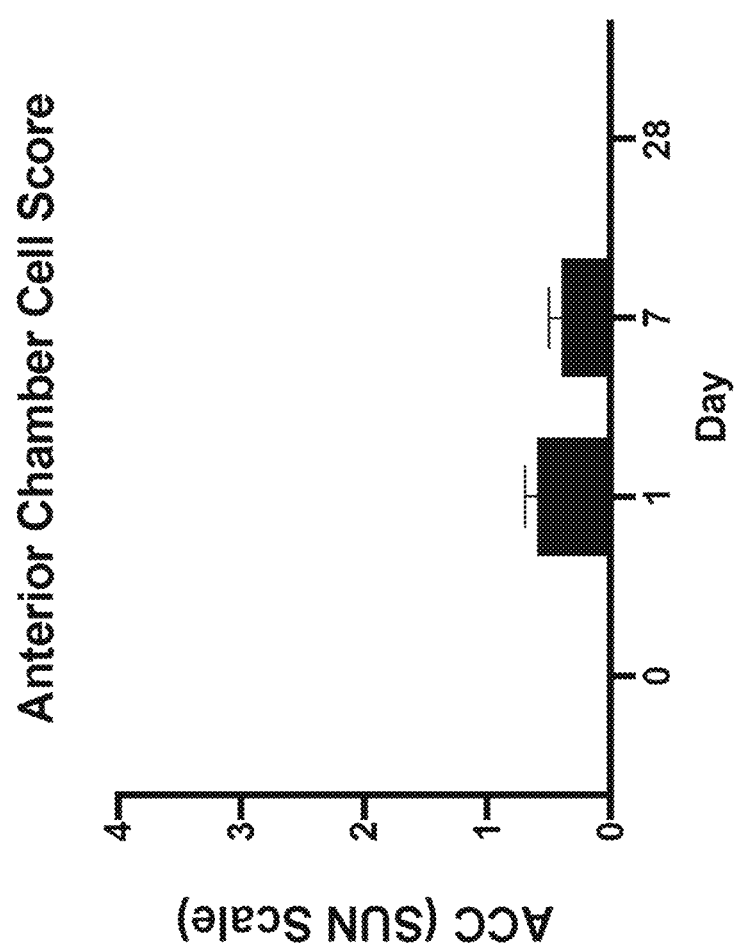
FIG. 48 illustrates anterior chamber cell (ACC) scores.

The mean anterior chamber cell (ACC) scores are shown in FIG. 48. Postoperative inflammation as was quantified by counting the number of cells in the anterior chamber within 1×1 mm slit beam as viewed through a slit-lamp biomicroscope and graded on the Standardization of Uveitis Nomenclature (SUN) scale shown in Table 15. The average ACC scores on days 1 and 7 were 0.6 and 0.4 according to the SUN scale, which is very minimal inflammation. By Day 28, there was no ACC observed. All subjects were pain-free at all postoperative visits.

TABLE 15

The SUN Working Group Grading Scheme For Anterior Chamber Cells

| Grade | Cells in Field† |
|---|---|
| 0 | <1 |
| 0.5+ | 1-5 |
| 1+ | 6-15 |
| 2+ | 16-25 |
| 3+ | 26-50 |
| 4+ | >50 |

*SUN = Standardization of uveitis nomenclature.
†Field size is a 1 mm by 1 mm slit beam.

Figure 49:
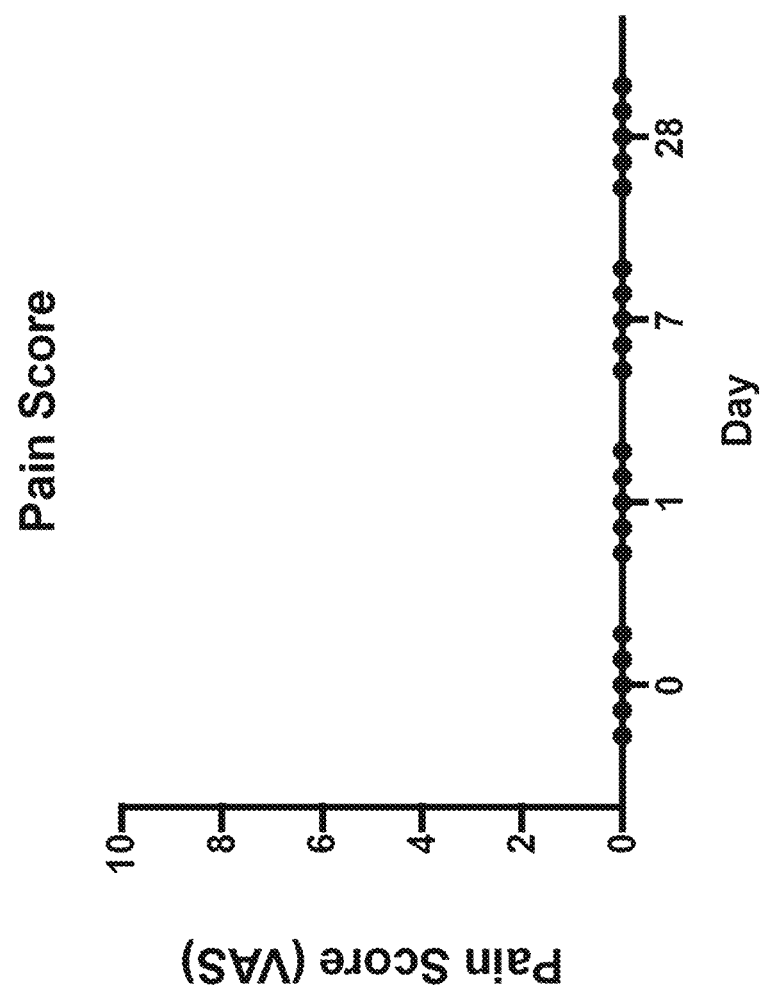
FIG. 49 shows pain scores for subjects at day 0, 1, 7 and 28.
Figure 51B:
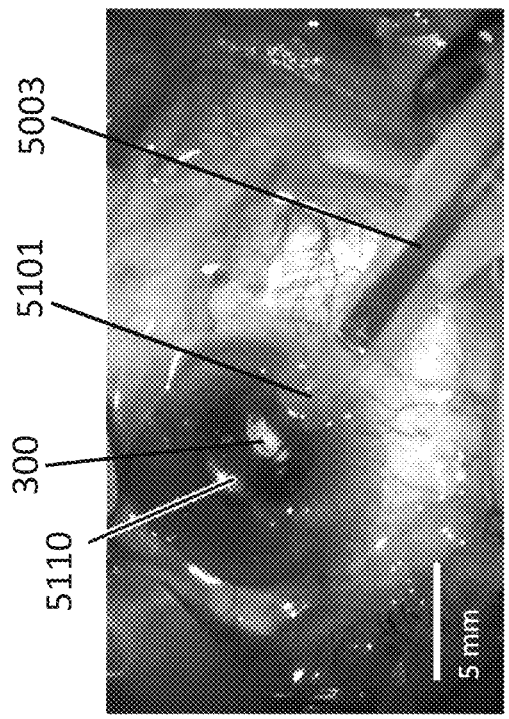
FIGS. 51A-51D illustrate surgical implantation of an IOL with an associated ophthalmic article into an eye of a human subject.
Figure 51D:
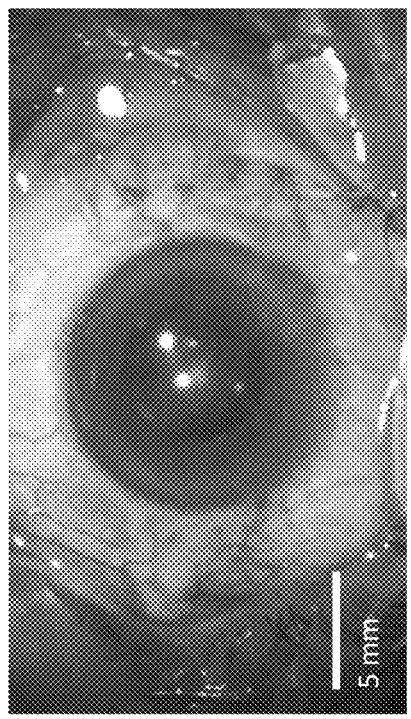
Figure 51A:
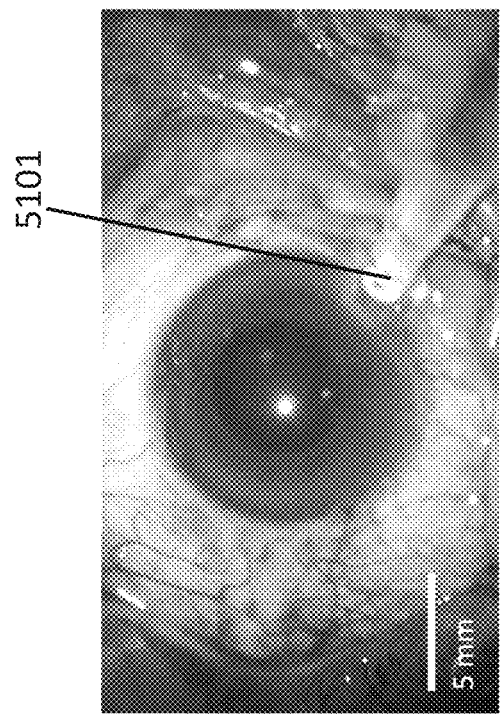
Figure 51C:
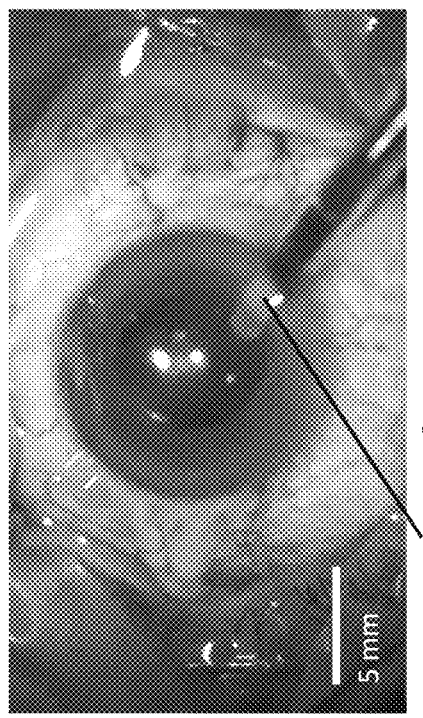

FIG. 49 shows pain scores for all subjects at day 0 (baseline), 1, 7 and 28.

Conclusion

There were no treatment-emergent adverse events related to the study drug. All of the adverse events reported were expected based on the subjects' ocular histories and receipt of cataract surgery. All of the adverse events were mild in grade, and there were no serious adverse events (SAEs).

Intraoperative Observations

Cataract surgery was performed in all subjects without complication. Surigical videos were recorded for all subjects. The ophthalmic articles (e.g., OcuRing-K) were attached to the IOL and inserted using standard surgical technique. In all cases, the IOLs were positioned inside the capsular bag, and there was no evidence that presence of the ophthalmic articles (e.g., OcuRing-K) affected the ability of the user (e.g., a surgeon) to position the IOLs.

FIGS. 50A-50D illustrate loading of an IOL 300 (e.g., Alcon AcrySof IQ Monofocal IOL SN60WF) with an attached ophthalmic article 100 (e.g., OcuRing-K) into the IOL injector cartridge 5001 designed for use with the IOL 300 (e.g. Alcon Monarch III injector system) just prior to surgical implantation. The haptic 302 of the IOL 300 with the attached ophthalmic article 100 is grasped with forceps 5005 (FIG. 50A) and then inserted into the rear of injector cartridge 5003 (FIG. 50B). The plunger 5003 of the injector 5001 advances IOL 300 with the attached ophthalmic article 100 mid-way through the injector cartridge, where the IOL 300 and attached ophthalmic article 100 appear partially rolled with the leading haptic 302 of the IOL 300 folded inward toward the center of the optic (FIG. 50C). As the IOL 300 and attached ophthalmic article 100 are advanced further, they are seen to be more completely rolled with both IOL haptics folded inward within the curled form of the IOL optic (FIG. 50D).

FIG. 51 illustrates surgical implantation of an IOL and attached ophthalmic article inside an eye of a human subject. The tip of the IOL injector cartridge 5101 is initially inserted into the anterior chamber through the corneal incision (FIG. 51A). The injector tip 5101 is then further advance through the pupil 5110 into the anterior opening of capsular bag, and the injector plunger 5003 is slowly advanced to deliver the IOL 300 and attached ophthalmic article into the capsular bag (FIG. 51B). After the IOL and attached ophthalmic article are fully delivered into the capsular bag, the tip of the plunger of the injector is used to position the IOL in the desired location and orientation (FIG. 51C). FIG. 51D shows the appearance of a properly positioned IOL inside the capsular bag. Note that due to the constriction of the pupil, the ophthalmic article is not visible in this image, but the intact ophthalmic article was visualized intraoperative by the surgeon confirming its original shape and position on the IOL haptic.

Visual acuity, intraocular pressure and corneal thickness were used as safety measures following the cataract surgery. The results of safety measurements are shown in Tables 16, 17 and 18. All subjects experienced improvement in visual acuity from day 0 (baseline) to day 28. Some subjects experienced greater improvement in visual acuity than others. For example, Subjects #4 and #5 achieved 20/20 vision by day 28.

Subjects #2 and #3 showed a suboptimal recovery of visual acuity. This may be explained by pre-existing ocular conditions unrelated to cataracts that limited their visual potential. subject #2 was diagnosed with suspected glaucoma based on excavation of her optic nerve. And subject #3 had a prior diagnosis of geographic atrophy confirmed by an optical coherence tomography (OCT). The suboptimal recovery of visual acuity in these subjects may be explained by these pre-existing conditions.

Table 16 shows the results for the change in visual acuity from day 0 (baseline) to day 28. Visual acuity was measured using a LogMAR chart and quantified by Snellen score.

TABLE 16

Change in Visual Acuity from Day 0 To Day 28

| Subject | Baseline Snellen | logMAR | Day 28 Snellen | logMAR |
|---|---|---|---|---|
| 1 | 20/70 | 0.54 | 20/50 | 0.4 |
| 2 | 20/150 | 0.88 | 20/40 | 0.3 |
| 3 | 20/150 | 0.88 | 20/100 | 0.7 |
| 4 | 20/1800 | 2 | 20/20 | 0 |
| 5 | 20/400 | 1.3 | 20/20 | 0 |

Table 17 shows interocular pressure (IOP) measurements for each subject on day 0, 1, 7 and 28. All of the subjects maintained normal IOP throughout the 28 days following the surgery. Transient increases in IOP were observed on day 1, which can be common immediately after cataract surgery; IOP measurements returned to baseline levels by day 7.

TABLE 17

Intraocular pressure Measurements

| | | Subject 001 | 002 | 003 | 004 | 005 |
|---|---|---|---|---|---|---|
| Day | 0 | 13 | 12 | 16 | 13 | 14 |
| | 1 | 20 | 15 | 17 | 15 | 22 |
| | 7 | 15 | 14 | 11 | 13 | 12 |
| | 28 | 16 | 12 | 12 | 11 | 14 |

Table 18 shows corneal thickness measurements for each subject on day 28 post-surgery. Corneal thickness measurements are a general indicator of corneal health. A damage to corneal endothelium from cataract surgery may be evidenced by increased corneal thickness. The corneal thickness measurements obtained on day 28 were normal for all subjects (Table 18).

TABLE 18

Corneal Thickness Measurements on Day 28

| Subject | Thinnest Point (μm) |
|---|---|
| 1 | 565 |
| 2 | 575 |
| 3 | 534 |
| 4 | 562 |
| 5 | 585 |

Figure 52B:
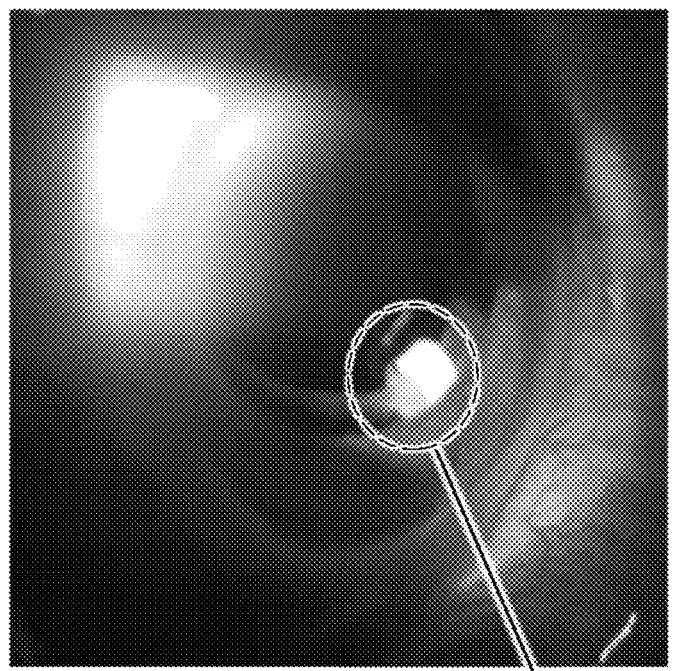
FIGS. 52A-52B illustrate slit lamp photographs for a subject.
Figure 52A:
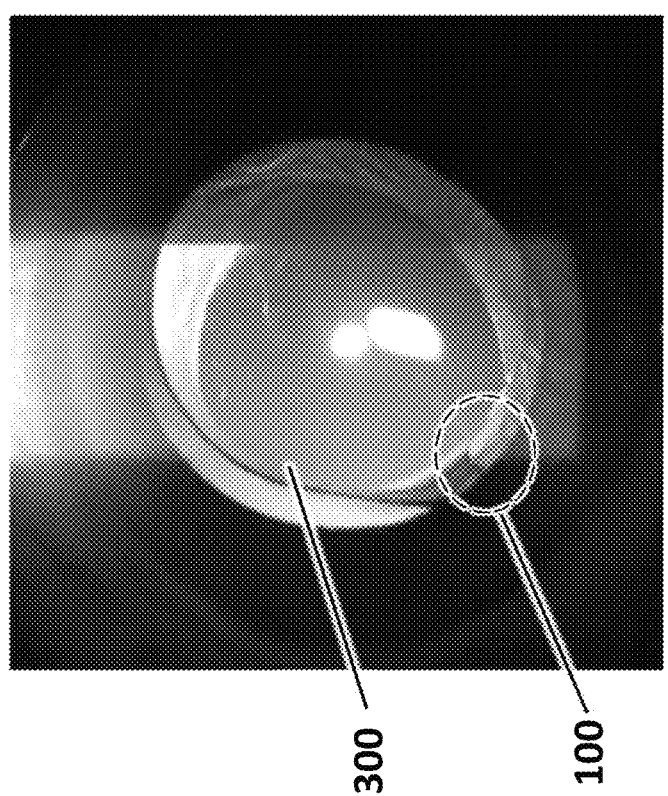

Slit lamp examinations were performed at all postoperative visits to assess the position of the ophthalmic article (e.g., OcuRing-K) and IOL within the study eye of each subjects. Representative slit lamp photographs from Day 28 are shown for a subject (FIGS. 52A and 52B). A portion of the ophthalmic article 100 attached to the IOL 300 is visible at margin of the eye pupil with the eye positioned in forward gaze. Retro-illumination of the study eye demonstrated centration of the IOL with no evidence of tilt (FIG. 52A), and there were no iris illumination defects, suggesting the ophthalmic article (e.g., OcuRing-K) was sufficiently posterior to the iris to avoid contact and did not cause iris thinning. This was further supported by the image obtained with the eye in inferotemporal gaze (FIG. 52B), which shows the ophthalmic article (e.g., OcuRing-K) 100 inside the capsular bag, posterior to the iris. These findings were consistent for all of the subjects studied at all postoperative time points.

Ultrasound biomicroscopy (UBM) scans were obtained in four of the five subjects at study completion. All UBM scans showed that the IOL was properly centered on the visual axis without significant tilt, and there was no evidence of impingement of the ophthalmic article or IOL on the iris or other intraocular tissues. FIG. 29 is a representative UBM image showing an ophthalmic article 100 positioned on the IOL haptic proximal to the optic portion of the IOL 301.

No safety issues involving the ophthalmic article (e.g., OcuRing-K) were identified. All treatment emergent adverse events (TEAE's) were mild grade and expected in relation to cataract surgery. The ophthalmic article (e.g., OcuRing-K) and IOL devices were properly positioned in the study eye of all the subjects.

Conclusion

The study described herein provided preliminary evidence of safety and efficacy of the ophthalmic article (e.g., OcuRing-K) implanted in subjects for treatment of postoperative inflammation in cataract surgery. All of the surgeries were performed using standard surgical technique without complication. The physical presence of the ophthalmic article (e.g., OcuRing-K) on the IOL did not affect the IOL insertion procedure or produce any untoward effects inside the eye after cataract surgery. The postoperative inflammatory response, measured by anterior chamber cell score, was minimal for all subjects and resolved completely by day 28. All subjects were pain-free throughout the postoperative period. A topical anti-inflammatory drug (e.g., NSAID) was not used and the ophthalmic article (e.g., OcuRing-K) was administered as monotherapy.

There were no drug-related adverse effects observed, which is consistent with the known safety profile of other ocular ketorolac formulations. Safety of the ophthalmic article (e.g., OcuRing-K) was evaluated by assessing potential adverse effects relating to the physical properties of the device and/or its polymer ingredients. No adverse effects were observed relating to the ophthalmic article (e.g., OcuRing-K). Slit lamp examinations demonstrated that the ophthalmic article (e.g., OcuRing-K) did not physically affect IOL position in the study eye of the subjects and/or come into contact with the iris. Furthermore, there was no evidence of "rebound" inflammation after the ketorolac had completely eluted by day 14; this observation can support a long-term biocompatibility of the ophthalmic article (e.g., OcuRing-K) and its polymer ingredients in human subjects.

Example 29: Glass Transition Temperature

Figure 53:
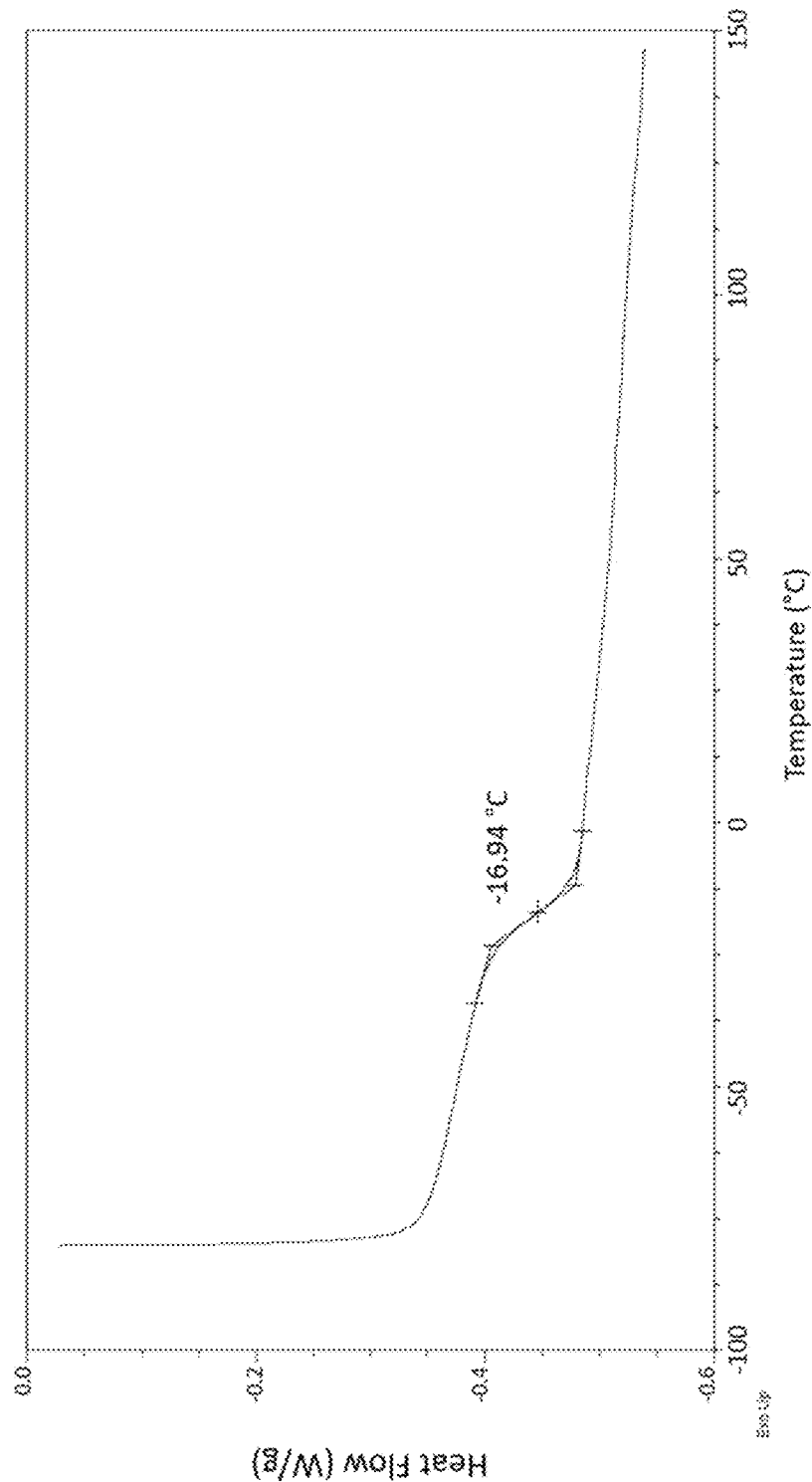
FIG. 53 illustrates differential scanning calorimetry of an ophthalmic article.

Differential scanning calorimetry (DSC) was performed to determine a glass transition temperature of a disc-shaped polymer sample, approximately 23 mm in dimeter and 10 mm thick, with approximately 4 g of mass. The disc-shaped polymer sample comprised of poly(L-lactide-co-caprolactone) at 60:40 ratio with a molecular mass of about 75 to 85 kDa. The experiment was performed using a TA Q2000 Differential Scanning calorimeter (DSC) over a temperature range of −80 to 150° C., heated at a rate of 10° C./min. The DSC curve is shown in FIG. 53. The glass transition temperature of the polymer can range from about −20° C. to about 50° C., and in this embodiment the polymer had a glass transition temperature of about −16.94° C.

Example 30: Dynamic Mechanical Analysis Testing

Figure 54:
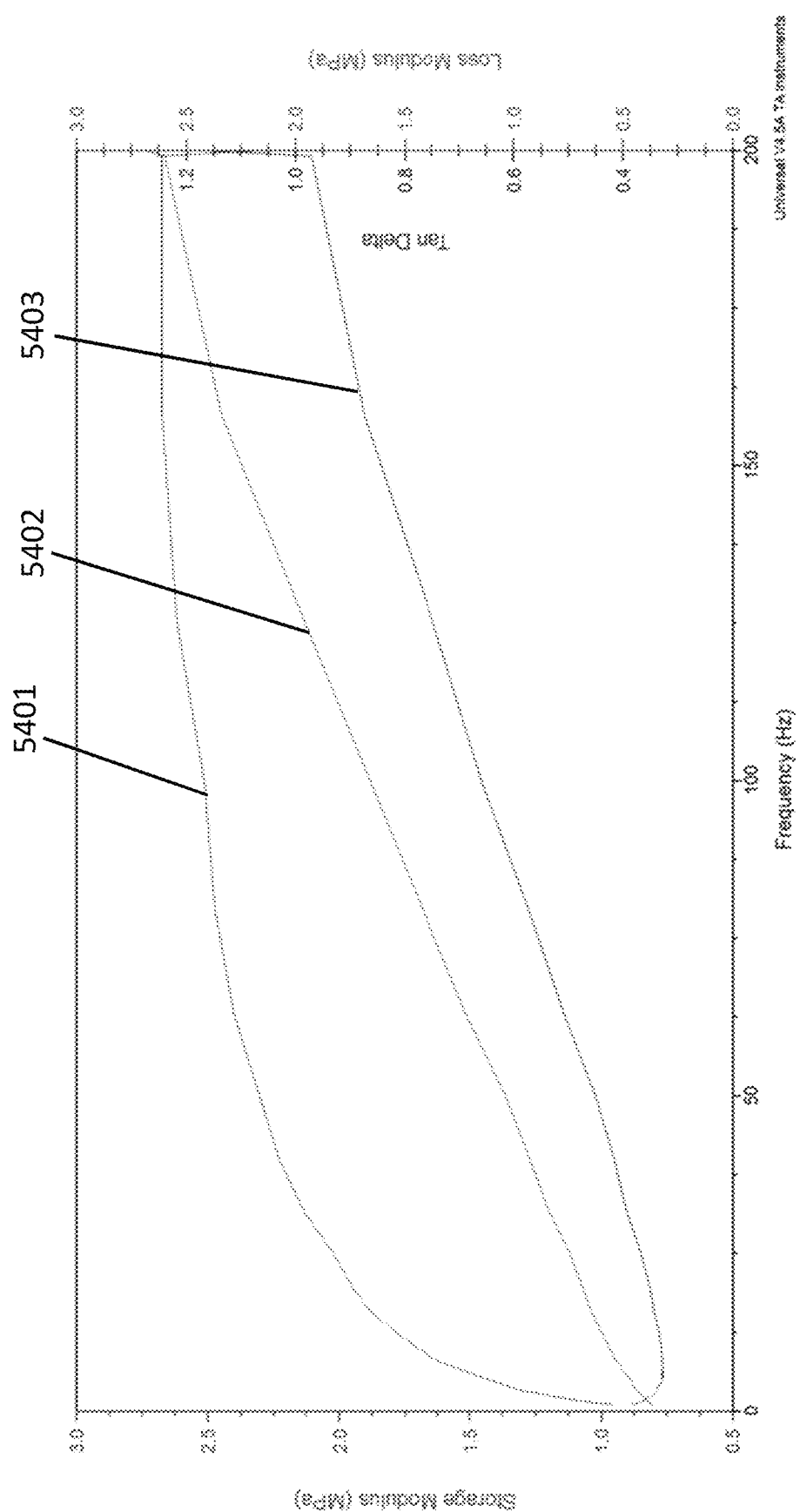
FIG. 54 illustrates a storage modulus curve, a loss modulus, and a tan delta curve for an ophthalmic article.

Dynamic mechanical analysis (DMA) testing was performed to determine the mechanical properties of a disc-shaped polymer sample, approximately 23 mm in dimeter and 10 mm thick, weighing approximately 4 g and comprised of poly(L-lactide-co-caprolactone) at 60:40 ratio with a molecular mass ($M_n$) of about 75 to 85 kDa. The experiment was performed using a Q800 Dynamic Mechanical Analyzer (DMA) manufactured by TA Instruments at 25° C. with a strain amplitude of 10 micrometer (μm) and frequency range of 1 Hz to 200 Hz. The DMA curves including a storage modulus curve 5401, a loss modulus 5402, and a tan delta curve 5403 are shown FIG. 54; a summary of the results are shown in table 19:

TABLE 19

Dynamic Mechanical Analysis Properties
DMA Properties as a Function of Frequency

| Frequency (Hz) | Storage Modulus (MPa) | Approximate Young's Modulus (MPa) | Loss Modulus (MPa) | Tan Delta |
|---|---|---|---|---|
| 1.0 | 0.96 | 0.96 | 0.37 | 0.38 |
| 1.3 | 1.03 | 1.03 | 0.38 | 0.37 |
| 1.6 | 1.09 | 1.09 | 0.40 | 0.36 |
| 2.0 | 1.16 | 1.16 | 0.41 | 0.35 |
| 2.5 | 1.22 | 1.22 | 0.42 | 0.35 |
| 3.2 | 1.30 | 1.30 | 0.44 | 0.34 |
| 5.0 | 1.44 | 1.44 | 0.47 | 0.33 |
| 6.3 | 1.53 | 1.53 | 0.50 | 0.33 |
| 7.9 | 1.63 | 1.63 | 0.53 | 0.33 |
| 10.0 | 1.71 | 1.71 | 0.56 | 0.33 |
| 12.6 | 1.79 | 1.79 | 0.60 | 0.34 |
| 15.8 | 1.88 | 1.88 | 0.65 | 0.34 |
| 19.0 | 1.94 | 1.94 | 0.68 | 0.35 |
| 25.0 | 2.03 | 2.03 | 0.75 | 0.37 |
| 31.6 | 2.14 | 2.14 | 0.84 | 0.39 |
| 39.8 | 2.23 | 2.23 | 0.93 | 0.42 |
| 50.0 | 2.30 | 2.30 | 1.04 | 0.45 |
| 63.0 | 2.40 | 2.40 | 1.22 | 0.51 |
| 79.5 | 2.47 | 2.47 | 1.42 | 0.57 |
| 100.0 | 2.52 | 2.52 | 1.66 | 0.66 |
| 125.0 | 2.62 | 2.62 | 1.96 | 0.75 |
| 158.0 | 2.68 | 2.68 | 2.34 | 0.87 |
| 199.0 | 2.68 | 2.68 | 2.60 | 0.97 |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An ophthalmic article, comprising:
   a. a biocompatible matrix comprising a copolymer derived from a caprolactone monomer and at least one other monomer; and
   b. an active agent or a diagnostic agent;
   wherein said ophthalmic article is toroid shaped to contact and enclose contiguously around an outer surface of a haptic of an intraocular lens (IOL).

2. The ophthalmic article of claim 1, wherein said copolymer is derived from about 20 wt % to about 60 wt % of said caprolactone monomer and from about 40 wt % to about 80 wt % of said at least one other monomer.

3. The ophthalmic article of claim 1, wherein said copolymer is derived from about 40 wt % of said caprolactone monomer and about 60 wt % of said at least one other monomer.

4. The ophthalmic article of claim 1, wherein said at least one other monomer is lactide, glycolide, or trimethylene carbonate.

5. The ophthalmic article of claim 1, wherein said ophthalmic article has a glass transition temperature of at most 24° C., as measured by differential scanning calorimetry.

6. The ophthalmic article of claim 1, wherein said ophthalmic article has an elasticity modulus of at most 10 MPa, as measured by dynamic mechanical analysis.

7. The ophthalmic article of claim 1, wherein said active agent is a corticosteroid, non-steroidal anti-inflammatory drug, or antibiotic.

8. The ophthalmic article of claim 1, wherein said ophthalmic article has a tensile strength of at least 0.5 megapascal (MPa).

9. The ophthalmic article of claim 1, wherein said ophthalmic article has an elongation at break of at least 100% as measured at from about 18° C. to 24° C.

10. The ophthalmic article of claim 1, wherein said ophthalmic article has an elongation at break from about 500% to 1500% as measured at from about 18° C. to 24° C.

11. The ophthalmic article of claim 1, wherein said ophthalmic article comprises an internal structure for contacting and enclosing contiguously around said outer surface of said haptic of said IOL.

12. The ophthalmic article of claim 11, wherein a perimeter or widest dimension of said internal structure is less than or equal to a perimeter or widest dimension of said haptic of said IOL.

13. The ophthalmic article of claim 1, wherein said ophthalmic article extends no more than 0.32 millimeter (mm) beyond said haptic of said IOL once said ophthalmic article is associated around said haptic of said IOL.

14. The ophthalmic article of claim 1, wherein said ophthalmic article comprises an outer diameter of at most 1.5 mm.

15. The ophthalmic article of claim 1, wherein said biocompatible matrix is sufficiently compressible such that said biocompatible matrix is compatible with injection through an IOL injector that comprises an injector tip inner diameter from about 0.5 mm to about 3 mm.

16. The ophthalmic article of claim 1, wherein said biocompatible matrix is sufficiently flexible such that said biocompatible matrix is compatible with injection through an IOL injector that comprises an injector tip inner diameter from about 0.5 mm to about 3 mm.

17. The ophthalmic article of claim 1, wherein said biocompatible matrix is sufficiently elastic such that said biocompatible matrix recovers its original shape after injection through an IOL injector that comprises an injector tip inner diameter from about 0.5 mm to about 3 mm.

18. The ophthalmic article of claim 1, wherein said ophthalmic article is sufficiently physically stable in a physiologic environment such that said ophthalmic article does not significantly change shape within at least 7 days after implantation of said ophthalmic article in an eye of a subject.

19. The ophthalmic article of claim 1, wherein said ophthalmic article comprises from about 1 microgram (μg) to about 800 μg of said active agent or said diagnostic agent.

20. The ophthalmic article of claim 1, wherein said copolymer is a random copolymer, a block copolymer, or a gradient copolymer.

21. An ophthalmic delivery system, comprising:
a. one or more ophthalmic articles comprising (1) a biocompatible matrix comprising a copolymer derived from a caprolactone monomer and at least one other monomer, and (2) one or more active agents or diagnostic agents; and
b. one or more intraocular lenses (IOL) comprising one or more haptics,
wherein said one or more ophthalmic articles is toroid shaped to contact and enclose contiguously around an outer surface of said one or more haptics of said one or more intraocular lenses.

22. The ophthalmic delivery system of claim 21, wherein about one of said one or more ophthalmic articles is associated with about one of said one or more haptics of said one or more intraocular lenses.

23. The ophthalmic delivery system of claim 21, wherein said copolymer is derived from about 20 wt % to about 60 wt % of said caprolactone monomer and from about 40 wt % to 80 wt % of said at least one other monomer.

24. The ophthalmic delivery system of claim 21, wherein said at least one other monomer is lactide, glycolide, or trimethylene carbonate.

25. The ophthalmic delivery system of claim 21, wherein said one or more active agents is a corticosteroid, non-steroidal anti-inflammatory drug, or antibiotic.

26. The ophthalmic delivery system of claim 21, wherein at least two ophthalmic articles are toroid shaped to contact and enclose contiguously around said outer surface of said one or more haptics of said one or more intraocular lenses.

27. A method of treating or preventing a disease, comprising:
implanting into an eye of a subject in need thereof an intraocular lens (IOL) for sustained intraocular drug delivery, wherein said IOL comprises one or more drug release articles associated thereto, wherein said one or more drug release articles comprises (a) a biocompatible matrix comprising a copolymer derived from a caprolactone monomer and at least one other monomer; and (b) one or more active agents, wherein said one or more drug release articles is toroid shaped to contact and enclose contiguously around an outer surface of one or more haptics of said IOL, wherein within 7 days after implantation said one or more drug release articles releases said one or more active agents and results in an inflammation score of at most 1 as measured by an anterior chamber cell score using slit lamp biomicroscopy or absence of eye pain as measured by a 10-point visual analog scale.

28. The method of claim 27, wherein said one or more active agents is a corticosteroid, non-steroidal anti-inflammatory drug, or antibiotic.

29. The method of claim 27, wherein said one or more drug release articles has a glass transition temperature of at most 24° C., as measured by differential scanning calorimetry.

30. The method of claim 27, wherein at least two drug release articles are toroid shaped to contact and enclose contiguously around said outer surface of said one or more haptics of said IOL.

* * * * *